United States Patent
Choi

(10) Patent No.: US 9,221,783 B2
(45) Date of Patent: Dec. 29, 2015

(54) PHENYLALKYL SULFAMATE COMPOUND AND MUSCLE RELAXANT COMPOSITION COMPRISING THE SAME

(71) Applicant: BIO-PHARM SOLUTIONS CO., LTD., Gyeonggi-do (KR)

(72) Inventor: Yong Moon Choi, Seoul (KR)

(73) Assignee: Bio-Pharm Solutions Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/401,990

(22) PCT Filed: Jun. 14, 2013

(86) PCT No.: PCT/KR2013/005279
§ 371 (c)(1),
(2) Date: Nov. 18, 2014

(87) PCT Pub. No.: WO2013/187727
PCT Pub. Date: Dec. 19, 2013

(65) Prior Publication Data
US 2015/0266848 A1    Sep. 24, 2015

Related U.S. Application Data

(60) Provisional application No. 61/660,064, filed on Jun. 15, 2012.

(51) Int. Cl.
C07D 317/72 (2006.01)
C07D 317/18 (2006.01)
C07D 317/34 (2006.01)

(52) U.S. Cl.
CPC ............ C07D 317/72 (2013.01); C07D 317/18 (2013.01); C07D 317/34 (2013.01)

(58) Field of Classification Search
CPC ..................................................... C07D 317/72
USPC ......................................... 514/462; 549/341
See application file for complete search history.

(56) References Cited

U.S. PATENT DOCUMENTS

| | | |
|---|---|---|
| 2,884,444 A | 4/1959 | Berger et al. |
| 2,937,119 A | 5/1960 | Berger et al. |
| 3,265,727 A | 8/1966 | Bossinger et al. |
| 3,313,692 A | 4/1967 | Bossinger et al. |
| 4,591,601 A | 5/1986 | Maryanoff et al. |
| 4,792,569 A | 12/1988 | Maryanoff et al. |
| 5,025,031 A | 6/1991 | Lo et al. |

*Primary Examiner* — Taofiq A Solola
(74) *Attorney, Agent, or Firm* — McDonnell Boehnen Hulbert & Berghoff LLP

(57) ABSTRACT

The present invention relates to novel phenylalkyl sulfamate compounds, a method for preventing or treating a disease associated with muscle spasm. The present invention ensures the enhancement of muscle relaxation activity essential for alleviation of muscle spasm, such that it is promising for preventing or treating various diseases associated with muscle spasm.

19 Claims, No Drawings

PHENYLALKYL SULFAMATE COMPOUND AND MUSCLE RELAXANT COMPOSITION COMPRISING THE SAME

BACKGROUND OF THE INVENTION

1. Field of the Invention

The present invention relates to novel phenylalkyl sulfamate compounds, a muscle relaxation and a method for preventing or treating a disease associated with muscle spasm.

2. Description of the Related Art

Myotony or spasm is frequently observed as a sequel of head injuries, and is difficult to treat.

Myotony is one of skeletal muscle dysfunctions resulting from muscle tone increase, and is caused by central nervous system damage due to wound and various other causes. The causes of muscle tone are abnormal posture, fatigue, degenerative change in spine, etc. And, Myotony can be induced by one of various causes including skeletal muscle spasticity and spastic paralysis causing serious hindrance to daily life. Particularly, spastic paralysis involves symptoms such as tension of the hand and feet, stiffness, difficulty when walking, etc., and causes serious hindrance to daily life. Centrally acting muscle relaxants block receptors related to the excitement of skeletal muscle function, or excite receptors related to the inhibition of skeletal muscle function, in order to relax muscle tone or decrease excessively activated reflection function thus causing muscle relaxation. The centrally acting muscle relaxants may include methocarbaamol, chlormezanon, carisoprodol, eperisone, phenprobamide, etc. However, these drugs act on spinal cord interneurons to inhibit monosynapse and polysynapse, and thus, have side effects including central nervous system depression and muscle weakness.

U.S. Pat. No. 3,313,692 describes racemic carbamate compounds useful as central nervous system drugs with significantly decreased side effects. U.S. Pat. No. 2,884,444, U.S. Pat. No. 2,937,119, and U.S. Pat. No. 3,265,727 describe dicarbamate compounds useful as central nervous system drugs, and N-isopropyl-2-methyl-2-propyl-1,3-propandiol dicarbamate described in U.S. Pat. No. 2,937,119 was released on the market as a muscle relaxant under the product name of Soma. Muscle relaxants are used as an agent for improving symptoms including hernia of an intervertebral disk related to muscle spasm that is involved in skeletal muscle diseases, and vascular disorders of the spinal cord, spastic paralysis of the spinal cord, cervical spondylosis, cerebral palsy, sequelae of injuries (spinal cord injuries, head injuries), spinocerebellar degeneration, etc., and Muscle relaxants are also used as an adjuvant to anesthetic agents.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY OF THE INVENTION

The present inventor has made intensive studies to develop a novel muscle relaxant with excellent activity and low toxicity which may be applied to effective treatment for various disease associated with muscle spasm. As results, the present inventors have discovered that the phenylalkyl sulfamate derivatives represented by above formula 1 provide highly enhanced muscle relaxation activity with significantly decreased side effects.

Accordingly, it is an object of this invention to provide a novel phenylalkyl sulfamate derivatives or pharmaceutically acceptable salt thereof:

It is another object of this invention to provide a method for muscle relaxation.

It is still another object of this invention to provide a method for preventing or treating a disease associated with muscle spasm.

It is still another object of this invention to provide a composition for preventing or treating a disease associated with muscle spasm.

Other objects and advantages of the present invention will become apparent from the following detailed description together with the appended claims and drawings.

DETAILED DESCRIPTION OF THE INVENTION

In one aspect of this invention, there is provided a compound represented by the following formula 1 or pharmaceutically acceptable salt thereof:

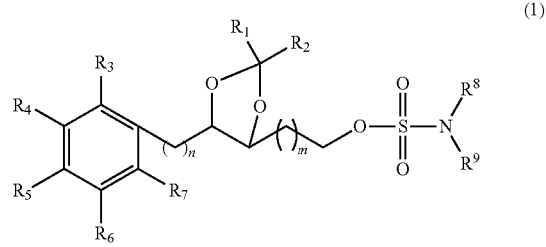

(1)

wherein $R^1$ and $R^2$ are each independently selected from the group consisting of hydrogen, $C_1$-$C_5$ alkyl group and $C_6$-$C_{10}$ aryl group or $R^1$ and $R^2$ together with the carbon atom to which they attach form $C_5$-$C_6$ cycloalkyl group; $R^3$, $R^4$, $R^5$, $R_6$ and $R^7$ are each independently selected from the group consisting of hydrogen, halogen, $C_1$-$C_5$ alkyl group, nitro group and unsubstituted or $C_1$-$C_3$ alkyl-substituted amine group; $R^8$ and $R^9$ are each independently hydrogen or $C_1$-$C_3$ alkyl group; n and m are each independently integer of 0-2.

The present inventor has made intensive studies to develop a novel muscle relaxant with excellent activity and low toxicity which may be applied to effective treatment for various disease associated with muscle spasm. As results, the present inventors have discovered that the novel phenylalkyl sulfamate derivatives represented by above formula 1 provide highly enhanced muscle relaxation activity with significantly decreased side effects.

The term "alkyl" as used herein, refers to a straight or branched chain of saturated hydrocarbon group, e.g., methyl, ethyl, propyl, butyl, isobutyl, tert butyl and pentyl. "$C_1$-$C_5$ alkyl group" as used herein, refers to an alkyl group with carbon number of 1-5.

The term "aryl" as used herein, refers to a totally or partially unsaturated monocylic or polycyclic carbon rings having aromaticity. The aryl group of the present invention is preferably monoaryl or biaryl.

The term "cycloalkyl" as used herein, refers to a monocyclic or polycyclic saturated ring comprising carbon and hydrogen atoms.

According to a concrete embodiment, $R^1$ and $R^2$ are each independently selected from the group consisting of hydrogen, $C_1$-$C_3$ alkyl group and phenyl group or $R^1$ and $R^2$ together with the carbon atom to which they attach form $C_5$-$C_6$ cycloalkyl group, and wherein $R^1$ and $R^2$ are not hydrogen at the same time.

According to a concrete embodiment, $R^3$, $R^4$, $R^5$, $R^6$ and $R^7$ are each independently selected from the group consisting of hydrogen, chlorine, fluorine, iodine, $C_1$-$C_3$ alkyl group, nitro group and unsubstituted or methyl-substituted amine group.

According to a concrete embodiment, $R^8$ and $R^9$ are hydrogen.

According to a concrete embodiment, n and m are each independently integer of 0-1.

According to more concrete embodiment, the compound is selected from the group consisting of:

(1) (5-(2-chlorophenyl)-2,2-dimethyl-1,3-dioxolan-4-yl)methylsulfamate;
(2) (5-(2-chlorophenyl)-2-methyl-1,3-dioxolan-4-yl) methyl sulfamate;
(3) (5-(2-chlorophenyl)-2,2-diethyl-1,3-dioxolan-4-yl)methyl sulfamate;
(4) (3-(2-chlorophenyl)-1,4-dioxaspiro[4,4]nonan-2-yl)methyl sulfamate;
(5) (3-(2-chlorophenyl)-1,4-dioxaspiro[4,5]decan-2-yl)methyl sulfamate;
(6) (5-(2-chlorophenyl)-2-phenyl-1,3-dioxolan-4-yl)methyl sulfamate;
(7) (5-(2-fluorophenyl)-2,2-dimethyl-1,3-dioxolan-4-yl)methyl sulfamate;
(8) (5-(2-fluorophenyl)-2-methyl-1,3-dioxolan-4-yl) methyl sulfamate;
(9) (5-(2-fluorophenyl)-2,2-diethyl-1,3-dioxolan-4-yl)methyl sulfamate;
(10) (3-(2-fluorophenyl)-1,4-dioxaspiro[4,4]nonan-2-yl)methyl sulfamate;
(11) (3-(2-fluorophenyl)-1,4-dioxaspiro[4,5]decan-2-yl)methyl sulfamate;
(12) (5-(2-fluorophenyl)-2-phenyl-1,3-dioxolan-4-yl)methyl sulfamate;
(13) (5-(2-iodophenyl)-2,2-dimethyl-1,3-dioxolan-4-yl)methyl sulfamate;
(14) (5-(2-iodophenyl)-2-methyl-1,3-dioxolan-4-yl) methyl sulfamate;
(15) (5-(2-iodophenyl)-2,2-diethyl-1,3-dioxolan-4-yl) methyl sulfamate;
(16) (3-(2-iodophenyl)-1,4-dioxaspiro[4,4]nonan-2-yl) methyl sulfamate;
(17) (3-(2-iodophenyl)-1,4-dioxaspiro[4,5]decan-2-yl)methyl sulfamate;
(18) (5-(2-iodophenyl)-2-phenyl-1,3-dioxolan-4-yl)methyl sulfamate;
(19) (5-(2,4-dichlorophenyl)-2,2-dimethyl-1,3-dioxolan-4-yl)methyl sulfamate;
(20) (5-(2,4-dichlorophenyl)-2-methyl-1,3-dioxolan-4-yl) methyl sulfamate;
(21) (5-(2,4-dichlorophenyl)-2,2-diethyl-1,3-dioxolan-4-yl) methyl sulfamate;
(22) (3-(2,4-dichlorophenyl)-1,4-dioxaspiro[4,4]nonan-2-yl)methyl sulfamate;
(23) (3-(2,4-dichlorophenyl)-1,4-dioxaspiro[4,5]decan-2-yl) methyl sulfamate;
(24) (5-(2,4-dichlorophenyl)-2-phenyl-1,3-dioxolan-4-yl) methyl sulfamate;
(25) (5-(2,6-dichlorophenyl)-2,2-dimethyl-1,3-dioxolan-4-yl)methylsulfamate;
(26) (5-(2,6-dichlorophenyl)-2-methyl-1,3-dioxolan-4-yl) methyl sulfamate;
(27) (5-(2,6-dichlorophenyl)-2,2-diethyl-1,3-dioxolan-4-yl) methyl sulfamate;
(28) (3-(2,6-dichlorophenyl)-1,4-dioxaspiro[4,4]nonan-2-yl)methyl sulfamate;
(29) (3-(2,6-dichlorophenyl)-1,4-dioxaspiro[4,5]decan-2-yl) methyl sulfamate;
(30) (5-(2,6-dichlorophenyl)-2-phenyl-1,3-dioxolan-4-yl) methyl sulfamate;
(31) (5-(2-aminophenyl)-2,2-dimethyl-1,3-dioxolan-4-yl) methyl sulfamate;
(32) (5-(2-aminophenyl)-2-methyl-1,3-dioxolan-4-yl)methyl sulfamate;
(33) (5-(2-aminophenyl)-2,2-diethyl-1,3-dioxolan-4-yl)methyl sulfamate;
(34) (3-(2-aminophenyl)-1,4-dioxaspiro[4,4]nonan-2-yl) methyl sulfamate;
(35) (3-(2-aminophenyl)-1,4-dioxaspiro[4,5]decan-2-yl)methyl sulfamate;
(36) (5-(2-aminophenyl)-2-phenyl-1,3-dioxolan-4-yl)methyl sulfamate;
(37) (5-(2-nitrophenyl)-2,2-dimethyl-1,3-dioxolan-4-yl)methyl sulfamate;
(38) (5-(2-nitrophenyl)-2-methyl-1,3-dioxolan-4-yl) methyl sulfamate;
(39) (5-(2-nitrophenyl)-2,2-diethyl-1,3-dioxolan-4-yl)methyl sulfamate;
(40) (3-(2-nitrophenyl)-1,4-dioxaspiro[4,4]nonan-2-yl)methyl sulfamate;
(41) (3-(2-nitrophenyl)-1,4-dioxaspiro[4,5]decan-2-yl)methyl sulfamate;
(42) (5-(2-nitrophenyl)-2-phenyl-1,3-dioxolan-4-yl)methyl sulfamate;
(43) (5-(2-nitrophenyl)-2-oxo-1,3-dioxolan-4-yl)methyl sulfamate;
(44) (5-(2-methylphenyl)-2,2-dimethyl-1,3-dioxolan-4-yl) methyl sulfamate;
(45) (5-(2-methylphenyl)-2-methyl-1,3-dioxolan-4-yl)methyl sulfamate;
(46) (5-(2-methylphenyl)-2,2-diethyl-1,3-dioxolan-4-yl)methyl sulfamate;
(47) (3-(2-methylphenyl)-1,4-dioxaspiro[4,4]nonan-2-yl) methyl sulfamate;
(48) (3-(2-methylphenyl)-1,4-dioxaspiro[4,5]decan-2-yl) methyl sulfamate;
(49) (5-(2-methylphenyl)-2-phenyl-1,3-dioxolan-4-yl)methyl sulfamate;
(50) (5-(2-methylaminophenyl)-2,2-dimethyl-1,3-dioxolan-4-yl)methyl methyl sulfamate;
(51) (5-phenyl-2,2-dimethyl-1,3-dioxolan-4-yl)methyl sulfamate;
(52) (5-phenyl-2,2-diethyl-1,3-dioxolan-4-yl)methyl sulfamate;
(53) (3-phenyl-1,4-dioxaspiro[4,4]nonan-2-yl)methyl sulfamate;
(54) (3-phenyl-1,4-dioxaspiro[4,5]decan-2-yl)methyl sulfamate;
(55) 2-(5-benzyl-2,2-dimethyl-1,3-dioxolan-4-yl)ethyl sulfamate;
(56) 2-(5-benzyl-2,2-diethyl-1,3-dioxolan-4-yl)ethyl sulfamate;
(57) 2-(3-benzyl-1,4-dioxaspiro[4,4]nonan-2-yl)ethyl sulfamate;
(58) 2-(3-benzyl-1,4-dioxaspiro[4,5]decane-2-yl)ethyl sulfamate;
(59) (5-benzyl-2,2-dimethyl-1,3-dioxolan-4-yl)methyl sulfamate;

(60) (5-benzyl-2,2-diethyl-1,3-dioxolan-4-yl)methyl sulfamate;
(61) (3-benzyl-1,4-dioxaspiro[4,4]nonan-2-yl)methyl sulfamate;
(62) (3-benzyl-1,4-dioxaspiro[4,5]decan-2-yl)methyl sulfamate;
(63) 2-(5-phenyl-2,2-dimethyl-1,3-dioxolan-4-yl)ethyl sulfamate;
(64) 2-(5-phenyl-2,2-diethyl-1,3-dioxolan-4-yl)ethyl sulfamate;
(65) 2-(3-phenyl-1,4-dioxaspiro[4,4]nonan-2-yl)ethyl sulfamate;
(66) 2-(3-phenyl-1,4-dioxaspiro[4,5]decan-2-yl)ethyl sulfamate;
(67) 2-(5-(2-chlorobenzyl)-2,2-dimethyl-1,3-dioxolan-4-yl) ethyl sulfamate;
(68) 2-(5-(2-chlorobenzyl)-2,2-diethyl-1,3-dioxolan-4-yl) ethyl sulfamate;
(69) 2-(3-(2-chlorobenzyl)-1,4-dioxaspiro[4,4]nonan-2-yl) ethyl sulfamate;
(70) 2-(3-(2-chlorobenzyl)-1,4-dioxaspiro[4,5]decan-2-yl) ethyl sulfamate;
(71) (5-(2-chlorobenzyl)-2,2-dimethyl-1,3-dioxolan-4-yl) methyl sulfamate;
(72) (5-(2-chlorobenzyl)-2,2-diethyl-1,3-dioxolan-4-yl)methyl sulfamate;
(73) (3-(2-chlorobenzyl)-1,4-dioxaspiro[4,4]nonan-2-yl) methyl sulfamate;
(74) (3-(2-chlorobenzyl)-1,4-dioxaspiro[4,5]decan-2-yl)methyl sulfamate;
(75) 2-(5-(2-chlorophenyl)-2,2-dimethyl-1,3-dioxolan-4-yl) ethyl sulfamate;
(76) 2-(5-(2-chlorophenyl)-2,2-diethyl-1,3-dioxolan-4-yl) ethyl sulfamate;
(77) 2-(3-(2-chlorophenyl)-1,4-dioxaspiro[4,4]nonan-2-yl) ethyl sulfamate; and
(78) 2-(3-(2-chlorophenyl)-1,4-dioxaspiro[4,5]decan-2-yl) ethyl sulfamate.

According to more concrete embodiment, the compound is selected from the group consisting of:
(1) (5-(2-chlorophenyl)-2,2-dimethyl-1,3-dioxolan-4-yl)methylsulfamate;
(2) (5-(2-chlorophenyl)-2-methyl-1,3-dioxolan-4-yl) methyl sulfamate;
(3) (5-(2-chlorophenyl)-2,2-diethyl-1,3-dioxolan-4-yl)methyl sulfamate;
(5) (3-(2-chlorophenyl)-1,4-dioxaspiro[4,5]decan-2-yl)methyl sulfamate;
(25) (5-(2,6-dichlorophenyl)-2,2-dimethyl-1,3-dioxolan-4-yl)methylsulfamate;
(43) (5-(2-nitrophenyl)-2-oxo-1,3-dioxolan-4-yl)methyl sulfamate;
(44) (5-(2-methylphenyl)-2,2-dimethyl-1,3-dioxolan-4-yl) methyl sulfamate;
(54) (3-phenyl-1,4-dioxaspiro[4,5]decan-2-yl)methyl sulfamate; and
(64) (5-phenyl-2,2-diethyl-1,3-dioxolan-4-yl)ethyl sulfamate.

According to a concrete embodiment, the compound is in the form of racemate, enantiomer, diastereomer, a mixture of enantiomer or a mixture of diastereomer.

As seen in the Examples, the present inventors have synthesized the compounds of various stereochemistries, and investigated their muscle relaxation activity by multilateral experiments.

The term "enantiomer" as used herein, refers to one of two stereoisomers that are mirror images of each other which are non-superposable due to existence of one or more chiral carbons. According to a concrete embodiment, the enantiomer of the present invention is one in which chiral carbons of $C_4$ and $C_5$ are diverse in stereo-configuration.

The term "diastereomer" as used herein, refers to stereoisomers that are not enantiomers, which occurs when two or more stereoisomers of a compound have different configurations at one or more (but not all) of the equivalent chiral centers thus are not mirror images of each other.

The term "racemate" as used herein, refers to one that has equal amounts of two enantiomers of different stereo-configuration, and lack in optical activity.

It would be obvious to the skilled artisan from the Examples below that the compounds of this invention are not limited to those with specific stereochemistry.

According to a concrete embodiment, the pharmaceutically acceptable salt is produced by reacting the compound with an inorganic acid, an organic acid, an amino acid, sulfonic acid, an alkali metal or ammonium ion.

The pharmaceutically acceptable salts of the present invention are those which can be manufactured by using a method known in the art, for example, but not limited to, salts with inorganic acids such as hydrochloric acid, bromic acid, sulfuric acid, sodium hydrogen sulfate, phosphate, nitrate and carbonate; and salts with organic acids such as formic acid, acetic acid, propionic acid, oxalic acid, succinic acid, benzoic acid, citric acid, maleic acid, malonic acid, tartaric acid, gluconic acid, lactic acid, gestisic acid, fumaric acid, lactobionic acid, salicylic acid, trifluoroacetic acid and acetylsalicylic acid (aspirin); or salts with amino acids such as glycine, alanine, valine, isoleucine, serine, cysteine, cystine, aspartic acid, glutamine, lysine, arginine, tyrosine, and proline; salts with sulfonic acid such as methane sulfonate, ethane sulfonate, benzene sulfonate and toluene sulfonate; metal salts by reaction with an alkali metal such as sodium and potassium; or salts with ammonium ion.

In another aspect of this invention, there is provided a method for muscle relaxation comprising administering pharmaceutically effective amount of the compound of the present invention or pharmaceutically acceptable salt thereof to a subject in need thereof.

As the common descriptions regarding the compounds of this invention are mentioned above, they are omitted herein to avoid excessive overlaps.

According to the present invention, the present inventor has observed that administration of the compound of the present invention significantly increased grip strength and residence time on rotarod rotating of mice, suggesting that the compound of the present invention may be effectively used for improving muscle relaxation activity.

In still another aspect of this invention, there is provided a method for preventing or treating a disease associated with muscle spasm comprising administering pharmaceutically effective amount of the compound of the present invention or pharmaceutically acceptable salt thereof to a subject in need thereof.

As discussed, the compound of the present invention has a superior activity for muscle relaxation with low toxicity. Therefore, it has potential to be developed as a therapeutic agent for preventing and treating various diseases associated with muscle spasm.

The term "disease associated with muscle spasm" as used herein, refers to a disease or disorder resulted from muscle spasm caused by dysfunctional muscle relaxation or excessive muscle tone; or disease or disorder inducing muscle spasm.

As used herein, "muscle spasm" is used interchangeably with "myotony".

According to a concrete embodiment, the disease associated with muscle spasm is selected from the group consisting of herniation of intervertebral disk, vascular disorders of the spinal cord, spastic spinal paralysis, cervical spondylosis, cerebral palsy, sequelae of spinal cord injuries, sequelae of head injuries.

In still another aspect of this invention, there is provided a composition for preventing or treating a disease associated with muscle spasm, comprising the compound of the present invention or pharmaceutically acceptable salt thereof as an active ingredient.

As the common descriptions regarding the compound of this invention and the diseases prevented or treated thereby are mentioned above, they are omitted herein to avoid excessive overlaps.

The composition of this invention may be provided as a pharmaceutical composition comprising a pharmaceutically effective amount of the compound or pharmaceutically acceptable salt thereof.

The term "pharmaceutically effective amount" as used herein, refers to an amount enough to show and accomplish efficacies and activities for preventing, alleviating, treating a disease associated with muscle spasm.

The pharmaceutical composition of this invention includes a pharmaceutically acceptable carrier besides the active ingredient compound. The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in Remington's Pharmaceutical Sciences (19th ed., 1995).

The pharmaceutical composition according to the present invention may be administered orally or parenterally, and concretely, administered parenterally. For parenteral administration, it may be administered intravenously, subcutaneously, intramuscularly, intraperitoneally, transdermally or intra-articularly. More concretely, it is administered intramuscularly or intraperitoneally.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, pharmaceutical composition of the present invention may be administered with a daily dosage of 0.001-10000 mg/kg (body weight).

According to the conventional techniques known to those skilled in the art, the pharmaceutical composition according to the present invention may be formulated with pharmaceutically acceptable carrier and/or vehicle as described above, finally providing several forms including a unit dose form and a multi-dose form. Non-limiting examples of the formulations include, but not limited to, a solution, a suspension or an emulsion in oil or aqueous medium, an elixir, a powder, a granule, a tablet and a capsule, and may further comprise a dispersion agent or a stabilizer.

In still another aspect of this invention, there is provided a method for preparing a compound represented by the following formula 2:

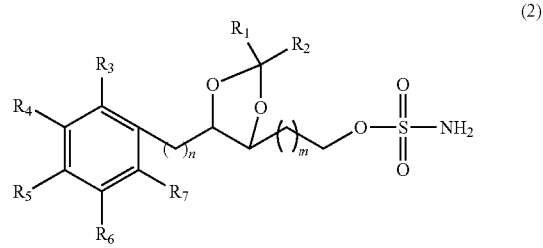

comprising:
(a) performing sulfamation of a compound represented by the following formula 3:

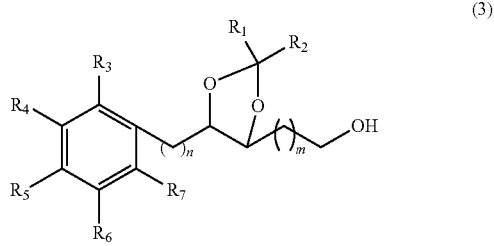

wherein $R_1$ to $R_7$, n and m are same as defined in formula 1.

The term "sulfamation" as used herein, refers to a reaction in which a sulfamate group is substituted on a hydroxyl group of an alcohol. Sulfamation may be performed by various reagents including, but not limited to, chlorosulfonyl isocyanate, sulfamide and sulfuryl chloride.

According to a concrete embodiment, the method further comprises reacting a compound represented by the following formula 4:

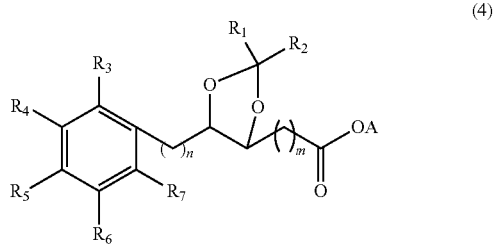

with a reducing agent to form the compound of formula 3 prior to the step (a), wherein $R^1$ to $R^7$, n and m are same as defined in formula 1, and, wherein A is $C_1$-$C_3$ alkoxy $C_1$-$C_3$ alkyl.

The reducing agent is used for reduction of the ester such that the compound of formula 3 is obtained. Non-limiting example of reducing agent is $LiAlH_4$, but any reducing agent which reduces ester to primary alcohol may be used in the present invention.

According to a more concrete embodiment, the method further comprises reacting a compound represented by the following formula 5:

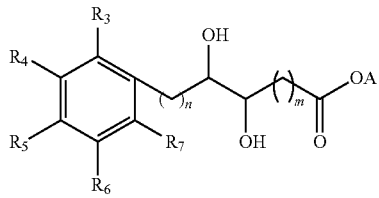

(5)

with and acid and a compound represented by the following formula 6-1 or formula 6-2 to form the compound of formula 4:

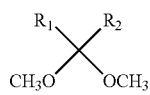

(6-1)

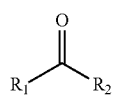

(6-2)

wherein $R_1$ to $R_7$, n, m and A are same as defined in formula 4

The acid of the present invention is used for protonations on methoxy groups in the compound of formula 6-1 or on carbonyl oxygen in the compound of formula 6-2 such that resultant methanols or water may leave well when diol of the compound of formula 5 reacts with the compound of formula 6-1 or 6-2.

According to even more concrete embodiment, the method further comprises performing dihydroxylation of a compound represented by the following formula 7:

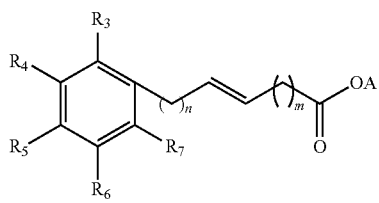

(7)

with an oxidant to form the compound of formula 5, wherein $R^3$ to $R^7$, n, m and A are same as defined in formula 4.

The term "dihydroxylation" as used herein, refers to a reaction in which an oxidant is added to alkenes to form vicinal diols. Concretely, the dihydroxylation is performed by syn-addition of two hydroxyl groups to an alkene. The dihydroxylation may be performed by oxidant including, but not limited to, $OsO_4$, $K_2OsO_4$, and $KMnO_4$.

According to even more concrete embodiment, the method further comprises performing dihydroxylation of a compound represented by the following formula 7:

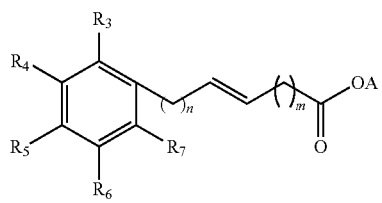

(7)

with an oxidant to form the compound of formula 5, wherein $R^3$ to $R^7$, n, m and A are same as defined in formula 4.

The term "dihydroxylation" as used herein, refers to a reaction in which an oxidant is added to alkenes to form vicinal diols. Concretely, the dihydroxylation is performed by syn-addition or anti-addition of two hydroxyl groups to an alkene. The dihydroxylation may be performed by oxidant including, but not limited to, $OsO_4$, $K_2OsO_4$, $K_2CO_3$ and $KMnO_4$.

In still another aspect of this invention, there is provided a compound represented by the following formula 3 or 4:

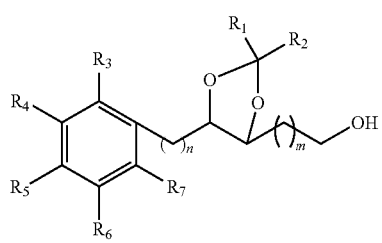

(3)

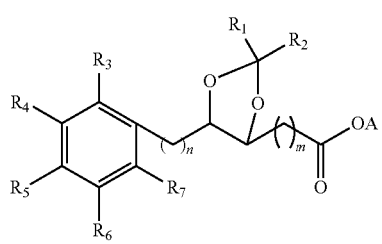

(4)

wherein $R^1$ to $R^7$, n, m and A are same as defined above

The present invention will now be described in further detail by examples. It would be obvious to those skilled in the art that these examples are intended to be more concretely illustrative and the scope of the present invention as set forth in the appended claims is not limited to or by the examples.

EXAMPLES

Reaction Formula 1

Synthesis of Dioxolan-Alcohol Compound

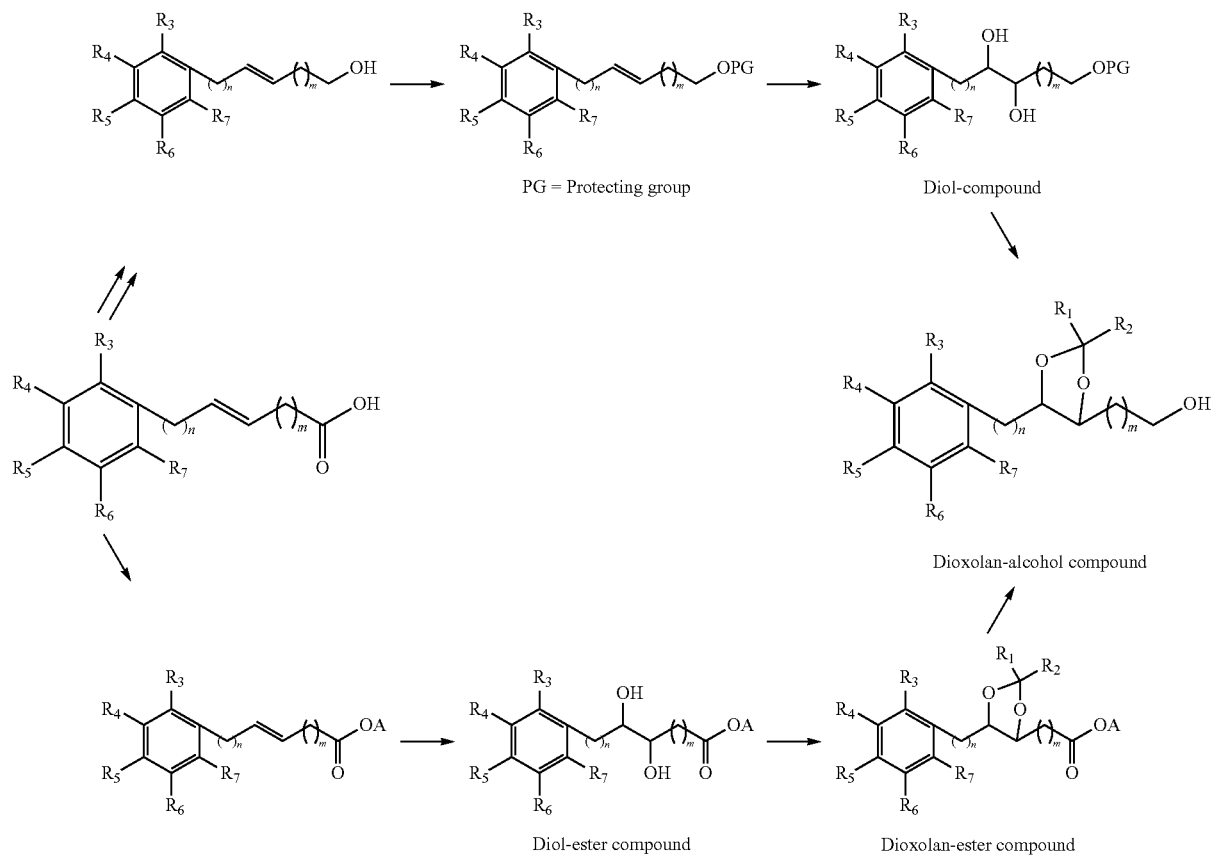

A dioxolan-alcohol compound used in the synthesis of a sulfamate compound is synthesized by dihydroxylation, condensation and a deprotection reaction Reaction Formula 2

Synthesis of Sulfamate Compound

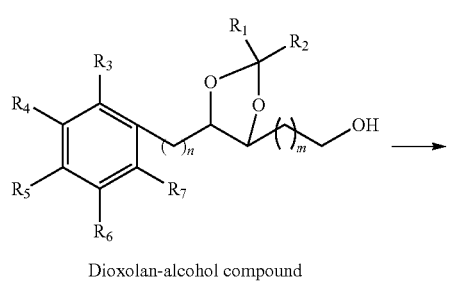

Dioxolan-alcohol compound

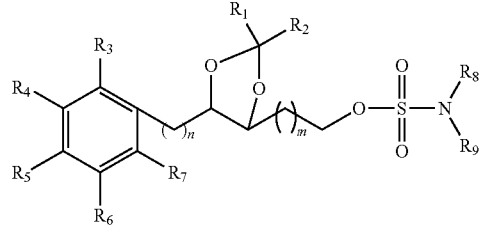

Sulfamate-compound

Preparation Example 1

(E)-3-(2-chlorophenyl)prop-2-en-1-ol

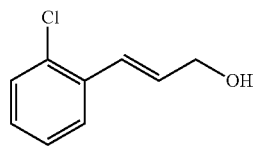

To a 100 ml round-bottomed flask, 2-Chlorocinnamic acid (5 g, 7.3 mmol) and THF (20 ml) were added and the reaction mixture was cooled to 0° C. Triethylamine (4.2 ml, 30.1 mmol) and Ethyl chloroformate (2.88 ml, 30.1 mmol) were added. The reaction mixture was precipitated as a white solid during stirring. After 2 hr, the reaction mixture was filtered with THF (white solid+yellow solution).

The yellow solution was added dropwise to Sodium borohydride (2.68 g, 142.3 mmol) in $H_2O$ at 0° C. and stirred for 2 hrs, quenched with 1N HCl solution. The reaction mixture was extracted by EtOAc and washed with $H_2O$. The combined organic extracts were dried over anhydrous magnesium sulfate ($MgSO_4$), filtered and concentrated under vacuum. The crude compound was purified by a silica gel column to produce the title compound (2.96 g, 60~70%).

$^1$H NMR (400 MHz, $CDCl_3$) δ1.67 (s, 1H), 4.39 (t, J=4.0, 2H), 6.37 (dt J=5.6, 16.0, 1H), 7.03 (d, J=16.0, 1H), 7.18~7.38 (m, 4H),

Preparation Example 2

(E)-1-chloro-2-(3-(methoxymethoxy)prop-1-enyl) benzene

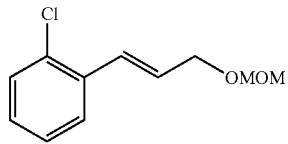

To a 250 ml round-bottomed flask, (E)-3-(2-chlorophenyl) prop-2-en-1-ol (2.96 g, 17.5 mmol, Preparation example 1) and Dichloromethane (17.5 ml) were added and the reaction mixture was cooled to 0° C. Diisopropylethylamine (6.1 ml, 35.1 mmol) was added and stirred at 0° C. Methyl chloromethyl ether (2.77 ml, 35.1 mmol) was added dropwise and stirred for overnight. The reaction mixture was quenched with 1N NaOH solution, extracted by dichloromethane. The combined organic extracts were dried over anhydrous magnesium sulfate ($MgSO_4$), filtered and concentrated under vacuum. The crude compound was purified by a silica gel column to produce the title compound (3.43 g, 85~95%).

$^1$H NMR (400 MHz, $CDCl_3$) δ3.44 (s, 3H), 4.30 (dd, J=8.0, 1.6, 1H), 4.73 (s, 2H), 6.30 (1H, dt, J=6.0, 16), 7.04 (d, J=16.0, 1H), 7.20~7.57 (m, 4H)

Preparation Example 3

(1R,2R)-1-(2-chlorophenyl)-3-(methoxymethoxy) propane-1,2-diol

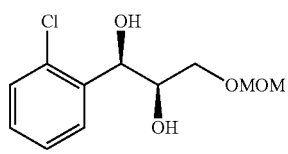

A 250 ml round-bottomed flask, equipped with a magnetic stirrer, was filled with 80 ml of tert-butyl alcohol, 80 ml of water, and $K_3Fe(CN)_6$ (15.93 g, 48.3 mmol), $K_2CO_3$ (6.7 g, 48.3 mmol), $(DHQD)_2$-PHAL (0.12 g, 0.16 mmol), $K_2OsO_2(OH)_4$, (11.8 mg, 0.03 mmol), and Methanesulfonamide (1.53 g, 16.1 mmol). Stirring at 0° C. (E)-1-chloro-2-(3-(methoxymethoxy)prop-1-enyl)benzene (3.43 g, 16.1 mmol, Preparation example 2) was added at once, and the mixture was stirred vigorously at 0° C. overnight. While the mixture was stirred at 0° C., solid sodium sulfite ($Na_2SO_3$, 24.4 g, 193.5 mmol) was added and the mixture was allowed to warm to room temperature. Ethyl acetate was added to the reaction mixture, and after the separation of the layers, the aqueous phase was further extracted with the organic solvent. The combined organic layers were washed with 2 N KOH. The combined organic extracts were dried over anhydrous magnesium sulfate ($MgSO_4$), filtered and concentrated under vacuum. The crude compound was purified by a silica gel column to produce the title compound (3.31 g, 75~90%).

$^1$H NMR (400 MHz, $CDCl_3$) δ3.09 (d, J=5.6, 1H), 3.27 (d, J=4.4, 1H), 3.41 (s, 3H), 3.69~3.77 (m, 2H), 3.96~3.99 (m, 1H), 4.69 (s, 2H), 5.19 (t, J=4.4, 1H), 7.23~7.61 (m, 1H)

Preparation Example 4

(1S,2S)-1-(2-chlorophenyl)-3-(methoxymethoxy) propane-1,2-diol

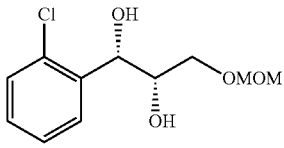

The substantially same method as described in Preparation Example 3 was conducted, except that $(DHQ)_2$-PHAL was used instead of $(DHQD)_2$-PHAL, to obtain the title compound. 3.1 g (75~90%).

$^1$H NMR (400 MHz, $CDCl_3$) δ3.09 (d, J=5.6, 1H), 3.27 (d, J=4.4, 1H), 3.41 (s, 3H), 3.69~3.77 (m, 2H), 3.96~3.99 (m, 1H), 4.69 (s, 2H), 5.19 (t, J=4.4, 1H), 7.23~7.61 (m, 4H)

Preparation Example 5

1-(2-chlorophenyl)-3-(methoxymethoxy)propane-1, 2-diol

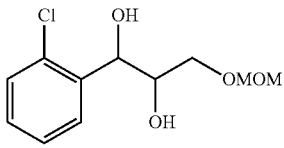

(E)-1-chloro-2-(3-(methoxymethoxy)prop-1-enyl)benzene (9.1 g, Preparation Example 2) was dissolved in 45 mL of a mixture of acetone/t-BuOH/$H_2O$ (5:1:1 V/V). At room temperature, N-methylmorpholine-N-oxide (7.51 g) and $OsO_4$ (0.54 g) were added thereto and stirred for 2-3 hours.

When the reaction was completed, the obtained product was washed with water and methylenechloride (MC). Then, the organic layer was dehydrated with anhydrous magnesium sulfate (MgSO$_4$), filtrated, and concentrated under reduced pressure. The crude compound was purified by a silica gel column to produce the title compound (7.42 g, 70~90%).

$^1$H NMR (400 MHz, CDCl$_3$) δ3.09 (d, J=5.6, 1H), 3.27 (d, J=4.4, 1H), 3.41 (s, 3H), 3.69~3.77 (m, 2H), 3.96~3.99 (m, 1H), 4.69 (s, 2H), 5.19 (t, J=4.4, 1H), 7.23~7.61 (m, 4H)

Preparation Example 6

((4R,5R)-5-(2-chlorophenyl)-2,2-dimethyl-1,3-dioxolan-4-yl)methanol

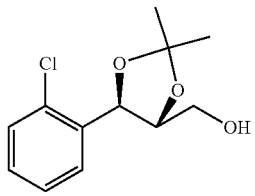 [SMILES: CC1(C)O[C@H](c2ccccc2Cl)[C@@H](CO)O1]

To (1R,2R)-1-(2-chlorophenyl)-3-(methoxymethoxy)propane-1,2-diol (3.31 g, 13.4 mmol, Preparation example 3), Dichloromethane was added and cooled to 0° C. 2,2-Dimethoxypropane (3.3 ml, 26.8 mmol) and p-toluenesulfonic acid (2 g, 10.7 mmol) was added and stirred at room temperature for 5 hrs. The reaction mixture was quenched with H2O, extracted with DCM, and washed with H2O. The organic layer was dried over anhydrous magnesium sulfate (MgSO$_4$), filtered and concentrated. The crude compound was purified by a silica gel column to produce the title compound (1.05 g, 30~40%).

$^1$H NMR (400 MHz, CDCl$_3$) δ1.57 (s, 3H), 1.63 (s, 3H), 1.95~1.98 (m, 1H), 3.88~3.89 (m, 1H), 3.90~3.96 (m, 2H), 5.41 (d, J=8.4, 1H), 7.25~7.66 (m, 4H)

Preparation Example 7

((4S,5S)-5-(2-chlorophenyl)-2,2-dimethyl-1,3-dioxolan-4-yl)methanol

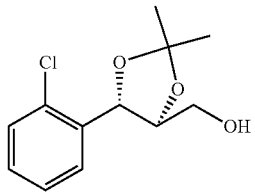

The substantially same method as described in Preparation Example 6 was conducted, except that (1S,2S)-1-(2-chlorophenyl)-3-(methoxymethoxy)propane-1,2-diol (Preparation example 4) was used instead of (1R,2R)-1-(2-chlorophenyl)-3-(methoxymethoxy)propane-1,2-diol (Preparation example 3), to obtain the title compound (1.1 g, 30~40%).

$^1$H NMR (400 MHz, CDCl$_3$) δ1.57 (s, 3H), 1.64 (s, 3H), 1.98 (m, 1H), 3.76~3.83 (m, 1H), 3.88~3.90 (m, 2H), 5.41 (d, J=8.4, 1H), 7.25~7.66 (m, 4H)

Preparation Example 8

(5-(2-chlorophenyl)-2,2-dimethyl-1,3-dioxolan-4-yl)methanol

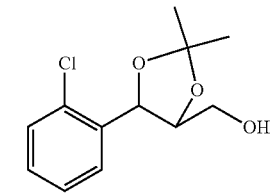 [SMILES: CC1(C)OC(CO)C(c2ccccc2Cl)O1]

The substantially same method as described in Preparation Example 6 was conducted, except that 1-(2-chlorophenyl)-3-(methoxymethoxy)propane-1,2-diol (Preparation example 5) was used instead of (1R,2R)-1-(2-chlorophenyl)-3-(methoxymethoxy)propane-1,2-diol (Preparation example 3), to obtain the title compound (2.1 g, 30~40%).

$^1$H NMR (400 MHz, CDCl$_3$) δ1.57 (s, 3H), 1.63 (s, 3H), 1.95~1.98 (m, 1H), 3.88~3.89 (m, 1H), 3.90~3.96 (m, 2H), 5.41 (d, J=8.4, 1H), 7.25~7.66 (m, 4H)

Preparation Example 9

(E)-3-(2-fluorophenyl)-acrylic acid

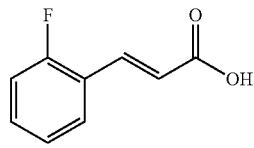 [SMILES: O=C(O)/C=C/c1ccccc1F]

Piperidine (247 mg, 2.90 mmol) was added to a stirred solution of malonic acid (3.1 g, 29.00 mmol) and 2-fluoroaldehyde (3 g, 24.17 mmol) in pyridine at room temperature under N$_2$ condition. The solution was cooled to room temperature, then quenched with HCl solution. The residue was treated with EA and H$_2$O. The organic layer was separated and the aqueous layer was extracted further with EA. The combined extracts were washed with brine. The organic layer was dried over Na$_2$SO$_4$, filtered and concentrated. The crude compound was purified by a silica gel column to produce the title compound (3.66 g, 70~90%).

¹H NMR (400 MHz, CDCl₃) δ6.60 (d, J=16.0, 1H), 7.24~7.50 (m, 3H), 7.66 (d, J=16.0, 1H), 7.84 (t, J=8.0, 1H)

Preparation Example 10

(E)-3-(2-fluorophenyl)-prop-2-en-1-ol

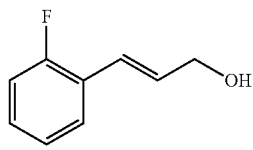

The substantially same method as described in Preparation Example 1 was conducted, except that (E)-3-(2-fluorophenyl)-acrylic acid (Preparation example 9) was used instead of 2-Chlorocinnamic acid, to obtain the title compound (1.6 g, 30~40%).
¹H NMR (400 MHz, CDCl₃) δ1.67 (s, 1H), 4.39 (t, J=4.0, 2H), 6.34~6.41 (m, 1H), 7.00~7.38 (m, 4H)

Preparation Example 11

(E)-1-Fluoro-2-(3-(methoxymethoxy)prop-1-enyl)benzene

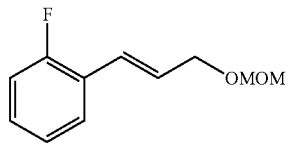

The substantially same method as described in Preparation Example 2 was conducted, except that (E)-3-(2-fluorophenyl)-prop-2-en-1-ol (Preparation example 10) was used instead of (E)-3-(2-chlorophenyl)-prop-2-en-1-ol (Preparation example 1), to obtain the title compound (2.23 g, 85~95%).
¹H NMR (400 MHz, CDCl₃) δ3.44 (s, 3H), 4.30 (dd, J=1.6, 8.0, 1H), 4.73 (s, 2H), 6.27~6.37 (m, 1H), 7.02~7.57 (m, 4H)

Preparation Example 12

(1R,2R)-1-(2-fluorophenyl)-3-(methoxymethoxy)propane-1,2-diol

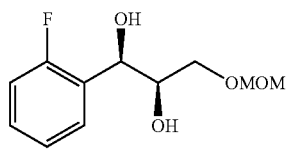

The substantially same method as described in Preparation Example 3 was conducted, except that (E)-1-Fluoro-2-(3-(methoxymethoxy)prop-1-enyl)benzene (Preparation example 11) was used instead of (E)-1-chloro-2-(3-(methoxymethoxy)prop-1-enyl)benzene (Preparation example 2), to obtain the title compound (2.13 g, 75~90%).
¹H NMR (400 MHz, CDCl₃) δ3.09 (d, J=5.6, 1H), 3.27 (d, J=4.4, 1H), 3.41 (s, 3H), 3.69~3.77 (m, 2H), 3.96~3.99 (m, 1H), 4.69 (s, 2H), 5.19 (t, J=4.4, 1H), 7.23~7.61 (m, 4H)

Preparation Example 13

((4R,5R)-5-(2-fluorophenyl)-2,2-dimethyl-1,3-dioxolan-4-yl)methanol

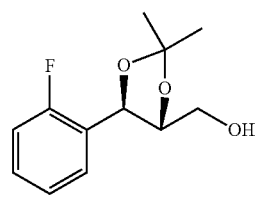 [SMILES: CC1(C)O[C@H](c2ccccc2F)[C@@H](CO)O1]

The substantially same method as described in Preparation Example 6 was conducted, except that (1R,2R)-1-(2-fluorophenyl)-3-(methoxymethoxy)propane-1,2-diol (Preparation example 12) was used instead of (1R,2R)-1-(2-chlorophenyl)-3-(methoxymethoxy)propane-1,2-diol (Preparation example 3), to obtain the title compound (1.73 g, 30~40%).
¹H NMR (400 MHz, CDCl₃) δ1.57 (s, 3H), 1.63 (s, 3H), 1.95~1.98 (m, 1H), 3.88~3.89 (m, 1H), 3.90~3.96 (m, 2H), 5.41 (d, J=8.4, 1H), 7.25~7.66 (m, 4H)

Preparation Example 14

(1S,2S)-1-(2-fluorophenyl)-3-(methoxymethoxy)propane-1,2-diol

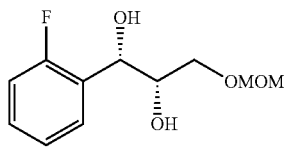

The substantially same method as described in Preparation Example 4 was conducted, except that (E)-1-Fluoro-2-(3-(methoxymethoxy)prop-1-enyl)benzene (Preparation example 11) was used instead of (E)-1-chloro-2-(3-(methoxymethoxy)prop-1-enyl)benzene (Preparation example 2), to obtain the title compound (2.13 g, 75~90%).
¹H NMR (400 MHz, CDCl₃) δ3.09 (d, J=5.6, 1H), 3.27 (d, J=4.4, 1H), 3.41 (s, 3H), 3.69~3.77 (m, 2H), 3.96~3.99 (m, 1H), 4.69 (s, 2H), 5.19 (t, J=4.4, 1H), 7.23~7.61 (m, 4H)

Preparation Example 15

((4S,5S)-5-(2-fluorophenyl)-2,2-dimethyl-1,3-dioxolan-4-yl)methanol

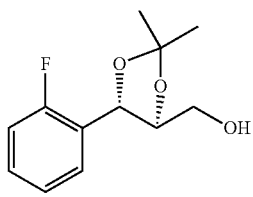 [SMILES: CC1(C)O[C@@H](CO)[C@H](c2ccccc2F)O1]

The substantially same method as described in Preparation Example 6 was conducted, except that (1S,2S)-1-(2-fluorophenyl)-3-(methoxymethoxy)propane-1,2-diol (Preparation example 14) was used instead of (1R,2R)-1-(2-chlorophenyl)-3-(methoxymethoxy)propane-1,2-diol (Preparation example 3), to obtain the title compound (1.73 g, 30~40%).

$^1$H NMR (400 MHz, CDCl$_3$) δ1.57 (s, 3H), 1.63 (s, 3H), 1.95~1.98 (m, 1H), 3.88~3.89 (m, 1H), 3.90~3.96 (m, 2H), 5.41 (d, J=8.4, 1H), 7.25~7.66 (m, 4H)

Preparation Example 16

2-Iodobenzenealdehyde

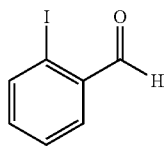

In a flask, 2-iodobenzyl alcohol (4 g, 17.09 mmol) was dissolved in dichloromethane (MC, 85 ml), and then, manganese oxide (MnO$_2$, 14.86 g, 170.92 mmol) was added thereto. The obtained reaction product was stirred under reflux. When the reaction was completed, the obtained reaction product was cooled to room temperature, and then, filtered and concentrated using celite, to obtain the title compound (3.6 g, yield 75~90%).

$^1$H NMR (400 MHz, CDCl$_3$) δ7.30~7.99 (m, 4H), 10.10 (s, 1H)

Preparation Example 17

(E)-3-(2-iodophenyl)-acrylic acid

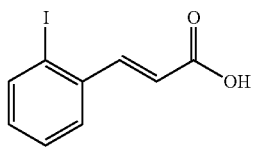 [SMILES: O=C(O)/C=C/c1ccccc1I]

The substantially same method as described in Preparation Example 9 was conducted, except that 2-Iodobenzenealdehyde(Preparation example 16) was used instead of 2-Fluoroaldehyde, to obtain the title compound (2.06 g, 70~90%)

$^1$H NMR (400 MHz, CDCl$_3$) δ6.60 (d, J=16.0, 1H), 7.24~7.50 (m, 3H), 7.66 (d, J=16.0, 1H), 7.84 (t, J=8.0, 1H)

Preparation Example 18

(E)-3-(2-iodophenyl)-prop-2-en-1-ol

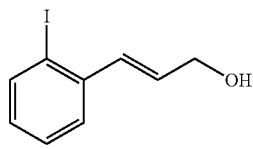 [SMILES: OC/C=C/c1ccccc1I]

The substantially same method as described in Preparation Example 1 was conducted, except that (E)-3-(2-iodophenyl)-acrylic acid (Preparation example 17) was used instead of 2-Chlorocinnamic acid, to obtain the title compound (1.08 g, 30~40%).

$^1$H NMR (400 MHz, CDCl$_3$) δ1.67 (s, 1H), 4.39 (t, J=4.0, 2H), 6.34~6.41 (m, 1H), 7.00~7.38 (m, 4H)

Preparation Example 19

(E)-1-Iodo-2-(3-(methoxymethoxy)prop-1-enyl)benzene

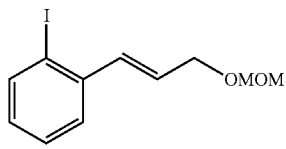

The substantially same method as described in Preparation Example 2 was conducted, except that (E)-3-(2-iodophenyl)-prop-2-en-1-ol (Preparation example 18) was used instead of (E)-3-(2-chlorophenyl)-prop-2-en-1-ol (Preparation example 1), to obtain the title compound (1.37 g, 85~95%).

$^1$H NMR (400 MHz, CDCl$_3$) δ3.44 (s, 3H), 4.30 (dd, J=8.0, 1.6, 1H), 4.73 (s, 2H), 6.27~6.34 (m, 1H), 7.02~7.57 (m, 4H)

Preparation Example 20

(1R,2R)-1-(2-iodophenyl)-3-(methoxymethoxy)propane-1,2-diol

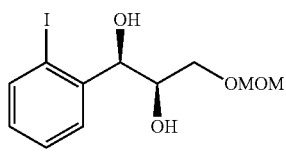

The substantially same method as described in Preparation Example 3 was conducted, except that (E)-1-Iodo-2-(3-(methoxymethoxy)prop-1-enyl)benzene (Preparation example 19) was used instead of (E)-1-chloro-2-(3-(methoxymethoxy)prop-1-enyl)benzene (Preparation example 2), to obtain the title compound (1.32 g, 75~90%).

¹H NMR (400 MHz, CDCl₃) δ3.09 (d, J=5.6, 1H), 3.27 (d, J=4.4, 1H), 3.41 (s, 3H), 3.69~3.77 (m, 2H), 3.96~3.99 (m, 1H), 4.69 (s, 2H), 5.19 (t, J=4.4, 1H), 7.23~7.61 (m, 4H)

Preparation Example 21

((4R,5R)-5-(2-iodophenyl)-2,2-dimethyl-1,3-dioxolan-4-yl)methanol

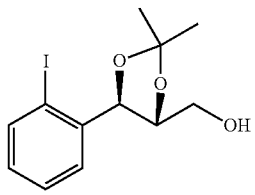 [SMILES: CC1(C)O[C@H](c2ccccc2I)[C@@H](CO)O1]

The substantially same method as described in Preparation Example 6 was conducted, except that (1R,2R)-1-(2-iodophenyl)-3-(methoxymethoxy)propane-1,2-diol (Preparation example 20) was used instead of (1R,2R)-1-(2-chlorophenyl)-3-(methoxymethoxy)propane-1,2-diol (Preparation example 3), to obtain the title compound (1.33 g, 30~40%).
¹H NMR (400 MHz, CDCl₃) δ1.57 (s, 3H), 1.63 (s, 3H), 1.95~1.98 (m, 1H), 3.88~3.89 (m, 1H), 3.90~3.96 (m, 2H), 5.41 (d, J=8.4, 1H), 7.25~7.66 (m, 4H)

Preparation Example 22

(1S,2S)-1-(2-Iodophenyl)-3-(methoxymethoxy)propane-1,2-diol

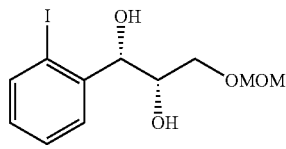

The substantially same method as described in Preparation Example 4 was conducted, except that (E)-1-Iodo-2-(3-(methoxymethoxy)prop-1-enyl)benzene (Preparation example 19) was used instead of (E)-1-chloro-2-(3-(methoxymethoxy)prop-1-enyl)benzene (Preparation example 2), to obtain the title compound (1.32 g, 75~90%).
¹H NMR (400 MHz, CDCl₃) δ3.09 (d, J=5.6, 1H), 3.27 (d, J=4.4, 1H), 3.41 (s, 3H), 3.69~3.77 (m, 2H), 3.96~3.99 (m, 1H), 4.69 (s, 2H), 5.19 (t, J=4.4, 1H), 7.23~7.61 (m, 4H)

Preparation Example 23

((4S,5S)-5-(2-iodophenyl)-2,2-dimethyl-1,3-dioxolan-4-yl)methanol

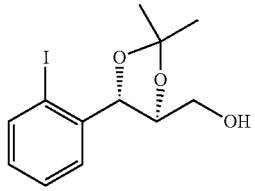 [SMILES: CC1(C)O[C@@H](CO)[C@H](c2ccccc2I)O1]

The substantially same method as described in Preparation Example 6 was conducted, except that (1S,2S)-1-(2-iodophenyl)-3-(methoxymethoxy)propane-1,2-diol (Preparation example 22) was used instead of (1R,2R)-1-(2-chlorophenyl)-3-(methoxymethoxy)propane-1,2-diol (Preparation example 3), to obtain the title compound (1.33 g, 30~40%).
¹H NMR (400 MHz, CDCl₃) δ1.57 (s, 3H), 1.63 (s, 3H), 1.95~1.98 (m, 1H), 3.88~3.89 (m, 1H), 3.90~3.96 (m, 2H), 5.41 (d, J=8.4, 1H), 7.25~7.66 (m, 4H)

Preparation Example 24

(E)-Methyl-3-(2-chlorophenyl)acrylate

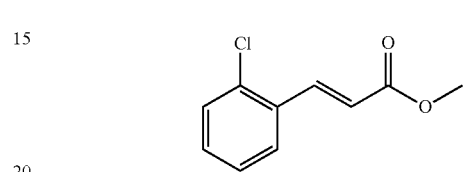

To a 250 ml round-bottomed flask, 2-Chlorocinnamic acid (25 g, 136.9 mmol) and MeOH(56 ml) were added. POCl₃ (1.27 ml, 13.6 mmol) was added dropwise. The reaction mixture was stirred under reflux for 3~4 h. The reaction mixture was cooled to room temperature, quenched with 1N NaOH solution. The mixture was extracted by EtOAc and washed with H₂O. The aqueous layer was further extracted with EtOAc. The combined organic layer was dried over anhydrous magnesium sulfate (MgSO₄), filtered and concentrated under vacuum. (26.98 g, 85~97%)
¹H NMR (400 MHz, CDCl₃) δ3.84 (s, 3H), 6.45 (d, J=16.0, 1H), 7.28~7.65 (m, 4H), 8.12 (d, J=16.0, 1H)

Preparation Example 25

(2R,3S)-methyl-3-(2-chlorophenyl)-2,3-dihydroxypropanoate

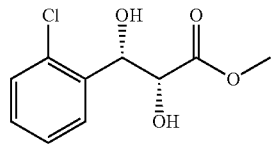

A 1000 ml round-bottomed flask, equipped with a magnetic stirrer, was filled with 362 ml of tert-butyl alcohol, 362 ml of water, K₃Fe(CN)₆ (135.53 g, 411.63 mmol), K₂CO₃ (56.89 g, 411.63 mmol), (DHQ)₂PHAL (1.06 g, 1.37 mmol), K₂OsO₂(OH)₄, (0.1 g, 0.27 mmol), and Methanesulfonamide (13.05 g, 137.21 mmol) and stirred at 0° C. (E)-Methyl-3-(2-chlorophenyl)acrylate (26.98 g, Preparation example 24) was added at once, and the mixture was stirred vigorously at 0° C. overnight. While the mixture was stirred at 0° C., solid sodium sulfite (Na₂SO₃, 24.4 g, 193.5 mmol), EtOAc and water was added and the mixture was allowed to warm to room temperature and stirred. After the separation of the layer, the aqueous layer was added to EtoAc, and the aqueous layer was separated. The combined organic layers were washed with 0.3M H₂SO₄/Na₂SO₄ solution (H₂SO₄ 76 ml, H₂O 2 L, Na₂SO₄ 360 g) twice. After separation of the organic layer, the organic layer was washed with H2O. After separating of the layer, the organic layer were dried over anhydrous MgSO4, filtered and concentrated under vacuum. The crude compound was purified by a silica gel column to produce the title compound (24.42 g, 7090%)

¹H NMR (400 MHz, CDCl₃) δ7.62~7.26 (4H, m), 5.51 (1H, dd, J=7.2, 2.4), 4.50 (1H, dd, J=5.6, 2.4), 3.86 (3H, s), 3.13 (1H, d, J=6.0), 2.79 (1H, d, J=7.2)

Preparation Example 26

(4R,5S)-methyl-5-(2-chlorophenyl)-2,2-dimethyl-1.3-dioxolane-4-carboxylate

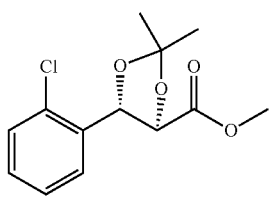 [SMILES: COC(=O)[C@@H]1OC(C)(C)O[C@H]1c1ccccc1Cl]

Dichloromethane(DMC) was added to (2S,3R)-methyl-3-(2-chlorophenyl)-2,3-dihydroxypropanoate (24.4 g, Preparation example 25) and cooled to 0° C. 2,2-Dimethoxypropane (26 ml, 211.77 mmol) and p-toluenesulfonic acid (2 g, 10.58 mmol) was added and stirred at room temperature. The reaction mixture was quenched with H₂O, extracted with DCM, washed with H₂O, dried over anhydrous magnesium sulfate, filtered and concentrated. The crude compound was purified by a silica gel column to produce the title compound (23.6 g, 70~95%).

¹H NMR (400 MHz, CDCl₃) δ1.63 (s, 3H), 1.65 (s, 3H), 3.78 (s, 3H), 4.30 (d, J=7.6, 1H), 5.62 (d, J=7.6, 1H), 7.28~7.64 (m, 4H)

Preparation Example 27(7)

((4S,5S)-5-(2-chlorophenyl)-2,2-dimethyl-1.3-dioxolane-4-yl)methanol

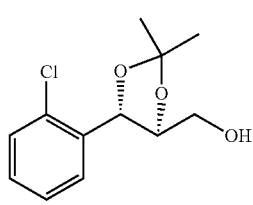

A solution of To a solution LAH(LiAlH₄ 3.31 g, 87.25 mmol) in THF was added dropwise to a solution of (4R,5S)-methyl 5-(2-chlorophenyl)-2,2-dimethyl-1,3-dioxolane-4-carboxylate (23.6 g, Preparation 26) in THF at 0° C., and the mixture stirred at room temp. The reaction mixture was quenched with H₂O at 0° C., cellite filtered with EtOAc, washed with EtOAc, dried over anhydrous magnesium sulfate (MgSO4), filtered and concentrated. The crude compound was purified by a silica gel column to produce the title compound (21.13 g 70~95%)

¹H NMR (400 MHz, CDCl₃) δ1.57 (s, 3H), 1.64 (s, 3H), 1.98 (m, 1H), 3.76~3.83 (m, 1H), 3.88~3.90 (m, 2H), 5.41 (d, J=8.4, 1H), 7.25~7.66 (m, 4H)

Preparation Example 28

(E)-Methyl-3-(2,4-dichlorophenyl)acrylate

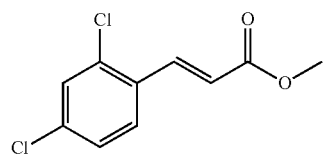

The substantially same method as described in Example 24 was conducted, except that 2,4-dichlorocinnamic acid was used instead of 2-chlorocinnamic acid, to obtain the title compound (9.7 g, 70~90%)

¹H NMR (400 MHz, CDCl₃): δ3.84 (s, 3H), 6.44 (d, J=16, 1H), 7.28~7.33 (m, 1H), 7.41 (d, J=2.0, 1H), 7.55 (d, J=8.4, 1H), 8.04 (d, J=16, 1H).

Preparation Example 29

(2R,3S)-methyl-3-(2,4-dichlorophenyl)-2,3-dihydroxypropanoate

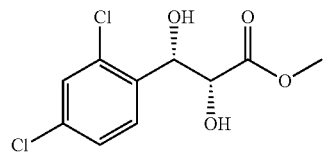 [SMILES: COC(=O)[C@H](O)[C@@H](O)c1ccc(Cl)cc1Cl]

The substantially same method as described in Example 25 was conducted, except that (E)-Methyl-3-(2,4-dichlorophenyl)acrylate (Preparation example 28) was used instead of (E)-Methyl-3-(2-chlorophenyl)acrylate (Preparation example 24), to obtain the title compound (3.8 g, 60~80%)

¹H NMR (400 MHz, CDCl₃): δ3.11 (s, 1H), 3.88 (s, 3H), 4.42 (d, J=2.4, 1H), 5.43 (d, J=2.0, 1H), 7.28~7.33 (m, 1H), 7.41 (d, J=2.0, 1H), 7.55 (d, J=8.4, 1H).

Preparation Example 30

(4R,5S)-methyl-5-(2,4-dichlorophenyl)-2,2-dimethyl-1.3-dioxolane-4-carboxylate

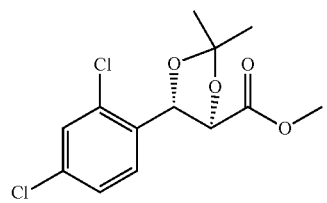 [SMILES: COC(=O)[C@@H]1OC(C)(C)O[C@H]1c1ccc(Cl)cc1Cl]

The substantially same method as described in Example 26 was conducted, except that (2R,3S)-methyl-3-(2,4-dichlorophenyl)-2,3-dihydroxypropanoate (Preparation example 29) was used instead of (2R,3S)-methyl-3-(2-chlorophenyl)-2,3-dihydroxypropanoate (Preparation example 25), to obtain the title compound (3.5 g, 60~80%)

$^1$H NMR (400 MHz, CDCl$_3$): δ1.59 (s, 3H), 1.63 (d, J=8.8, 3H), 3.78 (s, 3H), 4.25 (d, J=7.6, 1H), 5.56 (d, J=8.0, 1H), 7.28~7.33 (m, 1H), 7.41 (d, J=2.0, 1H), 7.56 (d, J=8.4, 1H).

Preparation Example 31

((4S,5S)-5-(2,4-dichlorophenyl)-2,2-dimethyl-1.3-dioxolane-4-yl)methanol

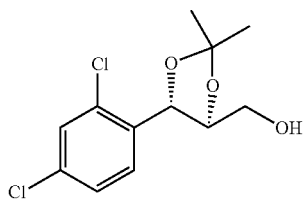 [SMILES: CC1(C)O[C@@H](CO)[C@H](c2ccc(Cl)cc2Cl)O1]

The substantially same method as described in Example 27 was conducted, except that (4R,5S)-methyl-5-(2,4-dichlorophenyl)-2,2-dimethyl-1.3-dioxolane-4-carboxylate (Preparation example 30) was used instead of (4R,5S)-methyl-5-(2-chlorophenyl)-2,2-dimethyl-1.3-dioxolane-4-carboxylate (Preparation example 26), to obtain the title compound (3.2 g, 70~95%)

$^1$H NMR (400 MHz, CDCl$_3$): δ1.56 (s, 3H), 1.62 (d, J=4.8, 6H), 1.97 (dd, J=7.6, J=7.2, 1H), 3.75~3.80 (m, 1H), 3.82~3.86 (m, 1H), 3.89~3.94 (m, 1H), 5.36 (d, J=8.4, 1H), 7.28~7.33 (m, 1H), 7.41 (d, J=2.0, 1H), 7.56 (d, J=8.4, 1H).

Preparation Example 32

(E)-Ethyl-3-(2,6-dichlorophenyl)acrylate

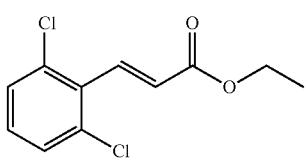

To a stirred solution of 2,6-dichlorobenzaldehyde (5.0 g, 28.56 mmol) in THF was added triethyl phosphono acetate (6.4 g, 28.56 mmol) at 0° C. The reaction mixture was added t-BuOK (3.2 g, 28.56 mmol) at room temperature. The mixture was stirred for 10 h then the resulting mixture was quenched with 1N HCl, diluted with ether, washed with water, dried over MgSO$_4$, filtered, and concentrated under reduced pressure. The crude product was purified by SiO$_2$ gel column chromatography (4.3 g 40~60%)

$^1$H NMR (400 MHz, CDCl$_3$): δ1.36 (t, J=3.6, 3H), 4.31 (q, J=3.7, 2H), 6.61 (d, J=16, 1H), 7.21 (t, J=4.2, 1H), 7.38 (d, J=5.2, 1H), 7.81 (d, J=16, 1H).

Preparation Example 33

(2R,3S)-ethyl-3-(2,6-dichlorophenyl)-2,3-dihydroxypropanoate

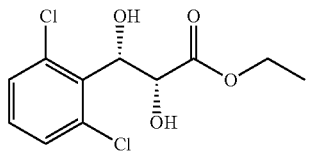 [SMILES: CCOC(=O)[C@H](O)[C@@H](O)c1c(Cl)cccc1Cl]

The substantially same method as described in Example 25 was conducted, except that (E)-ethyl-3-(2,6-dichlorophenyl)acrylate (Preparation example 32) was used instead of (E)-Methyl-3-(2-chlorophenyl)acrylate (Preparation example 24), to obtain the title compound (3.9 g, 60~80%)

$^1$H NMR (400 MHz, CDCl$_3$): δ1.21 (t, J=7.2, 3H), 3.22 (s, 1H), 3.69 (s, 1H), 4.20~4.28 (m, 1H), 4.70 (d, J=5.2, 1H), 5.62 (d, J=5.6, 1H), 7.19~7.36 (m, 3H).

Preparation Example 34

(4R,5S)-ethyl-5-(2,4-dichlorophenyl)-2,2-dimethyl-1.3-dioxolane-4-carboxylate

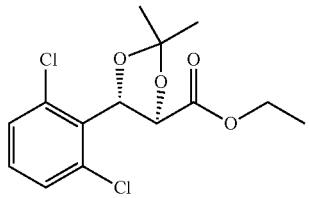 [SMILES: CCOC(=O)[C@@H]1OC(C)(C)O[C@H]1c1c(Cl)cccc1Cl]

The substantially same method as described in Example 26 was conducted, except that (2R,3S)-ethyl-3-(2,6-dichlorophenyl)-2,3-dihydroxypropanoate (Preparation example 29) was used instead of (2R,3S)-methyl-3-(2-chlorophenyl)-2,3-dihydroxypropanoate (Preparation example 25), to obtain the title compound (4.1 g, 60~90%)

$^1$H NMR (400 MHz, CDCl$_3$): δ1.26 (t, J=7.2, 3H), 1.58 (s, 3H), 1.70 (s, 3H), 3.77 (s, 3H), 4.24 (q, J=7.2, 1H), 4.95 (q, J=4.4, 1H), 5.95 (q, J=3.0, 1H), 7.20~7.39 (m, 3H).

Preparation Example 35

((4S,5S)-5-(2,6-dichlorophenyl)-2,2-dimethyl-1.3-dioxolane-4-yl)methanol

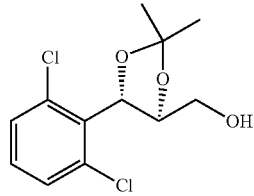 [SMILES: CC1(C)O[C@@H](CO)[C@H](c2c(Cl)cccc2Cl)O1]

The substantially same method as described in Example 27 was conducted, except that (4R,5S)-ethyl-5-(2,6-dichlororophenyl)-2,2-dimethyl-1,3-dioxolane-4-carboxylate (Preparation example 34) was used instead of (4R,5S)-methyl-5-(2-chlorophenyl)-2,2-dimethyl-1,3-dioxolane-4-carboxylate (Preparation example 26), to obtain the title compound (3.5 g, 70~95%)

$^1$H NMR (400 MHz, CDCl$_3$): δ1.55 (s, 3H), 1.68 (s, 3H), 3.66 (q, J=5.5, 1H), 3.85 (q, J=5.1, 1H), 4.56~4.61 (m, 1H), 5.78 (d, J=9.2, 1H), 7.19~7.37 (m, 3H).

Preparation Example 36

(2S,3R)-methyl-3-(2,4-dichlorophenyl)-2,3-dihydroxypropanoate

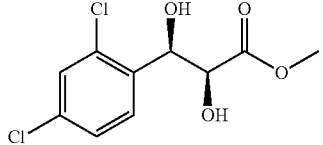 [SMILES: COC(=O)[C@@H](O)[C@H](O)c1ccc(Cl)cc1Cl]

The substantially same method as described in Preparation Example 3 was conducted, except that (E)-Methyl-3-(2,4-dichlorophenyl)acrylate (Preparation example 28) was used instead of (E)-1-chloro-2-(3-(methoxymethoxy)prop-1-enyl)benzene (Preparation example 2), to obtain the title compound (2.4 g, 75~90%).

$^1$H NMR (400 MHz, CDCl$_3$): δ3.11 (s, 1H), 3.88 (s, 3H), 4.42 (d, J=2.4, 1H), 5.43 (d, J=2.0, 1H), 7.28~7.33 (m, 1H), 7.41 (d, J=2.0, 1H), 7.55 (d, J=8.4, 1H).

Preparation Example 37

(4S,5R)-methyl-5-(2,4-dichlorophenyl)-2,2-dimethyl-1,3-dioxolane-4-carboxylate

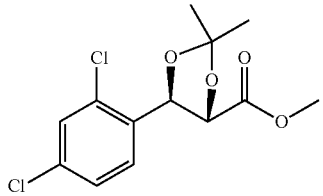 [SMILES: COC(=O)[C@H]1OC(C)(C)O[C@@H]1c1ccc(Cl)cc1Cl]

The substantially same method as described in Example 26 was conducted, except that (2S,3R)-methyl-3-(2,4-dichlorophenyl)-2,3-dihydroxypropanoate (Preparation example 36) was used instead of (2R,3S)-methyl-3-(2-chlorophenyl)-2,3-dihydroxypropanoate (Preparation example 25), to obtain the title compound (3.2 g, 60~80%)

$^1$H NMR (400 MHz, CDCl$_3$): δ1.59 (s, 3H), 1.63 (d, J=8.8, 3H), 3.78 (s, 3H), 4.25 (d, J=7.6, 1H), 5.56 (d, J=8.0, 1H), 7.28~7.33 (m, 1H), 7.41 (d, J=2.0, 1H), 7.56 (d, J=8.4, 1H).

Preparation Example 38

((4R,5R)-5-(2,4-dichlorophenyl)-2,2-dimethyl-1,3-dioxolane-4-yl)methanol

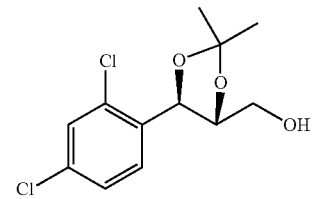 [SMILES: CC1(C)O[C@H](c2ccc(Cl)cc2Cl)[C@@H](CO)O1]

The substantially same method as described in Example 27 was conducted, except that (4S,5R)-methyl-5-(2,4-dichlorophenyl)-2,2-dimethyl-1,3-dioxolane-4-carboxylate (Preparation example 37) was used instead of (4R,5S)-methyl-5-(2-chlorophenyl)-2,2-dimethyl-1,3-dioxolane-4-carboxylate (Preparation example 26), to obtain the title compound (3.5 g, 70~95%)

$^1$H NMR (400 MHz, CDCl$_3$): δ1.56 (s, 3H), 1.62 (d, J=4.8, 6H), 1.97 (dd, J=7.6, J=7.2, 1H), 3.75~3.80 (m, 1H), 3.82~3.86 (m, 1H), 3.89~3.94 (m, 1H), 5.36 (d, J=8.4, 1H), 7.28~7.33 (m, 1H), 7.41 (d, J=2.0, 1H), 7.56 (d, J=8.4, 1H).

Preparation Example 39

(2S,3R)-ethyl-3-(2,6-dichlorophenyl)-2,3-dihydroxypropanoate

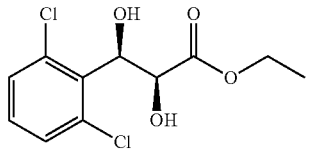 [SMILES: CCOC(=O)[C@@H](O)[C@H](O)c1c(Cl)cccc1Cl]

The substantially same method as described in Preparation Example 3 was conducted, except that (E)-ethyl-3-(2,6-dichlorophenyl)acrylate (Preparation example 32) was used instead of (E)-1-chloro-2-(3-(methoxymethoxy)prop-1-enyl)benzene (Preparation example 2), to obtain the title compound (2.8 g, 75~90%).

$^1$H NMR (400 MHz, CDCl$_3$): δ3.11 (s, 1H), 3.88 (s, 3H), 4.42 (d, J=2.4, 1H), 5.43 (d, J=2.0, 1H), 7.28~7.33 (m, 1H), 7.41 (d, J=2.0, 1H), 7.55 (d, J=8.4, 1H). $^1$H NMR (400 MHz, CDCl$_3$): δ=1.21 (t, J=7.2, 3H), 3.22 (s, 1H), 3.69 (s, 1H), 4.20~4.28 (m, 1H), 4.70 (d, J=5.2, 1H), 5.62 (d, J=5.6, 1H), 7.19~7.36 (m, 3H).

Preparation Example 40

(4S,5R)-ethyl-5-(2,4-dichlorophenyl)-2,2-dimethyl-1,3-dioxolane-4-carboxylate

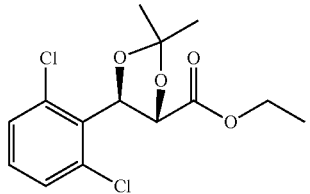 [SMILES: CCOC(=O)[C@H]1OC(C)(C)O[C@@H]1c1c(Cl)cccc1Cl]

The substantially same method as described in Example 26 was conducted, except that (2S,3R)-ethyl-3-(2,6-dichlorophenyl)-2,3-dihydroxypropanoate (Preparation example 39) was used instead of (2R,3S)-methyl-3-(2-chlorophenyl)-2,3-dihydroxypropanoate (Preparation example 25), to obtain the title compound (4.1 g, 60~90%)

¹H NMR (400 MHz, CDCl₃): δ1.26 (t, J=7.2, 3H), 1.58 (s, 3H), 1.70 (s, 3H), 3.77 (s, 3H), 4.24 (q, J=7.2, 1H), 4.95 (q, J=4.4, 1H), 5.95 (q, J=3.0, 1H), 7.20~7.39 (m, 3H).

Preparation Example 41

((4R,5R)-5-(2,6-dichlorophenyl)-2,2-dimethyl-1,3-dioxolane-4-yl)methanol

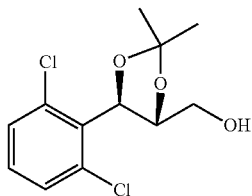 [SMILES: CC1(C)O[C@H](c2c(Cl)cccc2Cl)[C@@H](CO)O1]

The substantially same method as described in Example 27 was conducted, except that (4S,5R)-ethyl-5-(2,6-dichlorophenyl)-2,2-dimethyl-1,3-dioxolane-4-carboxylate (Preparation example 40) was used instead of (4R,5S)-methyl-5-(2-chlorophenyl)-2,2-dimethyl-1,3-dioxolane-4-carboxylate (Preparation example 26), to obtain the title compound (5.2 g, 70~95%)
¹H NMR (400 MHz, CDCl₃): δ1.55 (s, 3H), 1.68 (s, 3H), 3.66 (q, J=5.5, 1H), 3.85 (q, J=5.1, 1H), 4.56~4.61 (m, 1H), 5.78 (d, J=9.2, 1H), 7.19~7.37 (m, 3H).

Preparation Example 42

(E)-3-(2-nitrophenyl)-acrylic acid

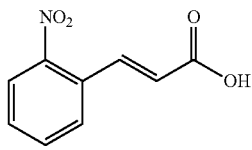 [SMILES: O=C(O)/C=C/c1ccccc1[N+](=O)[O-]]

The substantially same method as described in Preparation Example 9 was conducted, except that 2-nitrobenzenealdehyde was used instead of 2-Fluoroaldehyde, to obtain the title compound (2.06 g, 70~90%)
¹H NMR (400 MHz, DMSO) δ6.52 (d, J=15.6, 1H), 7.65 (t, J=8.1, 1H), 7.75 (t, J=7.4, 1H), 7.83 (d, J=15.8, 1H), 7.92 (dd, J=7.6, 1.1, 1H), 8.05 (dd, J=8.1, 1.2, 1H)

Preparation Example 43

(E)-Methyl-3-(2-nitrophenyl)acrylate

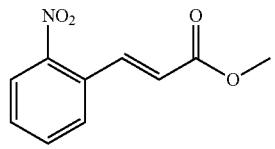

The substantially same method as described in Example 24 was conducted, except that (E)-3-(2-nitrophenyl)-acrylic acid (Preparation example 42) was used instead of 2-chlorocinnamic acid, to obtain the title compound (15.8 g, 70~90%)
¹H NMR (400 MHz, CDCl₃) δ 3.80 (s, 3H), 6.34 (d, J=15.9 Hz, 1H), 7.49~7.68 (m, 4H), 8.01 (d, J=7.9 Hz, 1H), 8.08 (d, J=15.9, 1H).

Preparation Example 44

(2S,3R)-methyl-3-(2-nitrophenyl)-2,3-dihydroxypropanoate

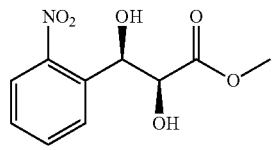 [SMILES: COC(=O)[C@@H](O)[C@H](O)c1ccccc1[N+](=O)[O-]]

The substantially same method as described in Preparation Example 3 was conducted, except that (E)-Methyl-3-(2-nitrophenyl)acrylate (Preparation example 43) was used instead of (E)-1-chloro-2-(3-(methoxymethoxy)prop-1-enyl) benzene (Preparation example 2), to obtain the title compound (12.5 g, 75~90%).
¹H NMR (400 MHz, CDCl₃): δ=4.31 (s, 3H), 5.44 (m, 4H), 5.89 (s, 1H), 7.53~7.90 (m, 4H).

Preparation Example 45

(4S,5R)-methyl-5-(2-nitrophenyl)-2,2-dimethyl-1,3-dioxolane-4-carboxylate

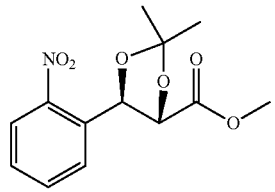 [SMILES: COC(=O)[C@H]1OC(C)(C)O[C@@H]1c1ccccc1[N+](=O)[O-]]

The substantially same method as described in Example 26 was conducted, except that (2S,3R)-methyl-3-(2-nitrophenyl)-2,3-dihydroxypropanoate (Preparation example 44) was used instead of (2R,3S)-methyl-3-(2-chlorophenyl)-2,3-dihydroxypropanoate (Preparation example 25), to obtain the title compound (11 g, 60~80%)
¹H NMR (400 MHz, CDCl₃): δ1.38 (s, 3H), 1.40 (s, 3H), 3.75 (s, 3H), 4.49 (d, J=7.4, 1H), 5.25 (d, J=7.4, 1H), 7.48~7.77 (m, 3H, 8.08 (m, 1H)

Preparation Example 46

((4R,5R)-5-(2-nitrophenyl)-2,2-dimethyl-1,3-dioxolane-4-yl)methanol

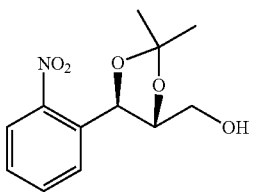

The substantially same method as described in Example 27 was conducted, except that (4S,5R)-methyl-5-(2-nitrophenyl)-2,2-dimethyl-1,3-dioxolane-4-carboxylate (Preparation example 45) was used instead of (4R,5S)-methyl-5-(2-chlorophenyl)-2,2-dimethyl-1.3-dioxolane-4-carboxylate (Preparation example 26), to obtain the title compound (13.1 g, 70~95%)

¹H NMR (400 MHz, CDCl₃): δ1.38 (s, 3H), 1.40 (s, 3H), 3.89 (d, J=4.1, 2H), 4.26 (dt, J=7.0, 4.1, 1H), 5.26 (d, J=7.0, 1H), 7.55~7.86 (m, 3H), 8.08 (m, 1H).

Preparation Example 47

((4R,5R)-5-(2-aminophenyl)-2,2-dimethyl-1.3-dioxolane-4-yl)methanol

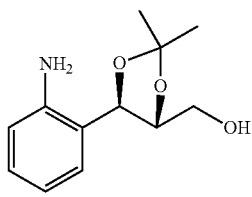 [SMILES: CC1(C)O[C@H](c2ccccc2[N+](=O)[O-])[C@@H](CO)O1]

To a stirred solution of ((4R,5R)-5-(2-nitrophenyl)-2,2-dimethyl-1.3-dioxolane-4-yl)methanol (Preparation example 46, 14 g) in EtOAc was added Pd(OH)₂ (20 wt%, 2.8 g) under hydrogen gas (balloon). The mixture was stirred for 6 h then the resulting mixture was filtered through celite and concentrated under reduced pressure. The crude product was purified by SiO₂ gel column chromatography to give title compound (7.5 g 65~85%)

¹H NMR (400 MHz, CDCl₃): δ1.39 (s, 3H), 1.40 (s, 3H), 3.88 (d, J=4.27, 2H), 3.99 (dt, J=7.02, J=4.30, 1H), 4.74 (d, J=7.02, 1H), 6.65-6.72 (m, 2H), 6.98 (m, 1H), 7.25 (m, 1H).

Preparation Example 48

(2R,3S)-methyl-3-(2-nitrophenyl)-2,3-dihydroxypropanoate

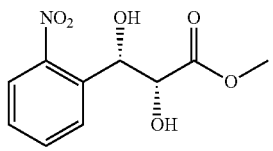 [SMILES: COC(=O)[C@H](O)[C@@H](O)c1ccccc1[N+](=O)[O-]]

The substantially same method as described in Example 25 was conducted, except that (E)-methyl-3-(2-nitrrophenyl) acrylate (Preparation example 43) was used instead of (E)-Methyl-3-(2-chlorophenyl)acrylate (Preparation example 24), to obtain the title compound (21.7 g, 60~80%)

¹H NMR (400 MHz, CDCl₃): δ4.31 (s, 3H), 5.44 (m, 4H), 5.89 (s, 1H), 7.53~7.90 (m, 4H)

Preparation Example 49

(4R,5S)-methyl-5-(2-nitrophenyl)-2,2-dimethyl-1.3-dioxolane-4-carboxylate

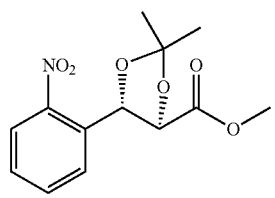 [SMILES: COC(=O)[C@@H]1OC(C)(C)O[C@H]1c1ccccc1[N+](=O)[O-]]

The substantially same method as described in Example 26 was conducted, except that (2R,3S)-methyl-3-(2-nitrophenyl)-2,3-dihydroxypropanoate (Preparation example 48) was used instead of (2R,3S)-methyl-3-(2-chlorophenyl)-2,3-dihydroxypropanoate (Preparation example 25), to obtain the title compound (21 g, 60~90%)

¹H NMR (400 MHz, CDCl₃): δ1.38 (s, 3H), 1.40 (s, 3H), 3.75 (s, 3H), 4.49 (d, J=7.4, 1H), 5.25 (d, J=7.4, 1H), 7.48~7.77 (m, 3H, 8.08 (m, 1H)

Preparation Example 50

((4S,5S)-5-(2-nitrophenyl)-2,2-dimethyl-1.3-dioxolane-4-yl)methanol

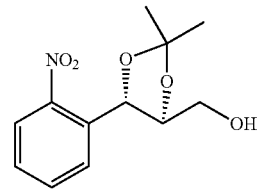 [SMILES: CC1(C)O[C@@H](CO)[C@H](c2ccccc2[N+](=O)[O-])O1]

The substantially same method as described in Example 27 was conducted, except that (4R,5S)-methyl-5-(2-nitrophenyl)-2,2-dimehtyl-1.3-dioxolane-4-carboxylate (Preparation example 49) was used instead of (4R,5S)-methyl-5-(2-chlorophenyl)-2,2-dimethyl-1.3-dioxolane-4-carboxylate (Preparation example 26), to obtain the title compound (14 g, 70~95%)

¹H NMR (400 MHz, CDCl₃): δ 61.38 (s, 3H), 1.40 (s, 3H), 3.89 (d, J=4.1, 2H), 4.26 (dt, J=7.0, 4.1, 1H), 5.26 (d, J=7.0, 1H), 7.55~7.86 (m, 3H), 8.08 (m, 1H).

Preparation Example 51

((4S,5S)-5-(2-aminophenyl)-2,2-dimethyl-1.3-dioxolane-4-yl)methanol

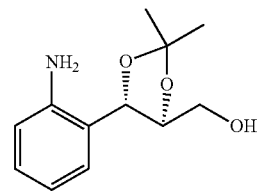 [SMILES: CC1(C)O[C@@H](CO)[C@H](c2ccccc2N)O1]

The substantially same method as described in Example 47 was conducted, except that (4S,5S)-methyl-5-(2-nitrophenyl)-2,2-dimethyl-1.3-dioxolane-4-carboxylate (Preparation example 50) was used instead of (4R,5R)-5-(2-nitrophenyl)-2,2-dimethyl-1.3-dioxolane-4-yl)methanol (Preparation example 46), to obtain the title compound (11 g, 70~95%)

$^1$H NMR (400 MHz, CDCl$_3$): δ 61.38 (s, 3H), 1.40 (s, 3H), 3.89 (d, J=4.1, 2H), 4.26 (dt, J=7.0, 4.1, 1H), 5.26 (d, J=7.0, 1H), 7.55~7.86 (m, 3H), 8.08 (m, 1H).

Preparation Example 52

(E)-3-o-tolyacrylic acid

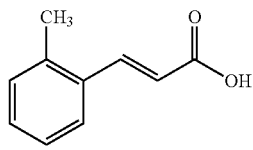

The substantially same method as described in Preparation Example 9 was conducted, except that 2-methylbenzenealdehyde was used instead of 2-Fluoroaldehyde, to obtain the title compound (1.5 g, 70~90%)

$^1$H NMR (400 MHz, CDCl$_3$): δ2.48 (s, 3H), 6.16 (d, J=15.1, 1H), 7.00~7.10 (m, 1H), 7.21~7.26 (m, 3H), 8.04 (d, J=15.1, 1H), 11.0 (s, 1H).

Preparation Example 53

(E)-Methyl-3-o-tolyacrylate

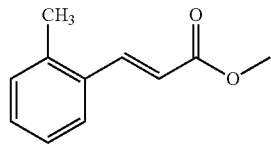

The substantially same method as described in Example 24 was conducted, except that (E)-3-o-tolyacrylic acid (Preparation example 52) was used instead of 2-chlorocinnamic acid, to obtain the title compound (1.5 g, 70~90%)

$^1$H NMR (400 MHz, CDCl$_3$): δ2.48 (s, 3H), 3.77 (s, 3H), 6.14 (d, J=15.1, 1H), 7.00~7.10 (m, 1H), 7.21~7.26 (m, 3H), 8.07 (d, J=15.1, 1H).

Preparation Example 54

(2S,3R)-methyl-3-(2-methylphenyl)-2,3-dihydroxypropanoate

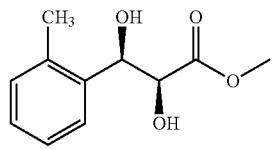

The substantially same method as described in Preparation Example 3 was conducted, except that (E)-Methyl-3-o-tolyacrylate (Preparation example 53) was used instead of (E)-1-chloro-2-(3-(methoxymethoxy)prop-1-enyl)benzene (Preparation example 2), to obtain the title compound (1.3 g, 75~90%).

$^1$H NMR (400 MHz, CDCl$_3$): δ2.34 (s, 3H), 2.80 (s, 1H), 3.65 (s, 1H), 3.68 (s, 3H), 4.52 (d, J=7.0, 1H), 5.22 (d, J=7.0, 1H), 7.19~7.39 (m, 4H).

Preparation Example 55

(4S,5R)-methyl-5-(2-methylphenyl)-2,2-dimethyl-1.3-dioxolane-4-carboxylate

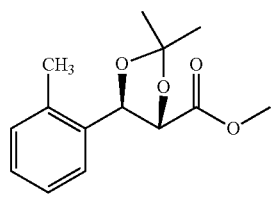 [SMILES: COC(=O)[C@H]1OC(C)(C)O[C@@H]1c1ccccc1C]

The substantially same method as described in Example 26 was conducted, except that (2S,3R)-methyl-3-(2-methylphenyl)-2,3-dihydroxypropanoate (Preparation example 54) was used instead of (2S,3R)-methyl-3-(2-chlorophenyl)-2,3-dihydroxypropanoate (Preparation example 25), to obtain the title compound (1.7 g, 60~80%)

$^1$H NMR (400 MHz, CDCl$_3$): δ1.27 (s, 6H), 2.34 (s, 3H), 3.68 (s, 3H), 5.11 (d, J=7.0, 1H), 5.81 (d, J=7.0, 1H), 7.19~7.26 (m, 3H), 7.37~7.39 (m, 1H).

Preparation Example 56

((4R,5R)-5-(2-methylphenyl)-2,2-dimethyl-1.3-dioxolane-4-yl)methanol

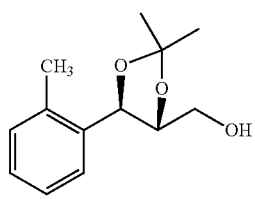 [SMILES: Cc1ccccc1[C@H]1OC(C)(C)O[C@@H]1CO]

The substantially same method as described in Example 27 was conducted, except that (4S,5R)-methyl-5-(2-methylphenyl)-2,2-dimethyl-1.3-dioxolane-4-carboxylate (Preparation example 55) was used instead of (4S,5R)-methyl-5-(2-chlorophenyl)-2,2-dimethyl-1.3-dioxolane-4-carboxylate (Preparation example 26), to obtain the title compound (1.3 g, 70~95%)

$^1$H NMR (400 MHz, CDCl$_3$): δ1.27 (s, 6H), 2.34 (s, 3H), 3.52~3.60 (m, 2H), 3.65 (s, 1H), 4.36 (dd, J=7.0, J=7.0, 1H), 5.17 (d, J=7.0, 1H), 7.19~7.26 (m, 3H), 7.37~7.39 (m, 1H).

Preparation Example 57

(2R,3S)-methyl-3-(2-methylphenyl)-2,3-dihydroxypropanoate

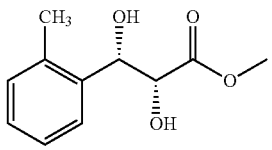

The substantially same method as described in Example 25 was conducted, except that (E)-methyl-3-o-tolyacrylate (Preparation example 53) was used instead of (E)-Methyl-3-(2-chlorophenyl)acrylate (Preparation example 24), to obtain the title compound (1.7 g, 60~80%)

$^1$H NMR (400 MHz, CDCl$_3$): δ2.34 (s, 3H), 2.80 (s, 1H), 3.65 (s, 1H), 3.68 (s, 3H), 4.52 (d, J=7.0, 1H), 5.22 (d, J=7.0, 1H), 7.19~7.39 (m, 4H).

Preparation Example 58

(4R,5S)-methyl-5-(2-methylphenyl)-2,2-dimethyl-1.3-dioxolane-4-carboxylate

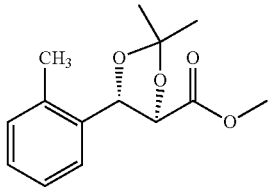

The substantially same method as described in Example 26 was conducted, except that (2R,3S)-methyl-3-(2-methylphenyl)-2,3-dihydroxypropanoate (Preparation example 57) was used instead of (2R,3S)-methyl-3-(2-chlorophenyl)-2,3-dihydroxypropanoate (Preparation example 25), to obtain the title compound (1.9 g, 60~90%)

$^1$H NMR (400 MHz, CDCl$_3$): δ1.27 (s, 6H), 2.34 (s, 3H), 3.68 (s, 3H), 5.11 (d, J=7.0, 1H), 5.81 (d, J=7.0, 1H), 7.19~7.26 (m, 3H), 7.37~7.39 (m, 1H).

Preparation Example 59

((4S,5S)-5-(2-methylphenyl)-2,2-dimethyl-1.3-dioxolane-4-yl)methanol

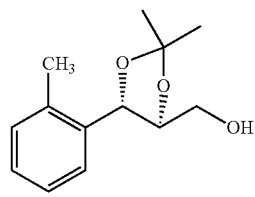

The substantially same method as described in Example 27 was conducted, except that (4R,5S)-methyl-5-(2-methylphenyl)-2,2-dimethyl-1.3-dioxolane-4-carboxylate (Preparation example 58) was used instead of (4R,5S)-methyl-5-(2-chlorophenyl)-2,2-dimethyl-1.3-dioxolane-4-carboxylate (Preparation example 26), to obtain the title compound (1.5 g, 70~95%)

$^1$H NMR (400 MHz, CDCl$_3$): δ1.27 (s, 6H), 2.34 (s, 3H), 3.52~3.60 (m, 2H), 3.65 (s, 1H), 4.36 (dd, J=7.0, J=7.0, 1H), 5.17 (d, J=7.0, 1H), 7.19~7.26 (m, 3H), 7.37~7.39 (m, 1H).

Preparation Example 60

((4S,5R)-methyl-5-(2-chlorophenyl)-2-methyl-1.3-dioxolane-4-carboxylate

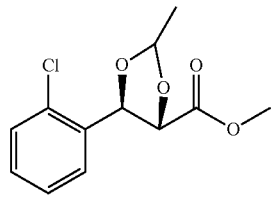

Dichloromethane (MC) was added to (2S,3R)-methyl-3-(2-chlorophenyl)-2,3-dihydroxypropanoate at room temperature. 1,1-Diethoxyethane (8 ml) and p-toluenesulfonic acid (0.27 g) was added and stirred at room temperature. The reaction mixture was quenched with H$_2$O, extracted with MC, washed with H$_2$O, dried over anhydrous magnesium sulfate (MgSO$_4$), filtered and concentrated. The crude compound was purified by a silica gel column to produce the title compound (3.6 g, 70~95%).

$^1$H NMR (400 MHz, CDCl$_3$) δ1.36 (d, J=6.4, 3H), 3.78 (s, 3H), 4.30 (d, J=7.6, 1H), 5.07 (m, 1H), 5.62 (d, J=7.6, 1H), 7.28~7.64 (m, 4H)

Preparation Example 61

((4R,5R)-5-(2-chlorophenyl)-2-methyl-1.3-dioxolane-4-yl)methanol

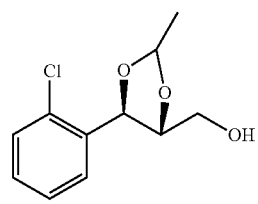

The substantially same method as described in Example 27 was conducted, except that (4R,5S)-methyl-5-(2-chlorophenyl)-2-methyl-1.3-dioxolane-4-carboxylate (Preparation example 60) was used instead of (4R,5S)-methyl-5-(2-chlorophenyl)-2,2-dimethyl-1.3-dioxolane-4-carboxylate (Preparation example 26), to obtain the title compound (3.1 g, 70~95%)

¹H NMR (400 MHz, CDCl₃): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.19~7.26 (m, 3H), 7.37~7.39 (m, 1H).

Preparation Example 62

((4R,5S)-methyl-5-(2-chlorophenyl)-2-methyl-1,3-dioxolane-4-carboxylate

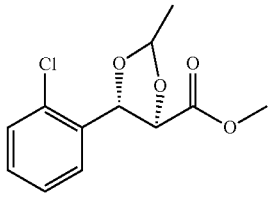

The substantially same method as described in Example 60 was conducted, except that (2R,3S)-methyl-3-(2-chlorophenyl)-2,3-dihydroxypropanote (Preparation example 25) was used instead of (2R,3S)-methyl-3-(2-chlorophenyl)-2,3-dihydroxypropanote, to obtain the title compound (2.1 g, 70~95%).

¹H NMR (400 MHz, CDCl₃) δ1.36 (d, J=6.4, 3H), 3.78 (s, 3H), 4.30 (d, J=7.6, 1H), 5.07 (m, 1H), 5.62 (d, J=7.6, 1H), 7.28~7.64 (m, 4H)

Preparation Example 63

((4S,5S)-5-(2-chlorophenyl)-2-methyl-1,3-dioxolane-4-yl)methanol

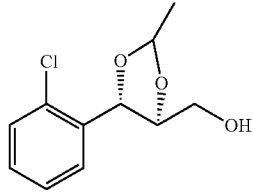

The substantially same method as described in Example 27 was conducted, except that (4S,5R)-methyl-5-(2-chlorophenyl)-2-methyl-1,3-dioxolane-4-carboxylate (Preparation example 60) was used instead of (4R,5S)-methyl-5-(2-chlorophenyl)-2,2-dimethyl-1,3-dioxolane-4-carboxylate (Preparation example 26), to obtain the title compound (3.1 g, 70~95%)

¹H NMR (400 MHz, CDCl₃): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.19~7.26 (m, 3H), 7.37~7.39 (m, 1H).

Preparation Example 64

(4S,5R)-methyl-5-(2-chlorophenyl)-2,2-diethyl-1,3-dioxolane-4-carboxylate

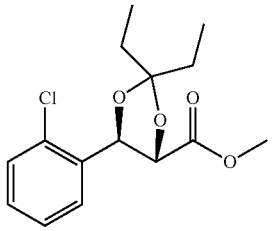 [SMILES: CCC1(CC)O[C@H](C(=O)OC)[C@@H](c2ccccc2Cl)O1]

3-pentanone was added to (2S,3R)-methyl-3-(2-chlorophenyl)-2,3-dihydroxypropanoate at room temperature. Sulfuric acid (H₂SO₄) was added and stirred at room temperature. The reaction mixture was quenched with H₂O, extracted with EA, washed with H₂O, dried over anhydrous sodium sulfate (Na₂SO₄), filtered and concentrated. The crude compound was purified by a silica gel column to produce the title compound (1.6 g, 60~85%).

¹H NMR (400 MHz, CDCl₃) δ0.96 (m, 6H), 1.59 (m, 4H), 3.67 (s, 3H), 5.11 (d, J=7.6, 1H), 5.81 (d, J=7.6, 1H), 7.22~7.60 (m, 4H)

Preparation Example 65

((4R,5R)-5-(2-chlorophenyl)-2,2-diethyl-1,3-dioxolane-4-yl)methanol

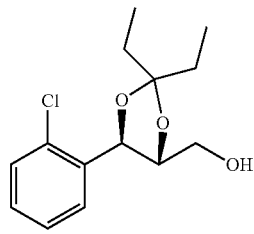 [SMILES: CCC1(CC)O[C@H](c2ccccc2Cl)[C@@H](CO)O1]

The substantially same method as described in Example 27 was conducted, except that (4S,5R)-methyl-5-(2-chlorophenyl)-2,2-diethyl-1,3-dioxolane-4-carboxylate (Preparation example 64) was used instead of (4R,5S)-methyl-5-(2-chlorophenyl)-2,2-dimethyl-1,3-dioxolane-4-carboxylate (Preparation example 26), to obtain the title compound (2.0 g, 70~95%)

¹H NMR (400 MHz, CDCl₃): δ0.96 (m, 6H), 1.59 (m, 4H), 3.66 (d, J=8.0, 2H), 5.09 (d, J=7.6, 1H), 5.88 (d, J=7.6, 1H), 7.26~7.62 (m, 4H).

Preparation Example 66

(4R,5S)-methyl-5-(2-chlorophenyl)-2,2-diethyl-1,3-dioxolane-4-carboxylate

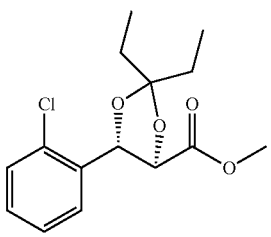 [SMILES: CCC1(CC)O[C@@H](C(=O)OC)[C@H](c2ccccc2Cl)O1]

The substantially same method as described in Example 64 was conducted, except that (2R,3S)-methyl-3-(2-chlorophenyl)-2,3-dihydroxypropanote (Preparation example 25) was used instead of (2S,3R)-methyl-3-(2-chlorophenyl)-2,3-dihydroxypropanote, to obtain the title compound (1.4 g, 70~95%).

¹H NMR (400 MHz, CDCl₃) δ0.96 (m, 6H), 1.59 (m, 4H), 3.67 (s, 3H), 5.11 (d, J=7.6, 1H), 5.81 (d, J=7.6, 1H), 7.22~7.60 (m, 4H)

Preparation Example 67

((4S,5S)-5-(2-chlorophenyl)-2,2-diethyl-1,3-dioxolane-4-yl)methanol

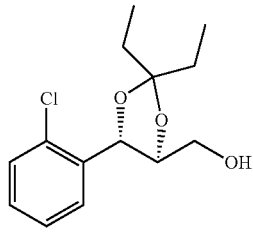 [SMILES: CCC1(CC)O[C@@H](CO)[C@H](c2ccccc2Cl)O1]

The substantially same method as described in Example 65 was conducted, except that (4R,5S)-methyl-5-(2-chlorophenyl)-2,2-diethyl-1,3-dioxolane-4-carboxylate (Preparation example 66) was used instead of (4S,5R)-methyl-5-(2-chlorophenyl)-2,2-diethyl-1,3-dioxolane-4-carboxylate (Preparation example 64), to obtain the title compound (2.2 g, 70~95%)

¹H NMR (400 MHz, CDCl₃): δ0.96 (m, 6H), 1.59 (m, 4H), 3.66 (d, J=8.0, 2H), 5.09 (d, J=7.6, 1H), 5.88 (d, J=7.6, 1H), 7.26~7.62 (m, 4H).

Preparation Example 68

(2S,3R)-methyl-3-(2-chlorophenyl)-1,4-dioxaspiro[4,4]nonane-2-carboxylate

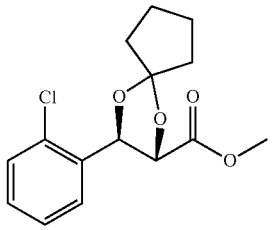 [SMILES: COC(=O)[C@H]1OC2(CCCC2)O[C@@H]1c1ccccc1Cl]

The substantially same method as described in Example 64 was conducted, except that cyclopentanone was used instead of 3-pentanone, to obtain the title compound (2.2 g, 70~95%).

¹H NMR (400 MHz, DMSO) δ1.69~1.71 (m, 4H), 1.82~1.86 (m, 1H), 1.91~2.00 (m, 3H), 3.68 (s, 3H), 4.40 (d, J=7.2, 1H), 5.39 (d, J=7.2, 1H), 7.39~7.61 (m, 4H)

Preparation Example 69

((4R,5R)-5-(2-chlorophenyl)-1,4-dioxaspiro[4,4]nonane-2-yl)methanol

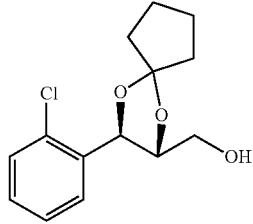 [SMILES: OC[C@H]1OC2(CCCC2)O[C@@H]1c1ccccc1Cl]

The substantially same method as described in Example 65 was conducted, except that (2S,3R)-methyl-3-(2-chlorophenyl)-1,4-dioxaspiro[4,4]nonane-2-carboxylate (Preparation example 68) was used instead of (4S,5R)-methyl-5-(2-chlorophenyl)-2,2-diethyl-1,3-dioxolane-4-carboxylate (Preparation example 64), to obtain the title compound (1.7 g, 70~95%)

¹H NMR (400 MHz, DMSO): δ1.60~1.72 (m, 4H), 1.83~1.94 (m, 1H), 3.52~3.65 (m, 2H), 3.82~3.86 (m, 1H), 4.90 (t, J=5.2, 1H), 5.12 (d, J=7.6, 1H), 7.34~7.58 (m, 4H)

Preparation Example 70

(2R,3S)-methyl-3-(2-chlorophenyl)-1,4-dioxaspiro[4,4]nonane-2-carboxylate

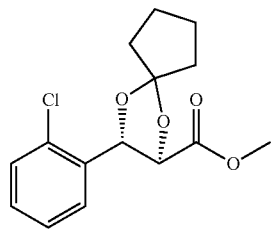 [SMILES: COC(=O)[C@@H]1OC2(CCCC2)O[C@H]1c1ccccc1Cl]

The substantially same method as described in Example 68 was conducted, except that (2R,3S)-methyl-3-(2-chlorophenyl)-2,3-dihydroxypropanoate (Preparation example 25) was used instead of (2S,3R)-methyl-3-(2-chlorophenyl)-2,3-dihydroxypropanoate, to obtain the title compound (1.5 g, 70~95%).

¹H NMR (400 MHz, DMSO) δ1.69~1.71 (m, 4H), 1.82~1.86 (m, 1H), 1.91~2.00 (m, 3H), 3.68 (s, 3H), 4.40 (d, J=7.2, 1H), 5.39 (d, J=7.2, 1H), 7.39~7.61 (m, 4H)

Preparation Example 71

((4R,5R)-5-(2-chlorophenyl)-1,4-dioxaspiro[4,4]nonane-2-yl)methanol

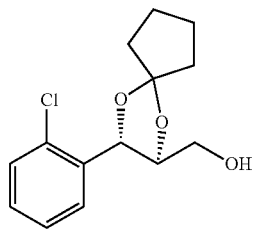 [SMILES: OC[C@@H]1OC2(CCCC2)O[C@H]1c1ccccc1Cl]

The substantially same method as described in Example 69 was conducted, except that (2R,3S)-methyl-3-(2-chlorophenyl)-1,4-dioxaspiro[4,4]nonane-2-carboxylate (Preparation example 70) was used instead of (2S,3R)-methyl-3-(2-chlorophenyl)-1,4-dioxaspiro[4,4]nonane-2-carboxylate (Preparation example 68), to obtain the title compound (1.8 g, 70~95%)

¹H NMR (400 MHz, DMSO): δ1.60~1.72 (m, 4H), 1.83~1.94 (m, 1H), 3.52~3.65 (m, 2H), 3.82~3.86 (m, 1H), 4.90 (t, J=5.2, 1H), 5.12 (d, J=7.6, 1H), 7.34~7.58 (m, 4H)

Preparation Example 72

(2S,3R)-methyl-3-(2-chlorophenyl)-1,4-dioxaspiro[4,5]decane-2-carboxylate

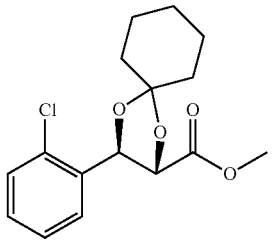 [SMILES: COC(=O)[C@H]1OC2(CCCCC2)O[C@@H]1c1ccccc1Cl]

The substantially same method as described in Example 64 was conducted, except that cyclohexanone was used instead of 3-pentanone, to obtain the title compound (1.2 g, 70~95%).
¹H NMR (400 MHz, DMSO) δ1.61~1.69 (m, 10H), 3.79 (s, 3H), 4.33 (d, J=8.0, 1H), 5.85 (d, J=8.0, 1H), 7.35~7.63 (m, 4H)

Preparation Example 73

((4R,5R)-5-(2-chlorophenyl)-1,4-dioxaspiro[4,5]decane-2-yl)methanol

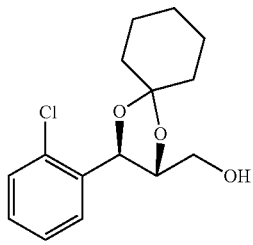

The substantially same method as described in Example 65 was conducted, except that (2S,3R)-methyl-3-(2-chlorophenyl)-1,4-dioxaspiro[4,5]decane-2-carboxylate (Preparation example 72) was used instead of (4S,5R)-methyl-5-(2-chlorophenyl)-2,2-diethyl-1,3-dioxolane-4-carboxylate (Preparation example 64), to obtain the title compound (1.8 g, 70~95%)
¹H NMR (400 MHz, DMSO): δ1.63~1.75 (m, 10H), 3.52~3.81 (m, 2H), 3.95 (t, J=8.0, 1H), 5.43 (d, J=7.6, 1H), 7.48~7.87 (m, 4H)

Preparation Example 74

(2R,3S)-methyl-3-(2-chlorophenyl)-1,4-dioxaspiro[4,5]decane-2-carboxylate

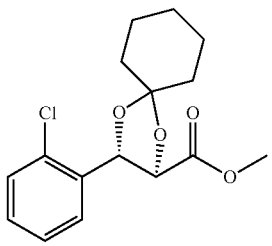 [SMILES: COC(=O)[C@@H]1OC2(CCCCC2)O[C@H]1c1ccccc1Cl]

The substantially same method as described in Example 72 was conducted, except that (2R,3S)-methyl-3-(2-chlorophenyl)-2,3-dihydroxypropanoate (Preparation example 25) was used instead of (2S,3R)-methyl-3-(2-chlorophenyl)-2,3-dihydroxypropanoate, to obtain the title compound (2.1 g, 70~95%).
¹H NMR (400 MHz, DMSO) δ1.61~1.69 (m, 10H), 3.79 (s, 3H), 4.33 (d, J=8.0, 1H), 5.85 (d, J=8.0, 1H), 7.35~7.63 (m, 4H)

Preparation Example 75

((4S,5S)-5-(2-chlorophenyl)-1,4-dioxaspiro[4,5]decane-2-yl)methanol

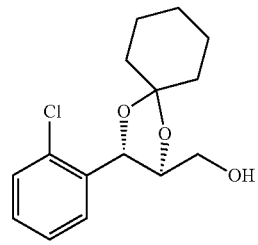 [SMILES: OC[C@@H]1OC2(CCCCC2)O[C@H]1c1ccccc1Cl]

The substantially same method as described in Example 65 was conducted, except that (2R,3S)-methyl-3-(2-chlorophenyl)-1,4-dioxaspiro[4,5]decane-2-carboxylate (Preparation example 74) was used instead of (4S,5R)-methyl-5-(2-chlorophenyl)-2,2-diethyl-1,3-dioxolane-4-carboxylate (Preparation example 64), to obtain the title compound (1.6 g, 70~95%)
¹H NMR (400 MHz, DMSO): δ1.63~1.75 (m, 10H), 3.52~3.81 (m, 2H), 3.95 (t, J=8.0, 1H), 5.43 (d, J=7.6, 1H), 7.48~7.87 (m, 4H)

Preparation Example 76

(2S,3R)-methyl-3-(2-chlorophenyl)-2-phenyl-1,3-dioxolane-4-carboxylate

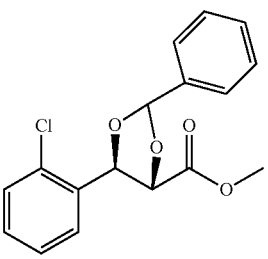

The substantially same method as described in Example 64 was conducted, except that benzaldehyde was used instead of 3-pentanone, to obtain the title compound (1.1 g, 50~70%).
¹H NMR (400 MHz, DMSO) δ1.61~1.69 (m, 10H), 3.79 (s, 3H), 4.33 (d, J=8.0, 1H), 5.85 (d, J=8.0, 1H), 7.35~7.63 (m, 4H)

Preparation Example 77

((4R,5R)-5-(2-chlorophenyl)-2-phenyl-1,3-dioxolane-4-yl)methanol

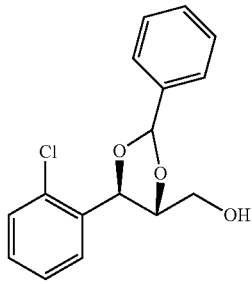

The substantially same method as described in Example 65 was conducted, except that (2S,3R)-methyl-3-(2-chlorophenyl)-2-phenyl-1,3-dioxolane-4-carboxylate (Preparation example 76) was used instead of (4S,5R)-methyl-5-(2-chlorophenyl)-2,2-diethyl-1.3-dioxolane-4-carboxylate (Preparation example 64), to obtain the title compound (0.7 g, 70~95%)

$^1$H NMR (400 MHz, DMSO): δ1.63~1.75 (m, 10H), 3.52~3.81 (m, 2H), 3.95 (t, J=8.0, 1H), 5.43 (d, J=7.6, 1H), 7.48~7.87 (m, 4H)

Preparation Example 78

(2R,3S)-methyl-3-(2-chlorophenyl)-2-phenyl-1,3-dioxolane-4-carboxylate

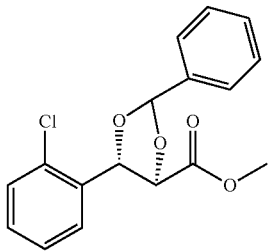

The substantially same method as described in Example 66 was conducted, except that benzaldehyde was used instead of 3-pentanone, to obtain the title compound (1.9 g, 50~70%).

$^1$H NMR (400 MHz, DMSO) δ1.61~1.69 (m, 10H), 3.79 (s, 3H), 4.33 (d, J=8.0, 1H), 5.85 (d, J=8.0, 1H), 7.35~7.63 (m, 4H)

Preparation Example 79

((4S,5S)-5-(2-chlorophenyl)-2-phenyl-1,3-dioxolane-4-yl)methanol

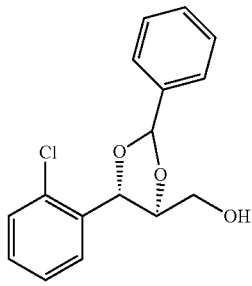

The substantially same method as described in Example 65 was conducted, except that (2R,3S)-methyl-3-(2-chlorophenyl)-2-phenyl-1,3-dioxolane-4-carboxylate (Preparation example 78) was used instead of (4S,5R)-methyl-5-(2-chlorophenyl)-2,2-diethyl-1.3-dioxolane-4-carboxylate (Preparation example 64), to obtain the title compound (1.3 g, 70~95%)

$^1$H NMR (400 MHz, DMSO): δ1.63~1.75 (m, 10H), 3.52~3.81 (m, 2H), 3.95 (t, J=8.0, 1H), 5.43 (d, J=7.6, 1H), 7.48~7.87 (m, 4H)

Preparation Example 80

(E)-Methyl-3-(2-fluorophenyl)acrylate

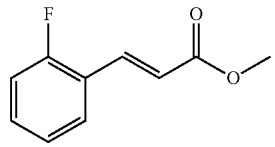

The substantially same method as described in Example 24 was conducted, except that (E)-3(2-fluorophenyl)-acrylic acid (Preparation example 9) was used instead of 2-chlorocinnamic acid, to obtain the title compound. (6.98 g, 70~90%)

$^1$H NMR (400 MHz, CDCl$_3$) δ3.84 (s, 3H), 6.45 (d, J=16.0, 1H), 7.24~7.62 (m, 4H), 8.12 (d, J=16.0, 1H)

Preparation Example 81

(2S,3R)-methyl-3-(2-fluorophenyl)-2,3-dihydroxypropanoate

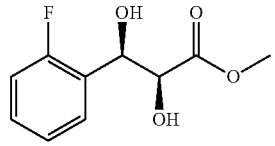

The substantially same method as described in Preparation Example 3 was conducted, except that (E)-Methyl-3-(2-fluorophenyl)acrylate (Preparation example 80) was used instead of (E)-1-chloro-2-(3-(methoxymethoxy)prop-1-enyl) benzene (Preparation example 2), to obtain the title compound (7.5 g, 75~90%).

$^1$H NMR (400 MHz, CDCl$_3$): β=4.31 (s, 3H), 5.44 (m, 4H), 5.89 (s, 1H), 7.32~7.70 (m, 4H).

Preparation Example 82

(2R,3S)-methyl-3-(2-fluorophenyl)-2,3-dihydroxypropanoate

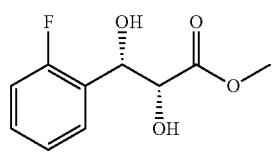

The substantially same method as described in Example 25 was conducted, except that (E)-methyl-3-(2-fluorophenyl)acrylate (Preparation example 80) was used instead of (E)-Methyl-3-(2-chlorophenyl)acrylate (Preparation example 24), to obtain the title compound (7.2 g, 60~80%)

¹H NMR (400 MHz, CDCl₃): β=4.31 (s, 3H), 5.44 (m, 4H), 5.89 (s, 1H), 7.32~7.70 (m, 4H).

Preparation Example 83

((4S,5R)-methyl-5-(2-fluorophenyl)-2-methyl-1.3-dioxolane-4-carboxylate

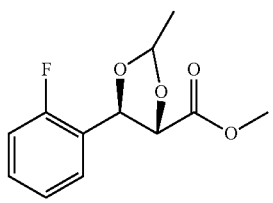

The substantially same method as described in Example 60 was conducted, except that (2S,3R)-methyl-3-(2-fluorophenyl)-2,3-dihydroxypropanoate (Preparation example 81) was used instead of ((2S,3R)-methyl-3-(2-chlorophenyl)-2,3-dihydroxypropanoate, to obtain the title compound (3.1 g, 70~95%).

¹H NMR (400 MHz, CDCl₃) δ1.36 (d, J=6.4, 3H), 3.78 (s, 3H), 4.30 (d, J=7.6, 1H), 5.07 (m, 1H), 5.62 (d, J=7.6, 1H), 7.29~7.67 (m, 4H)

Preparation Example 84

((4R,5R)-5-(2-fluorophenyl)-2-methyl-1.3-dioxolane-4-yl)methanol

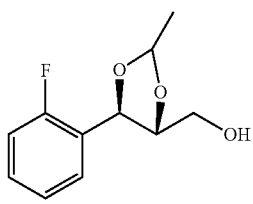

The substantially same method as described in Example 27 was conducted, except that (4S,5R)-methyl-5-(2-fluorophenyl)-2-methyl-1.3-dioxolane-4-carboxylate (Preparation example 83) was used instead of (4R,5S)-methyl-5-(2-chlorophenyl)-2,2-dimethyl-1.3-dioxolane-4-carboxylate (Preparation example 26), to obtain the title compound (3.3 g, 70~95%)

¹H NMR (400 MHz, CDCl₃): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.19~7.39 (m, 4H).

Preparation Example 85

((4R,5S)-methyl-5-(2-fluorophenyl)-2-methyl-1.3-dioxolane-4-carboxylate

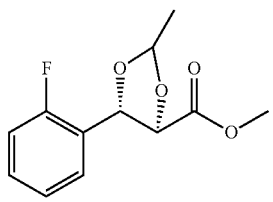

The substantially same method as described in Example 60 was conducted, except that (2R,3S)-methyl-3-(2-fluorophenyl)-2,3-dihydroxypropanote (Preparation example 82) was used instead of (2S,3R)-methyl-3-(2-chlorophenyl)-2,3-dihydroxypropanote, to obtain the title compound (2.9 g, 70~95%).

¹H NMR (400 MHz, CDCl₃) δ1.36 (d, J=6.4, 3H), 3.78 (s, 3H), 4.30 (d, J=7.6, 1H), 5.07 (m, 1H), 5.62 (d, J=7.6, 1H), 7.29~7.69 (m, 4H)

Preparation Example 86

((4S,5S)-5-(2-fluorophenyl)-2-methyl-1.3-dioxolane-4-yl)methanol

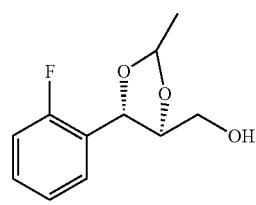

The substantially same method as described in Example 27 was conducted, except that (4R,5S)-methyl-5-(2-fluorophenyl)-2-methyl-1.3-dioxolane-4-carboxylate (Preparation example 85) was used instead of (4R,5S)-methyl-5-(2-chlorophenyl)-2,2-dimethyl-1.3-dioxolane-4-carboxylate (Preparation example 26), to obtain the title compound (3.8 g, 70~95%)

¹H NMR (400 MHz, CDCl₃): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.19~7.4.2 (m, 4H).

Preparation Example 87

(4S,5R)-methyl-5-(2-fluorophenyl)-2,2-diethyl-1.3-dioxolane-4-carboxylate

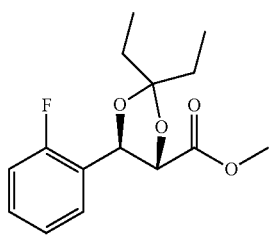

The substantially same method as described in Example 64 was conducted, except that (2S,3R)-methyl-3-(2-fluorophenyl)-2,3-dihydroxypropanoate (Preparation example 81) was used instead of (2S,3R)-methyl-3-(2-chlorophenyl)-2,3-dihydroxypropanoate, to obtain the title compound (2.1 g, 60~85%).

$^1$H NMR (400 MHz, CDCl$_3$) δ0.96 (m, 6H), 1.59 (m, 4H), 3.67 (s, 3H), 5.11 (d, J=7.6, 1H), 5.81 (d, J=7.6, 1H), 7.20~7.61 (m, 4H)

Preparation Example 88

((4R,5R)-5-(2-fluorophenyl)-2,2-diethyl-1.3-dioxolane-4-yl)methanol

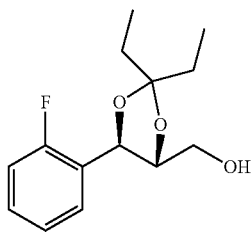

The substantially same method as described in Example 27 was conducted, except that (4S,5R)-methyl-5-(2-fluorophenyl)-2,2-diethyl-1.3-dioxolane-4-carboxylate (Preparation example 87) was used instead of (4R,5S)-methyl-5-(2-chlorophenyl)-2,2-dimethyl-1.3-dioxolane-4-carboxylate (Preparation example 26), to obtain the title compound (2.2 g, 70~95%)

$^1$H NMR (400 MHz, CDCl$_3$): δ0.96 (m, 6H), 1.59 (m, 4H), 3.66 (d, J=8.0, 2H), 5.09 (d, J=7.6, 1H), 5.88 (d, J=7.6, 1H), 7.23~7.60 (m, 4H).

Preparation Example 89

(4R,5S)-methyl-5-(2-fluorophenyl)-2,2-diethyl-1.3-dioxolane-4-carboxylate

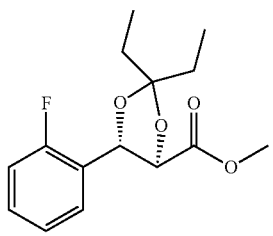

The substantially same method as described in Example 87 was conducted, except that (2R,3S)-methyl-3-(2-fluorophenyl)-2,3-dihydroxypropanoate (Preparation example 82) was used instead of (2S,3R)-methyl-3-(2-fluorophenyl)-2.3-dihydroxypropanote (Preparation example 81), to obtain the title compound (2.3 g, 70~95%).

$^1$H NMR (400 MHz, CDCl$_3$) δ0.96 (m, 6H), 1.59 (m, 4H), 3.67 (s, 3H), 5.11 (d, J=7.6, 1H), 5.81 (d, J=7.6, 1H), 7.20~7.61 (m, 4H)

Preparation Example 90

((4S,5S)-5-(2-fluorophenyl)-2,2-diethyl-1.3-dioxolane-4-yl)methanol

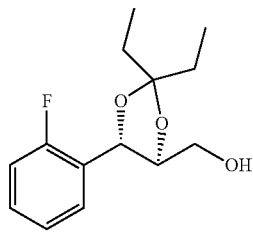

The substantially same method as described in Example 88 was conducted, except that (4R,5S)-methyl-5-(2-fluorophenyl)-2,2-diethyl-1.3-dioxolane-4-carboxylate (Preparation example 89) was used instead of (4S,5R)-methyl-5-(2-fluorophenyl)-2,2-diethyl-1.3-dioxolane-4-carboxylate (Preparation example 87), to obtain the title compound (2.2 g, 70~95%)

$^1$H NMR (400 MHz, CDCl$_3$): δ0.96 (m, 6H), 1.59 (m, 4H), 3.66 (d, J=8.0, 2H), 5.09 (d, J=7.6, 1H), 5.88 (d, J=7.6, 1H), 7.23~7.62 (m, 4H).

Preparation Example 91

(2S,3R)-methyl-3-(2-fluorophenyl)-1,4-dioxaspiro[4,4]nonane-2-carboxylate

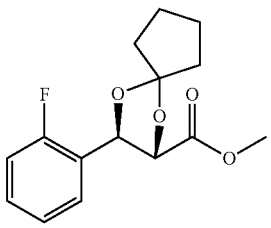 [SMILES: COC(=O)[C@H]1OC2(CCCC2)O[C@@H]1c1ccccc1F]

The substantially same method as described in Example 87 was conducted, except that cyclopentanone was used instead of 3-pentanone, to obtain the title compound (2.1 g, 70~95%).

$^1$H NMR (400 MHz, DMSO) δ1.69~1.71 (m, 4H), 1.82~1.86 (m, 1H), 1.91~2.00 (m, 3H), 3.68 (s, 3H), 4.40 (d, J=7.2, 1H), 5.39 (d, J=7.2, 1H), 7.33~7.62 (m, 4H)

Preparation Example 92

((4R,5R)-5-(2-fluorophenyl)-1,4-dioxaspiro[4,4]nonane-2-yl)methanol

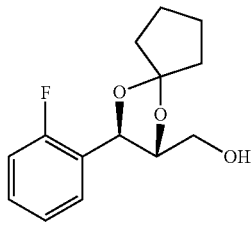 [SMILES: OC[C@H]1OC2(CCCC2)O[C@@H]1c1ccccc1F]

The substantially same method as described in Example 65 was conducted, except that (2S,3R)-methyl-3-(2-fluorophenyl)-1,4-dioxaspiro[4,4]nonane-2-carboxylate (Preparation example 91) was used instead of (4S,5R)-methyl-5-(2-chlorophenyl)-2,2-diethyl-1.3-dioxolane-4-carboxylate (Preparation example 64), to obtain the title compound (1.9 g, 70~95%)

$^1$H NMR (400 MHz, DMSO): δ1.60~1.72 (m, 4H), 1.83~1.94 (m, 1H), 3.52~3.65 (m, 2H), 3.82~3.86 (m, 1H), 4.90 (t, J=5.2, 1H), 5.12 (d, J=7.6, 1H), 7.32~7.57 (m, 4H)

Preparation Example 93

(2R,3S)-methyl-3-(2-fluorophenyl)-1,4-dioxaspiro[4,4]nonane-2-carboxylate

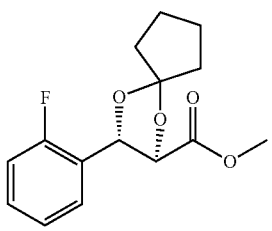

The substantially same method as described in Example 91 was conducted, except that (2R,3S)-methyl-3-(2-fluorophenyl)-2,3-dihydroxypropanoate (Preparation example 82) was used instead of (2S,3R)-methyl-3-(2-fluorophenyl)-2.3-dihydroxypropanote (Preparation example 81), to obtain the title compound (1.5 g, 70~95%).

$^1$H NMR (400 MHz, DMSO) δ1.69~1.71 (m, 4H), 1.82~1.86 (m, 1H), 1.91~2.00 (m, 3H), 3.68 (s, 3H), 4.40 (d, J=7.2, 1H), 5.39 (d, J=7.2, 1H), 7.39~7.61 (m, 4H)

Preparation Example 94

((4R,5R)-5-(2-fluorophenyl)-1,4-dioxaspiro[4,4]nonane-2-yl)methanol

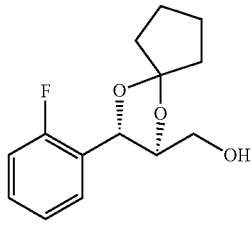

The substantially same method as described in Example 88 was conducted, except that (2R,3S)-methyl-3-(2-fluorophenyl)-1,4-dioxaspiro[4,4]nonane-2-carboxylate (Preparation example 93) was used instead of (4S,5R)-methyl-5-(2-fluorophenyl)-2,2-diethyl-1.3-dioxolane-4-carboxylate (Preparation example 87), to obtain the title compound (1.2 g, 70~95%)

$^1$H NMR (400 MHz, DMSO): δ1.60~1.72 (m, 4H), 1.83~1.94 (m, 1H), 3.52~3.65 (m, 2H), 3.82~3.86 (m, 1H), 4.90 (t, J=5.2, 1H), 5.12 (d, J=7.6, 1H), 7.38~7.63 (m, 4H)

Preparation Example 95

(2S,3R)-methyl-3-(2-fluorophenyl)-1,4-dioxaspiro[4,5]decane-2-carboxylate

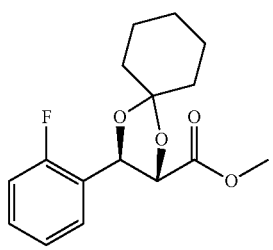

The substantially same method as described in Example 91 was conducted, except that cyclohexanone was used instead of cyclopentanone, to obtain the title compound (1.7 g, 70~95%).

$^1$H NMR (400 MHz, DMSO) δ1.61~1.69 (m, 10H), 3.79 (s, 3H), 4.33 (d, J=8.0, 1H), 5.85 (d, J=8.0, 1H), 7.37~7.63 (m, 4H)

Preparation Example 96

((4R,5R)-5-(2-fluorophenyl)-1,4-dioxaspiro[4,5]decane-2-yl)methanol

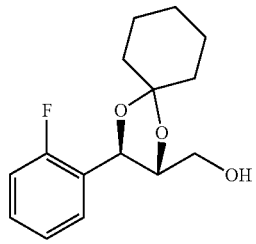 [SMILES: OC[C@H]1OC2(CCCCC2)O[C@@H]1c1ccccc1F]

The substantially same method as described in Example 73 was conducted, except that (2S,3R)-methyl-3-(2-fluorophenyl)-1,4-dioxaspiro[4,5]decane-2-carboxylate (Preparation example 95) was used instead of (2S,3R)-methyl-3-(2-chlorophenyl)-1,4-dioxaspiro[4,5]decane-2-carboxylate (Preparation example 72), to obtain the title compound (1.4 g, 70~95%)

$^1$H NMR (400 MHz, DMSO): δ1.63~1.75 (m, 10H), 3.52~3.81 (m, 2H), 3.95 (t, J=8.0, 1H), 5.43 (d, J=7.6, 1H), 7.42~7.89 (m, 4H)

Preparation Example 97

(2R,3S)-methyl-3-(2-fluorophenyl)-1,4-dioxaspiro[4,5]decane-2-carboxylate

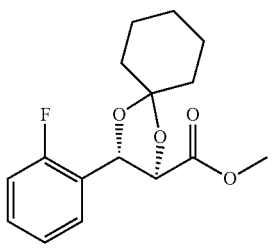

The substantially same method as described in Example 95 was conducted, except that (2R,3S)-methyl-3-(2-fluorophenyl)-2,3-dihydroxypropanoate (Preparation example 82) was used instead of (2S,3R)-methyl-3-(2-fluorophenyl)-2.3-dihydroxypropanote (Preparation example 81), to obtain the title compound (1.8 g, 70~95%).

$^1$H NMR (400 MHz, DMSO) δ1.61~1.69 (m, 10H), 3.79 (s, 3H), 4.33 (d, J=8.0, 1H), 5.85 (d, J=8.0, 1H), 7.32~7.64 (m, 4H)

Preparation Example 98

((4S,5S)-5-(2-fluorophenyl)-1,4-dioxaspiro[4,5]decane-2-yl)methanol

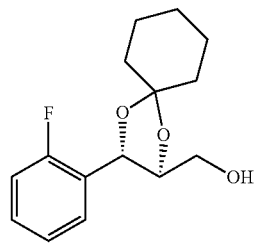

The substantially same method as described in Example 96 was conducted, except that (2R,3S)-methyl-3-(2-fluorophenyl)-1,4-dioxaspiro[4,5]decane-2-carboxylate (Preparation example 97) was used instead of (2S,3R)-methyl-3-(2-fluorophenyl)-1,4-dioxaspiro[4,5]decane-2-carboxylate (Preparation example 95), to obtain the title compound (1.5 g, 70~95%)

$^1$H NMR (400 MHz, DMSO): δ1.63~1.75 (m, 10H), 3.52~3.81 (m, 2H), 3.95 (t, J=8.0, 1H), 5.43 (d, J=7.6, 1H), 7.33~7.67 (m, 4H)

Preparation Example 99

(2S,3R)-methyl-3-(2-fluorophenyl)-2-phenyl-1,3-dioxolane-4-carboxylate

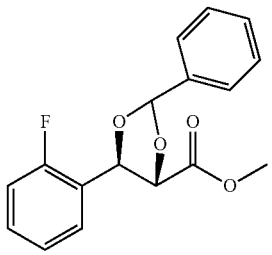

The substantially same method as described in Example 87 was conducted, except that benzaldehyde was used instead of 3-pentanone, to obtain the title compound (1.6 g, 50~70%).

$^1$H NMR (400 MHz, DMSO) δ1.61~1.69 (m, 10H), 3.79 (s, 3H), 4.33 (d, J=8.0, 1H), 5.85 (d, J=8.0, 1H), 7.33~7.64 (m, 4H)

Preparation Example 100

((4R,5R)-5-(2-fluorophenyl)-2-phenyl-1,3-dioxolane-4-yl)methanol

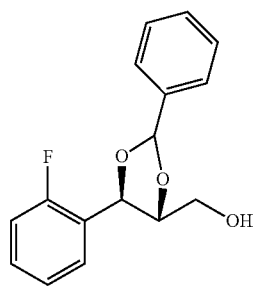

The substantially same method as described in Example 65 was conducted, except that (2S,3R)-methyl-3-(2-fluorophenyl)-2-phenyl-1,3-dioxolane-4-carboxylate (Preparation example 99) was used instead of (4S,5R)-methyl-5-(2-chlorophenyl)-2,2-diethyl-1.3-dioxolane-4-carboxylate (Preparation example 64), to obtain the title compound (1.3 g, 70~95%)

$^1$H NMR (400 MHz, DMSO): δ1.63~1.75 (m, 10H), 3.52~3.81 (m, 2H), 3.95 (t, J=8.0, 1H), 5.43 (d, J=7.6, 1H), 7.43~7.85 (m, 4H)

Preparation Example 101

(2R,3S)-methyl-3-(2-fluorophenyl)-2-phenyl-1,3-dioxolane-4-carboxylate

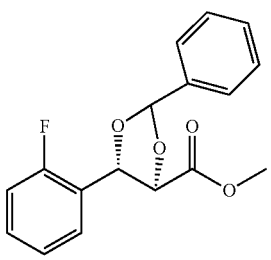

The substantially same method as described in Example 89 was conducted, except that benzaldehyde was used instead of 3-pentanone, to obtain the title compound (1.7 g, 50~70%).

$^1$H NMR (400 MHz, DMSO) δ1.61~1.69 (m, 10H), 3.79 (s, 3H), 4.33 (d, J=8.0, 1H), 5.85 (d, J=8.0, 1H), 7.33~7.64 (m, 4H)

Preparation Example 102

((4S,5S)-5-(2-fluorophenyl)-2-phenyl-1,3-dioxolane-4-yl)methanol

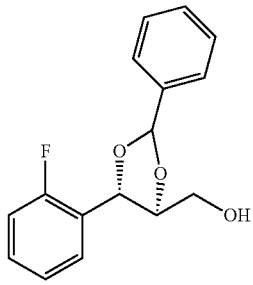

The substantially same method as described in Example 65 was conducted, except that (2R,3S)-methyl-3-(2-fluorophenyl)-2-phenyl-1,3-dioxolane-4-carboxylate (Preparation example 101) was used instead of (4S,5R)-methyl-5-(2-chlorophenyl)-2,2-diethyl-1.3-dioxolane-4-carboxylate (Preparation example 64), to obtain the title compound (1.1 g, 70~95%)

$^1$H NMR (400 MHz, DMSO): δ1.63~1.75 (m, 10H), 3.52~3.81 (m, 2H), 3.95 (t, J=8.0, 1H), 5.43 (d, J=7.6, 1H), 7.43~7.85 (m, 4H)

Preparation Example 103

(E)-Methyl-3-(2-iodophenyl)acrylate

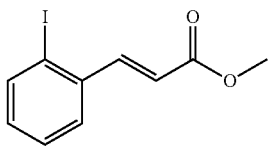

The substantially same method as described in Example 24 was conducted, except that (E)-3 (2-iodophenyl)-acrylic acid (Preparation example 17) was used instead of 2-chlorocinnamic acid, to obtain the title compound. (3.2 g, 70~90%)

$^1$H NMR (400 MHz, CDCl$_3$) δ3.84 (s, 3H), 6.45 (d, J=16.0, 1H), 7.01~7.35 (m, 4H), 8.09 (d, J=16.0, 1H)

Preparation Example 104

(2S,3R)-methyl-3-(2-iodophenyl)-2,3-dihydroxypropanoate

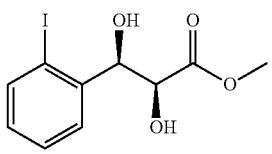

The substantially same method as described in Preparation Example 3 was conducted, except that (E)-Methyl-3-(2-iodophenyl)acrylate (Preparation example 103) was used instead of (E)-1-chloro-2-(3-(methoxymethoxy)prop-1-enyl)benzene (Preparation example 2), to obtain the title compound (3.2 g, 75~90%).

$^1$H NMR (400 MHz, CDCl$_3$): β=4.31 (s, 3H), 5.44 (m, 4H), 5.89 (s, 1H), 7.30~7.71 (m, 4H).

Preparation Example 105

(2R,3S)-methyl-3-(2-iodophenyl)-2,3-dihydroxypropanoate

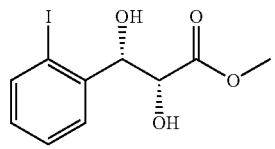

The substantially same method as described in Example 25 was conducted, except that (E)-methyl-3-(2-iodophenyl)acrylate (Preparation example 103) was used instead of (E)-Methyl-3-(2-chlorophenyl)acrylate (Preparation example 24), to obtain the title compound (3.1 g, 60~80%).

$^1$H NMR (400 MHz, CDCl$_3$): β=4.31 (s, 3H), 5.44 (m, 4H), 5.89 (s, 1H), 7.31~7.72 (m, 4H).

Preparation Example 106

((4S,5R)-methyl-5-(2-iodophenyl)-2-methyl-1.3-dioxolane-4-carboxylate

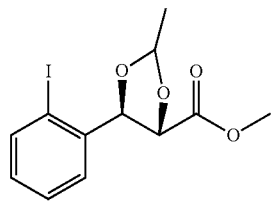

The substantially same method as described in Example 60 was conducted, except that (2S,3R)-methyl-3-(2-iodophenyl)-2,3-dihydroxypropanoate (Preparation example 104) was used instead of (2S,3R)-methyl-3-(2-chlorophenyl)-2,3-dihydroxypropanoate, to obtain the title compound (2.7 g, 70~95%).

$^1$H NMR (400 MHz, CDCl$_3$) δ1.36 (d, J=6.4, 3H), 3.78 (s, 3H), 4.30 (d, J=7.6, 1H), 5.07 (m, 1H), 5.62 (d, J=7.6, 1H), 7.29~7.70 (m, 4H)

Preparation Example 107

((4R,5R)-5-(2-iodophenyl)-2-methyl-1.3-dioxolane-4-yl)methanol

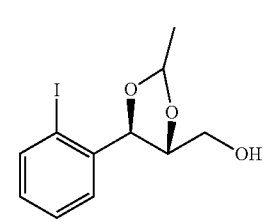

The substantially same method as described in Example 27 was conducted, except that (4S,5R)-methyl-5-(2-iodophenyl)-2-methyl-1,3-dioxolane-4-carboxylate (Preparation example 106) was used instead of (4R,5S)-methyl-5-(2-chlorophenyl)-2,2-dimethyl-1,3-dioxolane-4-carboxylate (Preparation example 26), to obtain the title compound (2.3 g, 70~95%)

¹H NMR (400 MHz, CDCl₃): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.17~7.41 (m, 4H).

Preparation Example 108

((4R,5S)-methyl-5-(2-iodophenyl)-2-methyl-1,3-dioxolane-4-carboxylate

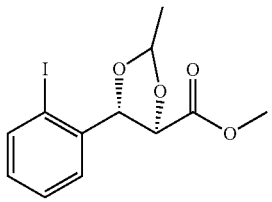

The substantially same method as described in Example 60 was conducted, except that (2R,3S)-methyl-3-(2-iodophenyl)-2,3-dihydroxypropanote (Preparation example 104) was used instead of (2S,3R)-methyl-3-(2-chlorophenyl)-2,3-dihydroxypropanote, to obtain the title compound (2.4 g, 70~95%).

¹H NMR (400 MHz, CDCl₃) δ1.36 (d, J=6.4, 3H), 3.78 (s, 3H), 4.30 (d, J=7.6, 1H), 5.07 (m, 1H), 5.62 (d, J=7.6, 1H), 7.29~7.70 (m, 4H)

Preparation Example 109

((4S,5S)-5-(2-iodophenyl)-2-methyl-1,3-dioxolane-4-yl)methanol

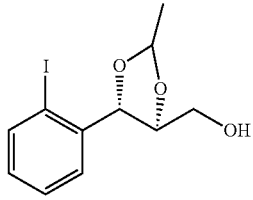

The substantially same method as described in Example 107 was conducted, except that (4R,5S)-methyl-5-(2-iodophenyl)-2-methyl-1,3-dioxolane-4-carboxylate (Preparation example 108) was used instead of (4S,5R)-methyl-5-(2-iodophenyl)-2-methyl-1,3-dioxolane-4-carboxylate (Preparation example 106), to obtain the title compound (1.9 g, 70~95%)

¹H NMR (400 MHz, CDCl₃): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.17~7.41 (m, 4H)

Preparation Example 110

(4S,5R)-methyl-5-(2-iodophenyl)-2,2-diethyl-1,3-dioxolane-4-carboxylate

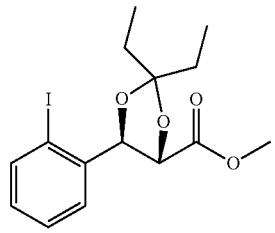 [SMILES: CCC1(CC)O[C@H](C(=O)OC)[C@@H](c2ccccc2I)O1]

The substantially same method as described in Example 64 was conducted, except that ((2S,3R)-methyl-3-(2-iodophenyl)-2,3-dihydroxypropanoate (Preparation example 104) was used instead of (2S,3R)-methyl-3-(2-chlorophenyl)-2,3-dihydroxypropanoate, to obtain the title compound (2.6 g, 60~85%).

¹H NMR (400 MHz, CDCl₃) δ0.96 (m, 6H), 1.59 (m, 4H), 3.67 (s, 3H), 5.11 (d, J=7.6, 1H), 5.81 (d, J=7.6, 1H), 7.23~7.65 (m, 4H)

Preparation Example 111

((4R,5R)-5-(2-iodophenyl)-2,2-diethyl-1,3-dioxolane-4-yl)methanol

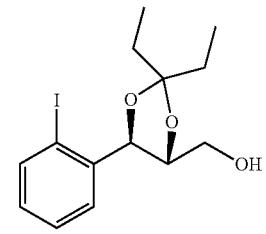

The substantially same method as described in Example 107 was conducted, except that (4S,5R)-methyl-5-(2-iodophenyl)-2,2-diethyl-1,3-dioxolane-4-carboxylate (Preparation example 110) was used instead of (4S,5R)-methyl-5-(2-iodophenyl)-2-methyl-1,3-dioxolane-4-carboxylate (Preparation example 106), to obtain the title compound (2.1 g, 70~95%)

¹H NMR (400 MHz, CDCl₃): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.17~7.41 (m, 4H)

Preparation Example 112

(4R,5S)-methyl-5-(2-iodophenyl)-2,2-diethyl-1,3-dioxolane-4-carboxylate

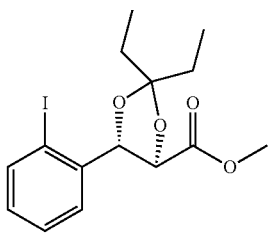 [SMILES: CCC1(CC)O[C@@H](C(=O)OC)[C@H](c2ccccc2I)O1]

The substantially same method as described in Example 110 was conducted, except that (2R,3S)-methyl-3-(2-iodophenyl)-2,3-dihydroxypropanoate (Preparation example 105) was used instead of (2S,3R)-methyl-3-(2-iodophenyl)-2,3-dihydroxypropanoate (Preparation example 104), to obtain the title compound (2.3 g, 60~85%).

$^1$H NMR (400 MHz, CDCl$_3$) δ0.96 (m, 6H), 1.59 (m, 4H), 3.67 (s, 3H), 5.11 (d, J=7.6, 1H), 5.81 (d, J=7.6, 1H), 7.20~7.61 (m, 4H)

Preparation Example 113

((4S,5S)-5-(2-iodophenyl)-2,2-diethyl-1,3-dioxolane-4-yl)methanol

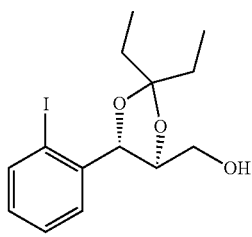 [SMILES: CCC1(CC)O[C@@H](CO)[C@H](c2ccccc2I)O1]

The substantially same method as described in Example 107 was conducted, except that (4R,5S)-methyl-5-(2-iodophenyl)-2,2-diethyl-1,3-dioxolane-4-carboxylate (Preparation example 112) was used instead of (4S,5R)-methyl-5-(2-iodophenyl)-2-methyl-1,3-dioxolane-4-carboxylate (Preparation example 106), to obtain the title compound (1.8 g, 70~95%)

$^1$H NMR (400 MHz, CDCl$_3$): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.17~7.41 (m, 4H)

Preparation Example 114

(2S,3R)-methyl-3-(2-iodophenyl)-1,4-dioxaspiro[4,4]nonane-2-carboxylate

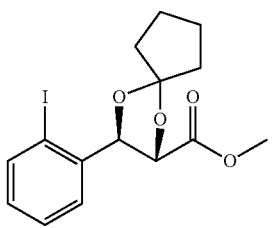 [SMILES: COC(=O)[C@H]1OC2(CCCC2)O[C@@H]1c1ccccc1I]

The substantially same method as described in Example 110 was conducted, except that cyclopentanone was used instead of 3-pentanone, to obtain the title compound (2.7 g, 70~95%).

$^1$H NMR (400 MHz, DMSO) δ1.69~4.71 (m, 4H), 1.82~1.86 (m, 1H), 1.91~2.00 (m, 3H), 3.68 (s, 3H), 4.40 (d, J=7.2, 1H), 5.39 (d, J=7.2, 1H), 7.19~7.44 (m, 4H)

Preparation Example 115

((4R,5R)-5-(2-iodophenyl)-1,4-dioxaspiro[4,4]nonane-2-yl)methanol

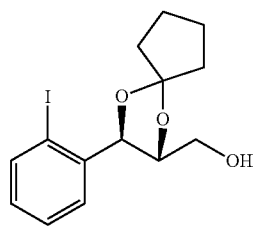

The substantially same method as described in Example 107 was conducted, except that (2S,3R)-methyl-3-(2-iodophenyl)-1,4-dioxaspiro[4,4]nonane-2-carboxylate (Preparation example 114) was used instead of (4S,5R)-methyl-5-(2-iodophenyl)-2-methyl-1,3-dioxolane-4-carboxylate (Preparation example 106), to obtain the title compound (2.1 g, 70~95%)

$^1$H NMR (400 MHz, DMSO): δ1.60~1.72 (m, 4H), 1.83~1.94 (m, 1H), 3.52~3.65 (m, 2H), 3.82~3.86 (m, 1H), 4.90 (t, J=5.2, 1H), 5.12 (d, J=7.6, 1H), 7.20~7.45 (m, 4H)

Preparation Example 116

(2R,3S)-methyl-3-(2-iodophenyl)-1,4-dioxaspiro[4,4]nonane-2-carboxylate

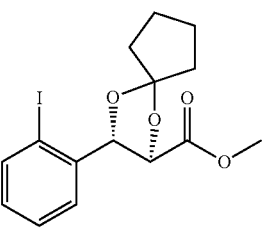 [SMILES: COC(=O)[C@@H]1OC2(CCCC2)O[C@H]1c1ccccc1I]

The substantially same method as described in Example 112 was conducted, except that cyclopentanone was used instead of 3-pentanone, to obtain the title compound (2.9 g, 70~95%).

$^1$H NMR (400 MHz, DMSO) δ1.69~4.71 (m, 4H), 1.82~1.86 (m, 1H), 1.91~2.00 (m, 3H), 3.68 (s, 3H), 4.40 (d, J=7.2, 1H), 5.39 (d, J=7.2, 1H), 7.19~7.44 (m, 4H)

Preparation example 117 ((4R,5R)-5-(2-iodophenyl)-1,4-dioxaspiro[4,4]nonane-2-yl)methanol

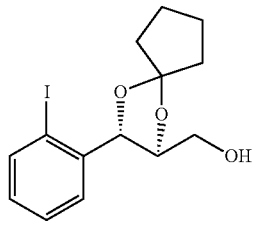 [SMILES: OC[C@@H]1OC2(CCCC2)O[C@H]1c1ccccc1I]

The substantially same method as described in Example 107 was conducted, except that (2R,3S)-methyl-3-(2-iodophenyl)-1,4-dioxaspiro[4,4]nonane-2-carboxylate (Preparation example 116) was used instead of (4S,5R)-methyl-5-(2-iodophenyl)-2-methyl-1,3-dioxolane-4-carboxylate (Preparation example 106), to obtain the title compound (1.5 g, 70~95%)

$^1$H NMR (400 MHz, DMSO) δ1.60~1.72 (m, 4H), 1.83~1.94 (m, 1H), 3.52~3.65 (m, 2H), 3.82~3.86 (m, 1H), 4.90 (t, J=5.2, 1H), 5.12 (d, J=7.6, 1H), 7.20~7.45 (m, 4H)

Preparation Example 118

(2S,3R)-methyl-3-(2-iodophenyl)-1,4-dioxaspiro[4,5]decane-2-carboxylate

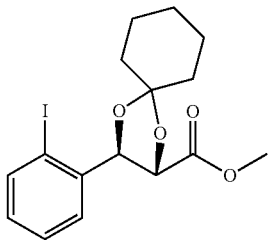

The substantially same method as described in Example 114 was conducted, except that cyclohexanone was used instead of cyclopentanone, to obtain the title compound (1.9 g, 70~95%).

$^1$H NMR (400 MHz, DMSO) δ1.61~1.69 (m, 10H), 3.79 (s, 3H), 4.33 (d, J=8.0, 1H), 5.85 (d, J=8.0, 1H), 7.17~7.43 (m, 4H)

Preparation Example 119

((4R,5R)-5-(2-iodophenyl)-1,4-dioxaspiro[4,5]decane-2-yl)methanol

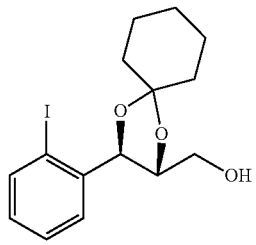 [SMILES: OC[C@H]1OC2(CCCCC2)O[C@@H]1c1ccccc1I]

The substantially same method as described in Example 107 was conducted, except that (2S,3R)-methyl-3-(2-iodophenyl)-1,4-dioxaspiro[4,5]decane-2-carboxylate (Preparation example 118) was used instead of (4S,5R)-methyl-5-(2-iodophenyl)-2-methyl-1,3-dioxolane-4-carboxylate (Preparation example 106), to obtain the title compound (1.3 g, 70~95%)

$^1$H NMR (400 MHz, DMSO) δ1.63~1.75 (m, 10H), 3.52~3.81 (m, 2H), 3.95 (t, J=8.0, 1H), 5.43 (d, J=7.6, 1H), 7.19~7.49 (m, 4H)

Preparation Example 120

(2R,3S)-methyl-3-(2-iodophenyl)-1,4-dioxaspiro[4,5]decane-2-carboxylate

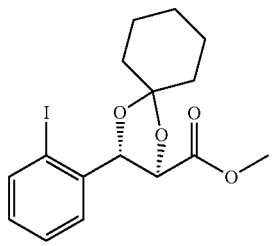 [SMILES: COC(=O)[C@@H]1OC2(CCCCC2)O[C@H]1c1ccccc1I]

The substantially same method as described in Example 116 was conducted, except that cyclohexanone was used instead of cyclopentanone, to obtain the title compound (2.3 g, 70~95%).

$^1$H NMR (400 MHz, DMSO) δ1.61~1.69 (m, 10H), 3.79 (s, 3H), 4.33 (d, J=8.0, 1H), 5.85 (d, J=8.0, 1H), 7.17~7.43 (m, 4H)

Preparation Example 121

((4S,5S)-5-(2-iodophenyl)-1,4-dioxaspiro[4,5]decane-2-yl)methanol

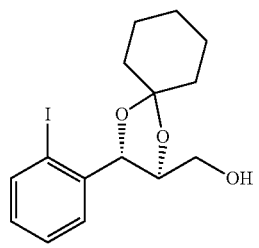 [SMILES: OC[C@@H]1OC2(CCCCC2)O[C@H]1c1ccccc1I]

The substantially same method as described in Example 107 was conducted, except that (2R,3S)-methyl-3-(2-iodophenyl)-1,4-dioxaspiro[4,5]decane-2-carboxylate (Preparation example 120) was used instead of (4S,5R)-methyl-5-(2-iodophenyl)-2-methyl-1,3-dioxolane-4-carboxylate (Preparation example 106), to obtain the title compound (1.7 g, 70~95%)

$^1$H NMR (400 MHz, DMSO) δ1.63~1.75 (m, 10H), 3.52~3.81 (m, 2H), 3.95 (t, J=8.0, 1H), 5.43 (d, J=7.6, 1H), 7.19~7.49 (m, 4H)

Preparation Example 122

(2S,3R)-methyl-3-(2-iodophenyl)-2-phenyl-1,3-dioxolane-4-carboxylate

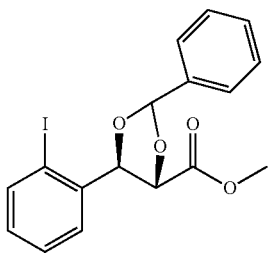

The substantially same method as described in Example 118 was conducted, except that benzaldehyde was used instead of cyclohexanone, to obtain the title compound (1.9 g, 50~70%).

¹H NMR (400 MHz, DMSO) δ3.67 (s, 3H), 5.11 (d, J=8.0, 1H), 5.81 (d, J=8.0, 1H), 6.18 (s, 1H), 6.96~7.57 (m, 9H)

Preparation Example 123

((4R,5R)-5-(2-iodophenyl)-2-phenyl-1,3-dioxolane-4-yl)methanol

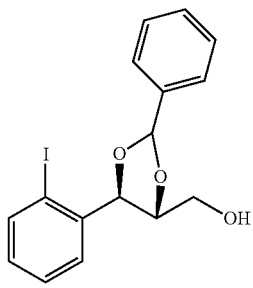

The substantially same method as described in Example 107 was conducted, except that (2S,3R)-methyl-3-(2-iodophenyl)-2-phenyl-1,3-dioxolane-4-carboxylate (Preparation example 122) was used instead of (4S,5R)-methyl-5-(2-iodophenyl)-2-methyl-1.3-dioxolane-4-carboxylate (Preparation example 106), to obtain the title compound (1.4 g, 70~95%)

¹H NMR (400 MHz, DMSO) δ3.66 (d, J=7.6, 2H), 4.36 (m, 1H), 5.17 (d, J=8.0, 1H), 6.18 (s, 1H), 6.94~7.59 (m, 9H)

Preparation Example 124

(2R,3S)-methyl-3-(2-iodophenyl)-2-phenyl-1,3-dioxolane-4-carboxylate

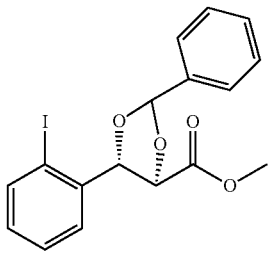

The substantially same method as described in Example 120 was conducted, except benzaldehyde that was used instead of cyclohexanone, to obtain the title compound (2.1 g, 50~70%).

¹H NMR (400 MHz, DMSO) δ3.67 (s, 3H), 5.11 (d, J=8.0, 1H), 5.81 (d, J=8.0, 1H), 6.18 (s, 1H), 6.96~7.57 (m, 9H)

Preparation Example 125

((4S,5S)-5-(2-iodophenyl)-2-phenyl-1,3-dioxolane-4-yl)methanol

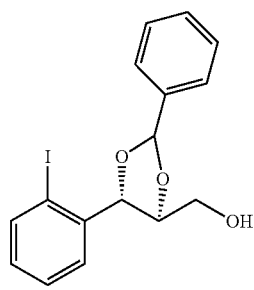

The substantially same method as described in Example 107 was conducted, except that (2R,3S)-methyl-3-(2-iodophenyl)-2-phenyl-1,3-dioxolane-4-carboxylate (Preparation example 124) was used instead of (4S,5R)-methyl-5-(2-iodophenyl)-2-methyl-1.3-dioxolane-4-carboxylate (Preparation example 106), to obtain the title compound (1.3 g, 70~95%)

¹H NMR (400 MHz, DMSO) δ3.66 (d, J=7.6, 2H), 4.36 (m, 1H), 5.17 (d, J=8.0, 1H), 6.18 (s, 1H), 6.94~7.59 (m, 9H)

Preparation Example 126

((4S,5R)-methyl-5-(2,4-dichlorophenyl)-2-methyl-1.3-dioxolane-4-carboxylate

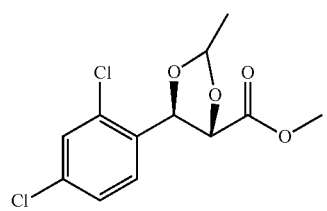

The substantially same method as described in Example 60 was conducted, except that (2S,3R)-methyl-3-(2,4-dichlorophenyl)-2,3-dihydroxypropanoate (Preparation example 36) was used instead of (2S,3R)-methyl-3-(2-chlorophenyl)-2,3-dihydroxypropanoate, to obtain the title compound (0.9 g, 70~95%).

¹H NMR (400 MHz, CDCl₃) δ1.36 (d, J=6.4, 3H), 3.78 (s, 3H), 4.30 (d, J=7.6, 1H), 5.07 (m, 1H), 5.62 (d, J=7.6, 1H), 7.07~7.21 (m, 3H)

Preparation Example 127

((4R,5R)-5-(2,4-dichlorophenyl)-2-methyl-1,3-dioxolane-4-yl)methanol

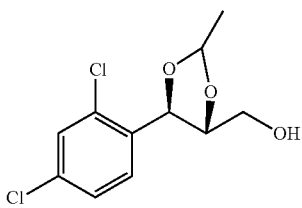

The substantially same method as described in Example 27 was conducted, except that (4S,5R)-methyl-5-(2,4-dichlorophenyl)-2-methyl-1,3-dioxolane-4-carboxylate (Preparation example 126) was used instead of (4R,5S)-methyl-5-(2-chlorophenyl)-2,2-dimethyl-1,3-dioxolane-4-carboxylate (Preparation example 26), to obtain the title compound (0.7 g, 70~95%)

$^1$H NMR (400 MHz, CDCl$_3$): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.08~7.39 (m, 3H).

Preparation Example 128

((4R,5S)-methyl-5-(2,4-dichlorophenyl)-2-methyl-1,3-dioxolane-4-carboxylate

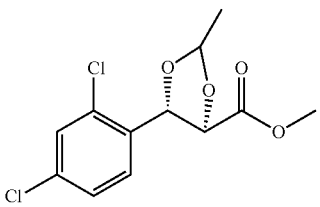

The substantially same method as described in Example 126 was conducted, except that (2R,3S)-methyl-3-(2,4-dichlorophenyl)-2,3-dihydroxypropanoate (Preparation example 29) was used instead of (2S,3R)-methyl-3-(2,4-dichlorophenyl)-2,3-dihydroxypropanoate (Preparation example 36), to obtain the title compound (1.9 g, 70~95%).

$^1$H NMR (400 MHz, CDCl$_3$) δ1.36 (d, J=6.4, 3H), 3.78 (s, 3H), 4.30 (d, J=7.6, 1H), 5.07 (m, 1H), 5.62 (d, J=7.6, 1H), 7.07~7.21 (m, 3H).

Preparation Example 129

((4S,5S)-5-(2,4-dichlorophenyl)-2-methyl-1,3-dioxolane-4-yl)methanol

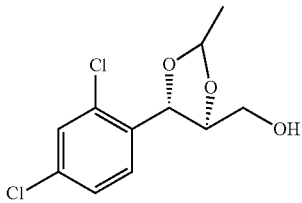

The substantially same method as described in Example 27 was conducted, except that (4R,5S)-methyl-5-(2,4-dichlorophenyl)-2-methyl-1,3-dioxolane-4-carboxylate (Preparation example 128) was used instead of (4R,5S)-methyl-5-(2-chlorophenyl)-2,2-dimethyl-1,3-dioxolane-4-carboxylate (Preparation example 26), to obtain the title compound (1.5 g, 70~95%)

$^1$H NMR (400 MHz, CDCl$_3$): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.08~7.39 (m, 3H).

Preparation Example 130

(4S,5R)-methyl-5-(2,4-dichlorophenyl)-2,2-diethyl-1,3-dioxolane-4-carboxylate

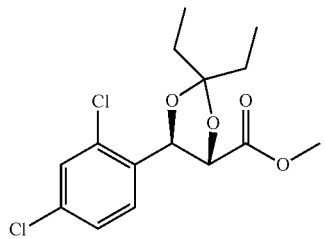 [SMILES: CCC1(CC)O[C@H](C(=O)OC)[C@@H](c2ccc(Cl)cc2Cl)O1]

The substantially same method as described in Example 64 was conducted, except that (2S,3R)-methyl-3-(2,4-dichlorophenyl)-2,3-dihydroxypropanoate (Preparation example 36) was used instead of (2S,3R)-methyl-3-(2-chlorophenyl)-2,3-dihydroxypropanoate, to obtain the title compound (2.2 g, 60~85%).

$^1$H NMR (400 MHz, CDCl$_3$) δ0.96 (m, 6H), 1.59 (m, 4H), 3.67 (s, 3H), 5.11 (d, J=7.6, 1H), 5.81 (d, J=7.6, 1H), 7.12~7.37 (m, 3H)

Preparation Example 131

((4R,5R)-5-(2,4-dichlorophenyl)-2,2-diethyl-1,3-dioxolane-4-yl)methanol

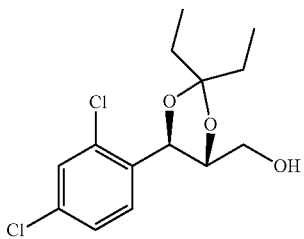 [SMILES: CCC1(CC)O[C@H](c2ccc(Cl)cc2Cl)[C@@H](CO)O1]

The substantially same method as described in Example 27 was conducted, except that (4S,5R)-methyl-5-(2,4-dichlorophenyl)-2,2-diethyl-1,3-dioxolane-4-carboxylate (Preparation example 130) was used instead of (4R,5S)-methyl-5-(2-chlorophenyl)-2,2-dimethyl-1,3-dioxolane-4-carboxylate (Preparation example 26), to obtain the title compound (1.4 g, 70~95%)

¹H NMR (400 MHz, CDCl₃): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.08~7.39 (m, 3H).

Preparation Example 132

(4R,5S)-methyl-5-(2,4-chlorophenyl)-2,2-diethyl-1,3-dioxolane-4-carboxylate

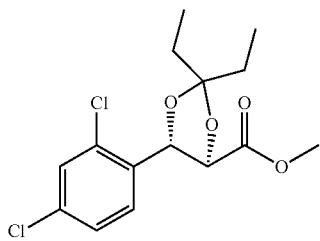 [SMILES: CCC1(CC)O[C@@H](C(=O)OC)[C@H](c2ccc(Cl)cc2Cl)O1]

The substantially same method as described in Example 130 was conducted, except that (2R,3S)-methyl-3-(2,4-dichlorophenyl)-2,3-dihydroxypropanoate (Preparation example 29) was used instead of (2S,3R)-methyl-3-(2,4-dichlorophenyl)-2,3-dihydroxypropanoate (Preparation example 36), to obtain the title compound (2.1 g, 70~95%).

¹H NMR (400 MHz, CDCl₃) δ0.96 (m, 6H), 1.59 (m, 4H), 3.67 (s, 3H), 5.11 (d, J=7.6, 1H), 5.81 (d, J=7.6, 1H), 7.12~7.37 (m, 3H)

Preparation Example 133

((4S,5S)-5-(2,4-chlorophenyl)-2,2-diethyl-1,3-dioxolane-4-yl)methanol

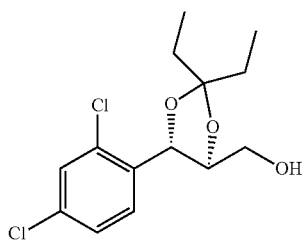 [SMILES: CCC1(CC)O[C@@H](CO)[C@H](c2ccc(Cl)cc2Cl)O1]

The substantially same method as described in Example 131 was conducted, except that (4R,5S)-methyl-5-(2,4-dichlorophenyl)-2,2-diethyl-1,3-dioxolane-4-carboxylate (Preparation example 132) was used instead of (4S,5R)-methyl-5-(2,4-dichlorophenyl)-2,2-diethyl-1,3-dioxolane-4-carboxylate (Preparation example 130), to obtain the title compound (1.2 g, 70~95%).

¹H NMR (400 MHz, CDCl₃): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.08~7.39 (m, 3H).

Preparation Example 134

(2S,3R)-methyl-3-(2,4-chlorophenyl)-1,4-dioxaspiro[4,4]nonane-2-carboxylate

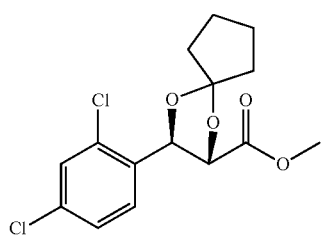 [SMILES: COC(=O)[C@H]1OC2(CCCC2)O[C@@H]1c1ccc(Cl)cc1Cl]

The substantially same method as described in Example 131 was conducted, except that cyclopentanone was used instead of 3-pentanone, to obtain the title compound (2.5 g, 70~95%).

¹H NMR (400 MHz, DMSO) δ1.69~4.71 (m, 4H), 1.82~1.86 (m, 1H), 1.91~2.00 (m, 3H), 3.68 (s, 3H), 4.40 (d, J=7.2, 1H), 5.39 (d, J=7.2, 1H), 7.03~7.36 (m, 3H)

Preparation Example 135

((4R,5R)-5-(2,4-chlorophenyl)-1,4-dioxaspiro[4,4]nonane-2-yl)methanol

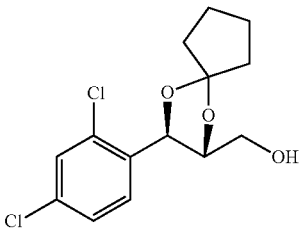 [SMILES: OC[C@H]1OC2(CCCC2)O[C@@H]1c1ccc(Cl)cc1Cl]

The substantially same method as described in Example 65 was conducted, except that (2S,3R)-methyl-3-(2,4-dichlorophenyl)-1,4-dioxaspiro[4,4]nonane-2-carboxylate (Preparation example 134) was used instead of (4S,5R)-methyl-5-(2-chlorophenyl)-2,2-diethyl-1,3-dioxolane-4-carboxylate (Preparation example 64), to obtain the title compound (1.8 g, 70~95%)

¹H NMR (400 MHz, DMSO) δ1.60~1.72 (m, 4H), 1.83~1.94 (m, 1H), 3.52~3.65 (m, 2H), 3.82~3.86 (m, 1H), 4.90 (t, J=5.2, 1H), 5.12 (d, J=7.6, 1H), 7.02~7.37 (m, 3H)

Preparation Example 136

(2R,3S)-methyl-3-(2,4-chlorophenyl)-1,4-dioxaspiro[4,4]nonane-2-carboxylate

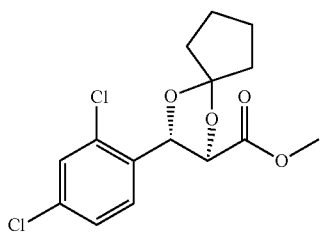 [SMILES: COC(=O)[C@@H]1OC2(CCCC2)O[C@H]1c1ccc(Cl)cc1Cl]

The substantially same method as described in Example 132 was conducted, except that cyclopentanone was used instead of 3-pentanone, to obtain the title compound (2.2 g, 70~95%).

¹H NMR (400 MHz, DMSO) δ1.69~4.71 (m, 4H), 1.82~1.86 (m, 1H), 1.91~2.00 (m, 3H), 3.68 (s, 3H), 4.40 (d, J=7.2, 1H), 5.39 (d, J=7.2, 1H), 7.03~7.36 (m, 3H)

Preparation Example 137

((4S,5S)-5-(2,4-chlorophenyl)-1,4-dioxaspiro[4,4]nonane-2-yl)methanol

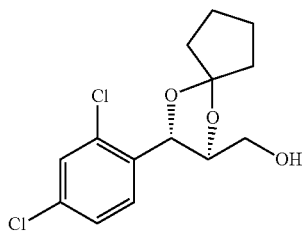 [SMILES: OC[C@@H]1OC2(CCCC2)O[C@H]1c1ccc(Cl)cc1Cl]

The substantially same method as described in Example 135 was conducted, except that (2R,3S)-methyl-3-(2,4-dichlorophenyl)-1,4-dioxaspiro[4,4]nonane-2-carboxylate (Preparation example 136) was used instead of (2S,3R)-methyl-3-(2,4-dichlorophenyl)-1,4-dioxaspiro[4,4]nonane-2-carboxylate (Preparation example 134), to obtain the title compound (1.2 g, 70~95%)

¹H NMR (400 MHz, DMSO) δ1.60~1.72 (m, 4H), 1.83~1.94 (m, 1H), 3.52~3.65 (m, 2H), 3.82~3.86 (m, 1H), 4.90 (t, J=5.2, 1H), 5.12 (d, J=7.6, 1H), 7.02~7.37 (m, 3H)

Preparation Example 138

(2S,3R)-methyl-3-(2,4-chlorophenyl)-1,4-dioxaspiro[4,5]decane-2-carboxylate

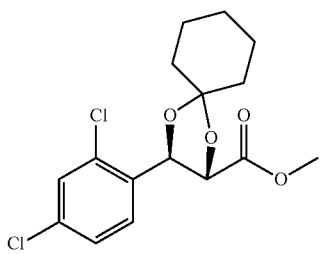 [SMILES: COC(=O)[C@H]1OC2(CCCCC2)O[C@@H]1c1ccc(Cl)cc1Cl]

The substantially same method as described in Example 134 was conducted, except that cyclohexanone was used instead of cyclopentanone, to obtain the title compound (1.8 g, 70~95%).

¹H NMR (400 MHz, DMSO) δ1.61~1.69 (m, 10H), 3.79 (s, 3H), 4.33 (d, J=8.0, 1H), 5.85 (d, J=8.0, 1H), 7.07~7.41 (m, 3H)

Preparation Example 139

((4R,5R)-5-(2,4-chlorophenyl)-1,4-dioxaspiro[4,5]decane-2-yl)methanol

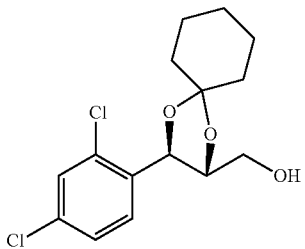 [SMILES: OC[C@H]1OC2(CCCCC2)O[C@@H]1c1ccc(Cl)cc1Cl]

The substantially same method as described in Example 73 was conducted, except that (2S,3R)-methyl-3-(2,4-dichlorophenyl)-1,4-dioxaspiro[4,5]decane-2-carboxylate (Preparation example 138) was used instead of (2S,3R)-methyl-3-(2-chlorophenyl)-1,4-dioxaspiro[4,5]decane-2-carboxylate (Preparation example 72), to obtain the title compound (1.3 g, 70~95%)

¹H NMR (400 MHz, DMSO) δ1.63~1.75 (m, 10H), 3.52~3.81 (m, 2H), 3.95 (t, J=8.0, 1H), 5.43 (d, J=7.6, 1H), 7.04~7.40 (m, 3H)

Preparation Example 140

(2R,3S)-methyl-3-(2,4-chlorophenyl)-1,4-dioxaspiro[4,5]decane-2-carboxylate

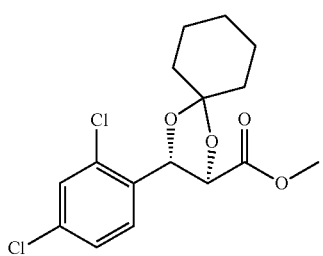 [SMILES: COC(=O)[C@@H]1OC2(CCCCC2)O[C@H]1c1ccc(Cl)cc1Cl]

The substantially same method as described in Example 136 was conducted, except that cyclohexanone was used instead of cyclopentanone, to obtain the title compound (1.6 g, 70~95%).

¹H NMR (400 MHz, DMSO) δ1.61~1.69 (m, 10H), 3.79 (s, 3H), 4.33 (d, J=8.0, 1H), 5.85 (d, J=8.0, 1H), 7.07~7.41 (m, 3H)

Preparation Example 141

((4S,5S)-5-(2,4-chlorophenyl)-1,4-dioxaspiro[4,5]decane-2-yl)methanol

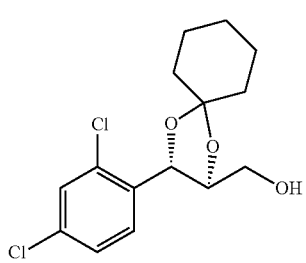 [SMILES: OC[C@@H]1OC2(CCCCC2)O[C@H]1c1ccc(Cl)cc1Cl]

The substantially same method as described in Example 139 was conducted, except that (2R,3S)-methyl-3-(2,4-dichlorophenyl)-1,4-dioxaspiro[4,5]decane-2-carboxylate (Preparation example 140) was used instead of (2S,3R)-methyl-3-(2,4-dichlorophenyl)-1,4-dioxaspiro[4,5]decane-2-carboxylate (Preparation example 138), to obtain the title compound (1.2 g, 70~95%)

¹H NMR (400 MHz, DMSO) δ1.63~1.75 (m, 10H), 3.52~3.81 (m, 2H), 3.95 (t, J=8.0, 1H), 5.43 (d, J=7.6, 1H), 7.04~7.40 (m, 3H)

Preparation Example 142

(2S,3R)-methyl-3-(2,4-chlorophenyl)-2-phenyl-1,3-dioxolane-4-carboxylate

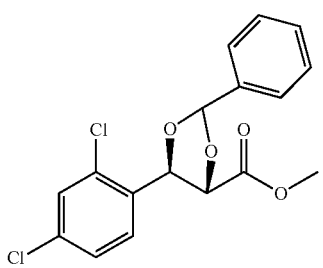

The substantially same method as described in Example 138 was conducted, except that benzaldehyde was used instead of cyclohexanone, to obtain the title compound (1.9 g, 50~70%).

¹H NMR (400 MHz, DMSO) δ1.61~1.69 (m, 10H), 3.79 (s, 3H), 4.33 (d, J=8.0, 1H), 5.85 (d, J=8.0, 1H), 7.03~7.41 (m, 3H)

Preparation Example 143

((4R,5R)-5-(2,4-chlorophenyl)-2-phenyl-1,3-dioxolane-4-yl)methanol

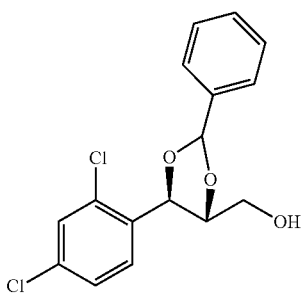

The substantially same method as described in Example 65 was conducted, except that (2S,3R)-methyl-3-(2,4-chlorophenyl)-2-phenyl-1,3-dioxolane-4-carboxylate (Preparation example 142) was used instead of (4S,5R)-methyl-5-(2-chlorophenyl)-2,2-diethyl-1.3-dioxolane-4-carboxylate (Preparation example 64), to obtain the title compound (1.5 g, 70~95%)

$^1$H NMR (400 MHz, DMSO) δ1.63~1.75 (m, 10H), 3.52~3.81 (m, 2H), 3.95 (t, J=8.0, 1H), 5.43 (d, J=7.6, 1H), 7.04~7.42 (m, 3H)

Preparation Example 144

(2R,3S)-methyl-3-(2,4-chlorophenyl)-2-phenyl-1,3-dioxolane-4-carboxylate

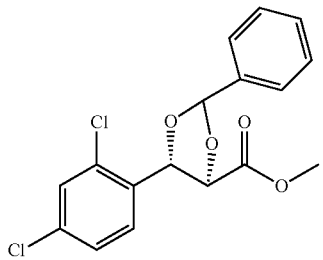

The substantially same method as described in Example 140 was conducted, except that benzaldehyde was used instead of cyclohexanone, to obtain the title compound (1.6 g, 50~70%).

$^1$H NMR (400 MHz, DMSO) δ1.61~1.69 (m, 10H), 3.79 (s, 3H), 4.33 (d, J=8.0, 1H), 5.85 (d, J=8.0, 1H), 7.03~7.41 (m, 3H)

Preparation Example 145

((4S,5S)-5-(2,4-chlorophenyl)-2-phenyl-1,3-dioxolane-4-yl)methanol

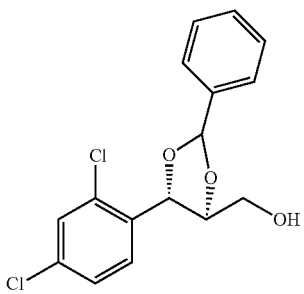

The substantially same method as described in Example 143 was conducted, except that (2R,3S)-methyl-3-(2,4-chlorophenyl)-2-phenyl-1,3-dioxolane-4-carboxylate (Preparation example 144) was used instead of (2S,3R)-methyl-3-(2,4-chlorophenyl)-2-phenyl-1,3-dioxolane-4-carboxylate (Preparation example 142), to obtain the title compound (1.2 g, 70~95%)

$^1$H NMR (400 MHz, DMSO) δ1.63~1.75 (m, 10H), 3.52~3.81 (m, 2H), 3.95 (t, J=8.0, 1H), 5.43 (d, J=7.6, 1H), 7.04~7.42 (m, 3H)

Preparation Example 146

((4S,5R)-ethyl-5-(2,6-dichlorophenyl)-2-methyl-1,3-dioxolane-4-carboxylate

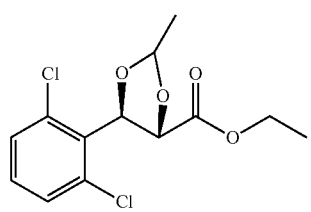

The substantially same method as described in Example 60 was conducted, except that (2S,3R)-ethyl-3-(2,6-dichlorophenyl)-2,3-dihydroxypropanoate (Preparation example 39) was used instead of (2S,3R)-methyl-3-(2-chlorophenyl)-2,3-dihydroxypropanoate, to obtain the title compound (1.7 g, 70~95%).

$^1$H NMR (400 MHz, CDCl$_3$) δ1.36 (d, J=6.4, 3H), 3.78 (s, 3H), 4.15 (m, 2H), 4.30 (d, J=7.6, 1H), 5.07 (m, 1H), 5.62 (d, J=7.6, 1H), 7.17~7.36 (m, 3H)

Preparation Example 147

((4R,5R)-5-(2,6-dichlorophenyl)-2-methyl-1,3-dioxolane-4-yl)methanol

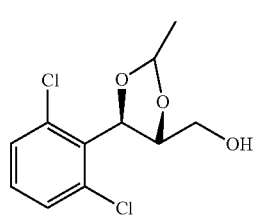

The substantially same method as described in Example 27 was conducted, except that (4S,5R)-ethyl-5-(2,6-dichlorophenyl)-2-methyl-1,3-dioxolane-4-carboxylate (Preparation example 146) was used instead of (4R,5S)-methyl-5-(2-chlorophenyl)-2,2-dimethyl-1,3-dioxolane-4-carboxylate (Preparation example 26), to obtain the title compound (1.2 g, 70~95%)

¹H NMR (400 MHz, CDCl₃): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.18~7.39 (m, 3H).

Preparation Example 148

((4R,5S)-ethyl-5-(2,6-dichlorophenyl)-2-methyl-1,3-dioxolane-4-carboxylate

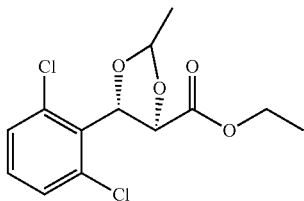

The substantially same method as described in Example 146 was conducted, except that (2R,3S)-ethyl-3-(2,6-ichlorophenyl)-2,3-dihydroxypropanoate (Preparation example 33) was used instead of (2S,3R)-methyl-3-(2,4-dichlorophenyl)-2,3-dihydroxypropanoate (Preparation example 39), to obtain the title compound (1.8 g, 70~95%).
¹H NMR (400 MHz, CDCl₃) δ1.36 (d, J=6.4, 3H), 3.78 (s, 3H), 4.15 (m, 2H), 4.30 (d, J=7.6, 1H), 5.07 (m, 1H), 5.62 (d, J=7.6, 1H), 7.17~7.36 (m, 3H).

Preparation Example 149

((4S,5S)-5-(2,6-dichlorophenyl)-2-methyl-1,3-dioxolane-4-yl)methanol

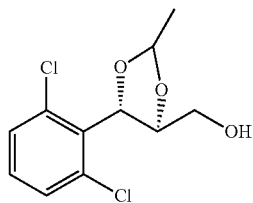

The substantially same method as described in Example 147 was conducted, except that (4R,5S)-ethyl-5-(2,6-dichlorophenyl)-2-methyl-1,3-dioxolane-4-carboxylate (Preparation example 148) was used instead of (4S,5R)-ethyl-5-(2,6-dichlorophenyl)-2-methyl-1,3-dioxolane-4-carboxylate (Preparation example 146), to obtain the title compound (1.3 g, 70~95%)
¹H NMR (400 MHz, CDCl₃): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.18~7.39 (m, 3H).

Preparation Example 150

(4S,5R)-ethyl-5-(2,6-dichlorophenyl)-2,2-diethyl-1,3-dioxolane-4-carboxylate

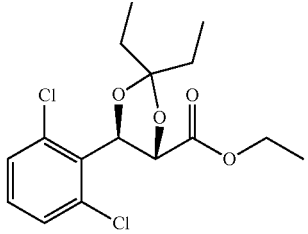 [SMILES: CCOC(=O)[C@H]1OC(CC)(CC)O[C@@H]1c1c(Cl)cccc1Cl]

The substantially same method as described in Example 130 was conducted, except that (2S,3R)-ethyl-3-(2,6-dichlorophenyl)-2,3-dihydroxypropanoate (Preparation example 39) was used instead of (2S,3R)-methyl-3-(2,6-dichlorophenyl)-2,3-dihydroxypropanoate (Preparation example 36), to obtain the title compound (1.8 g, 60~85%).
¹H NMR (400 MHz, CDCl₃) δ0.96 (m, 6H), 1.30 (t, J=8.0, 3H), 1.59 (m, 4H), 4.12 (m, 2H), 5.11 (d, J=7.6, 1H), 5.81 (d, J=7.6, 1H), 7.08~7.26 (m, 3H)

Preparation Example 151

((4R,5R)-5-(2,6-dichlorophenyl)-2,2-diethyl-1,3-dioxolane-4-yl)methanol

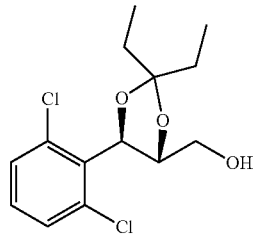 [SMILES: CCC1(CC)O[C@H](c2c(Cl)cccc2Cl)[C@@H](CO)O1]

The substantially same method as described in Example 147 was conducted, except that (4S,5R)-ethyl-5-(2,6-dichlorophenyl)-2,2-diethyl-1,3-dioxolane-4-carboxylate (Preparation example 150) was used instead of (4S,5R)-ethyl-5-(2,6-dichlorophenyl)-2-methyl-1,3-dioxolane-4-carboxylate (Preparation example 146), to obtain the title compound (1.2 g, 70~95%)
¹H NMR (400 MHz, CDCl₃): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.07~7.29 (m, 3H).

Preparation Example 152

(4R,5S)-ethyl-5-(2,6-chlorophenyl)-2,2-diethyl-1,3-dioxolane-4-carboxylate

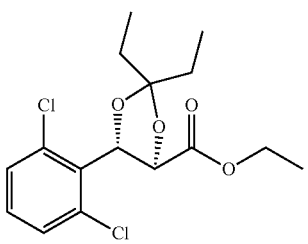 [SMILES: CCOC(=O)[C@@H]1OC(CC)(CC)O[C@H]1c1c(Cl)cccc1Cl]

The substantially same method as described in Example 150 was conducted, except that (2R,3S)-ethyl-3-(2,6-ichlorophenyl)-2,3-dihydroxypropanoate (Preparation example 33) was used instead of (2S,3R)-ethyl-3-(2,6-dichlorophenyl)-2,3-dihydroxypropanoate (Preparation example 39), to obtain the title compound (2.5 g, 70~95%).

¹H NMR (400 MHz, CDCl₃) δ0.96 (m, 6H), 1.30 (t, J=8.0, 3H), 1.59 (m, 4H), 4.12 (m, 2H), 5.11 (d, J=7.6, 1H), 5.81 (d, J=7.6, 1H), 7.08~7.26 (m, 3H)

Preparation Example 153

((4S,5S)-5-(2,6-chlorophenyl)-2,2-diethyl-1.3-dioxolane-4-yl)methanol

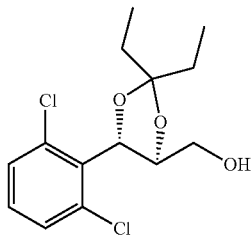 [SMILES: CCC1(CC)O[C@@H](CO)[C@H](c2c(Cl)cccc2Cl)O1]

The substantially same method as described in Example 151 was conducted, except that (4R,5S)-ethyl-5-(2,6-dichlorophenyl)-2,2-diethyl-1.3-dioxolane-4-carboxylate (Preparation example 152) was used instead of (4S,5R)-ethyl-5-(2,6-dichlorophenyl)-2,2-diethyl-1.3-dioxolane-4-carboxylate (Preparation example 150), to obtain the title compound (2.1 g, 70~95%)

¹H NMR (400 MHz, CDCl₃): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.07~7.29 (m, 3H).

Preparation Example 154

(2S,3R)-ethyl-3-(2,6-chlorophenyl)-1,4-dioxaspiro[4,4]nonane-2-carboxylate

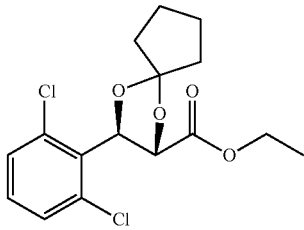 [SMILES: CCOC(=O)[C@H]1OC2(CCCC2)O[C@@H]1c1c(Cl)cccc1Cl]

The substantially same method as described in Example 150 was conducted, except that cyclopentanone was used instead of 3-pentanone, to obtain the title compound (2.1 g, 70~95%).

¹H NMR (400 MHz, DMSO) δ1.30 (t, J=7.8 hz, 3H), 1.69~1.71 (m, 4H), 1.73~1.86 (m, 4H), 4.07~4.14 (m, 2H), 5.11 (d, J=7.2, 1H), 5.81 (d, J=7.2, 1H), 7.07~7.31 (m, 3H)

Preparation Example 155

((2R,3R)-3-(2,6-chlorophenyl)-1,4-dioxaspiro[4,4]nonane-2-yl)methanol

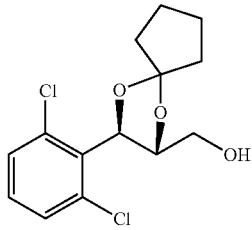 [SMILES: OC[C@H]1OC2(CCCC2)O[C@@H]1c1c(Cl)cccc1Cl]

The substantially same method as described in Example 151 was conducted, except that (2S,3R)-ethyl-3-(2,6-dichlorophenyl)-1,4-dioxaspiro[4,4]nonane-2-carboxylate (Preparation example 154) was used instead of (4S,5R)-ethyl-5-(2,6-dichlorophenyl)-2,2-diethyl-1.3-dioxolane-4-carboxylate (Preparation example 150), to obtain the title compound (1.7 g, 70~95%)

¹H NMR (400 MHz, DMSO) δ1.60~1.72 (m, 4H), 1.83~1.94 (m, 4H), 3.52~3.65 (m, 2H), 4.90 (t, J=5.2, 1H), 5.12 (d, J=7.6, 1H), 7.08~7.32 (m, 3H)

Preparation Example 156

(2R,3S)-ethyl-3-(2,6-chlorophenyl)-1,4-dioxaspiro[4,4]nonane-2-carboxylate

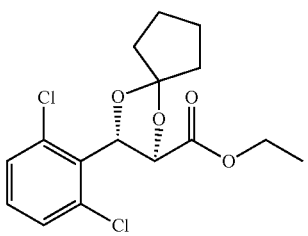 [SMILES: CCOC(=O)[C@@H]1OC2(CCCC2)O[C@H]1c1c(Cl)cccc1Cl]

The substantially same method as described in Example 152 was conducted, except that cyclopentanone was used instead of 3-pentanone, to obtain the title compound (2.5 g, 70~95%).

¹H NMR (400 MHz, DMSO) δ1.30 (t, J=7.8 hz, 3H), 1.69~1.71 (m, 4H), 1.73~1.86 (m, 4H), 4.07~4.14 (m, 2H), 5.11 (d, J=7.2, 1H), 5.81 (d, J=7.2, 1H), 7.07~7.31 (m, 3H)

Preparation Example 157

((2S,3S)-3-(2,6-chlorophenyl)-1,4-dioxaspiro[4,4]nonane-2-yl)methanol

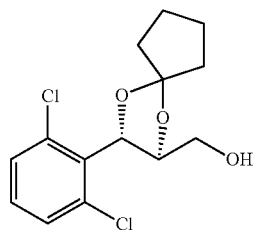 [SMILES: OC[C@@H]1OC2(CCCC2)O[C@H]1c1c(Cl)cccc1Cl]

The substantially same method as described in Example 155 was conducted, except that (2R,3S)-ethyl-3-(2,6-dichlorophenyl)-1,4-dioxaspiro[4,4]nonane-2-carboxylate (Preparation example 156) was used instead of (2S,3R)-ethyl-3-(2,6-dichlorophenyl)-1,4-dioxaspiro[4,4]nonane-2-carboxylate (Preparation example 154), to obtain the title compound (2.0 g, 70~95%)

¹H NMR (400 MHz, DMSO) δ1.60~1.72 (m, 4H), 1.83~1.94 (m, 4H), 3.52~3.65 (m, 2H), 4.90 (t, J=5.2, 1H), 5.12 (d, J=7.6, 1H), 7.08~7.32 (m, 3H)

Preparation Example 158

(2S,3R)-ethyl-3-(2,6-chlorophenyl)-1,4-dioxaspiro[4,5]decane-2-carboxylate

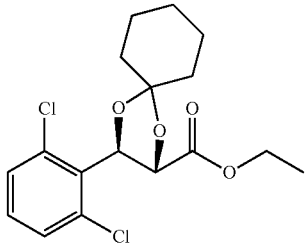 [SMILES: CCOC(=O)[C@H]1OC2(CCCCC2)O[C@@H]1c1c(Cl)cccc1Cl]

The substantially same method as described in Example 154 was conducted, except that cyclohexanone was used instead of cyclopentanone, to obtain the title compound (2.2 g, 70~95%).

¹H NMR (400 MHz, DMSO) δ1.30 (t, J=7.6, 3H), 1.61~1.69 (m, 10H), 4.08~4.18 (d, 2H), 4.33 (d, J=8.0, 1H), 5.85 (d, J=8.0, 1H), 7.07~7.31 (m, 3H)

Preparation Example 159

((2R,3R)-3-(2,6-chlorophenyl)-1,4-dioxaspiro[4,5]decane-2-yl)methanol

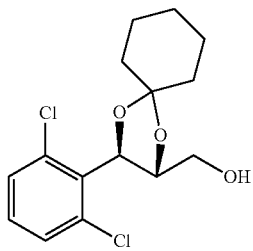 [SMILES: OC[C@H]1OC2(CCCCC2)O[C@@H]1c1c(Cl)cccc1Cl]

The substantially same method as described in Example 155 was conducted, except that (2S,3R)-ethyl-3-(2,6-dichlorophenyl)-1,4-dioxaspiro[4,5]decane-2-carboxylate (Preparation example 158) was used instead of (2S,3R)-ethyl-3-(2,6-dichlorophenyl)-1,4-dioxaspiro[4,4]nonane-2-carboxylate (Preparation example 154), to obtain the title compound (1.7 g, 70~95%)

¹H NMR (400 MHz, DMSO) δ1.63~1.75 (m, 10H), 3.52~3.81 (m, 2H), 3.95 (t, J=8.0, 1H), 5.43 (d, J=7.6, 1H), 7.05~7.30 (m, 3H)

Preparation Example 160

(2R,3S)-ethyl-3-(2,6-chlorophenyl)-1,4-dioxaspiro[4,5]decane-2-carboxylate

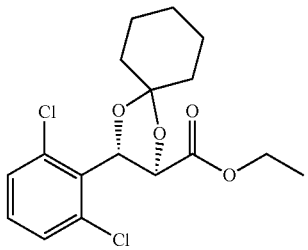 [SMILES: CCOC(=O)[C@@H]1OC2(CCCCC2)O[C@H]1c1c(Cl)cccc1Cl]

The substantially same method as described in Example 156 was conducted, except that cyclohexanone was used instead of cyclopentanone, to obtain the title compound (1.9 g, 70~95%).

¹H NMR (400 MHz, DMSO) δ1.30 (t, J=7.6, 3H), 1.61~1.69 (m, 10H), 4.08~4.18 (d, 2H), 4.33 (d, J=8.0, 1H), 5.85 (d, J=8.0, 1H), 7.07~7.31 (m, 3H)

Preparation Example 161

((2S,3S)-3-(2,6-chlorophenyl)-1,4-dioxaspiro[4,5]decane-2-yl)methanol

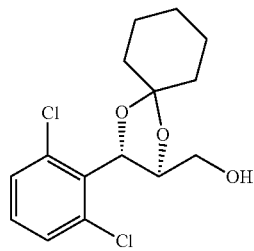 [SMILES: OC[C@@H]1OC2(CCCCC2)O[C@H]1c1c(Cl)cccc1Cl]

The substantially same method as described in Example 159 was conducted, except that (2R,3S)-ethyl-3-(2,6-dichlorophenyl)-1,4-dioxaspiro[4,5]decane-2-carboxylate (Preparation example 160) was used instead of (2S,3R)-ethyl-3-(2,6-dichlorophenyl)-1,4-dioxaspiro[4,5]decane-2-carboxylate (Preparation example 158), to obtain the title compound (1.5 g, 70~95%)

¹H NMR (400 MHz, DMSO) δ1.63~1.75 (m, 10H), 3.52~3.81 (m, 2H), 3.95 (t, J=8.0, 1H), 5.43 (d, J=7.6, 1H), 7.05~7.30 (m, 3H)

Preparation Example 162

(2S,3R)-ethyl-3-(2,6-chlorophenyl)-2-phenyl-1,3-dioxolane-4-carboxylate

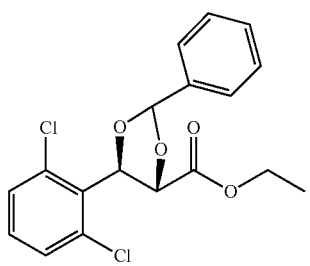

The substantially same method as described in Example 158 was conducted, except that benzaldehyde was used instead of cyclohexanone, to obtain the title compound (2.0 g, 50~70%).

¹H NMR (400 MHz, DMSO) δ1.30 (t, J=7.6, 3H), 4.08~4.18 (d, 2H), 5.13 (d, J=8.0, 1H), 5.85 (d, J=8.0, 1H), 6.18 (s, 1H), 7.03~7.22 (m, 8H)

Preparation Example 163

((4R,5R)-5-(2,6-chlorophenyl)-2-phenyl-1,3-dioxolane-4-yl)methanol

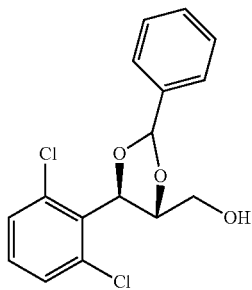

The substantially same method as described in Example 159 was conducted, except that (2S,3R)-ethyl-3-(2,6-chlorophenyl)-2-phenyl-1,3-dioxolane-4-carboxylate (Preparation example 162) was used instead of (2S,3R)-ethyl-3-(2,6-dichlorophenyl)-1,4-dioxaspiro[4,5]decane-2-carboxylate (Preparation example 158), to obtain the title compound (1.6 g, 70~95%)

$^1$H NMR (400 MHz, DMSO) δ3.50~3.79 (m, 2H), 5.13 (d, J=8.0, 1H), 5.85 (d, J=8.0, 1H), 6.18 (s, 1H), 7.03~7.22 (m, 8H)

Preparation Example 164

(2R,3S)-ethyl-3-(2,6-chlorophenyl)-2-phenyl-1,3-dioxolane-4-carboxylate

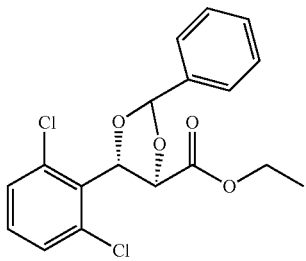

The substantially same method as described in Example 160 was conducted, except that benzaldehyde was used instead of cyclohexanone, to obtain the title compound (1.8 g, 50~70%).

$^1$H NMR (400 MHz, DMSO) δ1.30 (t, J=7.6, 3H), 4.08~4.18 (d, 2H), 5.13 (d, J=8.0, 1H), 5.85 (d, J=8.0, 1H), 6.18 (s, 1H), 7.03~7.22 (m, 8H)

Preparation Example 165

((4S,5S)-5-(2,6-chlorophenyl)-2-phenyl-1,3-dioxolane-4-yl)methanol

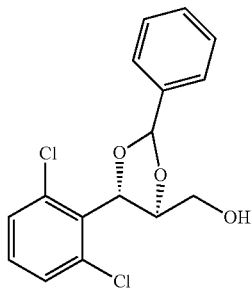

The substantially same method as described in Example 163 was conducted, except that (2R,3S)-ethyl-3-(2,6-chlorophenyl)-2-phenyl-1,3-dioxolane-4-carboxylate (Preparation example 164) was used instead of (2S,3R)-ethyl-3-(2,6-chlorophenyl)-2-phenyl-1,3-dioxolane-4-carboxylate (Preparation example 162), to obtain the title compound (1.4 g, 70~95%)

$^1$H NMR (400 MHz, DMSO) δ3.50~3.79 (m, 2H), 5.13 (d, J=8.0, 1H), 5.85 (d, J=8.0, 1H), 6.18 (s, 1H), 7.03~7.22 (m, 8H)

Preparation Example 166

((4S,5R)-methyl-5-(2-nitrophenyl)-2-methyl-1.3-dioxolane-4-carboxylate

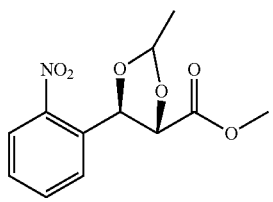

The substantially same method as described in Example 60 was conducted, except that (2S,3R)-methyl-3-(2-nitrophenyl)-2,3-dihydroxypropanoate (Preparation example 44) was used instead of (2S,3R)-methyl-3-(2-chlorophenyl)-2,3-dihydroxypropanoate, to obtain the title compound (2.3 g, 70~95%).

$^1$H NMR (400 MHz, CDCl$_3$) δ1.36 (d, J=6.4, 3H), 3.78 (s, 3H), 4.30 (d, J=7.6, 1H), 5.07 (m, 1H), 5.62 (d, J=7.6, 1H), 7.45~8.12 (m, 4H)

Preparation Example 167

((4R,5R)-5-(2-nitrophenyl)-2-methyl-1.3-dioxolane-4-yl)methanol

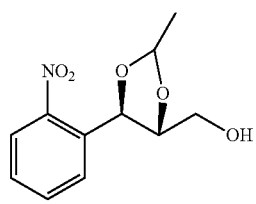

The substantially same method as described in Example 27 was conducted, except that (4S,5R) methyl-5-(2-nitrophenyl)-2-methyl-1.3-dioxolane-4-carboxylate (Preparation example 166) was used instead of (4R,5S)-methyl-5-(2-chlorophenyl)-2,2-dimethyl-1.3-dioxolane-4-carboxylate (Preparation example 26), to obtain the title compound (1.9 g, 70~95%)

$^1$H NMR (400 MHz, CDCl$_3$): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.47~8.11 (m, 4H).

Preparation Example 168

((4R,5S)-methyl-5-(2-nitrophenyl)-2-methyl-1.3-dioxolane-4-carboxylate

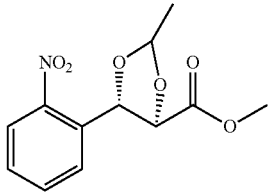

The substantially same method as described in Example 160 was conducted, except that (2R,3S)-methyl-3-(2-nitrophenyl)-2,3-dihydroxypropanoate (Preparation example 48) was used instead of (2S,3R)-methyl-3-(2-nitrophenyl)-2,3-dihydroxypropanoate (Preparation example 44), to obtain the title compound (2.0 g, 70~95%).
$^1$H NMR (400 MHz, CDCl$_3$) δ1.36 (d, J=6.4, 3H), 3.78 (s, 3H), 4.30 (d, J=7.6, 1H), 5.07 (m, 1H), 5.62 (d, J=7.6, 1H), 7.45~8.12 (m, 4H)

Preparation Example 169

((4S,5S)-5-(2-nitrophenyl)-2-methyl-1.3-dioxolane-4-yl)methanol

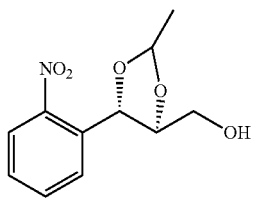

The substantially same method as described in Example 167 was conducted, except that (4R,5S)-methyl-5-(2-nitrophenyl)-2-methyl-1.3-dioxolane-4-carboxylate (Preparation example 168) was used instead of (4S,5R)-methyl-5-(2-nitrophenyl)-2-methyl-1.3-dioxolane-4-carboxylate (Preparation example 166), to obtain the title compound (1.6 g, 70~95%)
$^1$H NMR (400 MHz, CDCl$_3$): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.47~8.11 (m, 4H).

Preparation Example 170

(4S,5R)-methyl-5-(2-nitrophenyl)-2,2-diethyl-1.3-dioxolane-4-carboxylate

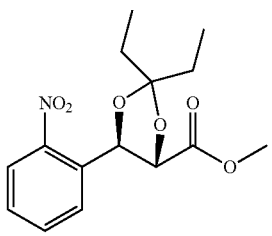 [SMILES: CCC1(CC)O[C@H](C(=O)OC)[C@@H](c2ccccc2[N+](=O)[O-])O1]

The substantially same method as described in Example 150 was conducted, except that (2S,3R)-methyl-3-(2-nitrophenyl)-2,3-dihydroxypropanoate (Preparation example 44) was used instead of (2S,3R)-ethyl-3-(2,6-dichlorophenyl)-2,3-dihydroxypropanoate (Preparation example 39), to obtain the title compound (2.4 g, 60~85%).
$^1$H NMR (400 MHz, CDCl$_3$) δ0.96 (m, 6H), 1.59 (m, 4H), 3.67 (s, 3H), 5.11 (d, J=7.6, 1H), 5.81 (d, J=7.6, 1H), 7.43~8.10 (m, 4H)

Preparation Example 171

((4R,5R)-5-(2-nitrophenyl)-2,2-diethyl-1.3-dioxolane-4-yl)methanol

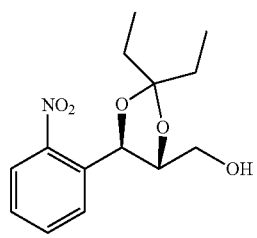 [SMILES: CCC1(CC)O[C@H](c2ccccc2[N+](=O)[O-])[C@@H](CO)O1]

The substantially same method as described in Example 167 was conducted, except that (4S,5R)-methyl-5-(2-nitrophenyl)-2,2-diethyl-1.3-dioxolane-4-carboxylate (Preparation example 170) was used instead of (4S,5R)-methyl-5-(2-nitrophenyl)-2-methyl-1.3-dioxolane-4-carboxylate (Preparation example 166), to obtain the title compound (1.9 g, 70~95%)
$^1$H NMR (400 MHz, CDCl$_3$): δ0.96 (m, 6H), 1.59 (m, 4H), 3.62~3.70 (m, 2H), 4.36 (dd, J=7.0, J=7.0, 1H), 5.17 (d, J=7.0, 1H), 7.37~8.09 (m, 4H)

Preparation Example 172

(4R,5S)-methyl-5-(2-nitrophenyl)-2,2-diethyl-1.3-dioxolane-4-carboxylate

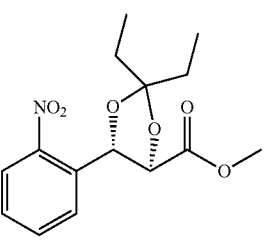 [SMILES: CCC1(CC)O[C@@H](C(=O)OC)[C@H](c2ccccc2[N+](=O)[O-])O1]

The substantially same method as described in Example 170 was conducted, except that (2R,3S)-methyl-3-(2-nitrophenyl)-2,3-dihydroxypropanoate (Preparation example 48) was used instead of (2S,3R)-methyl-3-(2-nitrophenyl)-2,3-dihydroxypropanoate (Preparation example 44), to obtain the title compound (2.5 g, 60~85%).
$^1$H NMR (400 MHz, CDCl$_3$) δ0.96 (m, 6H), 1.59 (m, 4H), 3.67 (s, 3H), 5.11 (d, J=7.6, 1H), 5.81 (d, J=7.6, 1H), 7.43~8.10 (m, 4H)

Preparation Example 173

((4S,5S)-5-(2-nitrophenyl)-2,2-diethyl-1.3-dioxolane-4-yl)methanol

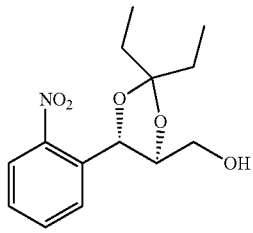 [SMILES: CCC1(CC)O[C@@H](CO)[C@H](c2ccccc2[N+](=O)[O-])O1]

The substantially same method as described in Example 171 was conducted, except that (4R,5S)-methyl-5-(2-nitrophenyl)-2,2-diethyl-1.3-dioxolane-4-carboxylate (Preparation example 172) was used instead of (4S,5R)-methyl-5-(2-nitrophenyl)-2,2-diethyl-1.3-dioxolane-4-carboxylate (Preparation example 170), to obtain the title compound (2.0 g, 70~95%)

$^1$H NMR (400 MHz, CDCl$_3$): δ0.96 (m, 6H), 1.59 (m, 4H), 3.62~3.70 (m, 2H), 4.36 (dd, J=7.0, J=7.0, 1H), 5.17 (d, J=7.0, 1H), 7.37~8.09 (m, 4H)

Preparation Example 174

(2S,3R)-methyl-3-(2-nitrophenyl)-1,4-dioxaspiro[4,4]nonane-2-carboxylate

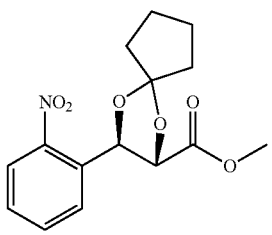 [SMILES: COC(=O)[C@H]1OC2(CCCC2)O[C@@H]1c1ccccc1[N+](=O)[O-]]

The substantially same method as described in Example 170 was conducted, except that cyclopentanone was used instead of 3-pentanone, to obtain the title compound (2.5 g, 70~95%).

$^1$H NMR (400 MHz, DMSO) δ1.69~1.71 (m, 4H), 1.82~1.86 (m, 4H), 3.68 (s, 3H), 4.40 (d, J=7.2, 1H), 5.39 (d, J=7.2, 1H), 7.44~8.06 (m, 4H)

Preparation Example 175

((4R,5R)-5-(2-nitrophenyl)-1,4-dioxaspiro[4,4]nonane-2-yl)methanol

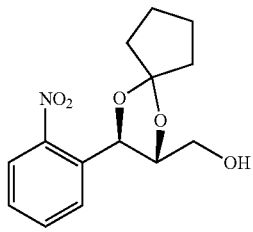 [SMILES: O=[N+]([O-])c1ccccc1[C@H]1OC2(CCCC2)O[C@@H]1CO]

The substantially same method as described in Example 171 was conducted, except that (2S,3R)-methyl-3-(2-nitrophenyl)-1,4-dioxaspiro[4,4]nonane-2-carboxylate (Preparation example 174) was used instead of (4S,5R)-methyl-5-(2-nitrophenyl)-2,2-diethyl-1.3-dioxolane-4-carboxylate (Preparation example 170), to obtain the title compound (2.1 g, 70~95%)

$^1$H NMR (400 MHz, DMSO) δ1.60~1.72 (m, 4H), 1.83~1.94 (m, 4H), 3.52~3.65 (m, 2H), 4.90 (t, J=5.2, 1H), 5.12 (d, J=7.6, 1H), 7.46~8.09 (m, 4H)

Preparation Example 176

(2R,3S)-methyl-3-(2-nitrophenyl)-1,4-dioxaspiro[4,4]nonane-2-carboxylate

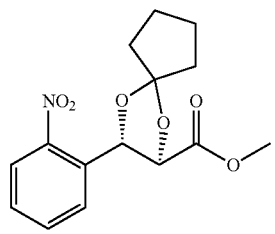 [SMILES: COC(=O)[C@@H]1OC2(CCCC2)O[C@H]1c1ccccc1[N+](=O)[O-]]

The substantially same method as described in Example 172 was conducted, except that cyclopentanone was used instead of 3-pentanone, to obtain the title compound (2.9 g, 70~95%).

$^1$H NMR (400 MHz, DMSO) δ1.69~1.71 (m, 4H), 1.82~1.86 (m, 4H), 3.68 (s, 3H), 4.40 (d, J=7.2, 1H), 5.39 (d, J=7.2, 1H), 7.44~8.06 (m, 4H)

Preparation Example 177

((2S,3S)-3-(2-nitrophenyl)-1,4-dioxaspiro[4,4]nonane-2-yl)methanol

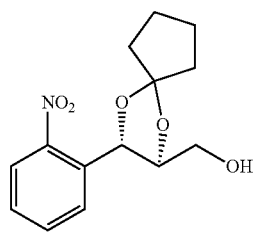 [SMILES: O=[N+]([O-])c1ccccc1[C@@H]1OC2(CCCC2)O[C@H]1CO]

The substantially same method as described in Example 175 was conducted, except that (2R,3S)-methyl-3-(2-nitrophenyl)-1,4-dioxaspiro[4,4]nonane-2-carboxylate (Preparation example 176) was used instead of (2S,3R)-methyl-3-(2-nitrophenyl)-1,4-dioxaspiro[4,4]nonane-2-carboxylate (Preparation example 174), to obtain the title compound (2.0 g, 70~95%)

¹H NMR (400 MHz, DMSO) δ1.60~1.72 (m, 4H), 1.83~1.94 (m, 4H), 3.52~3.65 (m, 2H), 4.90 (t, J=5.2, 1H), 5.12 (d, J=7.6, 1H), 7.46~8.09 (m, 4H)

Preparation Example 178

(2S,3R)-methyl-3-(2-nitrophenyl)-1,4-dioxaspiro[4,5]decane-2-carboxylate

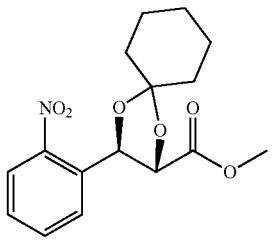 [SMILES: COC(=O)[C@H]1OC2(CCCCC2)O[C@@H]1c1ccccc1[N+](=O)[O-]]

The substantially same method as described in Example 174 was conducted, except that cyclohexanone was used instead of cyclopentanone, to obtain the title compound (1.7 g, 70~95%).
¹H NMR (400 MHz, DMSO) δ1.61~1.69 (m, 10H), 3.79 (s, 3H), 4.33 (d, J=8.0, 1H), 5.85 (d, J=8.0, 1H), 7.45~8.12 (m, 4H)

Preparation Example 179

((2R,3R)-3-(2-nitrophenyl)-1,4-dioxaspiro[4,5]decane-2-yl)methanol

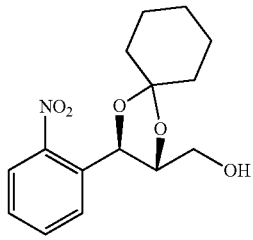 [SMILES: O=[N+]([O-])c1ccccc1[C@H]1OC2(CCCCC2)O[C@@H]1CO]

The substantially same method as described in Example 175 was conducted, except that (2R,3S)-methyl-3-(2-nitrophenyl)-1,4-dioxaspiro[4,5]decane-2-carboxylate (Preparation example 178) was used instead of (2R,3S)-methyl-3-(2-nitrophenyl)-1,4-dioxaspiro[4,4]nonane-2-carboxylate (Preparation example 174), to obtain the title compound (1.4 g, 70~95%)
¹H NMR (400 MHz, DMSO) δ1.63~1.75 (m, 10H), 3.52~3.81 (m, 2H), 3.95 (t, J=8.0, 1H), 5.43 (d, J=7.6, 1H), 7.46~8.09 (m, 4H)

Preparation Example 180

(2R,3S)-methyl-3-(2-nitrophenyl)-1,4-dioxaspiro[4,5]decane-2-carboxylate

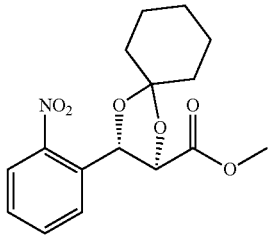 [SMILES: COC(=O)[C@@H]1OC2(CCCCC2)O[C@H]1c1ccccc1[N+](=O)[O-]]

The substantially same method as described in Example 176 was conducted, except that cyclohexanone was used instead of cyclopentanone, to obtain the title compound (2.2 g, 70~95%).
¹H NMR (400 MHz, DMSO) δ1.61~1.69 (m, 10H), 3.79 (s, 3H), 4.33 (d, J=8.0, 1H), 5.85 (d, J=8.0, 1H), 7.45~8.12 (m, 4H)

Preparation Example 181

((2S,3S)-3-(2-nitrophenyl)-1,4-dioxaspiro[4,5]decane-2-yl)methanol

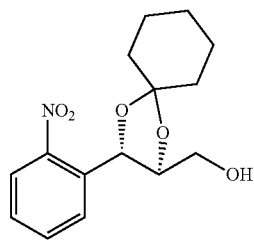 [SMILES: O=[N+]([O-])c1ccccc1[C@@H]1OC2(CCCCC2)O[C@H]1CO]

The substantially same method as described in Example 179 was conducted, except that (2S,3R)-methyl-3-(2-nitrophenyl)-1,4-dioxaspiro[4,5]decane-2-carboxylate (Preparation example 180) was used instead of (2R,3S)-methyl-3-(2-nitrophenyl)-1,4-dioxaspiro[4,5]decane-2-carboxylate (Preparation example 178), to obtain the title compound (1.5 g, 70~95%)
¹H NMR (400 MHz, DMSO) δ1.63~1.75 (m, 10H), 3.52~3.81 (m, 2H), 3.95 (t, J=8.0, 1H), 5.43 (d, J=7.6, 1H), 7.19~7.49 (m, 4H)

Preparation Example 182

(2S,3R)-methyl-3-(2-nitrophenyl)-2-phenyl-1,3-dioxolane-4-carboxylate

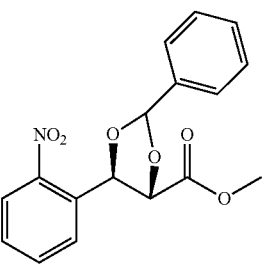

The substantially same method as described in Example 178 was conducted, except that benzaldehyde was used instead of cyclohexanone, to obtain the title compound (1.9 g, 50~70%).
¹H NMR (400 MHz, DMSO) δ3.67 (s, 3H), 5.11 (d, J=8.0, 1H), 5.81 (d, J=8.0, 1H), 6.18 (s, 1H), 6.96~8.12 (m, 9H)

Preparation Example 183

((4R,5R)-5-(2-nitrophenyl)-2-phenyl-1,3-dioxolane-4-yl)methanol

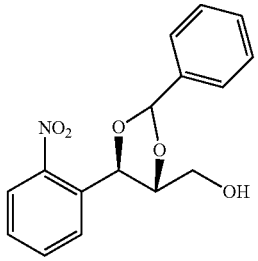

The substantially same method as described in Example 179 was conducted, except that (2S,3R)-methyl-3-(2-nitrophenyl)-2-phenyl-1,3-dioxolane-4-carboxylate (Preparation example 182) was used instead of (2S,3R)-methyl-3-(2-nitrophenyl)-1,4-dioxaspiro[4,4]nonane-2-carboxylate (Preparation example 174), to obtain the title compound (1.5 g, 70~95%)

$^1$H NMR (400 MHz, DMSO) δ3.66 (d, J=7.6, 2H), 4.36 (m, 1H), 5.17 (d, J=8.0, 1H), 6.18 (s, 1H), 7.06~8.14 (m, 9H)

Preparation Example 184

(2R,3S)-methyl-3-(2-nitrophenyl)-2-phenyl-1,3-dioxolane-4-carboxylate

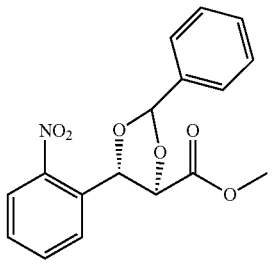

The substantially same method as described in Example 180 was conducted, except benzaldehyde that was used instead of cyclohexanone, to obtain the title compound (1.8 g, 50~70%).

$^1$H NMR (400 MHz, DMSO) δ3.67 (s, 3H), 5.11 (d, J=8.0, 1H), 5.81 (d, J=8.0, 1H), 6.18 (s, 1H), 6.96~8.12 (m, 9H)

Preparation Example 185

((4S,5S)-5-(2-nitrophenyl)-2-phenyl-1,3-dioxolane-4-yl)methanol

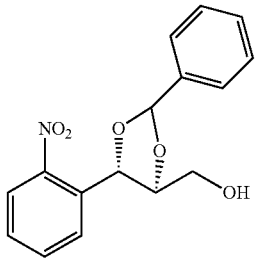

The substantially same method as described in Example 183 was conducted, except that (2R,3S)-methyl-3-(2-nitrophenyl)-2-phenyl-1,3-dioxolane-4-carboxylate (Preparation example 184) was used instead of (2S,3R)-methyl-3-(2-nitrophenyl)-2-phenyl-1,3-dioxolane-4-carboxylate (Preparation example 182), to obtain the title compound (1.3 g, 70~95%)

$^1$H NMR (400 MHz, DMSO) δ3.66 (d, J=7.6, 2H), 4.36 (m, 1H), 5.17 (d, J=8.0, 1H), 6.18 (s, 1H), 7.06~8.14 (m, 9H)

Preparation Example 186

(4S,5R)-methyl-5-(2-methylphenyl)-2-methyl-1.3-dioxolane-4-carboxylate

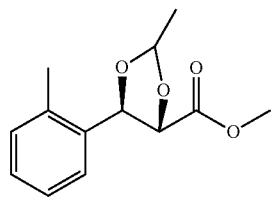

The substantially same method as described in Example 60 was conducted, except that (2S,3R)-methyl-3-(2-methylphenyl)-2,3-dihydroxypropanoate (Preparation example 54) was used instead of (2S,3R)-methyl-3-(2-chlorophenyl)-2,3-dihydroxypropanoate, to obtain the title compound (2.1 g, 70~95%).

$^1$H NMR (400 MHz, CDCl$_3$) δ1.36 (d, J=6.4, 3H), 2.35 (s, 3H), 3.68 (s, 3H), 5.07 (m, 1H), 5.11 (d, J=7.6, 1H), 5.82 (d, J=7.6, 1H), 7.19~7.39 (m, 4H)

Preparation Example 187

((4R,5R)-5-(2-methylphenyl)-2-methyl-1,3dioxolane-4-yl)methanol

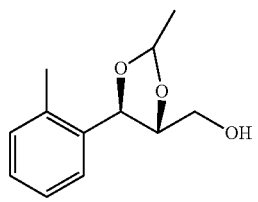

The substantially same method as described in Example 185 was conducted, except that (4S,5R)-methyl-5-(2-methylphenyl)-2-methyl-1.3-dioxolane-4-carboxylate (Preparation example 186) was used instead of (2R,3S)-methyl-3-(2-nitrophenyl)-2-phenyl-1,3-dioxolane-4-carboxylate (Preparation example 184), to obtain the title compound (1.7 g, 70~95%)

$^1$H NMR (400 MHz, CDCl$_3$): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.17~7.41 (m, 4H).

Preparation Example 188

(4R,5S)-methyl-5-(2-methylphenyl)-2-methyl-1.3-dioxolane-4-carboxylate

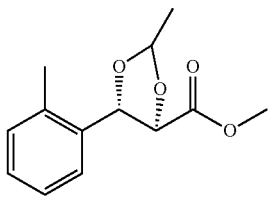

The substantially same method as described in Example 186 was conducted, except that (2R,3S)-methyl-3-(2-methylphenyl)-2,3-dihydroxypropanoate (Preparation example 57) was used instead of (2S,3R)-methyl-3-(2-methylphenyl)-2,3-dihydroxypropanoate (Preparation example 54), to obtain the title compound (1.8 g, 70~95%).

$^1$H NMR (400 MHz, CDCl$_3$) δ1.36 (d, J=6.4, 3H), 2.35 (s, 3H), 3.68 (s, 3H), 5.07 (m, 1H), 5.11 (d, J=7.6, 1H), 5.82 (d, J=7.6, 1H), 7.19~7.39 (m, 4H)

Preparation Example 189

((4S,5S)-5-(2-methylphenyl)-2-methyl-1.3-dioxolane-4-yl)methanol

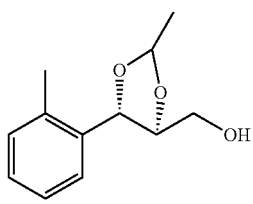

The substantially same method as described in Example 187 was conducted, except that (4R,5S)-methyl-5-(2-methylphenyl)-2-methyl-1.3-dioxolane-4-carboxylate (Preparation example 188) was used instead of (4S,5R)-methyl-5-(2-methylphenyl)-2-methyl-1.3-dioxolane-4-carboxylate (Preparation example 186), to obtain the title compound (1.6 g, 70~95%)

$^1$H NMR (400 MHz, CDCl$_3$): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.17~7.41 (m, 4H).

Preparation Example 190

(4S,5R)-methyl-5-(2-methylphenyl)-2,2-diethyl-1.3-dioxolane-4-carboxylate

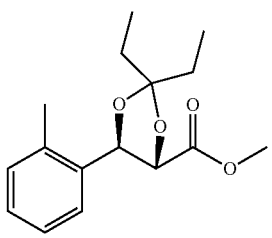 [SMILES: CCC1(CC)O[C@H](C(=O)OC)[C@@H](c2ccccc2C)O1]

The substantially same method as described in Example 170 was conducted, except that (2S,3R)-methyl-3-(2-methylphenyl)-2,3-dihydroxypropanoate (Preparation example 54) was used instead of (2S,3R)-methyl-3-(2-nitrophenyl)-2,3-dihydroxypropanoate (Preparation example 44), to obtain the title compound (2.1 g, 60~85%).

$^1$H NMR (400 MHz, CDCl$_3$) δ0.96 (m, 6H), 1.59 (m, 4H), 2.33 (s, 1H), 3.67 (s, 3H), 5.11 (d, J=7.6, 1H), 5.81 (d, J=7.6, 1H), 7.00~7.17 (m, 4H)

Preparation Example 191

((4R,5R-5-(2-methylphenyl)-2,2-diethyl-1.3-dioxolane-4-yl)methanol

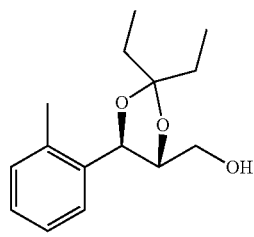 [SMILES: CCC1(CC)O[C@H](c2ccccc2C)[C@@H](CO)O1]

The substantially same method as described in Example 187 was conducted, except that (4S,5R)-methyl-2,2-diethyl-5-(2-methylphenyl)-1.3-dioxolane-4-carboxylate (Preparation example 190) was used instead of (4S,5R)-methyl-2-methyl-5-(2-methylphenyl)-1.3-dioxolane-4-carboxylate (Preparation example 186), to obtain the title compound (1.7 g, 70~95%)

$^1$H NMR (400 MHz, CDCl$_3$): δ0.96 (m, 6H), 1.59 (m, 4H), 2.37 (s, 3H), 3.62~3.70 (m, 2H), 4.36 (dd, J=7.0, J=7.0, 1H), 5.17 (d, J=7.0, 1H), 7.15~7.39 (m, 4H)

Preparation Example 192

(4R,5S)-methyl-5-(2-methylphenyl)-2,2-diethyl-1.3-dioxolane-4-carboxylate

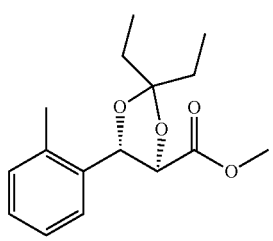 [SMILES: CCC1(CC)O[C@@H](C(=O)OC)[C@H](c2ccccc2C)O1]

The substantially same method as described in Example 190 was conducted, except that ((2R,3S)-methyl-3-(2-methylphenyl)-2,3-dihydroxypropanoate (Preparation example 57) was used instead of (2S,3R)-methyl-3-(2-methylphenyl)-2,3-dihydroxypropanoate (Preparation example 54), to obtain the title compound (2.2 g, 60~85%).

$^1$H NMR (400 MHz, CDCl$_3$) δ0.96 (m, 6H), 1.59 (m, 4H), 2.33 (s, 1H), 3.67 (s, 3H), 5.11 (d, J=7.6, 1H), 5.81 (d, J=7.6, 1H), 7.00~7.17 (m, 4H)

Preparation Example 193

((4S,5S)-5-(2-methylphenyl)-2,2-diethyl-1,3-diox-olane-4-yl)methanol

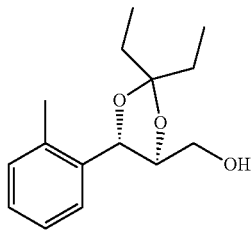 [SMILES: CCC1(CC)O[C@@H](CO)[C@H](c2ccccc2C)O1]

The substantially same method as described in Example 191 was conducted, except that (4R,5S)-methyl-5-(2-methylphenyl)-2,2-diethyl 1,3-dioxolane-4-carboxylate (Preparation example 192) was used instead of (4S,5R)-methyl-5-(2-methylphenyl)-2,2-diethyl-1,3-dioxolane-4-carboxylate (Preparation example 190), to obtain the title compound (1.8 g, 70~95%)

$^1$H NMR (400 MHz, CDCl$_3$): δ0.96 (m, 6H), 1.59 (m, 4H), 2.37 (s, 3H), 3.62~3.70 (m, 2H), 4.36 (dd, J=7.0, J=7.0, 1H), 5.17 (d, J=7.0, 1H), 7.15~7.39 (m, 4H)

Preparation Example 194

(2S,3R)-methyl-3-(2-methylphenyl)-1,4-dioxaspiro[4,4]nonane-2-carboxylate

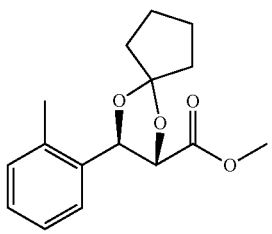 [SMILES: COC(=O)[C@H]1OC2(CCCC2)O[C@@H]1c1ccccc1C]

The substantially same method as described in Example 190 was conducted, except that cyclopentanone was used instead of 3-pentanone, to obtain the title compound (2.1 g, 70~95%).

$^1$H NMR (400 MHz, DMSO) δ1.49~1.57 (m, 4H), 1.72~1.81 (m, 4H), 2.35 (s, 3H), 3.68 (s, 3H), 5.14 (d, J=7.2, 1H), 5.89 (d, J=7.2, 1H), 7.02~7.25 (m, 4H)

Preparation Example 195

((2R,3R)-3-(2-methylphenyl)-1,4-dioxaspiro[4,4]nonane-2-yl)methanol

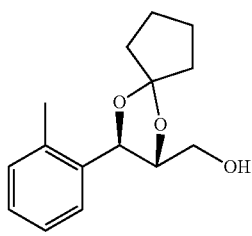 [SMILES: Cc1ccccc1[C@H]1OC2(CCCC2)O[C@@H]1CO]

The substantially same method as described in Example 191 was conducted, except that (2S,3R)-methyl-3-(2-methylphenyl)-1,4-dioxaspiro[4,4]nonane-2-carboxylate (Preparation example 194) was used instead of (4S,5R)-methyl-5-(2-methylphenyl)-2,2-diethyl-1,3-dioxolane-4-carboxylate (Preparation example 190), to obtain the title compound (1.6 g, 70~95%)

$^1$H NMR (400 MHz, DMSO) δ1.49~1.57 (m, 4H), 1.72~1.81 (m, 4H), 2.35 (s, 3H), 3.52~3.65 (m, 2H), 4.90 (t, J=5.2, 1H), 5.12 (d, J=7.6, 1H), 7.02~7.25 (m, 4H)

Preparation Example 196

(2R,3S)-methyl-3-(2-methylphenyl)-1,4-dioxaspiro[4,4]nonane-2-carboxylate

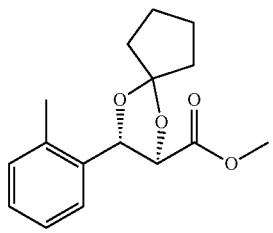 [SMILES: COC(=O)[C@@H]1OC2(CCCC2)O[C@H]1c1ccccc1C]

The substantially same method as described in Example 192 was conducted, except that cyclopentanone was used instead of 3-pentanone, to obtain the title compound (2.5 g, 70~95%).

$^1$H NMR (400 MHz, DMSO) δ1.49~1.57 (m, 4H), 1.72~1.81 (m, 4H), 2.35 (s, 3H), 3.68 (s, 3H), 5.14 (d, J=7.2, 1H), 5.89 (d, J=7.2, 1H), 7.02~7.25 (m, 4H)

Preparation Example 197

((2R,3R)-3-(2-methylphenyl)-1,4-dioxaspiro[4,4]nonane-2-yl)methanol

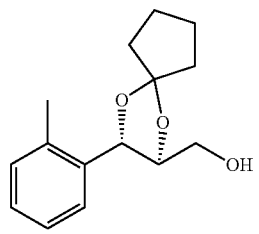 [SMILES: Cc1ccccc1[C@@H]1OC2(CCCC2)O[C@H]1CO]

The substantially same method as described in Example 195 was conducted, except that (2R,3S)-methyl-3-(2-methylphenyl)-1,4-dioxaspiro[4,4]nonane-2-carboxylate (Preparation example 196) was used instead of (2S,3R)-methyl-3-(2methylphenyl)-1,4-dioxaspiro[4,4]nonane-2-carboxylate (Preparation example 194), to obtain the title compound (2.0 g, 70~95%)

$^1$H NMR (400 MHz, DMSO) δ1.49~1.57 (m, 4H), 1.72~1.81 (m, 4H), 2.35 (s, 3H), 3.52~3.65 (m, 2H), 4.90 (t, J=5.2, 1H), 5.12 (d, J=7.6, 1H), 7.02~7.25 (m, 4H)

Preparation Example 198

(2S,3R)-methyl-3-(2-methylphenyl)-1,4-dioxaspiro[4,5]decane-2-carboxylate

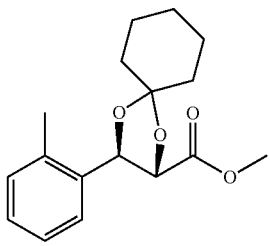 [SMILES: COC(=O)[C@H]1OC2(CCCCC2)O[C@@H]1c1ccccc1C]

The substantially same method as described in Example 194 was conducted, except that cyclohexanone was used instead of cyclopentanone, to obtain the title compound (1.8 g, 70~95%).

$^1$H NMR (400 MHz, DMSO) δ1.61~1.69 (m, 10H), 2.34 (s, 3H), 3.79 (s, 3H), 4.33 (d, J=8.0, 1H), 5.85 (d, J=8.0, 1H), 7.01~7.30 (m, 4H)

Preparation Example 199

((2R,3R)-3-(2-methylphenyl)-1,4-dioxaspiro[4,5]decane-2-yl)methanol

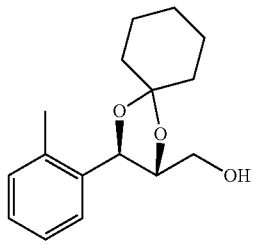 [SMILES: Cc1ccccc1[C@H]1OC2(CCCCC2)O[C@@H]1CO]

The substantially same method as described in Example 195 was conducted, except that (2S,3R)-methyl-3-(2-methylphenyl)-1,4-dioxaspiro[4,5]decane-2-carboxylate (Preparation example 198) was used instead of (2S,3R)-methyl-3-(2-methylphenyl)-1,4-dioxaspiro[4,4]nonane-2-carboxylate (Preparation example 194), to obtain the title compound (1.5 g, 70~95%)

$^1$H NMR (400 MHz, DMSO) δ1.63~1.75 (m, 10H), 2.33 (s, 3H), 3.52~3.81 (m, 2H), 3.95 (t, J=8.0, 1H), 5.43 (d, J=7.6, 1H), 7.02~7.28 (m, 4H)

Preparation Example 200

(2R,3S)-methyl-3-(2-methylphenyl)-1,4-dioxaspiro[4,5]decane-2-carboxylate

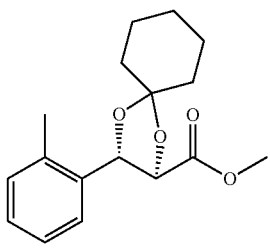 [SMILES: COC(=O)[C@@H]1OC2(CCCCC2)O[C@H]1c1ccccc1C]

The substantially same method as described in Example 196 was conducted, except that cyclohexanone was used instead of cyclopentanone, to obtain the title compound (2.2 g, 70~95%).

$^1$H NMR (400 MHz, DMSO) δ1.61~1.69 (m, 10H), 2.34 (s, 3H), 3.79 (s, 3H), 4.33 (d, J=8.0, 1H), 5.85 (d, J=8.0, 1H), 7.01~7.30 (m, 4H)

Preparation Example 201

((2S,3S)-3-(2-methylphenyl)-1,4-dioxaspiro[4,5]decane-2-yl)methanol

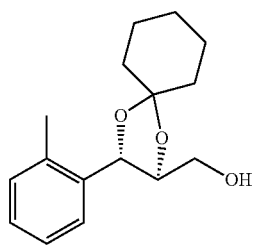 [SMILES: Cc1ccccc1[C@@H]1OC2(CCCCC2)O[C@H]1CO]

The substantially same method as described in Example 199 was conducted, except that (2R,3S)-methyl-3-(2-methylphenyl)-1,4-dioxaspiro[4,5]decane-2-carboxylate (Preparation example 200) was used instead of (2S,3R)-methyl-3-(2-methylphenyl)-1,4-dioxaspiro[4,5]decane-2-carboxylate (Preparation example 198), to obtain the title compound (1.5 g, 70~95%)

$^1$H NMR (400 MHz, DMSO) δ1.63~1.75 (m, 10H), 2.33 (s, 3H), 3.52~3.81 (m, 2H), 3.95 (t, J=8.0, 1H), 5.43 (d, J=7.6, 1H), 7.02~7.28 (m, 4H)

Preparation Example 202

(4S,5R)-methyl-5-(2-methylphenyl)-2-phenyl-1,3-dioxolane-4-carboxylate

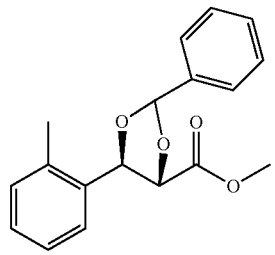

The substantially same method as described in Example 198 was conducted, except that benzaldehyde was used instead of cyclohexanone, to obtain the title compound (2.2 g, 50~70%).

$^1$H NMR (400 MHz, DMSO) δ2.33 (s, 3H), 3.67 (s, 3H), 5.11 (d, J=8.0, 1H), 5.81 (d, J=8.0, 1H), 6.18 (s, 1H), 6.96~7.32 (m, 9H)

Preparation Example 203

((4R,5R)-5-(2-methylphenyl)-2-phenyl-1,3-dioxolane-4-yl)methanol

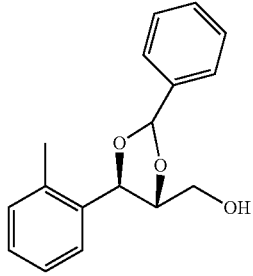

The substantially same method as described in Example 199 was conducted, except that (4S,5R)-methyl-5-(2-methylphenyl)-2-phenyl-1,3-dioxolane-4-carboxylate (Preparation example 202) was used instead of (2S,3R)-methyl-3-(2-methylphenyl)-1,4-dioxaspiro[4,5]decane-2-carboxylate (Preparation example 198), to obtain the title compound (1.6 g, 70~95%)

$^1$H NMR (400 MHz, DMSO) δ2.32 (s, 3H), 3.66 (d, J=7.6, 2H), 4.36 (m, 1H), 5.17 (d, J=8.0, 1H), 6.18 (s, 1H), 6.99~7.33 (m, 9H)

Preparation Example 204

(4R,5S)-methyl-5-(2-methylphenyl)-2-phenyl-1,3-dioxolane-4-carboxylate

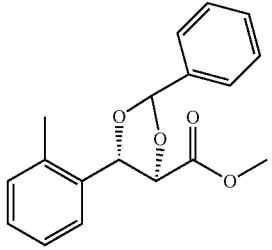

The substantially same method as described in Example 200 was conducted, except benzaldehyde that was used instead of cyclohexanone, to obtain the title compound (1.9 g, 50~70%).

$^1$H NMR (400 MHz, DMSO) δ2.33 (s, 3H), 3.67 (s, 3H), 5.11 (d, J=8.0, 1H), 5.81 (d, J=8.0, 1H), 6.18 (s, 1H), 6.96~7.32 (m, 9H)

Preparation Example 205

((4S,5S)-5-(2-methylphenyl)-2-phenyl-1,3-dioxolane-4-yl)methanol

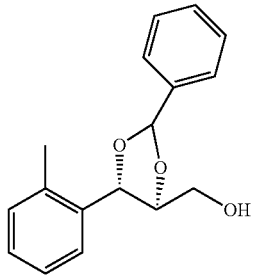

The substantially same method as described in Example 203 was conducted, except that (4R,5S)-methyl-5-(2-methylphenyl)-2-phenyl-1,3-dioxolane-4-carboxylate (Preparation example 204) was used instead of (2S,3R)-methyl-3-(2-methylphenyl)-2-phenyl-1,3-dioxolane-4-carboxylate (Preparation example 202), to obtain the title compound (1.3 g, 70~95%)

$^1$H NMR (400 MHz, DMSO) δ2.32 (s, 3H), 3.66 (d, J=7.6, 2H), 4.36 (m, 1H), 5.17 (d, J=8.0, 1H), 6.18 (s, 1H), 6.99~7.33 (m, 9H)

Preparation Example 206

((4R,5R)-5-(2-aminophenyl)-2-methyl-1,3-dioxolane-4-yl)methanol

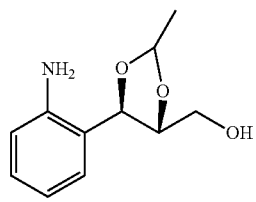

The substantially same method as described in Example 47 was conducted, except that ((4R,5R)-5-(2-nitrophenyl)-2-methyl-1,3-dioxolane-4-yl)methanol (Preparation example 167) was used instead of ((4R,5R)-5-(2-nitrophenyl)-2,2-dimethyl-1,3-dioxolane-4-yl)methanol (Preparation example 46), to obtain the title compound (1.5 g, 65~85%)

$^1$H NMR (400 MHz, CDCl$_3$): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.57~8.08 (m, 4H).

Preparation Example 207

((4S,5S)-5-(2-aminophenyl)-2-methyl-1,3-dioxolane-4-yl)methanol

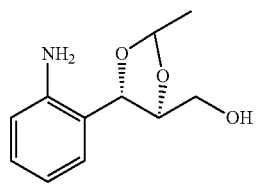

The substantially same method as described in Example 47 was conducted, except that ((4S,5S)-5-(2-nitrophenyl)-2-methyl-1,3-dioxolane-4-yl)methanol (Preparation example 169) was used instead of ((4R,5R)-5-(2-nitrophenyl)-2,2-dimethyl-1,3-dioxolane-4-yl)methanol (Preparation example 46), to obtain the title compound (1.1 g, 65~85%)

$^1$H NMR (400 MHz, CDCl$_3$): δ1.37 (d, J=6.0, 3H), 3.62~3.70 (m, 2H), 4.36 (dd, J=7.0, J=7.0, 1H), 5.06 (m, 1H), 5.17 (d, J=7.0, 1H), 7.57~8.08 (m, 4H).

Preparation Example 208

((4R,5R)-5-(2-aminohenyl)-2,2-diethyl-1.3-dioxolane-4-yl)methanol

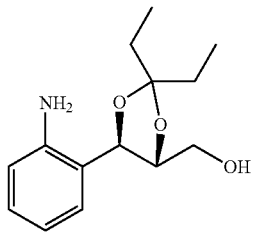 [SMILES: CCC1(CC)O[C@H](c2ccccc2N)[C@@H](CO)O1]

The substantially same method as described in Example 47 was conducted, except that ((4R,5R)-5-(2-nitrophenyl)-2,2-diethyl-1.3-dioxolane-4-yl)methanol (Preparation example 171) was used instead of ((4R,5R)-5-(2-nitrophenyl)-2,2-dimethyl-1.3-dioxolane-4-yl)methanol (Preparation example 46), to obtain the title compound (1.5 g, 65~85%)

$^1$H NMR (400 MHz, CDCl$_3$): δ0.96 (m, 6H), 1.59 (m, 4H), 3.62~3.70 (m, 2H), 4.36 (dd, J=7.0, J=7.0, 1H), 5.17 (d, J=7.0, 1H), 7.55~8.09 (m, 4H)

Preparation Example 209

((4S,5S)-5-(2-aminophenyl)-2,2-diethyl-1.3-dioxolane-4-yl)methanol

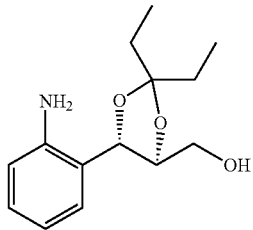 [SMILES: CCC1(CC)O[C@@H](CO)[C@H](c2ccccc2N)O1]

The substantially same method as described in Example 47 was conducted, except that ((4S,5S)-5-(2-nitrophenyl)-2,2-diethyl-1.3-dioxolane-4-yl)methanol (Preparation example 173) was used instead of ((4R,5R)-5-(2-nitrophenyl)-2,2-dimethyl-1.3-dioxolane-4-yl)methanol (Preparation example 46), to obtain the title compound (1.4 g, 65~85%)

$^1$H NMR (400 MHz, CDCl$_3$): δ0.96 (m, 6H), 1.59 (m, 4H), 3.62~3.70 (m, 2H), 4.36 (dd, J=7.0, J=7.0, 1H), 5.17 (d, J=7.0, 1H), 7.55~8.09 (m, 4H)

Preparation Example 210

((2R,3R)-3-(2-aminophenyl)-1,4-dioxaspiro[4,4]nonane-2-yl)methanol

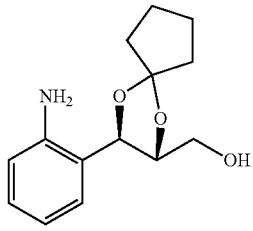 [SMILES: Nc1ccccc1[C@H]1OC2(CCCC2)O[C@@H]1CO]

The substantially same method as described in Example 47 was conducted, except that ((2R,3R)-3-(2-nitrophenyl)-1,4-dioxaspiro[4,4]nonane-2-yl)methanol (Preparation example 175) was used instead of ((4R,5R)-5-(2-nitrophenyl)-2,2-dimethyl-1.3-dioxolane-4-yl)methanol (Preparation example 46), to obtain the title compound (1.7 g, 65~85%)

$^1$H NMR (400 MHz, DMSO) δ1.62~1.73 (m, 4H), 1.82~1.95 (m, 4H), 3.52~3.65 (m, 2H), 4.90 (t, J=5.2, 1H), 5.12 (d, J=7.6, 1H), 7.56~8.11 (m, 4H)

Preparation Example 211

((2R,3R)-3-(2-aminophenyl)-1,4-dioxaspiro[4,4]nonane-2-yl)methanol

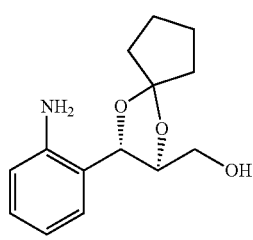 [SMILES: Nc1ccccc1[C@@H]1OC2(CCCC2)O[C@H]1CO]

The substantially same method as described in Example 47 was conducted, except that ((2S,2S)-3-(2-nitrophenyl)-1,4-dioxaspiro[4,4]nonane-2-yl)methanol (Preparation example 177) was used instead of ((4R,5R)-5-(2-nitrophenyl)-2,2-dimethyl-1.3-dioxolane-4-yl)methanol (Preparation example 46), to obtain the title compound (1.6 g, 65~85%)

$^1$H NMR (400 MHz, DMSO) δ1.62~1.73 (m, 4H), 1.82~1.95 (m, 4H), 3.52~3.65 (m, 2H), 4.90 (t, J=5.2, 1H), 5.12 (d, J=7.6, 1H), 7.56~8.11 (m, 4H)

Preparation Example 212

((2R,3R)-3-(2-aminophenyl)-1,4-dioxaspiro[4,5]decane-2-yl)methanol

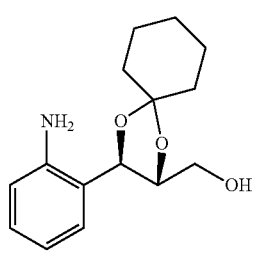 [SMILES: Nc1ccccc1[C@H]1OC2(CCCCC2)O[C@@H]1CO]

The substantially same method as described in Example 47 was conducted, except that ((2R,3R)-3-(2-nitrophenyl)-1,4-dioxaspiro[4,5]decane-2-yl)methanol (Preparation example 179) was used instead of ((4R,5R)-5-(2-nitrophenyl)-2,2-dimethyl-1.3-dioxolane-4-yl)methanol (Preparation example 46), to obtain the title compound (1.1 g, 65~85%)

$^1$H NMR (400 MHz, DMSO) δ1.61~1.75 (m, 10H), 3.52~3.81 (m, 2H), 3.95 (t, J=8.0, 1H), 5.43 (d, J=7.6, 1H), 7.49~8.12 (m, 4H)

Preparation Example 213

((2S,3S)-3-(2-aminophenyl)-1,4-dioxaspiro[4,5]decane-2-yl)methanol

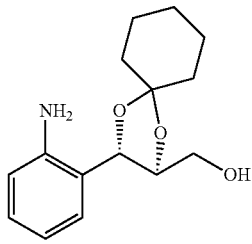 [SMILES: Nc1ccccc1[C@@H]1OC2(CCCCC2)O[C@H]1CO]

The substantially same method as described in Example 47 was conducted, except that ((2S,3S)-3-(2-nitrophenyl)-1,4-dioxaspiro[4,5]decane-2-yl)methanol (Preparation example 181) was used instead of ((4R,5R)-5-(2-nitrophenyl)-2,2-dimethyl-1.3-dioxolane-4-yl)methanol (Preparation example 46), to obtain the title compound (1.0 g, 65~85%)

$^1$H NMR (400 MHz, DMSO) δ1.61~1.75 (m, 10H), 3.52~3.81 (m, 2H), 3.95 (t, J=8.0, 1H), 5.43 (d, J=7.6, 1H), 7.49~8.12 (m, 4H)

Preparation Example 214

((4R,5R)-5-(2-aminophenyl)-2-phenyl-1,3-dioxolane-4-yl)methanol

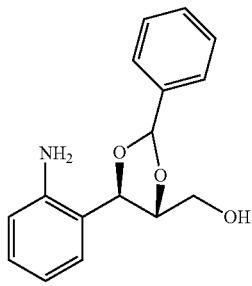

The substantially same method as described in Example 47 was conducted, except that ((4R,5R)-5-(2-nitrophenyl)-2-phenyl-1,3-dioxolane-4-yl)methanol (Preparation example 183) was used instead of ((4R,5R)-5-(2-nitrophenyl)-2,2-dimethyl-1.3-dioxolane-4-yl)methanol (Preparation example 46), to obtain the title compound (1.2 g, 65~85%)

$^1$H NMR (400 MHz, DMSO) δ3.66 (d, J=7.6, 2H), 4.36 (m, 1H), 5.17 (d, J=8.0, 1H), 6.18 (s, 1H), 7.06~8.14 (m, 9H)

Preparation Example 215

((4S,5S)-5-(2-aminophenyl)-2-phenyl-1,3-dioxolane-4-yl)methanol

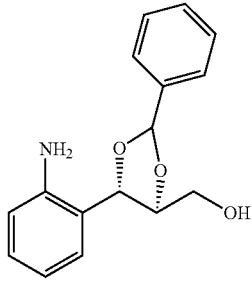

The substantially same method as described in Example 47 was conducted, except that ((4S,5S)-5-(2-nitrophenyl)-2-phenyl-1,3-dioxolane-4-yl)methanol (Preparation example 185) was used instead of ((4R,5R)-5-(2-nitrophenyl)-2,2-dimethyl-1.3-dioxolane-4-yl)methanol (Preparation example 46), to obtain the title compound (0.9 g, 65~85%)

$^1$H NMR (400 MHz, DMSO) δ3.66 (d, J=7.6, 2H), 4.36 (m, 1H), 5.17 (d, J=8.0, 1H), 6.18 (s, 1H), 7.06~8.14 (m, 9H)

Preparation Example 216

(E)-Methyl cinnamate

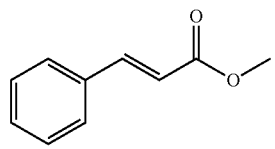

To a round-bottomed flask, trans-cinnamic acid (7 g, 47.25 mmol) and MeOH(70 mL) were added. POCl$_3$ (0.43 mL, 4.73 mmol) was added dropwise. The reaction mixture was stirred under reflux for 3 h. The reaction mixture was cooled to room temperature, quenched with 1N NaOH solution. The mixture was extracted by EtOAc and washed with H$_2$O. The aqueous layer was further extracted with EtOAc. The combined organic layer was dried over anhydrous magnesium sulfate (MgSO$_4$), filtered and concentrated under vacuum (7.1 g, 80~95%)

$^1$H NMR (400 MHz, CDCl$_3$): δ3.81 (s, 3H), 6.42 (d, J=15.9, 1H), 7.37~7.39 (m, 3H), 7.50~7.53 (m, 2H), 7.67 (d, J=15.9, 1H)

Preparation Example 217

(2S,3R)-methyl-3-phenyl-2,3-dihydroxypropanoate

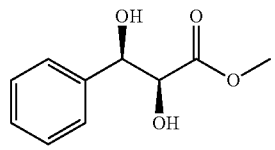

The substantially same method as described in Example 36 was conducted, except that (E)-Methyl cinnamate (Preparation example 216) was used instead of (E)-methyl-3-(2,4-dichlorophenyl)acrylate (Preparation example 28), to obtain the title compound (6.2 g, 70~95%)

$^1$H NMR (400 MHz, CDCl$_3$): δ2.70 (bs, 1H), 3.08 (bs, 1H), 3.82 (s, 3H), 4.38 (d, J=2.9, 1H), 5.03 (d, J=2.9, 1H), 7.30~7.42 (m, 5H)

Preparation Example 218

(4S,5R)-methyl-2,2-dimethyl-5-phenyl-1,3-dioxolane-4-carboxylate

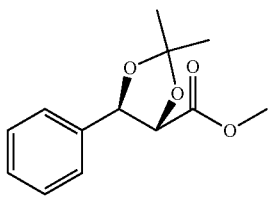 [SMILES: COC(=O)[C@H]1OC(C)(C)O[C@@H]1c1ccccc1]

The substantially same method as described in Example 45 was conducted, except that (2S,3R)-methyl-3-phenyl-2,3-dihydroxypropanoate (Preparation example 217) was used instead of (2S,3R)-methyl-3-(2-nitrophenyl)-2,3-dihydroxypropanoate (Preparation example 44), to obtain the title compound (5.6 g, 70~95%)

$^1$H NMR (400 MHz, CDCl$_3$): δ1.56 (s, 3H), 1.61 (s, 3H), 3.79 (s, 3H), 4.36 (d, J=7.8, 1H), 5.17 (d, J=7.8, 1H), 7.31~7.40 (m, 5H)

Preparation Example 219

((4R,5R)-5-phenyl-2,2-dimethyl-1,3-dioxolane-4-yl)methanol

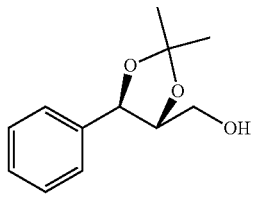

The substantially same method as described in Example 46 was conducted, except that (4S,5R)-methyl-2,2-dimethyl-5-phenyl-1,3-dioxolane-4-carboxylate (Preparation example 218) was used instead of (4S,5R)-methyl-5-(2-nitrophenyl)-1,3-dioxolane-4-carboxylate (Preparation example 45), to obtain the title compound (4.4 g, 70~95%)

$^1$H NMR (400 MHz, CDCl$_3$): δ1.41 (s, 3H), 1.46 (s, 3H), 2.79 (bs, 1H), 3.48~3.52 (m, 1H), 3.68~3.76 (m, 2H), 4.76 (d, J=8.8, 1H), 7.18~7.28 (m, 5H)

Preparation Example 220

(2R,3S)-methyl-3-phenyl-2,3-dihydroxypropanoate

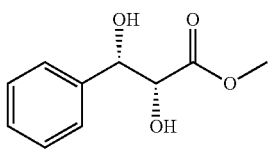

The substantially same method as described in Example 30 was conducted, except that (E)-Methyl cinnamate (Preparation example 216) was used instead of (E)-methyl-3-(2,4-dichlorophenyl)acrylate (Preparation example 28), to obtain the title compound (8.6 g, 70~95%)

$^1$H NMR (400 MHz, CDCl$_3$): δ2.70 (bs, 1H), 3.08 (bs, 1H), 3.82 (s, 3H), 4.38 (d, J=2.9, 1H), 5.03 (d, J=2.9, 1H), 7.30~7.42 (m, 5H)

Preparation Example 221

(4R,5S)-methyl-2,2-dimethyl-5-phenyl-1,3-dioxolane-4-carboxylate

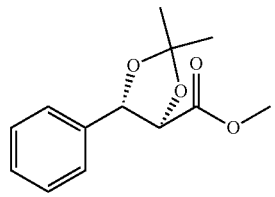 [SMILES: COC(=O)[C@@H]1OC(C)(C)O[C@H]1c1ccccc1]

The substantially same method as described in Example 45 was conducted, except that (2S,3R)-methyl-3-phenyl-2,3-dihydroxypropanoate (Preparation example 217) was used instead of (2S,3R)-methyl-3-(2-nitrophenyl)-2,3-dihydroxypropanoate (Preparation example 44), to obtain the title compound (5.6 g, 70~95%)

$^1$H NMR (400 MHz, CDCl$_3$): δ1.56 (s, 3H), 1.61 (s, 3H), 3.79 (s, 3H), 4.36 (d, J=7.8, 1H), 5.17 (d, J=7.8, 1H), 7.31~7.40 (m, 5H)

Preparation Example 222

((4S,5S)-5-phenyl-2,2-dimethyl-1,3-dioxolane-4-yl)methanol

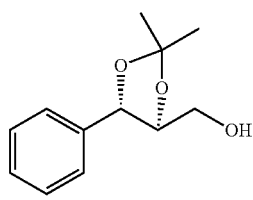

The substantially same method as described in Example 46 was conducted, except that (4R,5S)-methyl-2,2-dimethyl-5-phenyl-1,3-dioxolane-4-carboxylate (Preparation example 221) was used instead of (4S,5R)-methyl-5-(2-nitrophenyl)-1,3-dioxolane-4-carboxylate (Preparation example 45), to obtain the title compound (6.5 g, 70~95%)

$^1$H NMR (400 MHz, CDCl$_3$): δ1.41 (s, 3H), 1.46 (s, 3H), 2.79 (bs, 1H), 3.48~3.52 (m, 1H), 3.68~3.76 (m, 2H), 4.76 (d, J=8.8, 1H), 7.18~7.28 (m, 5H)

Preparation Example 223

(4S,5R)-methyl-2,2-diethyl-5-phenyl-1,3-dioxolane-4-carboxylate

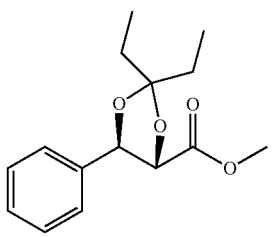 [SMILES: CCC1(CC)O[C@H](C(=O)OC)[C@@H](c2ccccc2)O1]

The substantially same method as described in Example 190 was conducted, except that (2S,3R)-methyl-3-phenyl-2,3-dihydroxypropanoate (Preparation example 217) was used instead of (2S,3R)-methyl-3-(2-methylphenyl)-2,3-dihydroxypropanoate (Preparation example 54), to obtain the title compound (1.9 g, 70~95%)

$^1$H NMR (400 MHz, CDCl$_3$): δ=1.01 (t, J=7.4, 1H), 1.06 (t, J=7.6, 3H), 1.78~1.90 (m, 4H), 3.78 (s, 3H), 5.12 (d, J=8.4, 1H), 7.32~7.45 (m, 5H)

Preparation Example 224

((4R,5R)-5-phenyl-2,2-diethyl-1,3-dioxolane-4-yl)methanol

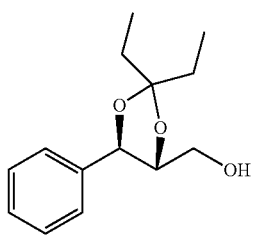 [SMILES: CCC1(CC)O[C@H](c2ccccc2)[C@@H](CO)O1]

The substantially same method as described in Example 219 was conducted, except that (4S,5R)-methyl-2,2-diethyl-5-phenyl-1,3-dioxolane-4-carboxylate (Preparation example 223) was used instead of (4S,5R)-methyl-2,2-dimethyl-5-phenyl-1,3-dioxolane-4-carboxylate (Preparation example 218), to obtain the title compound (1.3 g, 70~95%)

$^1$H NMR (400 MHz, CDCl$_3$): β=1.00 (t, J=7.6, 1H), 1.06 (t, J=7.4, 1H), 1.74~1.90 (m, 4H), 3.64 (ddd, J=3.4, 8.4, 12.1, 1H), 3.84~3.91 (m, 2H), 4.89 (d, J=8.8, 1H), 7.30~7.43 (m, 5H)

Preparation Example 225

(4R,5S)-methyl-2,2-diethyl-5-phenyl-1,3-dioxolane-4-carboxylate

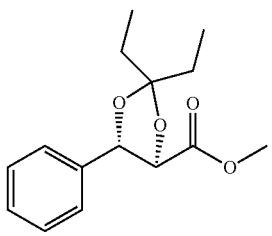 [SMILES: CCC1(CC)O[C@@H](C(=O)OC)[C@H](c2ccccc2)O1]

The substantially same method as described in Example 223 was conducted, except that (2R,3S)-methyl-3-phenyl-2,3-dihydroxypropanoate (Preparation example 220) was used instead of (2S,3R)-methyl-3-phenyl-2,3-dihydroxypropanoate (Preparation example 217), to obtain the title compound (5.6 g, 70~95%)

$^1$H NMR (400 MHz, CDCl$_3$): β=1.01 (t, J=7.4, 1H), 1.06 (t, J=7.6, 3H), 1.78~1.90 (m, 4H), 3.78 (s, 3H), 5.12 (d, J=8.4, 1H), 7.32~7.45 (m, 5H)

Preparation Example 226

((4S,5S)-5-phenyl-2,2-dimethyl-1,3-dioxolane-4-yl)methanol

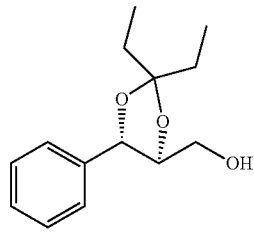 [SMILES: CCC1(CC)O[C@@H](CO)[C@H](c2ccccc2)O1]

The substantially same method as described in Example 224 was conducted, except that (4R,5S)-methyl-2,2-dimethyl-5-phenyl-1,3-dioxolane-4-carboxylate (Preparation example 225) was used instead of (4S,5R)-methyl-2,2-dimethyl-5-phenyl-1,3-dioxolane-4-carboxylate (Preparation example 218), to obtain the title compound (6.5 g, 70~95%)

$^1$H NMR (400 MHz, CDCl$_3$): β=1.00 (t, J=7.6, 1H), 1.06 (t, J=7.4, 1H), 1.74~1.90 (m, 4H), 3.64 (ddd, J=3.4, 8.4, 12.1, 1H), 3.84~3.91 (m, 2H), 4.89 (d, J=8.8, 1H), 7.30~7.43 (m, 5H)

Preparation Example 227

(2S,3R)-methyl-3-phenyl-1,4-dioxapiro[4,4]nonane-2-carboxylate

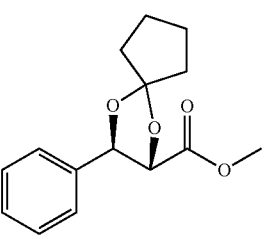 [SMILES: COC(=O)[C@H]1OC2(CCCC2)O[C@@H]1c1ccccc1]

The substantially same method as described in Example 223 was conducted, except that cyclopetanone was used instead of 3-pantanone, to obtain the title compound (0.9 g, 50~75%)

$^1$H NMR (400 MHz, CDCl$_3$): β=1.71~1.80 (m, 4H), 1.87~1.94 (m, 1H), 2.00~2.08 (m, 3H), 3.79 (s, 3H), 4.35 (d, J=7.2, 1H), 5.08 (d, J=7.2, 1H), 7.32~7.45 (m, 5H)

Preparation Example 228

((2R,3R)-3-phenyl-1,4-dioxapiro[4,4]nonan-2-yl) methanol

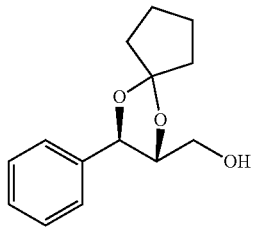 [SMILES: OC[C@H]1OC2(CCCC2)O[C@@H]1c1ccccc1]

The substantially same method as described in Example 224 was conducted, except that (2S,3R)-methyl-3-phenyl-1,4-dioxapiro[4,4]nonane-2-carboxylate (Preparation example 227) was used instead of (4S,5R)-methyl-2,2-diethyl-5-phenyl-1,3-dioxolane-4-carboxylate (Preparation example 223), to obtain the title compound (0.7 g, 70~95%)

$^1$H NMR (400 MHz, CDCl$_3$): δ=1.69~1.82 (m, 4H), 1.85~2.03 (m, 4H), 3.66 (ddd, J=3.7, 8.1, 12.1, 1H), 3.83~3.90 (m, 2H), 4.84 (d, J=8.4, 1H), 7.26~7.41 (m, 5H)

Preparation Example 229

(2R,3S)-methyl-3-phenyl-1,4-dioxapiro[4,4]nonane-2-carboxylate

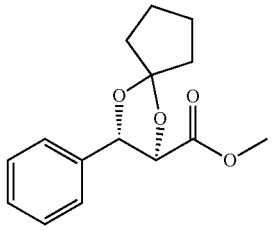 [SMILES: COC(=O)[C@@H]1OC2(CCCC2)O[C@H]1c1ccccc1]

The substantially same method as described in Example 225 was conducted, except that cyclopetanone was used instead of 3-pantanone, to obtain the title compound (0.8 g, 50~75%)

$^1$H NMR (400 MHz, CDCl$_3$): δ=1.71~1.80 (m, 4H), 1.87~1.94 (m, 1H), 2.00~2.08 (m, 3H), 3.79 (s, 3H), 4.35 (d, J=7.2, 1H), 5.08 (d, J=7.2, 1H), 7.32~7.45 (m, 5H)

Preparation Example 230

((2S,3S)-3-phenyl-1,4-dioxapiro[4,4]nonan-2-yl) methanol

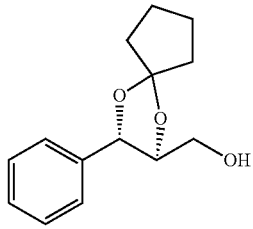 [SMILES: OC[C@@H]1OC2(CCCC2)O[C@H]1c1ccccc1]

The substantially same method as described in Example 228 was conducted, except that (2R,3S)-methyl-3-phenyl-1,4-dioxapiro[4,4]nonane-2-carboxylate (Preparation example 229) was used instead (2S,3R)-methyl-3-phenyl-1,4-dioxapiro[4,4]nonane-2-carboxylate (Preparation example 227), to obtain the title compound (0.5 g, 70~95%)

$^1$H NMR (400 MHz, CDCl$_3$): δ=1.69~1.82 (m, 4H), 1.85~2.03 (m, 4H), 3.66 (ddd, J=3.7, 8.1, 12.1, 1H), 3.83~3.90 (m, 2H), 4.84 (d, J=8.4, 1H), 7.26~7.41 (m, 5H)

Preparation Example 231

(2S,3R)-methyl-3-phenyl-1,4-dioxapiro[4,5]decane-2-carboxylate

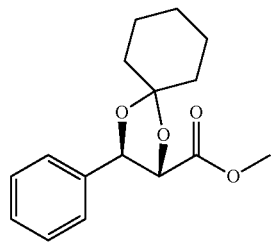 [SMILES: COC(=O)[C@H]1OC2(CCCCC2)O[C@@H]1c1ccccc1]

The substantially same method as described in Example 227 was conducted, except that cyclohexanone was used instead of cyclopetanone, to obtain the title compound (1.4 g, 50~75%)

$^1$H NMR (400 MHz, CDCl$_3$): δ=1.41~1.49 (m, 2H), 1.58~1.76 (m, 4H), 1.79~1.90 (m, 4H), 3.78 (s, 3H), 4.36 (d, J=7.6, 1H), 5.16 (d, J=7.2, 1H), 7.31~7.44 (m, 5H)

Preparation Example 232

((2R,3R)-3-phenyl-1,4-dioxapiro[4,5]decan-2-yl) methanol

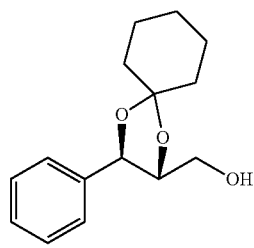 [SMILES: OC[C@H]1OC2(CCCCC2)O[C@@H]1c1ccccc1]

The substantially same method as described in Example 224 was conducted, except that (2S,3R)-methyl-3-phenyl-1,4-dioxapiro[4,5]decane-2-carboxylate (Preparation example 231) was used instead of (4S,5R)-methyl-2,2-diethyl-5-phenyl-1,3-dioxolane-4-carboxylate (Preparation example 223), to obtain the title compound (1.0 g, 70~95%)

$^1$H NMR (400 MHz, CDCl$_3$): δ=1.41~1.50 (m, 2H), 1.61~1.89 (m, 8H), 3.60~3.66 (m, 1H), 3.85~3.90 (m, 2H), 4.91 (d, J=8.4, 1H), 7.30~7.42 (m, 5H)

Preparation Example 233

(2R,3S)-methyl-3-phenyl-1,4-dioxapiro[4,5]decane-2-carboxylate

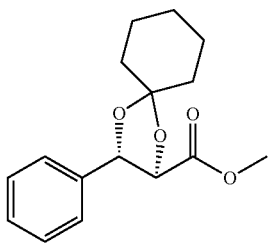 [SMILES: COC(=O)[C@@H]1OC2(CCCCC2)O[C@H]1c1ccccc1]

The substantially same method as described in Example 229 was conducted, except that cyclohexanone was used instead of cyclopetanone, to obtain the title compound (1.2 g, 50~75%)

$^1$H NMR (400 MHz, CDCl$_3$): δ=1.41~1.49 (m, 2H), 1.58~1.76 (m, 4H), 1.79~1.90 (m, 4H), 3.78 (s, 3H), 4.36 (d, J=7.6, 1H), 5.16 (d, J=7.2, 1H), 7.31~7.44 (m, 5H)

Preparation Example 234

((2S,3S)-3-phenyl-1,4-dioxapiro[4,5]decane-2-yl)methanol

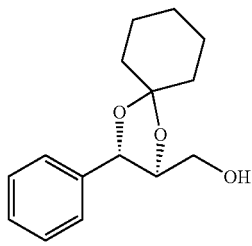 [SMILES: OC[C@@H]1OC2(CCCCC2)O[C@H]1c1ccccc1]

The substantially same method as described in Example 232 was conducted, except that (2R,3S)-methyl-3-phenyl-1,4-dioxapiro[4,5]decane-2-carboxylate (Preparation example 233) was used instead of (2S,3R)-methyl-3-phenyl-1,4-dioxapiro[4,5]decane-2-carboxylate (Preparation example 231), to obtain the title compound (0.8 g, 70~95%)

$^1$H NMR (400 MHz, CDCl$_3$): δ=1.41~1.50 (m, 2H), 1.61~1.89 (m, 8H), 3.60~3.66 (m, 1H), 3.85~3.90 (m, 2H), 4.91 (d, J=8.4, 1H), 7.30~7.42 (m, 5H)

Preparation Example 235

(E)-5-phenylpent-3-enoic acid

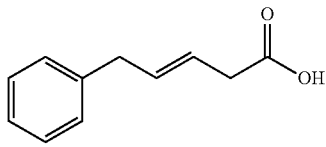 [SMILES: O=C(O)C/C=C/Cc1ccccc1]

A solution of malonic acid (17.06 g, 163.96 mmol) in DMSO (65 mL) was treated with a solution of AcOH (0.1 mL, 1.49 mmol) and piperidine (0.15 mL, 1.49 mmol) in DMSO (4 mL). The reaction solution was warmed to 65° C. and hydrocinnamaldehyde (10 g, 74.53 mmol) was added dropwise within 1.5 hr. After the addition ended, the reaction mixture was stirred for further 2 h at 65° C. The solution was cooled to room temperature, taken up in H$_2$O and extracted with Et$_2$O. The combined organic extracts were washed with 5% aqueous KHSO$_4$ and brine, dried over MgSO$_4$, and evaporated to dryness. The crude compound was purified by a silica gel column to produce the title compound (10.4 g, 75~90%)

$^1$H NMR (400 MHz, CDCl$_3$): δ=3.19 (d, J=6.9, 2H), 3.46 (d, J=6.9, 2H), 5.69~5.78 (m, 1H), 5.83~5.91 (m, 1H), 7.01~7.56 (m, 5H), 11.79 (s, 1H)

Preparation Example 236

(E)-5-phenylpent-3-en-1-ol

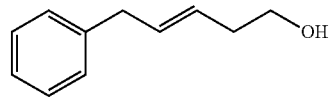 [SMILES: OCC/C=C/Cc1ccccc1]

To stirred solution of LAH(LiAlH$_4$, 3.3 g, 86.73 mmol) in THF(66 mL) was added dropwise a solution (E)-5-phenylpent-3-enoic acid (Preparation example 235, 11.0 g, 57.82 mmol) in THF(44 mL) at 0° C. then stirred at room temperature for 1 h. The reaction mixture was quenched with H$_2$O at 0° C., filtered through celite, washed with EtOAc, dried over anhydrous magnesium sulfate (MgSO$_4$), filtered and concentrated. The crude compound was purified by a silica gel column to produce the title compound (7.2 g, 70~90%)

$^1$H NMR (400 MHz, CDCl$_3$): δ=1.40 (bs, 1H), 2.31 (q, J=6.3, 2H), 3.37 (d, J=6.8, 2H), 3.66 (t, J=6.4, 2H), 5.49 (dt, J=4.9, 11.0, 1H), 5.73 (dt, J=4.8, 10.9, 1H), 7.17~7.31 (m, 5H)

Preparation Example 237

(E)-tert-butyldimethyl(5-phenyl pent-3-enyloxy)silane

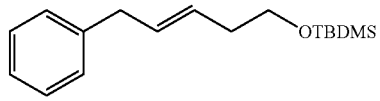 [SMILES: CC(C)(C)[Si](C)(C)OCC/C=C/Cc1ccccc1]

To a stirred solution of (E)-5-phenylpent-3-en-1-ol (Preparation example 236, 6.3 g, 38.83 mmol) in CH$_2$Cl$_2$ was added imidazole (3.4 g, 50.48 mmol) and TBDMS-Cl (7.6 g, 50.48 mmol) at 0° C. then stirred for 1 h at room temperature. The resulting mixture was diluted with EtOAc, washed with water, dried over MgSO$_4$, filtered, and concentrated under reduced pressure. The crude compound was purified by a silica gel column to produce the title compound (10.6 g, 80~98%)

¹H NMR (400 MHz, CDCl₃): δ=0.00 (s, 6H), 0.84 (s, 9H), 2.21 (ddd, J=6.8, 13.6, 0.8, 2H), 3.29 (d, J=6.8, 2H), 3.59 (t, J=6.8, 2H), 5.41~5.49 (m, 1H), 5.56~5.63 (m, 1H), 7.13~7.26 (m, 5H)

Preparation Example 238

(E)-5-phenylpent-3-enyl pivalate

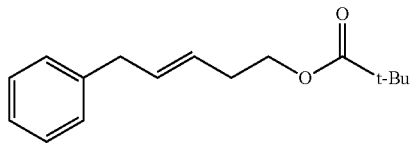 [SMILES: CC(C)(C)C(=O)OCC/C=C/Cc1ccccc1]

To a stirred solution of (E)-5-phenylpent-3-en-1-ol (Preparation example 236, 3.8 g, 23.42 mmol) in CH₂Cl₂ (40 mL) was added pyridine (2.3 mL, 28.1 mmol) and pivaloyl chloride (3.5 mL, 28.1 mmol) at 0° C. under N₂. The mixture was stirred for 14 h. The resulting mixture was diluted with CH₂Cl₂, washed with water, dried over MgSO₄, filtered, and concentrated under reduced pressure. The crude compound was purified by a silica gel column to produce the title compound (5.5 g, 80~95%)

¹H NMR (400 MHz, CDCl₃): δ=1.17 (s, 9H), 2.36 (q, J=6.7, 2H), 3.34 (d, J=6.8, 2H), 4.09 (t, J=6.8, 2H), 5.45~5.51 (m, 1H), 5.64~5.69 (m, 1H), 7.16~7.21 (m, 3H), 7.26~7.30 (m, 2H)

Preparation Example 239

(2S,3S)-5-(tert-butyldimethylsilyloxy)-1-phenylpentane-2,3-diol

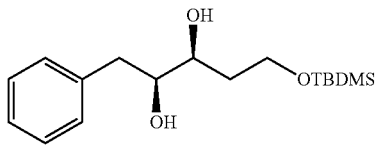 [SMILES: CC(C)(C)[Si](C)(C)OCC[C@H](O)[C@@H](O)Cc1ccccc1]

The substantially same method as described in Example 217 was conducted, except that (E)-tert-butyldimethyl(5-phenylpent-3-enyloxy)silane (Preparation example 237) was used instead of (E)-Methyl cinnamate (Preparation example 216), to obtain the title compound (8.7 g, 70~95%)

¹H NMR (400 MHz, CDCl₃): δ=0.00 (s, 6H), 0.82 (s, 9H), 1.57~1.62 (m, 1H), 1.73~1.80 (m, 1H), 2.51 (d, J=6.0, 1H), 2.77 (dq, J=6.9, 14.9, 2H), 3.50 (d, J=3.6, 1H), 3.59~3.62 (m, 1H), 3.66 (dq, J=3.1, 5.4, 1H), 3.72~3.82 (m, 2H), 7.12~7.25 (m, 5H)

Preparation Example 240

(2-((4S,5S)-5-benzyl-2,2-dimethyl-1,3-dioxolane-4-yl)ethoxy)(tert-butyl)dimethylsilane

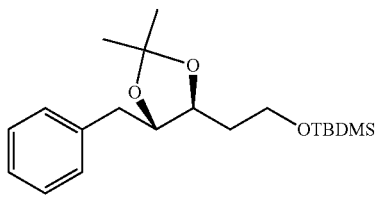 [SMILES: CC1(C)O[C@@H](CCO[Si](C)(C)C(C)(C)C)[C@H](Cc2ccccc2)O1]

The substantially same method as described in Example 218 was conducted, except that (2S,3S)-5-(tert-butyldimeth-ylsilyloxy)-1-phenylpentane-2,3-diol (Preparation example 239) was used instead of (2R,3S)-methyl-3-phenyl-2,3-dihydroxypropanoate (Preparation example 217), to obtain the title compound (9.5 g, 70~95%)

¹H NMR (400 MHz, CDCl₃): δ=0.00 (s, 6H), 0.85 (s, 9H), 1.29 (s, 3H), 1.34 (s, 3H), 1.52~1.58 (m, 2H), 2.87 (dq, J=5.5, 14.2, 2H), 3.64~3.69 (m, 2H), 3.80~3.88 (m, 2H), 7.18~7.27 (m, 5H)

Preparation Example 241

2-((4S,5S)-5-benzyl-2,2-dimethyl-1,3-dioxolane-4-yl)ethanol

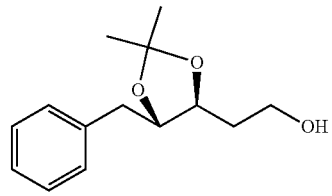 [SMILES: CC1(C)O[C@@H](CCO)[C@H](Cc2ccccc2)O1]

To a stirred solution of (2-((4S,5S)-5-benzyl-2,2-dimethyl-1,3-dioxolan-4-yl)ethoxy)(tert-butyl)dimethylsilane (Preparation example 240, 11.5 g, 32.80 mmol) in THF (115 mL) was slowly added tetrabutylammonium fluoride (TBAF, 1.0M in THF, 48.8 mL, 48.8 mmol) at room temperature. The mixture was stirred for 5 h. The resulting mixture was diluted with EtOAc, washed with water, dried over anhydrous magnesium sulfate, filtered and concentrated. The crude compound was purified by a silica gel column to produce the title compound (7.3 g, 80~95%)

¹H NMR (400 MHz, CDCl₃): δ=1.38 (s, 3H), 1.40 (s, 3H), 1.50~1.63 (m, 2H), 2.29 (t, J=5.4, 1H), 2.82 (dd, J=5.8, 13.8, 1H), 3.01 (dd, J=6.4, 14.0, 1H), 3.72 (q, J=5.5, 2H), 3.86 (dt, J=3.2, 8.4, 1H), 3.92~3.97 (m, 1H), 7.22~7.32 (m, 5H)

Preparation Example 242

(2R,3R)-5-(tert-butyldimethylsilyloxy)-1-phenylpentane-2,3-diol

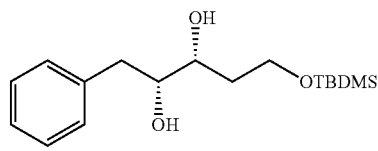 [SMILES: CC(C)(C)[Si](C)(C)OCC[C@@H](O)[C@H](O)Cc1ccccc1]

The substantially same method as described in Example 220 was conducted, except that (E)-tert-butyldimethyl(5-phenylpent-3-enyloxy)silane (Preparation example 237) was used instead of (E)-Methyl cinnamate (Preparation example 216), to obtain the title compound (10.6 g, 70~95%)

¹H NMR (400 MHz, CDCl₃): δ=0.00 (s, 6H), 0.82 (s, 9H), 1.57~1.62 (m, 1H), 1.73~1.80 (m, 1H), 2.51 (d, J=6.0, 1H), 2.77 (dq, J=6.9, 14.9, 2H), 3.50 (d, J=3.6, 1H), 3.59~3.62 (m, 1H), 3.66 (dq, J=3.1, 5.4, 1H), 3.72~3.82 (m, 2H), 7.12~7.25 (m, 5H)

Preparation Example 243

(2-((4R,5R)-5-benzyl-2,2-dimethyl-1,3-dioxolane-4-yl)ethoxy)(tert-butyl)dimethylsilane

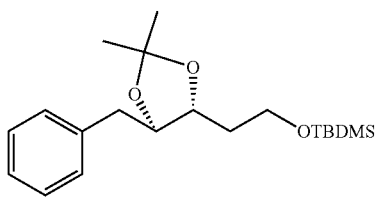 [SMILES: CC1(C)O[C@H](CCO[Si](C)(C)C(C)(C)C)[C@@H](Cc2ccccc2)O1]

The substantially same method as described in Example 221 was conducted, except that (2R,3R)-5-(tert-butyldimethylsilyloxy)-1-phenylpentane-2,3-diol (Preparation example 242) was used instead of (2R,3S)-methyl-3-phenyl-2,3-dihydroxypropanoate (Preparation example 217), to obtain the title compound (11.5 g, 70~95%)

$^1$H NMR (400 MHz, CDCl$_3$): δ=0.00 (s, 6H), 0.85 (s, 9H), 1.29 (s, 3H), 1.34 (s, 3H), 1.52~1.58 (m, 2H), 2.87 (dq, J=5.5, 14.2, 2H), 3.64~3.69 (m, 2H), 3.80~3.88 (m, 2H), 7.18~7.27 (m, 5H)

Preparation Example 244

2-((4R,5R)-5-benzyl-2,2-dimethyl-1,3-dioxolane-4-yl)ethanol

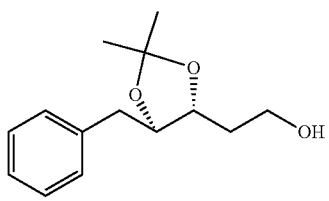 [SMILES: CC1(C)O[C@H](CCO)[C@@H](Cc2ccccc2)O1]

The substantially same method as described in Example 241 was conducted, except that (2-((4R,5R)-5-benzyl-2,2-dimethyl-1,3-dioxolan-4-yl)ethoxy)(tert-butyl)dimethylsilane (Preparation example 243) was used instead of (2-((4S,5S)-5-benzyl-2,2-dimethyl-1,3-dioxolan-4-yl)ethoxy)(tert-butyl)dimethylsilane (Preparation example 240), to obtain the title compound (7.4 g, 80~95%)

$^1$H NMR (400 MHz, CDCl$_3$): δ=1.38 (s, 3H), 1.40 (s, 3H), 1.50~1.63 (m, 2H), 2.29 (t, J=5.4, 1H), 2.82 (dd, J=5.8, 13.8, 1H), 3.01 (dd, J=6.4, 14.0, 1H), 3.72 (q, J=5.5, 2H), 3.86 (dt, J=3.2, 8.4, 1H), 3.92~3.97 (m, 1H), 7.22~7.32 (m, 5H)

Preparation Example 245

(3S,4S)-3,4-dihydroxy-5-phenylpentyl pivalate

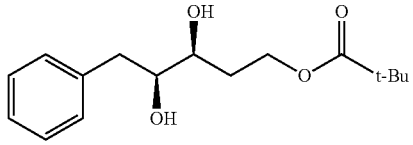 [SMILES: CC(C)(C)C(=O)OCC[C@H](O)[C@@H](O)Cc1ccccc1]

The substantially same method as described in Example 239 was conducted, except that (E)-5-phenylpent-3-enyl pivalate (Preparation example 238) was used instead of (E)-tert-butyldimethyl(5-phenylpent-3-enyloxy)silane (Preparation example 237), to obtain the title compound (5.5 g, 70~95%)

$^1$H NMR (400 MHz, CDCl$_3$): δ=1.16 (s, 9H), 1.83~1.88 (m, 2H), 2.08 (d, J=4.8, 1H), 2.67 (d, J=5.2, 1H), 2.80 (dd, J=8.0, 13.6, 1H), 2.92 (dd, J=5.2, 13.6, 1H), 3.50~3.55 (m, 1H), 3.66~3.71 (m, 1H), 4.09~4.19 (m, 1H), 4.35~4.41 (m, 1H), 7.22~7.25 (m, 3H), 7.29~7.33 (m, 2H)

Preparation Example 246

(2-((4S,5S)-5-benzyl-2,2-diethyl-1,3-dioxolane-4-yl)ethyl pivalate

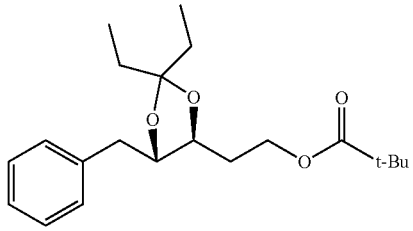 [SMILES: CCC1(CC)O[C@@H](CCOC(=O)C(C)(C)C)[C@H](Cc2ccccc2)O1]

The substantially same method as described in Example 223 was conducted, except that (3S,4S)-3,4-dihydroxy-5-phenylpentyl pivalate (Preparation example 245) was used instead of (2R,3S)-methyl-3-phenyl-2,3-dihydroxypropanoate (Preparation example 217), to obtain the title compound (0.9 g, 70~95%)

$^1$H NMR (400 MHz, CDCl$_3$): δ=1.15 (s, 9H), 1.76 (q, J=7.6, 2H), 1.84~1.90 (m, 2H), 2.00~2.07 (m, 2H), 3.85 (dt, J=3.7, 8.5, 1H), 4.14~4.27 (m, 2H), 5.17 (d, J=8.4, 1H), 7.22~7.28 (m, 1H), 7.32~7.38 (m, 2H), 7.64 (dd, J=1.4, 7.8, 1H)

Preparation Example 247

2-((4S,5S)-5-benzyl-2,2-diethyl-1,3-dioxolane-4-yl)ethanol

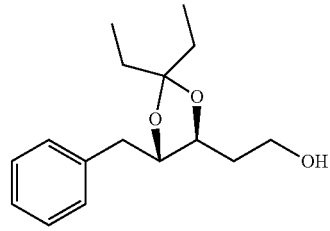 [SMILES: CCC1(CC)O[C@@H](CCO)[C@H](Cc2ccccc2)O1]

To a stirred solution of (2-((4S,5S)-5-benzyl-2,2-diethyl-1,3-dioxolan-4-yl)ethyl pivalate (Preparation example 246, 1.0 g, 2.87 mmol) in MeOH (10 mL) was added NaOMe (0.47 g, 8.61 mmol) and then warm to 45° C. The mixture was stirred for 14 h. The resulting mixture was diluted with EtOAc, washed with water, dried over MgSO4, filtered, and concentrated under reduced pressure. The crude compound was purified by a silica gel column to produce the title compound (0.7 g, 80~95%);

$^1$H NMR (400 MHz, CDCl$_3$): δ=0.89 (t, J=7.4, 6H), 1.44~1.50 (m, 1H), 1.54~1.66 (m, 5H), 2.37 (t, J=5.6, 1H), 2.80 (dd, J=5.6, 14.0, 1H), 3.03 (dd, J=6.4, 14.0, 1H), 3.72 (q, J=5.5, 2H), 3.80~3.85 (m, 1H), 3.89~3.94 (m, 1H), 7.21~7.24 (m, 3H), 7.28~7.31 (m, 2H)

Preparation Example 248

(3R,4R)-3,4-dihydroxy-5-phenylpentyl pivalate

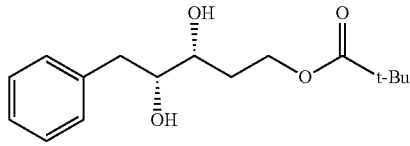 [SMILES: CC(C)(C)C(=O)OCC[C@@H](O)[C@H](O)Cc1ccccc1]

The substantially same method as described in Example 242 was conducted, except that (E)-5-phenylpent-3-enyl pivalate (Preparation example 238) was used instead of (E)-tert-butyldimethyl(5-phenylpent-3-enyloxy)silane (Preparation example 237), to obtain the title compound (4.5 g, 70~95%)

$^1$H NMR (400 MHz, CDCl$_3$): δ=1.16 (s, 9H), 1.83~1.88 (m, 2H), 2.08 (d, J=4.8, 1H), 2.67 (d, J=5.2, 1H), 2.80 (dd, J=8.0, 13.6, 1H), 2.92 (dd, J=5.2, 13.6, 1H), 3.50~3.55 (m, 1H), 3.66~3.71 (m, 1H), 4.09~4.19 (m, 1H), 4.35~4.41 (m, 1H), 7.22~7.25 (m, 3H), 7.29~7.33 (m, 2H)

Preparation Example 249

(2-((4R,5R)-5-benzyl-2,2-diethyl-1,3-dioxolane-4-yl)ethyl pivalate

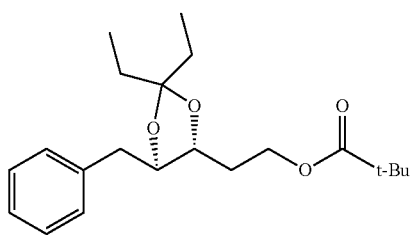 [SMILES: CCC1(CC)O[C@H](CCOC(=O)C(C)(C)C)[C@@H](Cc2ccccc2)O1]

The substantially same method as described in Example 246 was conducted, except that (3R,4R)-3,4-dihydroxy-5-phenylpentyl pivalate (Preparation example 248) was used instead of (3S,4S)-3,4-dihydroxy-5-phenylpentyl pivalate (Preparation example 245), to obtain the title compound (1.1 g, 70~95%)

$^1$H NMR (400 MHz, CDCl$_3$): δ=1.15 (s, 9H), 1.76 (q, J=7.6, 2H), 1.84~1.90 (m, 2H), 2.00~2.07 (m, 2H), 3.85 (dt, J=3.7, 8.5, 1H), 4.14~4.27 (m, 2H), 5.17 (d, J=8.4, 1H), 7.22~7.28 (m, 1H), 7.32~7.38 (m, 2H), 7.64 (dd, J=1.4, 7.8, 1H)

Preparation Example 250

2-((4R,5R)-5-benzyl-2,2-diethyl-1,3-dioxolane-4-yl)ethanol

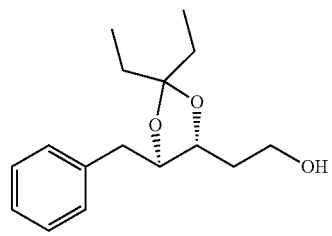 [SMILES: CCC1(CC)O[C@H](CCO)[C@@H](Cc2ccccc2)O1]

The substantially same method as described in Example 247 was conducted, except that (2-((4R,5R)-5-benzyl-2,2-diethyl-1,3-dioxolan-4-yl)ethyl pivalate (Preparation example 249) was used instead of (2-((4S,5S)-5-benzyl-2,2-diethyl-1,3-dioxolan-4-yl)ethyl pivalate (Preparation example 246), to obtain the title compound (0.9 g, 80~95%)

$^1$H NMR (400 MHz, CDCl$_3$): δ=0.89 (t, J=7.4, 6H), 1.44~1.50 (m, 1H), 1.54~1.66 (m, 5H), 2.37 (t, J=5.6, 1H), 2.80 (dd, J=5.6, 14.0, 1H), 3.03 (dd, J=6.4, 14.0, 1H), 3.72 (q, J=5.5, 2H), 3.80~3.85 (m, 1H), 3.89~3.94 (m, 1H), 7.21~7.24 (m, 3H), 7.28~7.31 (m, 2H)

Preparation Example 251

2-((2S,3S)-3-benzyl-1,4-dioxaspiro[4.4]nonane-2-yl) ethyl pivalate

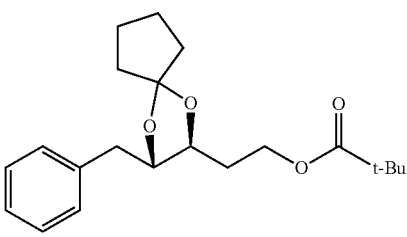 [SMILES: CC(C)(C)C(=O)OCC[C@@H]1OC2(CCCC2)O[C@H]1Cc1ccccc1]

The substantially same method as described in Example 246 was conducted, except that cyclopetanone was used instead of 3-pantanone, to obtain the title compound (1.2 g, 60~85%)

$^1$H NMR (400 MHz, CDCl$_3$): δ=1.18 (s, 9H), 1.53~1.80 (m, 10H), 2.81 (dd, J=6.0, 13.6, 1H), 3.00 (dd, J=6.4, 14.0, 1H), 3.75~3.80 (m, 1H), 3.84~3.89 (m, 1H), 4.05~4.16 (m, 2H), 7.20~7.24 (m, 3H), 7.27~7.31 (m, 2H)

Preparation Example 252

2-((2S,3S)-3-benzyl-1,4-dioxaspiro[4.4]nonane-2-yl)ethanol

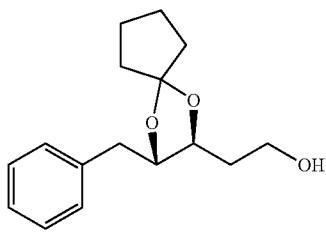 [SMILES: OCC[C@@H]1OC2(CCCC2)O[C@H]1Cc1ccccc1]

The substantially same method as described in Example 247 was conducted, except that 2-((2S,3S)-3-benzyl-1,4-dioxaspiro[4.4]nonan-2-yl)ethyl pivalate (Preparation example 251) was used instead of (2-((4S,5S)-5-benzyl-2,2-diethyl-1,3-dioxolan-4-yl)ethyl pivalate (Preparation example 246), to obtain the title compound (0.7 g, 80~95%)

$^1$H NMR (400 MHz, CDCl$_3$): δ=1.44~1.51 (m, 1H), 1.56~1.60 (m, 1H), 1.63~1.70 (m, 4H), 1.72~1.81 (m, 4H), 2.26 (t, J=5.4, 1H), 2.80 (dd, J=6.0, 14.0, 1H), 3.03 (dd, J=6.4, 14.0, 1H), 3.71 (q, J=5.5, 2H), 3.81~3.92 (m, 2H), 7.22~7.24 (m, 3H), 7.28~7.32 (m, 2H)

Preparation example 253

2-((2R,3R)-3-benzyl-1,4-dioxaspiro[4.4]nonane-2-yl)ethyl pivalate

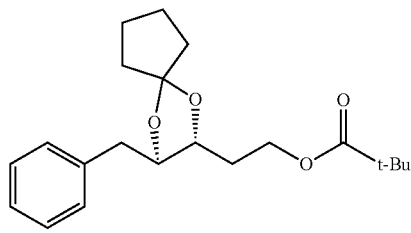 [SMILES: CC(C)(C)C(=O)OCC[C@H]1OC2(CCCC2)O[C@@H]1Cc1ccccc1]

The substantially same method as described in Example 249 was conducted, except that cyclopetanone was used instead of 3-pantanone, to obtain the title compound (1.7 g, 60~85%)

$^1$H NMR (400 MHz, CDCl$_3$): δ=1.18 (s, 9H), 1.53~1.80 (m, 10H), 2.81 (dd, J=6.0, 13.6, 1H), 3.00 (dd, J=6.4, 14.0, 1H), 3.75~3.80 (m, 1H), 3.84~3.89 (m, 1H), 4.05~4.16 (m, 2H), 7.20~7.24 (m, 3H), 7.27~7.31 (m, 2H)

Preparation Example 254

2-((2R,3R)-3-benzyl-1,4-dioxaspiro[4.4]nonane-2-yl)ethanol

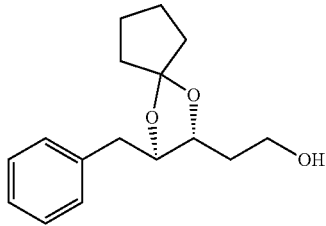 [SMILES: OCC[C@H]1OC2(CCCC2)O[C@@H]1Cc1ccccc1]

The substantially same method as described in Example 252 was conducted, except that 2-((2R,3R)-3-benzyl-1,4-dioxaspiro[4.4]nonan-2-yl)ethyl pivalate (Preparation example 253) was used instead of 2-((2S,3S)-3-benzyl-1,4-dioxaspiro[4.4]nonan-2-yl)ethyl pivalate (Preparation example 251), to obtain the title compound (0.8 g, 80~95%)

$^1$H NMR (400 MHz, CDCl$_3$): δ=1.44~1.51 (m, 1H), 1.56~1.60 (m, 1H), 1.63~1.70 (m, 4H), 1.72~1.81 (m, 4H), 2.26 (t, J=5.4, 1H), 2.80 (dd, J=6.0, 14.0, 1H), 3.03 (dd, J=6.4, 14.0, 1H), 3.71 (q, J=5.5, 2H), 3.81~3.92 (m, 2H), 7.22~7.24 (m, 3H), 7.28~7.32 (m, 2H)

Preparation Example 255

2-((2S,3S)-3-benzyl-1,4-dioxaspiro[4.5]decane-2-yl)ethyl pivalate

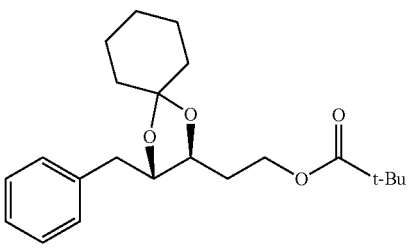 [SMILES: CC(C)(C)C(=O)OCC[C@@H]1OC2(CCCCC2)O[C@H]1Cc1ccccc1]

The substantially same method as described in Example 251 was conducted, except that cyclohexanone was used instead of cyclopetanone, to obtain the title compound (1.4 g, 60~85%)

$^1$H NMR (400 MHz, CDCl$_3$): δ=1.18 (s, 9H), 1.53~1.60 (m, 10H), 1.61~1.66 (m, 2H), 2.83 (dd, J=5.6, 14.0, 1H), 2.98 (dd, J=6.0, 14.0, 1H), 3.78 (dt, J=3.5, 8.2, 1H), 3.86~3.91 (m, 1H), 4.11~4.15 (m, 2H), 7.20~7.31 (m, 5H)

Preparation Example 256

2-((2S,3S)-3-benzyl-1,4-dioxaspiro[4.5]decane-2-yl)ethanol

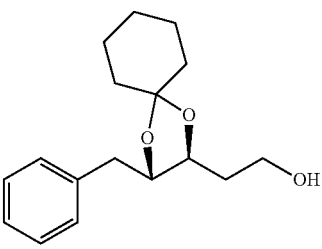 [SMILES: OCC[C@@H]1OC2(CCCCC2)O[C@H]1Cc1ccccc1]

The substantially same method as described in Example 254 was conducted, except that 2-((2S,3S)-3-benzyl-1,4-dioxaspiro[4.5]decan-2-yl)ethyl pivalate (Preparation example 255) was used instead of 2-((2R,3R)-3-benzyl-1,4-dioxaspiro[4.4]nonan-2-yl)ethyl pivalate (Preparation example 253), to obtain the title compound (1.0 g, 80~95%)

$^1$H NMR (400 MHz, CDCl$_3$): δ=1.34~1.43 (m, 2H), 1.48~1.61 (m, 10H), 2.42 (t, J=5.6, 1H), 2.81 (dd, J=5.6, 14.0, 1H), 3.02 (dd, J=6.2, 13.8, 1H), 3.72 (q, J=5.5, 2H), 3.82~3.87 (m, 1H), 3.91~3.96 (m, 1H), 7.21~7.31 (m, 5H)

Preparation Example 257

2-((2R,3R)-3-benzyl-1,4-dioxaspiro[4.5]decane-2-yl)ethyl pivalate

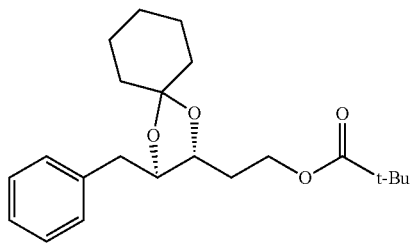 [SMILES: CC(C)(C)C(=O)OCC[C@H]1OC2(CCCCC2)O[C@@H]1Cc1ccccc1]

The substantially same method as described in Example 253 was conducted, except that cyclohexanone was used instead of cyclopetanone, to obtain the title compound (1.6 g, 60~85%)

$^1$H NMR (400 MHz, CDCl$_3$): δ=1.18 (s, 9H), 1.53~1.60 (m, 10H), 1.61~1.66 (m, 2H), 2.83 (dd, J=5.6, 14.0, 1H), 2.98 (dd, J=6.0, 14.0, 1H), 3.78 (dt, J=3.5, 8.2, 1H), 3.86~3.91 (m, 1H), 4.11~4.15 (m, 2H), 7.20~7.31 (m, 5H)

Preparation Example 258

2-((2R,3R)-3-benzyl-1,4-dioxaspiro[4.5]decane-2-yl)ethanol

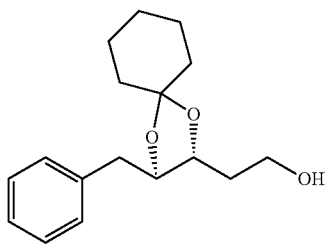 [SMILES: OCC[C@H]1OC2(CCCCC2)O[C@@H]1Cc1ccccc1]

The substantially same method as described in Example 256 was conducted, except that 2-((2R,3R)-3-benzyl-1,4-dioxaspiro[4.5]decan-2-yl)ethyl pivalate (Preparation example 257) was used instead of 2-((2S,3S)-3-benzyl-1,4-dioxaspiro[4.5]decan-2-yl)ethyl pivalate (Preparation example 255), to obtain the title compound (1.1 g, 80~95%)

$^1$H NMR (400 MHz, CDCl$_3$): δ=1.34~1.43 (m, 2H), 1.48~1.61 (m, 10H), 2.42 (t, J=5.6, 1H), 2.81 (dd, J=5.6, 14.0, 1H), 3.02 (dd, J=6.2, 13.8, 1H), 3.72 (q, J=5.5, 2H), 3.82~3.87 (m, 1H), 3.91~3.96 (m, 1H), 7.21~7.31 (m, 5H)

Preparation Example 259

(E)-methyl-4-phenylbut-2-enoate

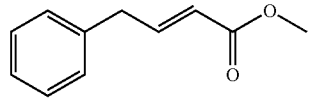

To a solution of phenyl acetaldehyde (5.0 g, 41.61 mmol) in toluene (500 mL) was added methyl (triphenylphosphoranylidene)acetate (13.9 g, 41.61 mmol). The reaction mixture was stirred at reflux for 3 h. The resulting mixture was diluted with EtOAc, washed with water, dried over MgSO$_4$, filtered, and concentrated under reduced pressure. The crude product was added ether/hexane (=1:1, v/v) at 0° C. then stirred for 30 min. The filtrate was concentrated then purified by a silica gel column to produce the title compound (5.9 g, 70~90%)

$^1$H NMR (400 MHz, CDCl$_3$): δ=3.47 (d, J=6.8, 2H), 3.67 (s, 3H), 5.79 (d, J=15.4, 1H), 7.06 (dt, J=15.4, 6.8, 1H), 7.28~7.12 (m, 5H)

Preparation Example 260

(2R,3S)-methyl 2,3-dihydroxy-4-phenylbutanoate

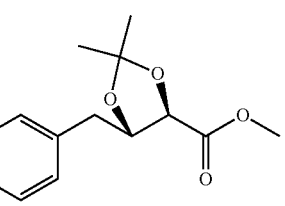

The substantially same method as described in Example 245 was conducted, except that (E)-methyl-4-phenylbut-2-enoate (Preparation example 259) was used instead of (E)-5-phenylpent-3-enyl pivalate (Preparation example 238), to obtain the title compound (3.5 g, 70~95%)

$^1$H NMR (400 MHz, CDCl$_3$): δ=2.96 (ddd, J=7.3, 13.5, 17.1, 2H), 3.10 (d, J=5.2, 1H), 3.80 (s, 3H), 4.08 (dd, J=1.4, 5.4, 1H), 7.23~7.34 (m, 5H)

Preparation Example 261

(4R,5S)-methyl-5-benzyl-2,2-dimethyl-1,3-dioxolane-4-carboxylate

The substantially same method as described in Example 240 was conducted, except that (2R,3S)-methyl 2,3-dihydroxy-4-phenylbutanoate (Preparation example 260) was used instead of (2S,3S)-5-(tert-butyldimethylsilyloxy)-1-phenylpentane-2,3-diol (Preparation example 239), to obtain the title compound (3.1 g, 70~95%)

$^1$H NMR (400 MHz, CDCl$_3$): δ=1.42 (s, 3H), 1.43 (s, 3H), 3.01 (dd, J=6.8, 14.4, 1H), 3.12 (dd, J=4.4, 14.4, 1H), 3.72 (s, 3H), 4.19 (d, J=7.6, 1H), 4.40 (ddd, J=4.4, 7.0, 7.8, 1H), 7.22~7.33 (m, 5H)

Preparation Example 262

((4S,5S)-5-benzyl-2,2-dimethyl-1,3-dioxolan-4-yl)methanol

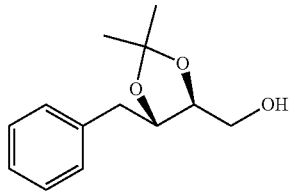 [SMILES: CC1(C)O[C@@H](CO)[C@H](Cc2ccccc2)O1]

The substantially same method as described in Example 234 was conducted, except that (4R,5S)-methyl 5-benzyl-2,2-dimethyl-1,3-dioxolane-4-carboxylate (Preparation example 261) was used instead of (4S,5R)-methyl-3-phenyl-1,4-dioxapiro[4,5]decane-2-carboxylate (Preparation example 233), to obtain the title compound (2.3 g, 70~95%)

$^1$H NMR (400 MHz, CDCl$_3$): δ=1.41 (s, 6H), 1.79 (q, J=4.3, 1H), 2.83 (dd, J=6.2, 13.8, 1H), 3.07 (dd, J=6.4, 14.0, 1H), 3.29 (ddd, J=4.7, 7.5, 12.1, 1H), 3.54 (ddd, J=2.8, 5.2, 12.0, 1H), 3.83 (ddd, J=3.9, 3.9, 7.1, 1H), 4.15 (q, J=7.1, 1H), 7.22~7.32 (m, 5H)

Preparation Example 263

(4R,5S)-methyl-5-benzyl-2,2-diethyl-1,3-dioxolane-4-carboxylate

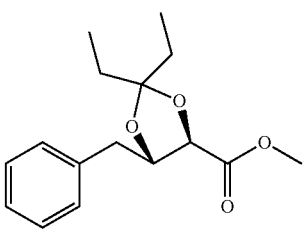 [SMILES: CCC1(CC)O[C@@H](Cc2ccccc2)[C@H](C(=O)OC)O1]

To a stirred solution of (2R,3S)-methyl 2,3-dihydroxy-4-phenylbutanoate (Preparation example 260, 2.0 g, 9.51 mmol) in 3-pentanone (5 mL, 47.55 mmol) was added a catalytic amount of H$_2$SO$_4$ (0.051 mL, 0.951 mmol) at room temperature. The mixture was stirred for 20 h. The resulting mixture was diluted with EtOAc, washed with water, dried over MgSO$_4$, filtered, and concentrated under reduced pressure. The crude compound was purified by a silica gel column to produce the title compound (1.2 g, 50~75%)

$^1$H NMR (400 MHz, CDCl$_3$): δ=0.85 (t, J=6.0, 3H), 0.92 (t, J=7.6, 3H), 1.66 (dq, J=7.6, 14.7, 4H), 3.01 (dd, J=6.6, 14.2, 1H), 3.10 (dd, J=4.4, 14.4, 1H), 3.71 (s, 3H), 4.17 (d, J=8.4, 1H), 4.32~4.37 (m, 1H), 7.23~7.32 (m, 5H)

Preparation Example 264

((4S,5S)-5-benzyl-2,2-diethyl-1,3-dioxolan-4-yl)methanol

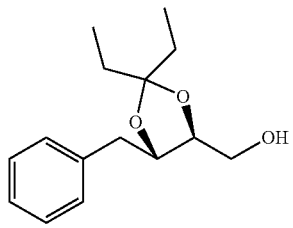 [SMILES: CCC1(CC)O[C@@H](CO)[C@H](Cc2ccccc2)O1]

The substantially same method as described in Example 262 was conducted, except that (4R,5S)-methyl-5-benzyl-2,2-dimethyl-1,3-dioxolane-4-carboxylate (Preparation example 263) was used instead of (4R,5S)-methyl 5-benzyl-2,2-dimethyl-1,3-dioxolane-4-carboxylate (Preparation example 261), to obtain the title compound (0.8 g, 70~95%)

$^1$H NMR (400 MHz, CDCl$_3$): δ=0.91 (dt, J=1.9, 7.5, 6H), 1.61~1.68 (m, 4H), 1.77 (t, J=6.2, 1H), 2.81 (dd, J=6.4, 14.0, 1H), 3.09 (dd, J=6.2, 13.8, 1H), 3.24~3.30 (m, 1H), 3.49~3.54 (m, 1H), 3.78~3.82 (m, 1H), 4.08~4.13 (m, 1H), 7.21~7.32 (m, 5H)

Preparation Example 265

(2R,3S)-methyl 3-benzyl-1,4-dioxaspiro[4.4]nonane-2-carboxylate

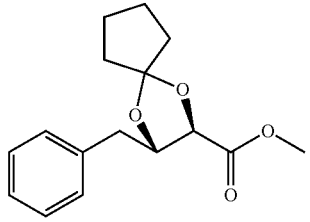 [SMILES: COC(=O)[C@@H]1OC2(CCCC2)O[C@H]1Cc1ccccc1]

The substantially same method as described in Example 263 was conducted, except that cyclopetanone was used instead of 3-pantanone, to obtain the title compound (1.3 g, 60~85%)

$^1$H NMR (400 MHz, CDCl$_3$): δ=1.61~1.79 (m, 5H), 1.85~1.92 (m, 3H), 3.00~3.11 (m, 2H), 3.70 (s, 3H), 4.17 (d, J=7.2, 1H), 4.32 (dt, J=4.9, 7.0, 1H), 7.21~7.33 (m, 5H)

Preparation Example 266

((2S,3S)-3-benzyl-1,4-dioxaspiro[4.4]nonane-2-yl)methanol

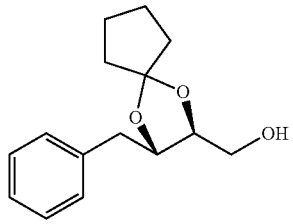 [SMILES: OC[C@@H]1OC2(CCCC2)O[C@H]1Cc1ccccc1]

The substantially same method as described in Example 264 was conducted, except that (2R,3S)-methyl 3-benzyl-1,4-dioxaspiro[4.4]nonane-2-carboxylate (Preparation example 265) was used instead of (4R,5S)-methyl-5-benzyl-2,2-dimethyl-1,3-dioxolane-4-carboxylate (Preparation example 263), to obtain the title compound (0.8 g, 70~95%)

¹H NMR (400 MHz, CDCl₃): δ=1.57~1.88 (m, 8H), 2.82 (dd, J=6.6, 13.8, 1H), 3.08 (dd, J=6.4, 14.0, 1H), 3.27~3.33 (m, 1H), 3.47~3.52 (m, 1H), 3.79~3.83 (m, 1H), 4.07 (q, J=6.8, 1H), 7.21~7.32 (m, 5H)

Preparation Example 267

(2R,3S)-methyl-3-benzyl-1,4-dioxaspiro[4.5]decane-2-carboxylate

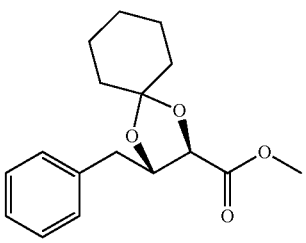 [SMILES: COC(=O)[C@@H]1OC2(CCCCC2)O[C@H]1Cc1ccccc1]

The substantially same method as described in Example 265 was conducted, except that cyclohexanone was used instead of cyclopetanone, to obtain the title compound (1.5 g, 60~85%)

¹H NMR (400 MHz, CDCl₃): δ=1.54~1.74 (m, 10H), 2.99~3.12 (m, 2H), 3.70 (s, 3H), 4.18 (d, J=7.6, 1H), 4.36~4.41 (m, 1H), 7.21~7.32 (m, 5H)

Preparation Example 268

((2S,3S)-3-benzyl-1,4-dioxaspiro[4.4]decan-2-yl)methanol

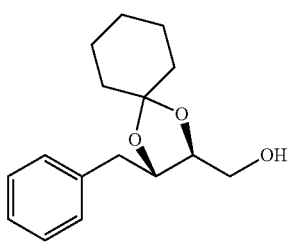 [SMILES: OC[C@@H]1OC2(CCCCC2)O[C@H]1Cc1ccccc1]

The substantially same method as described in Example 266 was conducted, except that (2R,3S)-methyl-3-benzyl-1,4-dioxaspiro[4.5]decane-2-carboxylate (Preparation example 267) was used instead of (2R,3S)-methyl 3-benzyl-1,4-dioxaspiro[4.4]nonane-2-carboxylate (Preparation example 265), to obtain the title compound (0.8 g, 70~95%)

¹H NMR (400 MHz, CDCl₃): δ=1.53~1.65 (m, 10H), 2.82 (dd, J=6.2, 13.8, 1H), 3.07 (dd, J=6.4, 13.6, 1H), 3.24~3.30 (m, 1H), 3.52~3.56 (m, 1H), 3.80~3.84 (m, 1H), 4.10~4.15 (m, 1H), 7.21~7.31 (m, 5H)

Preparation Example 269

(2S,3R)-methyl-2,3-dihydroxy-4-phenylbutanoate

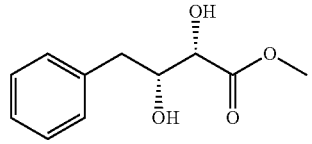

The substantially same method as described in Example 242 was conducted, except that (E)-methyl-4-phenylbut-2-enoate (Preparation example 259) was used instead of (E)-tert-butyldimethyl(5-phenylpent-3-enyloxy)silane (Preparation example 237), to obtain the title compound (3.5 g, 70~95%)

¹H NMR (400 MHz, CDCl₃): δ=2.96 (ddd, J=7.3, 13.5, 17.1, 2H), 3.10 (d, J=5.2, 1H), 3.80 (s, 3H), 4.08 (dd, J=1.4, 5.4, 1H), 7.23~7.34 (m, 5H)

Preparation Example 270

(4S,5R)-methyl-5-benzyl-2,2-dimethyl-1,3-dioxolane-4-carboxylate

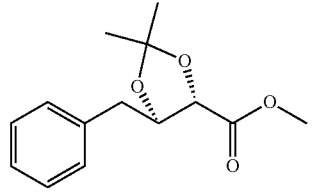 [SMILES: COC(=O)[C@H]1OC(C)(C)O[C@@H]1Cc1ccccc1]

The substantially same method as described in Example 261 was conducted, except that (2S,3R)-methyl-2,3-dihydroxy-4-phenylbutanoate (Preparation example 269) was used instead of (2R,3S)-methyl 2,3-dihydroxy-4-phenylbutanoate (Preparation example 260), to obtain the title compound (3.4 g, 70~95%)

¹H NMR (400 MHz, CDCl₃): δ=1.41 (s, 6H), 1.79 (q, J=4.3, 1H), 2.83 (dd, J=6.2, 13.8, 1H), 3.07 (dd, J=6.4, 14.0, 1H), 3.29 (ddd, J=4.7, 7.5, 12.1, 1H), 3.54 (ddd, J=2.8, 5.2, 12.0, 1H), 3.83 (ddd, J=3.9, 3.9, 7.1, 1H), 4.15 (q, J=7.1, 1H), 7.22~7.32 (m, 5H)

Preparation Example 271

((4R,5R)-5-benzyl-2,2-dimethyl-1,3-dioxolan-4-yl)methanol

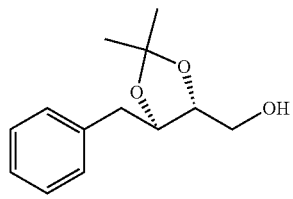 [SMILES: CC1(C)O[C@H](CO)[C@@H](Cc2ccccc2)O1]

The substantially same method as described in Example 262 was conducted, except that (4S,5R)-methyl-5-benzyl-2,2-dimethyl-1,3-dioxolane-4-carboxylate (Preparation example 270) was used instead of (4R,5S)-methyl 5-benzyl-2,2-dimethyl-1,3-dioxolane-4-carboxylate (Preparation example 261), to obtain the title compound (2.7 g, 70~95%)

¹H NMR (400 MHz, CDCl₃): δ=1.41 (s, 6H), 1.79 (q, J=4.3, 1H), 2.83 (dd, J=6.2, 13.8, 1H), 3.07 (dd, J=6.4, 14.0, 1H), 3.29 (ddd, J=4.7, 7.5, 12.1, 1H), 3.54 (ddd, J=2.8, 5.2, 12.0, 1H), 3.83 (ddd, J=3.9, 3.9, 7.1, 1H), 4.15 (q, J=7.1, 1H), 7.22~7.32 (m, 5H)

Preparation Example 272

(4S,5R)-methyl-5-benzyl-2,2-diethyl-1,3-dioxolane-4-carboxylate

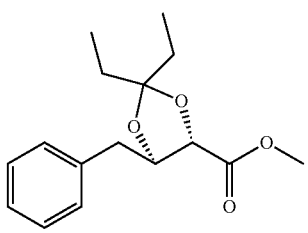 [SMILES: CCC1(CC)O[C@H](C(=O)OC)[C@@H](Cc2ccccc2)O1]

The substantially same method as described in Example 263 was conducted, except that (2S,3R)-methyl-2,3-dihydroxy-4-phenylbutanoate (Preparation example 269) was used instead of (2,3-dihydroxy-4-phenylbutanoate (Preparation example 260), to obtain the title compound (1.5 g, 50~75%)

¹H NMR (400 MHz, CDCl₃): δ=0.85 (t, J=6.0, 3H), 0.92 (t, J=7.6, 3H), 1.66 (dq, J=7.6, 14.7, 4H), 3.01 (dd, J=6.6, 14.2, 1H), 3.10 (dd, J=4.4, 14.4, 1H), 3.71 (s, 3H), 4.17 (d, J=8.4, 1H), 4.32~4.37 (m, 1H), 7.23~7.32 (m, 5H)

Preparation Example 273

((4R,5R)-5-benzyl-2,2-diethyl-1,3-dioxolan-4-yl)methanol

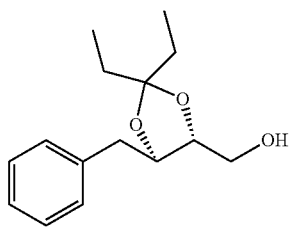 [SMILES: CCC1(CC)O[C@H](CO)[C@@H](Cc2ccccc2)O1]

The substantially same method as described in Example 264 was conducted, except that (4S,5R)-methyl-5-benzyl-2,2-dimethyl-1,3-dioxolane-4-carboxylate (Preparation example 272) was used instead of (4R,5S)-methyl-5-benzyl-2,2-dimethyl-1,3-dioxolane-4-carboxylate (Preparation example 263), to obtain the title compound (1.2 g, 70~95%)

¹H NMR (400 MHz, CDCl₃): δ=0.91 (dt, J=1.9, 7.5, 6H), 1.61~1.68 (m, 4H), 1.77 (t, J=6.2, 1H), 2.81 (dd, J=6.4, 14.0, 1H), 3.09 (dd, J=6.2, 13.8, 1H), 3.24~3.30 (m, 1H), 3.49~3.54 (m, 1H), 3.78~3.82 (m, 1H), 4.08~4.13 (m, 1H), 7.21~7.32 (m, 5H)

Preparation Example 274

(2S,3R)-methyl-3-benzyl-1,4-dioxaspiro[4.4]nonane-2-carboxylate

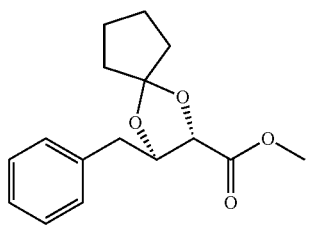 [SMILES: COC(=O)[C@H]1OC2(CCCC2)O[C@@H]1Cc1ccccc1]

The substantially same method as described in Example 272 was conducted, except that cyclopetanone was used instead of 3-pantanone, to obtain the title compound (1.2 g, 60~85%)

¹H NMR (400 MHz, CDCl₃): δ=1.61~1.79 (m, 5H), 1.85~1.92 (m, 3H), 3.00~3.11 (m, 2H), 3.70 (s, 3H), 4.17 (d, J=7.2, 1H), 4.32 (dt, J=4.9, 7.0, 1H), 7.21~7.33 (m, 5H)

Preparation Example 275

((2R,3R)-3-benzyl-1,4-dioxaspiro[4.4]nonane-2-yl)methanol

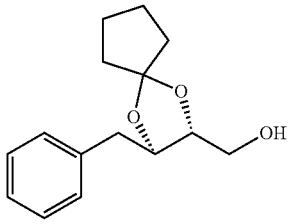 [SMILES: OC[C@H]1OC2(CCCC2)O[C@@H]1Cc1ccccc1]

The substantially same method as described in Example 266 was conducted, except that (2S,3R)-methyl-3-benzyl-1,4-dioxaspiro[4.4]nonane-2-carboxylate (Preparation example 274) was used instead of (2R,3S)-methyl-3-benzyl-1,4-dioxaspiro[4.4]nonane-2-carboxylate (Preparation example 265), to obtain the title compound (1.1 g, 70~95%)

¹H NMR (400 MHz, CDCl₃): δ=1.57~1.88 (m, 8H), 2.82 (dd, J=6.6, 13.8, 1H), 3.08 (dd, J=6.4, 14.0, 1H), 3.27~3.33 (m, 1H), 3.47~3.52 (m, 1H), 3.79~3.83 (m, 1H), 4.07 (q, J=6.8, 1H), 7.21~7.32 (m, 5H)

Preparation Example 276

(2S,3R)-methyl-3-benzyl-1,4-dioxaspiro[4.5]decane-2-carboxylate

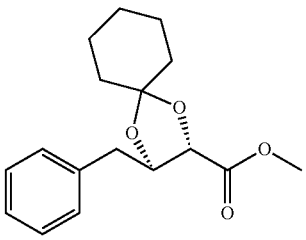 [SMILES: COC(=O)[C@H]1OC2(CCCCC2)O[C@@H]1Cc1ccccc1]

The substantially same method as described in Example 274 was conducted, except that cyclohexanone was used instead of cyclopetanone, to obtain the title compound (1.4 g, 60~85%)

$^1$H NMR (400 MHz, CDCl$_3$): δ=1.54~1.74 (m, 10H), 2.99~3.12 (m, 2H), 3.70 (s, 3H), 4.18 (d, J=7.6, 1H), 4.36~4.41 (m, 1H), 7.21~7.32 (m, 5H)

Preparation Example 277

((2R,3R)-3-benzyl-1,4-dioxaspiro[4.4]nonane-2-yl)methanol

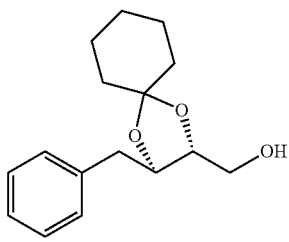 [SMILES: OC[C@H]1OC2(CCCCC2)O[C@@H]1Cc1ccccc1]

The substantially same method as described in Example 268 was conducted, except that (2S,3R)-methyl-3-benzyl-1,4-dioxaspiro[4.5]decane-2-carboxylate (Preparation example 276) was used instead of (2R,3S)-methyl-3-benzyl-1,4-dioxaspiro[4.5]decane-2-carboxylate (Preparation example 267), to obtain the title compound (1.4 g, 70~95%)

$^1$H NMR (400 MHz, CDCl$_3$): δ=1.53~1.65 (m, 10H), 2.82 (dd, J=6.2, 13.8, 1H), 3.07 (dd, J=6.4, 13.6, 1H), 3.24~3.30 (m, 1H), 3.52~3.56 (m, 1H), 3.80~3.84 (m, 1H), 4.10~4.15 (m, 1H), 7.21~7.31 (m, 5H)

Preparation Example 278

(E)-4-phenylbut-3-enoic acid

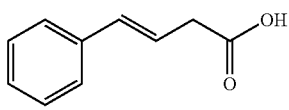 [SMILES: O=C(O)C/C=C/c1ccccc1]

To a stirred solution of 2-phenylacetaldehyde (5.0 g, 32.3 mmol) and malonic acid (4.0 g, 38.8 mmol) in pyridine (25.0 mL) was added a catalytic amount of piperidine (0.64 mL, 6.46 mmol) then heated to reflux. After 3 h, the resulting mixture was cooled to room temperature and concentrated under reduced pressure. The crude product was slowly added 2N HCl. The white precipitate was filtered off and dried under vacuum to produce the title compound (3.5 g, 55~80%)

$^1$H NMR (400 MHz, CDCl$_3$): δ=3.39 (d, J=8.8, 2H), 6.31 (td, J=7.9, 14.8, 1H), 6.94 (d, J=16, 1H), 7.17~7.45 (m, 3H), 7.56~7.59 (m, 1H)

Preparation Example 279

(E)-4-phenylbut-3-en-1-ol

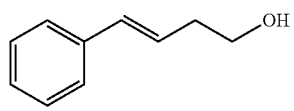 [SMILES: OCC/C=C/c1ccccc1]

To stirred solution of Zn(BH$_4$)$_2$ (40.0 mL, 20.0 mmol) in THF(40 mL) was added dropwise a solution 1 (2.0 g, 10.0 mmol) in THF(5 mL) at 0° C. then heated to reflux for 0.5 h. The reaction mixture was quenched with H$_2$O at 0° C., filtered through celite, washed with EtOAc, dried over anhydrous magnesium sulfate (MgSO$_4$), filtered and concentrated. The crude compound was purified by a silica gel column to produce the title compound (1.0 g, 50~75%)

$^1$H NMR (400 MHz, CDCl$_3$): δ=2.55 (ddd, J=4.1, 11.9, 21.5, 2H), 3.82 (t, J=5.8, 2H), 6.24 (td, J=7.2, 15.7, 1H), 6.87 (d, J=14.8, 1H), 7.12~7.25 (m, 3H), 7.36 (dd, J=1.2, 8.0, 1H), 7.52 (dd, J=1.6, 9.2, 1H)

Preparation Example 280

(E)-tert-butyldimethyl(4-phenylbut-3-enyloxy)silane

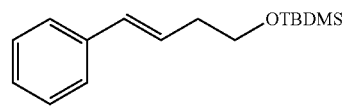 [SMILES: CC(C)(C)[Si](C)(C)OCC/C=C/c1ccccc1]

The substantially same method as described in Example 237 was conducted, except that (E)-4-phenylbut-3-en-1-ol (Preparation example 279) was used instead of (E)-5-phenylpent-3-en-1-ol (Preparation example 236), to obtain the title compound (1.7 g, 80~98%)

$^1$H NMR (400 MHz, CDCl$_3$): δ=0.07 (s, 3H), 0.10 (s, 3H), 0.92 (d, J=6.4, 9H), 2.51 (q, J=4.5, 2H), 3.78 (t, J=6.6, 2H), 6.26 (td, J=7.2, 15.7, 1H), 6.84 (d, J=15.6, 1H), 7.13~7.24 (m, 3H), 7.36 (dd, J=5.6, 12.4, 1H), 7.53 (dd, J=1.4, 7.8, 1H)

Preparation Example 281

(E)-4-phenylbut-3-enyl pivalate

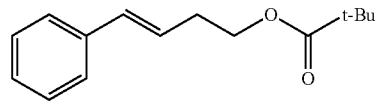 [SMILES: CC(C)(C)C(=O)OCC/C=C/c1ccccc1]

The substantially same method as described in Example 238 was conducted, except that (E)-4-phenylbut-3-en-1-ol (Preparation example 279) was used instead of (E)-5-phenylpent-3-en-1-ol (Preparation example 236), to obtain the title compound (10.8 g, 75~95%)

¹H NMR (400 MHz, CDCl₃): δ=1.22 (s, 9H), 2.57 (ddd, J=1.3, 6.7, 13.5, 2H), 4.22 (t, J=6.6, 2H), 6.19 (td, J=7.0, 16.0, 1H), 6.49 (d, J=16.0, 1H), 7.23~7.26 (m, 1H), 7.31~7.41 (m, 4H)

Preparation Example 282

(1R,2R)-4-(tert-butyldimethylsilyloxy)-1-phenylbutane-1,2-diol

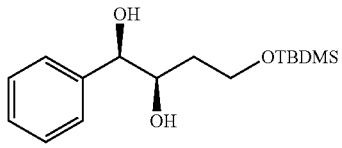 [SMILES: CC(C)(C)[Si](C)(C)OCC[C@@H](O)[C@H](O)c1ccccc1]

The substantially same method as described in Example 239 was conducted, except that (E)-tert-butyldimethyl(4-phenylbut-3-enyloxy)silane (Preparation example 280) was used instead of (E)-tert-butyldimethyl(5-phenylpent-3-enyloxy)silane (Preparation example 237), to obtain the title compound (0.8 g, 70~95%)

¹H NMR (400 MHz, CDCl₃): δ=0.10 (s, 3H), 0.11 (s, 3H), 0.92 (s, 9H), 1.69~1.70 (m, 1H), 1.93~2.07 (m, 1H), 3.51 (d, J=4.8, 1H), 3.86 (d, J=3.2, 1H), 3.87 (dd, J=3.2, 9.2, 1H), 3.91~3.96 (m, 1H), 4.01~4.06 (m, 1H), 5.05 (t, J=4.6, 1H), 7.22~7.26 (m, 1H), 7.31~7.37 (m, 2H), 7.59 (dd, J=1.2, 7.6, 1H)

Preparation Example 283

(3R,4R)-3,4-dihydroxy-4-phenylbutyl pivalate

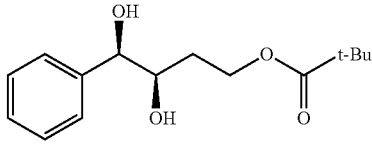 [SMILES: CC(C)(C)C(=O)OCC[C@@H](O)[C@H](O)c1ccccc1]

The substantially same method as described in Example 282 was conducted, except that (E)-4-phenylbut-3-enyl pivalate (Preparation example 281) was used instead of (E)-tert-butyldimethyl(4-phenylbut-3-enyloxy)silane (Preparation example 280), to obtain the title compound (8.7 g, 70~95%)

¹H NMR (400 MHz, CDCl₃): δ=1.18 (s, 9H), 1.65~1.74 (m, 2H), 2.83 (d, J=2.4, 1H), 2.96 (d, J=3.2, 1H), 3.74~3.79 (m, 1H), 4.10~4.17 (m, 1H), 4.33 (ddd, J=4.0, 7.2, 12.6, 1H), 4.49 (d, J=5.6, 1H), 7.31~7.41 (m, 5H)

Preparation Example 284 tert-butyl(2-((4R,5R)-5-phenyl-2,2-dimethyl-1,3-dioxolan-4-yl)ethoxy)dimethylsilane

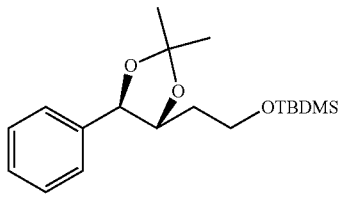 [SMILES: CC1(C)O[C@H](c2ccccc2)[C@@H](CCO[Si](C)(C)C(C)(C)C)O1]

The substantially same method as described in Example 218 was conducted, except that (1R,2R)-4-(tert-butyldimethylsilyloxy)-1-phenylbutane-1,2-diol (Preparation example 282) was used instead of (2R,3S)-methyl-3-phenyl-2,3-dihydroxypropanoate (Preparation example 217), to obtain the title compound (1.6 g, 70~95%)

¹H NMR (400 MHz, CDCl₃): δ=0.02 (s, 3H), 0.07 (s, 3H), 0.86 (s, 9H), 1.50 (s, 3H), 1.58 (s, 3H), 1.82~1.99 (m, 2H), 3.68~3.78 (m, 2H), 3.95 (dt, J=3.3, 8.7, 1H), 5.16 (d, J=8.4, 1H), 7.21~7.27 (m, 1H), 7.31~7.38 (m, 2H), 7.60 (dd, J=1.6, 7.6, 1H)

Preparation Example 285

2-((4R,5R)-5-phenyl-2,2-dimethyl-1,3-dioxolan-4-yl)ethanol

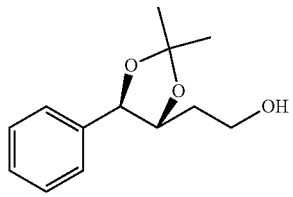 [SMILES: CC1(C)O[C@H](c2ccccc2)[C@@H](CCO)O1]

The substantially same method as described in Example 244 was conducted, except that tert-butyl(2-((4R,5R)-5-phenyl-2,2-dimethyl-1,3-dioxolan-4-yl)ethoxy)dimethylsilane (Preparation example 284) was used instead of (2-((4R,5R)-5-benzyl-2,2-dimethyl-1,3-dioxolan-4-yl)ethoxy)(tert-butyl)dimethylsilane (Preparation example 243), to obtain the title compound (1.4 g, 80~95%).

¹H NMR (400 MHz, CDCl₃): δ=1.56 (s, 3H), 1.62 (s, 3H), 1.92~2.04 (m, 2H), 2.26 (q, J=3.7, 1H), 3.75~3.90 (m, 2H), 3.94 (td, J=3.9, 8.5, 1H), 5.23 (d, J=15.6, 1H), 7.22~7.27 (m, 1H), 7.33~7.39 (m, 2H), 7.62 (dd, J=1.6, 7.6, 1H)

Preparation Example 286

(1S,2S)-4-(tert-butyldimethylsilyloxy)-1-phenylbutane-1,2-diol

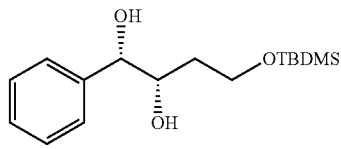 [SMILES: CC(C)(C)[Si](C)(C)OCC[C@H](O)[C@@H](O)c1ccccc1]

The substantially same method as described in Example 242 was conducted, except that (E)-tert-butyldimethyl(4-phenylbut-3-enyloxy)silane (Preparation example 280) was used instead of (E)-tert-butyldimethyl(5-phenylpent-3-enyloxy)silane (Preparation example 237), to obtain the title compound (0.7 g, 70~95%)

¹H NMR (400 MHz, CDCl₃): δ=0.10 (s, 3H), 0.11 (s, 3H), 0.92 (s, 9H), 1.69~1.70 (m, 1H), 1.93~2.07 (m, 1H), 3.51 (d, J=4.8, 1H), 3.86 (d, J=3.2, 1H), 3.87 (dd, J=3.2, 9.2, 1H), 3.91~3.96 (m, 1H), 4.01~4.06 (m, 1H), 5.05 (t, J=4.6, 1H), 7.22~7.26 (m, 1H), 7.31~7.37 (m, 2H), 7.59 (dd, J=1.2, 7.6, 1H)

Preparation Example 287

(3S,4S)-3,4-dihydroxy-4-phenylbutyl pivalate

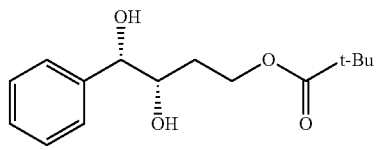 [SMILES: CC(C)(C)C(=O)OCC[C@H](O)[C@@H](O)c1ccccc1]

The substantially same method as described in Example 286 was conducted, except that (E)-4-phenylbut-3-enyl pivalate (Preparation example 281) was used instead of (E)-tert-butyldimethyl(4-phenylbut-3-enyloxy)silane (Preparation example 280), to obtain the title compound (10.4 g, 70~95%)

$^1$H NMR (400 MHz, CDCl$_3$): δ=1.18 (s, 9H), 1.65~1.74 (m, 2H), 2.83 (d, J=2.4, 1H), 2.96 (d, J=3.2, 1H), 3.74~3.79 (m, 1H), 4.10~4.17 (m, 1H), 4.33 (ddd, J=4.0, 7.2, 12.6, 1H), 4.49 (d, J=5.6, 1H), 7.31~7.41 (m, 5H)

Preparation Example 288 tert-butyl(2-((4S,5S)-5-phenyl-2,2-dimethyl-1,3-dioxolan-4-yl)ethoxy)dimethylsilane

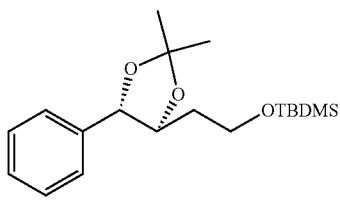 [SMILES: CC1(C)O[C@@H](CCO[Si](C)(C)C(C)(C)C)[C@H](c2ccccc2)O1]

The substantially same method as described in Example 284 was conducted, except that (1S,2S)-4-(tert-butyldimethylsilyloxy)-1-phenylbutane-1,2-diol (Preparation example 286) was used instead of (1R,2R)-4-(tert-butyldimethylsilyloxy)-1-phenylbutane-1,2-diol (Preparation example 282), to obtain the title compound (0.7 g, 70~95%)

$^1$H NMR (400 MHz, CDCl$_3$): δ=0.02 (s, 3H), 0.07 (s, 3H), 0.86 (s, 9H), 1.50 (s, 3H), 1.58 (s, 3H), 1.82~1.99 (m, 2H), 3.68~3.78 (m, 2H), 3.95 (dt, J=3.3, 8.7, 1H), 5.16 (d, J=8.4, 1H), 7.21~7.27 (m, 1H), 7.31~7.38 (m, 2H), 7.60 (dd, J=1.6, 7.6, 1H)

Preparation Example 289

2-((4S,5S)-5-phenyl-2,2-dimethyl-1,3-dioxolan-4-yl)ethanol

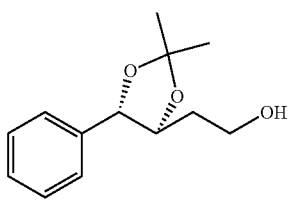 [SMILES: CC1(C)O[C@@H](CCO)[C@H](c2ccccc2)O1]

The substantially same method as described in Example 285 was conducted, except that tert-butyl(2-((4S,5S)-5-phenyl-2,2-dimethyl-1,3-dioxolan-4-yl)ethoxy)dimethylsilane (Preparation example 288) was used instead of that tert-butyl (2-((4R,5R)-5-phenyl-2,2-dimethyl-1,3-dioxolan-4-yl)ethoxy)dimethylsilane (Preparation example 284), to obtain the title compound (0.4 g, 80~95%)

$^1$H NMR (400 MHz, CDCl$_3$): δ=1.56 (s, 3H), 1.62 (s, 3H), 1.92~2.04 (m, 2H), 2.26 (q, J=3.7, 1H), 3.75~3.90 (m, 2H), 3.94 (td, J=3.9, 8.5, 1H), 5.23 (d, J=15.6, 1H), 7.22~7.27 (m, 1H), 7.33~7.39 (m, 2H), 7.62 (dd, J=1.6, 7.6, 1H)

Preparation Example 290

2-((4R,5R)-2,2-diethyl-5-phenyl-1,3-dioxolan-4-yl)ethyl pivalate

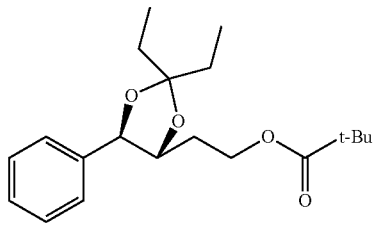 [SMILES: CCC1(CC)O[C@H](c2ccccc2)[C@@H](CCOC(=O)C(C)(C)C)O1]

The substantially same method as described in Example 264 was conducted, except that (3R,4R)-3,4-dihydroxy-4-phenylbutyl pivalate (Preparation example 283) was used instead of (4R,5S)-methyl-5-benzyl-2,2-dimethyl-1,3-dioxolane-4-carboxylate (Preparation example 263), to obtain the title compound (1.8 g, 70~95%)

$^1$H NMR (400 MHz, CDCl$_3$): δ=1.00 (t, J=7.4, 3H), 1.08 (t, J=7.6, 3H), 1.14 (s, 9H), 1.76 (q, J=7.5, 2H), 1.81~1.89 (m, 2H), 1.91~1.98 (m, 2H), 3.87 (td, J=5.8, 8.8, 1H), 4.13~4.18 (m, 1H), 4.22~4.28 (m, 1H), 4.58 (d, J=8.8, 1H), 7.31~7.43 (m, 5H)

Preparation Example 291

2-((4R,5R)-2,2-diethyl-5-phenyl-1,3-dioxolan-4-yl)ethyl pivalate

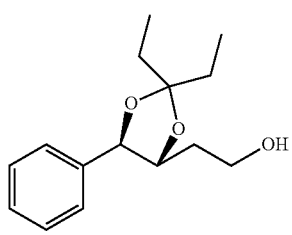 [SMILES: CCC1(CC)O[C@H](c2ccccc2)[C@@H](CCO)O1]

The substantially same method as described in Example 258 was conducted, except that 2-((4R,5R)-2,2-diethyl-5-phenyl-1,3-dioxolan-4-yl)ethyl pivalate (Preparation example 290) was used instead of 2-((2R,3R)-3-benzyl-1,4-dioxaspiro[4.5]decan-2-yl)ethyl pivalate (Preparation example 257), to obtain the title compound (0.9 g, 80~95%)

$^1$H NMR (400 MHz, CDCl$_3$): δ=1.01 (t, J=7.4, 3H), 1.07 (t, J=7.6, 3H), 1.79 (q, J=7.5, 2H), 1.83~1.90 (m, 4H), 2.38 (q, J=3.7, 1H), 3.75~3.87 (m, 2H), 3.90~3.95 (m, 1H), 4.63 (d, J=8.8, 1H), 7.32~7.43 (m, 5H)

Preparation Example 292

2-((2R,3R)-3-phenyl-1,4-dioxaspiro[4.4]nonan-2-yl) ethyl pivalate

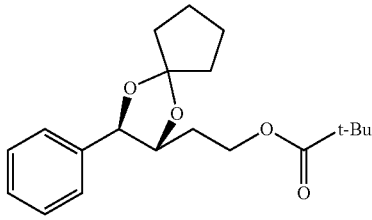 [SMILES: CC(C)(C)C(=O)OCC[C@H]1OC2(CCCC2)O[C@@H]1c1ccccc1]

The substantially same method as described in Example 290 was conducted, except that cyclopetanone was used instead of 3-pantanone, to obtain the title compound (1.8 g, 60~85%)

$^1$H NMR (400 MHz, CDCl$_3$): δ=1.14 (s, 9H), 1.67~1.83 (m, 4H), 1.88~2.07 (m, 6H), 3.84 (td, J=6.0, 8.4, 1H), 4.13 (td, J=7.0, 11.1, 1H), 4.24 (td, J=6.4, 11.2, 1H), 4.55 (d, J=8.4, 1H), 7.31~7.39 (m, 5H)

Preparation Example 293

2-((2R,3R)-3-phenyl-1,4-dioxaspiro[4.4]nonan-2-yl) ethanol

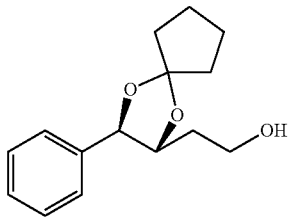 [SMILES: OCC[C@H]1OC2(CCCC2)O[C@@H]1c1ccccc1]

The substantially same method as described in Example 291 was conducted, except that 2-((2R,3R)-3-phenyl-1,4-dioxaspiro[4.4]nonan-2-yl)ethyl pivalate (Preparation example 292) was used instead of that 2-((4S,5S)-2,2-diethyl-5-phenyl-1,3-dioxolan-4-yl)ethyl pivalate (Preparation example 290), to obtain the title compound (0.9 g, 80~95%)

$^1$H NMR (400 MHz, CDCl$_3$): δ=1.71~1.81 (m, 4H), 1.87~2.07 (m, 6H), 2.27 (q, J=3.7, 1H), 3.79~3.85 (m, 2H), 3.89~3.92 (m, 1H), 4.59 (d, J=8.4, 1H), 7.32~7.41 (m, 5H)

Preparation Example 294

2-((2R,3R)-3-phenyl-1,4-dioxaspiro[4.5]decan-2-yl) ethyl pivalate

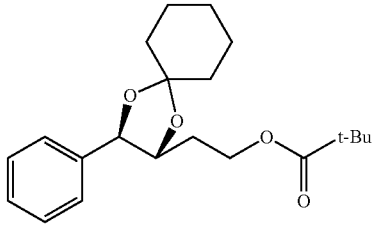 [SMILES: CC(C)(C)C(=O)OCC[C@H]1OC2(CCCCC2)O[C@@H]1c1ccccc1]

The substantially same method as described in Example 292 was conducted, except that cyclohexanone was used instead of cyclopetanone, to obtain the title compound (2.0 g, 60~85%)

$^1$H NMR (400 MHz, CDCl$_3$): δ=1.14 (s, 9H), 1.67~1.83 (m, 4H), 1.88~2.07 (m, 6H), 3.84 (td, J=6.0, 8.4, 1H), 4.10~4.17 (m, 1H), 4.21~4.27 (m, 1H), 4.55 (d, J=8.4, 1H), 7.31~7.39 (m, 5H)

Preparation Example 295

2-((2R,3R)-3-phenyl-1,4-dioxaspiro[4.5]decan-2-yl) ethanol

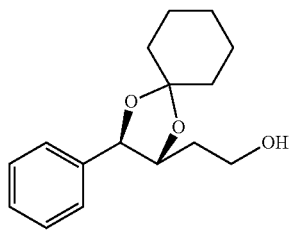 [SMILES: OCC[C@H]1OC2(CCCCC2)O[C@@H]1c1ccccc1]

The substantially same method as described in Example 293 was conducted, except that 2-((2R,3R)-3-phenyl-1,4-dioxaspiro[4.5]decan-2-yl)ethyl pivalate (Preparation example 294) was used instead of that 2-((2R,3R)-3-phenyl-1,4-dioxaspiro[4.4]nonan-2-yl)ethyl pivalate (Preparation example 292), to obtain the title compound (1.2 g, 80~95%)

$^1$H NMR (400 MHz, CDCl$_3$): δ=1.71~1.83 (m, 4H), 1.87~2.05 (m, 6H), 2.27 (q, J=3.7, 1H), 3.79~3.85 (m, 2H), 3.86~3.91 (m, 1H), 4.59 (d, J=8.4, 1H), 7.32~7.41 (m, 5H)

Preparation Example 296

2-((4S,5S)-2,2-diethyl-5-phenyl-1,3-dioxolan-4-yl) ethyl pivalate

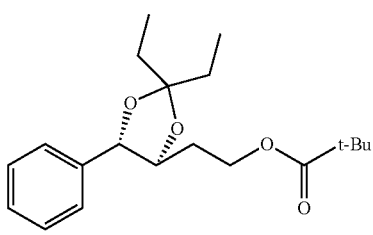 [SMILES: CCC1(CC)O[C@@H](CCOC(=O)C(C)(C)C)[C@H](c2ccccc2)O1]

The substantially same method as described in Example 290 was conducted, except that (3S,4S)-3,4-dihydroxy-4-phenylbutyl pivalate (Preparation example 287) was used instead of (3R,4R)-3,4-dihydroxy-4-phenylbutyl pivalate (Preparation example 283), to obtain the title compound (2.2 g, 70~95%)

$^1$H NMR (400 MHz, CDCl$_3$): δ=1.00 (t, J=7.4, 3H), 1.08 (t, J=7.6, 3H), 1.14 (s, 9H), 1.76 (q, J=7.5, 2H), 1.81~1.89 (m, 2H), 1.91~1.98 (m, 2H), 3.87 (td, J=5.8, 8.8, 1H), 4.13~4.18 (m, 1H), 4.22~4.28 (m, 1H), 4.58 (d, J=8.8, 1H), 7.31~7.43 (m, 5H)

Preparation Example 297

2-((4S,5S)-2,2-diethyl-5-phenyl-1,3-dioxolan-4-yl)ethyl pivalate

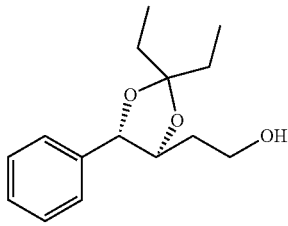 [SMILES: CCC1(CC)O[C@@H](CCO)[C@H](c2ccccc2)O1]

The substantially same method as described in Example 295 was conducted, except 2-((4S,5S)-2,2-diethyl-5-phenyl-1,3-dioxolan-4-yl)ethyl pivalate (Preparation example 296) was used instead of 2-((2R,3R)-3-phenyl-1,4-dioxaspiro[4.5]decan-2-yl)ethyl pivalate (Preparation example 294), to obtain the title compound (0.7 g, 80~95%)

$^1$H NMR (400 MHz, CDCl$_3$): δ=1.01 (t, J=7.4, 3H), 1.07 (t, J=7.6, 3H), 1.79 (q, J=7.5, 2H), 1.83~1.90 (m, 4H), 2.38 (q, J=3.7, 1H), 3.75~3.87 (m, 2H), 3.90~3.95 (m, 1H), 4.63 (d, J=8.8, 1H), 7.32~7.43 (m, 5H)

Preparation Example 298

2-((2S,3S)-3-phenyl-1,4-dioxaspiro[4.4]nonan-2-yl)ethyl pivalate

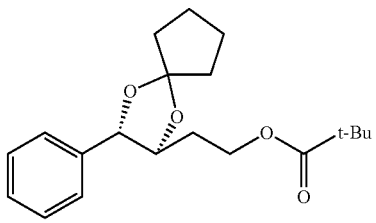 [SMILES: CC(C)(C)C(=O)OCC[C@@H]1OC2(CCCC2)O[C@H]1c1ccccc1]

The substantially same method as described in Example 296 was conducted, except that cyclopetanone was used instead of 3-pantanone, to obtain the title compound (2.4 g, 60~85%)

$^1$H NMR (400 MHz, CDCl$_3$): δ=1.14 (s, 9H), 1.67~1.83 (m, 4H), 1.88~2.07 (m, 6H), 3.84 (td, J=6.0, 8.4, 1H), 4.13 (td, J=7.0, 11.1, 1H), 4.24 (td, J=6.4, 11.2, 1H), 4.55 (d, J=8.4, 1H), 7.31~7.39 (m, 5H)

Preparation Example 299

2-((2S,3S)-3-phenyl-1,4-dioxaspiro[4.4]nonan-2-yl)ethanol

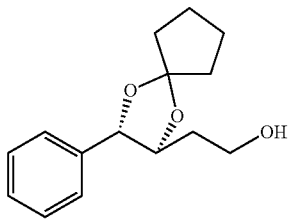 [SMILES: OCC[C@@H]1OC2(CCCC2)O[C@H]1c1ccccc1]

The substantially same method as described in Example 297 was conducted, except that 2-((2S,3S)-3-phenyl-1,4-dioxaspiro[4.4]nonan-2-yl)ethyl pivalate (Preparation example 298) was used instead of that 2-((4S,5S)-2,2-diethyl-5-phenyl-1,3-dioxolan-4-yl)ethyl pivalate (Preparation example 296), to obtain the title compound (07 g, 80~95%)

$^1$H NMR (400 MHz, CDCl$_3$): δ=1.71~1.81 (m, 4H), 1.87~2.07 (m, 6H), 2.27 (q, J=3.7, 1H), 3.79~3.85 (m, 2H), 3.89~3.92 (m, 1H), 4.59 (d, J=8.4, 1H), 7.32~7.41 (m, 5H)

Preparation Example 300

2-((2S,3S)-3-phenyl-1,4-dioxaspiro[4.5]decan-2-yl)ethyl pivalate

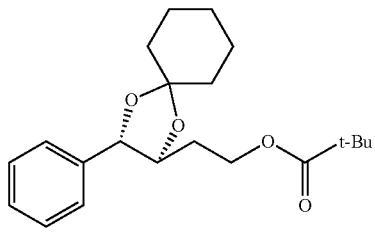 [SMILES: CC(C)(C)C(=O)OCC[C@@H]1OC2(CCCCC2)O[C@H]1c1ccccc1]

The substantially same method as described in Example 298 was conducted, except that cyclohexanone was used instead of cyclopetanone, to obtain the title compound (2.4 g, 60~85%)

$^1$H NMR (400 MHz, CDCl$_3$): δ=1.14 (s, 9H), 1.67~1.83 (m, 4H), 1.88~2.07 (m, 6H), 3.84 (td, J=6.0, 8.4, 1H), 4.10~4.17 (m, 1H), 4.21~4.27 (m, 1H), 4.55 (d, J=8.4, 1H), 7.31~7.39 (m, 5H)

Preparation Example 301

2-((2S,3S)-3-phenyl-1,4-dioxaspiro[4.5]decan-2-yl)ethanol

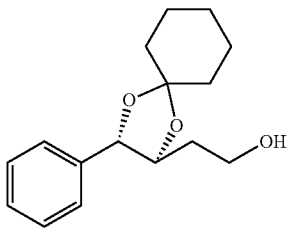 [SMILES: OCC[C@@H]1OC2(CCCCC2)O[C@H]1c1ccccc1]

The substantially same method as described in Example 299 was conducted, except that 2-((2S,3S)-3-phenyl-1,4-dioxaspiro[4.5]decan-2-yl)ethyl pivalate (Preparation example 300) was used instead of that 2-((2S,3S)-3-phenyl-1,4-dioxaspiro[4.4]nonan-2-yl)ethyl pivalate (Preparation example 298), to obtain the title compound (1.2 g, 80~95%)

$^1$H NMR (400 MHz, CDCl$_3$): δ=1.71~1.83 (m, 4H), 1.87~2.05 (m, 6H), 2.27 (q, J=3.7, 1H), 3.79~3.85 (m, 2H), 3.86~3.91 (m, 1H), 4.59 (d, J=8.4, 1H), 7.32~7.41 (m, 5H)

Preparation Example 302

(E)-5-(2-chlorophenyl)pent-3-enoic acid

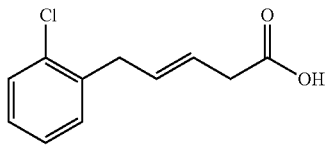 [SMILES: O=C(O)C/C=C/Cc1ccccc1Cl]

The substantially same method as described in Example 235 was conducted, except that 3-(2-chlorophenyl)propanal was used instead of that hydrocinnamaldehyde (6.1 g, 70~90%)

$^1$H NMR (400 MHz, CDCl$_3$): δ=3.15 (dd, J=0.8, 6.8, 2H), 3.53 (d, J=6.4, 2H), 5.61~5.69 (m, 1H), 5.75~5.82 (m, 1H), 7.16~7.28 (m, 3H), 7.36~7.38 (m, 1H)

Preparation Example 303

(E)-5-(2-chlorophenyl)pent-3-en-1-ol

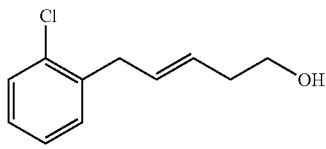 [SMILES: OCC/C=C/Cc1ccccc1Cl]

The substantially same method as described in Example 236 was conducted, except that (E)-5-(2-chlorophenyl)pent-3-enoic acid (Preparation example 302) was used instead of that (E)-5-phenylpent-3-enoic acid (Preparation example 235), to obtain the title compound (4.6 g, 70~90%)

$^1$H NMR (400 MHz, CDCl$_3$): δ=2.33 (dq, J=1.0, 6.5, 2H), 3.50 (dd, J=1.8, 5.0, 2H), 3.67 (q, J=6.0, 2H), 5.45~5.53 (m, 1H), 5.70~5.77 (m, 1H), 7.15~7.37 (m, 4H)

Preparation Example 304

(E)-tert-butyl(5-(2-chlorophenyl)pent-3-enyloxy)dimethylsilane

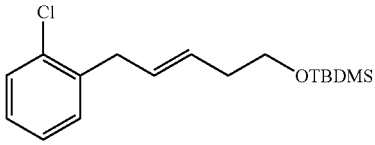 [SMILES: CC(C)(C)[Si](C)(C)OCC/C=C/Cc1ccccc1Cl]

The substantially same method as described in Example 237 was conducted, except that (E)-5-(2-chlorophenyl)pent-3-en-1-ol (Preparation example 303) was used instead of that (E)-5-phenylpent-3-en-1-ol (Preparation example 236), to obtain the title compound (4.9 g, 75~95%)

$^1$H NMR (400 MHz, CDCl$_3$): δ=0.60 (s, 6H), 0.90 (s, 9H), 2.28 (dq, J=1.0, 6.7, 2H), 3.47 (d, J=6.4, 2H), 3.65 (t, J=6.8, 2H), 5.49~5.56 (m, 1H), 5.62~5.70 (m, 1H), 7.14~7.36 (m, 4H)

Preparation Example 305

(E)-5-(2-chlorophenyl)pent-3-enyl pivalate

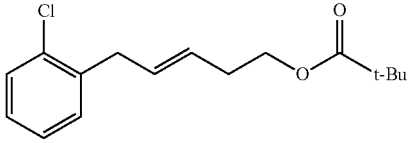 [SMILES: CC(C)(C)C(=O)OCC/C=C/Cc1ccccc1Cl]

The substantially same method as described in Example 238 was conducted, except that (E)-5-(2-chlorophenyl)pent-3-en-1-ol (Preparation example 303) was used instead of that (E)-5-phenylpent-3-en-1-ol (Preparation example 236), to obtain the title compound (7.2 g, 75~95%)

$^1$H NMR (400 MHz, CDCl$_3$): δ=1.18 (s, 9H), 2.36 (q, J=6.7, 2H), 3.45 (d, J=6.4, 2H), 4.08 (t, J=6.6, 2H), 5.43~5.50 (m, 1H), 5.63~5.70 (m, 1H), 7.12~7.35 (m, 4H)

Preparation Example 306

(2S,3S)-5-(tert-butyldimethylsilyloxy)-1-(2-chlorophenyl)pentane-2,3-diol

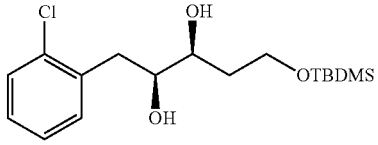 [SMILES: CC(C)(C)[Si](C)(C)OCC[C@H](O)[C@@H](O)Cc1ccccc1Cl]

The substantially same method as described in Example 239 was conducted, except that (E)-tert-butyl(5-(2-chlorophenyl)pent-3-enyloxy)dimethylsilane (Preparation example 304) was used instead of that (E)-tert-butyldimethyl(5-phenylpent-3-enyloxy)silane (Preparation example 237), to obtain the title compound (2.8 g, 90%)

$^1$H NMR (400 MHz, CDCl$_3$): δ=0.11 (s, 6H), 0.92 (s, 9H), 1.68~1.77 (m, 1H), 1.87~1.96 (m, 1H), 2.64 (d, J=6.0, 1H), 2.93 (dd, J=8.2, 13.4, 1H), 3.07 (dd, J=4.8, 13.6, 1H), 3.68 (d, J=3.2, 1H), 3.76~3.96 (m, 4H), 7.17~7.25 (m, 2H), 7.35~7.39 (m, 2H)

Preparation Example 307

(2-(4S,5S)-5-(2chlorobenzyl)-2,2-dimethyl-1,3-dioxolan-4-yl)ethoxy)(tert-butyl)dimethylsilane

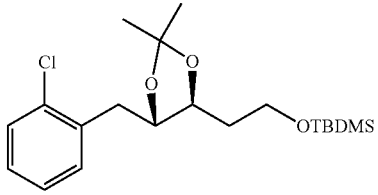 [SMILES: CC1(C)O[C@@H](CCO[Si](C)(C)C(C)(C)C)[C@H](Cc2ccccc2Cl)O1]

The substantially same method as described in Example 240 was conducted, except that (2S,3S)-5-(tert-butyldimethylsilyloxy)-1-(2-chlorophenyl)pentane-2,3-diol (Preparation example 306) was used instead of that (2S,3S)-5-(tert-butyldimethylsilyloxy)-1-phenylpentane-2,3-diol (Preparation example 239), to obtain the title compound (3.6 g, 75~90%)

¹H NMR (400 MHz, CDCl₃): δ=0.06 (s, 6H), 0.91 (s, 9H), 1.39 (s, 3H), 1.40 (s, 3H), 1.69 (q, J=6.5, 2H), 3.05 (dq, J=5.8, 15.1, 2H), 3.70~3.80 (m, 2H), 3.86~3.93 (m, 1H), 3.97~4.02 (m, 1H), 7.17~7.25 (m, 2H), 7.36~7.38 (m, 2H)

Preparation Example 308

2-((4S,5S)-5-(2-chlorobenzyl)-2,2-dimethyl-1,3-dioxolan-4-yl)ethanol

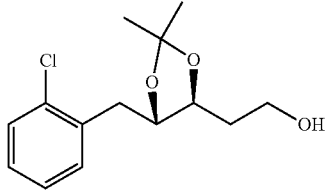 [SMILES: CC1(C)O[C@@H](CCO)[C@H](Cc2ccccc2Cl)O1]

The substantially same method as described in Example 241 was conducted, except that (2-(4S,5S)-5-(2chlorobenzyl)-2,2-dimethyl-1,3-dioxolan-4-yl)ethoxy)(tert-butyl)dimethylsilane (Preparation example 307) was used instead of that (2-(4S,5S)-5-benzyl-2,2-dimethyl-1,3-dioxolan-4-yl)ethoxy)(tert-butyl) dimethylsilane (Preparation example 240), to obtain the title compound (3.2 g, 80~95%)

¹H NMR (400 MHz, CDCl₃): δ=1.38 (s, 3H), 1.40 (s, 3H), 1.50~1.63 (m, 2H), 2.29 (t, J=5.4, 1H), 2.82 (dd, J=5.8, 13.8, 1H), 3.01 (dd, J=6.4, 14.0, 1H), 3.72 (q, J=5.5, 2H), 3.86 (dt, J=3.2, 8.4, 1H), 3.92~3.97 (m, 1H), 7.17~7.25 (m, 2H), 7.36~7.38 (m, 2H)

Preparation Example 309

(2R,3R)-5-(tert-butyldimethylsilyloxy)-1-(2-chlorophenyl)pentane-2,3-diol

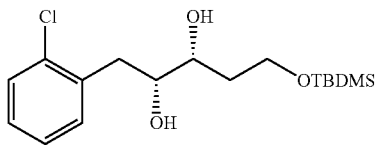 [SMILES: CC(C)(C)[Si](C)(C)OCC[C@@H](O)[C@H](O)Cc1ccccc1Cl]

The substantially same method as described in Example 242 was conducted, except that (E)-tert-butyl(5-(2-chlorophenyl)pent-3-enyloxy)dimethylsilane (Preparation example 304) was used instead of that (E)-tert-butyldimethyl(5-phenylpent-3-enyloxy)silane (Preparation example 237), to obtain the title compound (4.4 g, 90%)

¹H NMR (400 MHz, CDCl₃): δ=0.11 (s, 6H), 0.92 (s, 9H), 1.68~1.77 (m, 1H), 1.87~1.96 (m, 1H), 2.64 (d, J=6.0, 1H), 2.93 (dd, J=8.2, 13.4, 1H), 3.07 (dd, J=4.8, 13.6, 1H), 3.68 (d, J=3.2, 1H), 3.76~3.96 (m, 4H), 7.17~7.25 (m, 2H), 7.35~7.39 (m, 2H)

Preparation Example 310

(2-(4R,5R)-5-(2chlorobenzyl)-2,2-dimethyl-1,3-dioxolan-4-yl)ethoxy)(tert-butyl)dimethylsilane

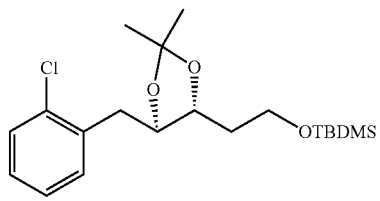 [SMILES: CC1(C)O[C@H](CCO[Si](C)(C)C(C)(C)C)[C@@H](Cc2ccccc2Cl)O1]

The substantially same method as described in Example 307 was conducted, except that (2R,3R)-5-(tert-butyldimethylsilyloxy)-1-(2-chlorophenyl)pentane-2,3-diol (Preparation example 309) was used instead of (2S,3S)-5-(tert-butyldimethylsilyloxy)-1-(2-chlorophenyl)pentane-2,3-diol (Preparation example 306), to obtain the title compound (4.6 g, 70~95%)

¹H NMR (400 MHz, CDCl₃): δ=0.06 (s, 6H), 0.91 (s, 9H), 1.39 (s, 3H), 1.40 (s, 3H), 1.69 (q, J=6.5, 2H), 3.05 (dq, J=5.8, 15.1, 2H), 3.70~3.80 (m, 2H), 3.86~3.93 (m, 1H), 3.97~4.02 (m, 1H), 7.17~7.25 (m, 2H), 7.36~7.38 (m, 2H)

Preparation Example 311

2-((4R,5R)-5-(2-chlorobenzyl)-2,2-dimethyl-1,3-dioxolan-4-yl)ethanol

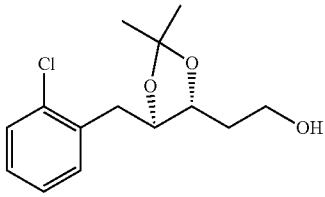 [SMILES: CC1(C)O[C@H](CCO)[C@@H](Cc2ccccc2Cl)O1]

The substantially same method as described in Example 241 was conducted, except that (2-(4S,5S)-5-(2chlorobenzyl)-2,2-dimethyl-1,3-dioxolan-4-yl)ethoxy)(tert-butyl)dimethylsilane (Preparation example 307) was used instead of that (2-(4S,5S)-5-benzyl-2,2-dimethyl-1,3-dioxolan-4-yl)ethoxy)(tert-butyl)dimethylsilane (Preparation example 240), to obtain the title compound (3.0 g, 80~95%)

¹H NMR (400 MHz, CDCl₃): δ=1.38 (s, 3H), 1.40 (s, 3H), 1.50~1.63 (m, 2H), 2.29 (t, J=5.4, 1H), 2.82 (dd, J=5.8, 13.8,

1H), 3.01 (dd, J=6.4, 14.0, 1H), 3.72 (q, J=5.5, 2H), 3.86 (dt, J=3.2, 8.4, 1H), 3.92~3.97 (m, 1H), 7.17~7.25 (m, 2H), 7.36~7.38 (m, 2H)

Preparation Example 312

(3S,4S)-3,4-dihydroxy-5-(2chlorophenyl)pentyl pivalate

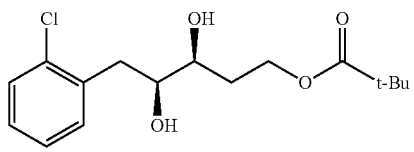

The substantially same method as described in Example 306 was conducted, except that (E)-5-(2-chlorophenyl)pent-3-enyl pivalate (Preparation example 305) was used instead of (E)-tert-butyl(5-(2-chlorophenyl)pent-3-enyloxy)dimethylsilane (Preparation example 304), to obtain the title compound (6.0 g, 70~95%)

$^1$H NMR (400 MHz, CDCl$_3$): δ=1.16 (s, 9H), 1.85~1.91 (m, 2H), 2.17 (d, J=6.0, 1H), 2.73 (d, J=5.2, 1H), 2.91 (dd, J=8.4, 13.6, 1H), 3.08 (dd, J=5.6, 13.6, 1H), 3.52~3.55 (m, 1H), 3.77~3.80 (m, 1H), 4.11~4.19 (m, 1H), 4.37~4.41 (m, 1H), 7.18~7.23 (m, 2H), 7.31 (dd, J=2.2, 7.0, 1H), 7.36 (dd, J=1.8, 7.4, 1H)

Preparation Example 313

2-((4S,5S)-5-(2-chlorobenzyl)-2,2-diethyl-1,3-dioxolan-4-yl)ethyl pivalate

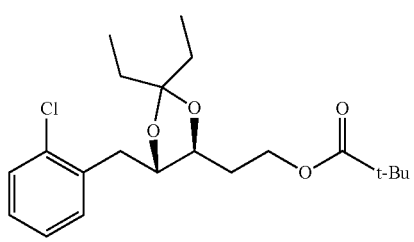 [SMILES: CCC1(CC)O[C@@H](CCOC(=O)C(C)(C)C)[C@H](Cc2ccccc2Cl)O1]

The substantially same method as described in Example 246 was conducted, except that (3S,4S)-3,4-dihydroxy-5-(2chlorophenyl)pentyl pivalate (Preparation example 312) was used instead of (3S,4S)-3,4-dihydroxy-5-phenylpentyl pivalate (Preparation example 245), to obtain the title compound (1.7 g, 70~95%)

$^1$H NMR (400 MHz, CDCl$_3$): δ=0.90 (t, J=7.4, 6H), 1.21 (s, 9H), 1.58~1.66 (m, 4H), 1.70~1.77 (m, 2H), 3.06 (d, J=5.6, 2H), 3.81~3.86 (m, 1H), 3.94~3.99 (m, 1H), 4.15~4.25 (m, 2H), 7.18~7.24 (m, 2H), 7.36~7.38 (m, 2H)

Preparation Example 314

2-((4S,5S)-5-(2-chlorobenzyl)-2,2-dimethyl-1,3-dioxolan-4-yl)ethanol

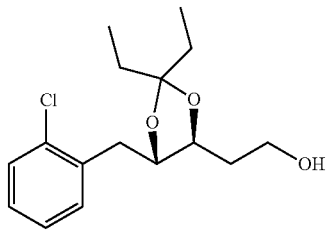 [SMILES: CCC1(CC)O[C@@H](CCO)[C@H](Cc2ccccc2Cl)O1]

The substantially same method as described in Example 247 was conducted, except that 2-((4S,5S)-5-(2-chlorobenzyl)-2,2-diethyl-1,3-dioxolan-4-yl)ethyl pivalate (Preparation example 313) was used instead of 2-((4S,5S)-5-benzyl-2,2-diethyl-1,3-dioxolan-4-yl)ethyl pivalate (Preparation example 246), to obtain the title compound (0.9 g, 80~95%);

$^1$H NMR (400 MHz, CDCl$_3$): δ=0.91 (dt, J=2.5, 7.5, 6H), 1.46~1.79 (m, 6H), 2.42 (t, J=5.6, 1H), 3.01~3.12 (m, 2H), 3.79 (q, J=5.6, 2H), 3.88~3.93 (m, 1H), 3.98~4.06 (m, 1H), 7.18~7.25 (m, 2H), 7.35~7.39 (m, 2H)

Preparation Example 315

(3R,4R)-3,4-dihydroxy-5-(2-chlorophenyl)pentyl pivalate

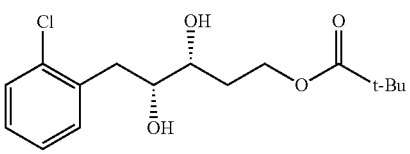 [SMILES: CC(C)(C)C(=O)OCC[C@@H](O)[C@H](O)Cc1ccccc1Cl]

The substantially same method as described in Example 309 was conducted, except that (E)-5-(2-chlorophenyl)pent-3-enyl pivalate (Preparation example 305) was used instead of (E)-tert-butyl(5-(2-chlorophenyl)pent-3-enyloxy)dimethylsilane (Preparation example 304), to obtain the title compound (4.4 g, 70~95%)

$^1$H NMR (400 MHz, CDCl$_3$): δ=0.11 (s, 6H), 0.92 (s, 9H), 1.68~1.77 (m, 1H), 1.87~1.96 (m, 1H), 2.64 (d, J=6.0, 1H), 2.93 (dd, J=8.2, 13.4, 1H), 3.07 (dd, J=4.8, 13.6, 1H), 3.68 (d, J=3.2, 1H), 3.76~3.96 (m, 4H), 7.17~7.25 (m, 2H), 7.35~7.39 (m, 2H)

Preparation Example 316

2-((4R,5R)-5-(2-chlorobenzyl)-2,2-diethyl-1,3-dioxolan-4-yl)ethyl pivalate

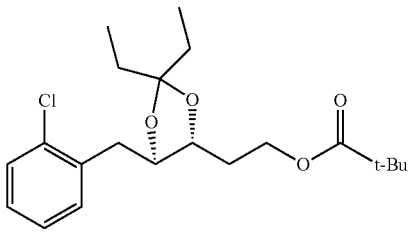 [SMILES: CCC1(CC)O[C@H](CCOC(=O)C(C)(C)C)[C@@H](Cc2ccccc2Cl)O1]

The substantially same method as described in Example 313 was conducted, except that (3R,4R)-3,4-dihydroxy-5-(2chlorophenyl)pentyl pivalate (Preparation example 315) was used instead of (3S,4S)-3,4-dihydroxy-5-(2chlorophenyl)pentyl pivalate (Preparation example 312), to obtain the title compound (1.7 g, 70~95%)

$^1$H NMR (400 MHz, CDCl$_3$): δ=0.90 (t, J=7.4, 6H), 1.21 (s, 9H), 1.58~1.66 (m, 4H), 1.70~1.77 (m, 2H), 3.06 (d, J=5.6, 2H), 3.81~3.86 (m, 1H), 3.94~3.99 (m, 1H), 4.15~4.25 (m, 2H), 7.18~7.24 (m, 2H), 7.36~7.38 (m, 2H)

Preparation Example 317

2-((4R,5R)-5-(2-chlorobenzyl)-2,2-dimethyl-1,3-dioxolan-4-yl)ethanol

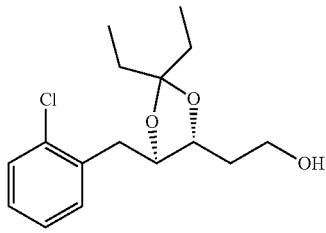 [SMILES: CCC1(CC)O[C@H](CCO)[C@@H](Cc2ccccc2Cl)O1]

The substantially same method as described in Example 314 was conducted, except that 2-((4R,5R)-5-(2-chlorobenzyl)-2,2-diethyl-1,3-dioxolan-4-yl)ethyl pivalate (Preparation example 316) was used instead of 2-((4S,5S)-5-(2-chlorobenzyl)-2,2-diethyl-1,3-dioxolan-4-yl)ethyl pivalate (Preparation example 313), to obtain the title compound (0.9 g, 80~95%)

$^1$H NMR (400 MHz, CDCl$_3$): δ=0.91 (dt, J=2.5, 7.5, 6H), 1.46~1.79 (m, 6H), 2.42 (t, J=5.6, 1H), 3.01~3.12 (m, 2H), 3.79 (q, J=5.6, 2H), 3.88~3.93 (m, 1H), 3.98~4.06 (m, 1H), 7.18~7.25 (m, 2H), 7.35~7.39 (m, 2H)

Preparation Example 318

2-((2S,3S)-3-(2-chlorobenzyl)-1,4-dioxaspiro[4.4]nonan-2-yl)ethyl pivalate

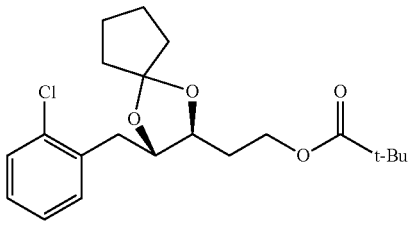 [SMILES: CC(C)(C)C(=O)OCC[C@@H]1OC2(CCCC2)O[C@H]1Cc1ccccc1Cl]

The substantially same method as described in Example 313 was conducted, except that cyclopetanone was used instead of 3-pantanone, to obtain the title compound (1.2 g, 60~85%)

$^1$H NMR (400 MHz, CDCl$_3$): δ=1.21 (s, 9H), 1.64~1.74 (m, 5H), 1.75~1.88 (m, 5H), 3.03~3.11 (m, 2H), 3.81~3.86 (m, 1H), 3.97 (q, J=6.5, 1H), 4.12~4.22 (m, 2H), 7.18~7.25 (m, 2H), 7.34~7.39 (m, 2H)

Preparation Example 319

2-((2S,3S)-3-(2-chlorobenzyl)-1,4-dioxaspiro[4.4]nonan-2-yl)ethanol

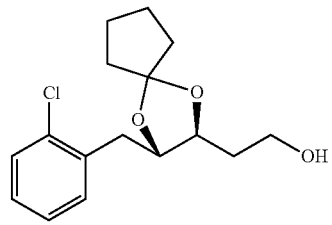 [SMILES: OCC[C@@H]1OC2(CCCC2)O[C@H]1Cc1ccccc1Cl]

The substantially same method as described in Example 317 was conducted, except that 2-((2S,3S)-3-(2-chlorobenzyl)-1,4-dioxaspiro[4.4]nonan-2-yl)ethyl pivalate (Preparation example 318) was used instead of 2-((4R,5R)-5-(2-chlorobenzyl)-2,2-diethyl-1,3-dioxolan-4-yl)ethyl pivalate (Preparation example 316), to obtain the title compound (0.7 g, 80~95%)

$^1$H NMR (400 MHz, CDCl$_3$): δ=1.62~1.74 (m, 6H), 1.75~1.88 (m, 4H), 2.28 (t, J=5.6, 1H), 3.03~3.12 (m, 2H), 3.78 (q, J=5.6, 1H), 3.88~3.95 (m, 1H), 3.97~4.06 (m, 1H), 7.18~7.26 (m, 2H), 7.34~7.39 (m, 2H)

Preparation Example 320

2-((2R,3R)-3-(2-chlorobenzyl)-1,4-dioxaspiro[4.4]nonan-2-yl)ethyl pivalate

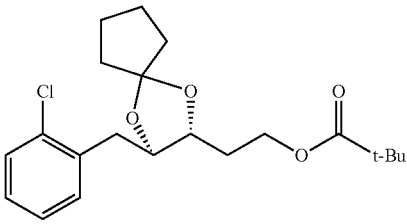 [SMILES: CC(C)(C)C(=O)OCC[C@H]1OC2(CCCC2)O[C@@H]1Cc1ccccc1Cl]

The substantially same method as described in Example 316 was conducted, except that cyclopetanone was used instead of 3-pantanone, to obtain the title compound (1.4 g, 60~85%)

$^1$H NMR (400 MHz, CDCl$_3$): δ=1.21 (s, 9H), 1.64~1.74 (m, 5H), 1.75~1.88 (m, 5H), 3.03~3.11 (m, 2H), 3.81~3.86 (m, 1H), 3.97 (q, J=6.5, 1H), 4.12~4.22 (m, 2H), 7.18~7.25 (m, 2H), 7.34~7.39 (m, 2H)

Preparation Example 321

2-((2R,3R)-3-(2-chlorobenzyl)-1,4-dioxaspiro[4.4]nonan-2-yl)ethanol

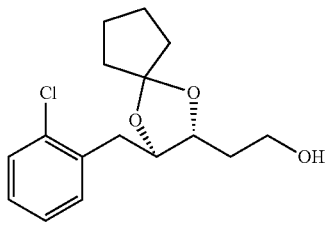 [SMILES: OCC[C@H]1OC2(CCCC2)O[C@@H]1Cc1ccccc1Cl]

The substantially same method as described in Example 319 was conducted, except that 2-((2R,3R)-3-(2-chlorobenzyl)-1,4-dioxaspiro[4.4]nonan-2-yl)ethyl pivalate (Preparation example 320) was used instead of 2-((2S,3S)-3-(2-chlorobenzyl)-1,4-dioxaspiro[4.4]nonan-2-yl)ethyl pivalate (Preparation example 318), to obtain the title compound (0.8 g, 80~95%)

$^1$H NMR (400 MHz, CDCl$_3$): δ=1.62~1.74 (m, 6H), 1.75~1.88 (m, 4H), 2.28 (t, J=5.6, 1H), 3.03~3.12 (m, 2H), 3.78 (q, J=5.6, 1H), 3.88~3.95 (m, 1H), 3.97~4.06 (m, 1H), 7.18~7.26 (m, 2H), 7.34~7.39 (m, 2H)

Preparation Example 322

2-((2S,3S)-3-(2-chlorobenzyl)-1,4-dioxaspiro[4.5]decan-2-yl)ethyl pivalate

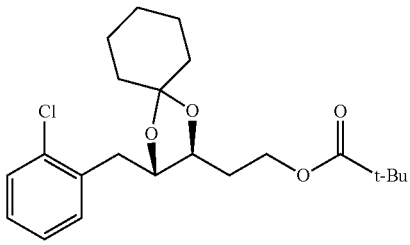 [SMILES: CC(C)(C)C(=O)OCC[C@@H]1OC2(CCCCC2)O[C@H]1Cc1ccccc1Cl]

The substantially same method as described in Example 318 was conducted, except that cyclohexanone was used instead of cyclopetanone, to obtain the title compound (1.1 g, 60~85%)

$^1$H NMR (400 MHz, CDCl$_3$): δ=1.21 (s, 9H), 1.58~1.61 (m, 8H), 1.77 (q, J=6.8, 2H), 3.07 (d, J=6.0, 2H), 3.81~3.88 (m, 1H), 3.96~4.01 (m, 1H), 4.16~4.22 (m, 2H), 7.17~7.25 (m, 2H), 7.36~7.39 (m, 2H)

Preparation Example 323

2-((2S,3S)-3-(2-chlorobenzyl)-1,4-dioxaspiro[4.5]decan-2-yl)ethanol

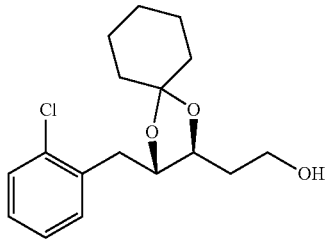 [SMILES: OCC[C@@H]1OC2(CCCCC2)O[C@H]1Cc1ccccc1Cl]

The substantially same method as described in Example 321 was conducted, except that 2-((2S,3S)-3-(2-chlorobenzyl)-1,4-dioxaspiro[4.5]decan-2-yl)ethyl pivalate (Preparation example 322) was used instead of 2-((2R,3R)-3-(2-chlorobenzyl)-1,4-dioxaspiro[4.4]nonan-2-yl)ethyl pivalate (Preparation example 320), to obtain the title compound (0.7 g, 80~95%)

$^1$H NMR (400 MHz, CDCl$_3$): δ=1.51~1.64 (m, 8H), 1.65~1.74 (m, 2H), 2.59~2.63 (m, 1H), 3.06 (d, J=6.0, 2H), 3.76~3.78 (m, 2H), 3.89~3.94 (m, 1H), 3.99~4.04 (m, 1H), 7.16~7.24 (m, 2H), 7.35~7.38 (m, 2H)

Preparation Example 324

2-((2R,3R)-3-(2-chlorobenzyl)-1,4-dioxaspiro[4.5]decan-2-yl)ethyl pivalate

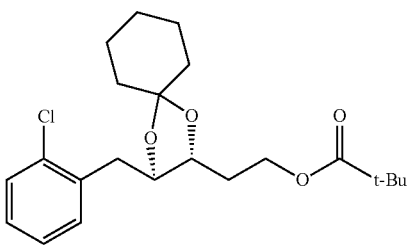 [SMILES: CC(C)(C)C(=O)OCC[C@H]1OC2(CCCCC2)O[C@@H]1Cc1ccccc1Cl]

The substantially same method as described in Example 320 was conducted, except that cyclohexanone was used instead of cyclopetanone, to obtain the title compound (1.5 g, 60~85%)

$^1$H NMR (400 MHz, CDCl$_3$): δ=1.21 (s, 9H), 1.58~1.61 (m, 8H), 1.77 (q, J=6.8, 2H), 3.07 (d, J=6.0, 2H), 3.81~3.88 (m, 1H), 3.96~4.01 (m, 1H), 4.16~4.22 (m, 2H), 7.17~7.25 (m, 2H), 7.36~7.39 (m, 2H)

Preparation Example 325

2-((2R,3R)-3-(2-chlorobenzyl)-1,4-dioxaspiro[4.5]decan-2-yl)ethanol

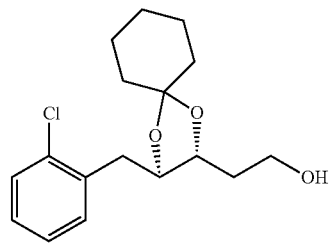 [SMILES: OCC[C@H]1OC2(CCCCC2)O[C@@H]1Cc1ccccc1Cl]

The substantially same method as described in Example 323 was conducted, except that 2-((2R,3R)-3-(2-chlorobenzyl)-1,4-dioxaspiro[4.5]decan-2-yl)ethyl pivalate (Preparation example 324) was used instead of 2-((2S,3S)-3-(2-chlorobenzyl)-1,4-dioxaspiro[4.5]decan-2-yl)ethyl pivalate (Preparation example 322), to obtain the title compound (0.9 g, 80~95%)

$^1$H NMR (400 MHz, CDCl$_3$): δ=1.51~1.64 (m, 8H), 1.65~1.74 (m, 2H), 2.59~2.63 (m, 1H), 3.06 (d, J=6.0, 2H), 3.76~3.78 (m, 2H), 3.89~3.94 (m, 1H), 3.99~4.04 (m, 1H), 7.16~7.24 (m, 2H), 7.35~7.38 (m, 2H)

Preparation Example 326

(E)-methyl-4-(2-chlorophenyl)but-2-enoate

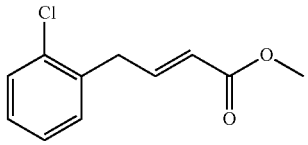

The substantially same method as described in Example 259 was conducted, except that 2-chlorophenyl acetaldehyde was used instead of phenyl acetaldehyde, to obtain the title compound (5.0 g, 65~85%)

$^1$H NMR (400 MHz, CDCl$_3$): δ=3.47 (d, J=6.8, 2H), 3.67 (s, 3H), 5.79 (d, J=15.4, 1H), 7.06 (dt, J=15.4, 6.8, 1H), 7.12~7.28 (m, 4H)

Preparation Example 327

(2R,3S)-methyl-4-(2chlorophenyl)-2,3-dihydroxybutanoate

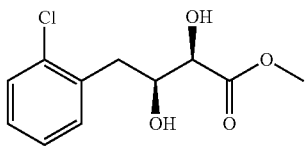 [SMILES: COC(=O)[C@H](O)[C@@H](O)Cc1ccccc1Cl]

The substantially same method as described in Example 260 was conducted, except that (E)-methyl-4-(2-chlorophenyl)but-2-enoate (Preparation example 326) was used instead of (E)-methyl-4-phenylbut-2-enoate (Preparation example 259), to obtain the title compound (3.0 g, 70~95%)

$^1$H NMR (400 MHz, CDCl$_3$): δ=3.08~3.17 (m, 2H), 3.84 (s, 3H), 4.12 (dd, J=1.6, 5.2, 1H), 4.28~4.34 (m, 1H), 7.20~7.27 (m, 2H), 7.33~7.36 (m, 1H), 7.39~7.41 (m, 1H)

Preparation Example 328

(4R,5S)-methyl-5-(2-chlorobenzyl)-2,2-dimethyl-1,3-dioxolane-4-carboxylate

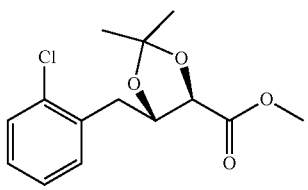 [SMILES: COC(=O)[C@@H]1OC(C)(C)O[C@H]1Cc1ccccc1Cl]

The substantially same method as described in Example 261 was conducted, except that (2R,3S)-methyl-4-(2chlorophenyl)-2,3-dihydroxybutanoate (Preparation example 327) was used instead of (2R,3S)-methyl 2,3-dihydroxy-4-phenylbutanoate (Preparation example 260), to obtain the title compound (0.6 g, 70~95%)

$^1$H NMR (400 MHz, CDCl$_3$): δ=1.45 (s, 3H), 1.49 (s, 3H), 3.11 (dd, J=7.6, 14.4, 1H), 3.35 (dd, J=4.4, 14.4, 1H), 3.74 (s, 3H), 4.30 (d, J=7.6, 1H), 4.50 (dt, J=4.0, 7.6, 1H), 7.19~7.26 (m, 2H), 7.36~7.40 (m, 2H)

Preparation Example 329

((4S,5S)-5-(2-chlorobenzyl)-2,2-dimethyl-1,3-dioxolan-4-yl)methanol

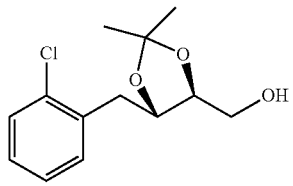 [SMILES: CC1(C)O[C@@H](CO)[C@H](Cc2ccccc2Cl)O1]

The substantially same method as described in Example 262 was conducted, except that (4R,5S)-methyl-5-(2-chlorobenzyl)-2,2-dimethyl-1,3-dioxolane-4-carboxylate (Preparation example 328) was used instead of (4R,5S)-methyl 5-benzyl-2,2-dimethyl-1,3-dioxolane-4-carboxylate (Preparation example 261), to obtain the title compound (0.5 g, 70~95%)

$^1$H NMR (400 MHz, CDCl$_3$): δ=1.43 (s, 6H), 1.83 (q, J=4.3, 1H), 3.06~3.17 (m, 2H), 3.45 (ddd, J=4.6, 7.4, 12.0, 1H), 3.68 (ddd, J=3.2, 5.2, 12.0, 1H), 3.91 (ddd, J=3.3, 4.7, 8.0, 1H), 4.22~4.27 (m, 1H), 7.20~7.26 (m, 2H), 7.35~7.40 (m, 2H)

Preparation Example 330

(4R,5S)-methyl-5-(2-chlorobenzyl)-2,2-diethyl-1,3-dioxolane-4-carboxylate

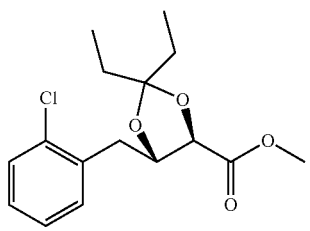 [SMILES: CCC1(CC)O[C@@H](Cc2ccccc2Cl)[C@H](C(=O)OC)O1]

The substantially same method as described in Example 263 was conducted, except that (2R,3S)-methyl-4-(2chlorophenyl)-2,3-dihydroxybutanoate (Preparation example 327) was used instead of (2R,3S)-methyl 2,3-dihydroxy-4-phenylbutanoate (Preparation example 260), to obtain the title compound (0.8 g, 50~75%)

$^1$H NMR (400 MHz, CDCl$_3$): δ=0.93 (t, J=7.4, 6H), 1.67~1.74 (m, 4H), 3.10 (dd, J=8.0, 14.4, 1H), 3.35 (dd, J=4.0, 14.4, 1H), 3.73 (s, 3H), 4.27 (d, J=8.4, 1H), 4.42~4.47 (m, 1H), 7.18~7.26 (m, 2H), 7.37~7.40 (m, 2H)

Preparation Example 331

((4S,5S)-5-(2-chlorobenzyl)-2,2-diethyl-1,3-dioxolan-4-yl)methanol

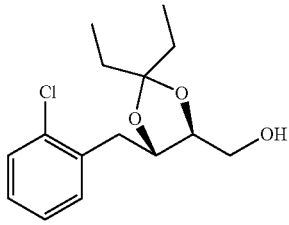 [SMILES: CCC1(CC)O[C@@H](CO)[C@H](Cc2ccccc2Cl)O1]

The substantially same method as described in Example 329 was conducted, except that (4R,5S)-methyl-5-(2-chlorobenzyl)-2,2-dimethyl-1,3-dioxolane-4-carboxylate (Preparation example 330) was used instead of (4R,5S)-methyl-5-(2-chlorobenzyl)-2,2-dimethyl-1,3-dioxolane-4-carboxylate (Preparation example 328), to obtain the title compound (0.6 g, 70~95%)

$^1$H NMR (400 MHz, CDCl$_3$): δ=0.93 (dt, J=2.1, 7.5, 6H), 1.62~1.70 (m, 4H), 1.83 (q, J=4.3, 1H), 3.11 (ddd, J=6.0, 14.2, 28.0, 2H), 3.44 (ddd, J=4.8, 7.2, 12.0, 1H), 3.64~3.69 (m, 1H), 3.88 (ddd, J=3.3, 4.9, 8.3, 1H), 4.18~4.24 (m, 1H), 7.19~7.26 (m, 2H), 7.36~7.39 (m, 2H)

Preparation Example 332

(2R,3S)-methyl-3-(2-chlorobenzyl)-1,4-dioxaspiro[4.4]nonane-2-carboxylate

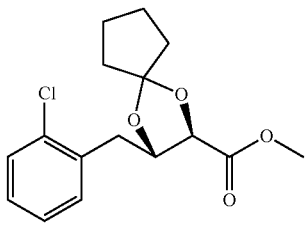 [SMILES: COC(=O)[C@@H]1OC2(CCCC2)O[C@H]1Cc1ccccc1Cl]

The substantially same method as described in Example 330 was conducted, except that cyclopetanone was used instead of 3-pantanone, to obtain the title compound (0.8 g, 60~85%)

$^1$H NMR (400 MHz, CDCl$_3$): δ=1.65~1.80 (m, 5H), 1.89~2.00 (m, 3H), 3.13 (dd, J=7.8, 14.2, 1H), 3.32 (dd, J=4.6, 14.2, 1H), 3.72 (s, 3H), 4.28 (d, J=7.2, 1H), 4.41~4.46 (m, 1H), 7.19~7.26 (m, 2H), 7.35~7.40 (m, 2H)

Preparation Example 333

((2S,3S)-3-(2chlorobenzyl)-1,4-dioxaspiro[4.4]nonan-2-yl)methanol

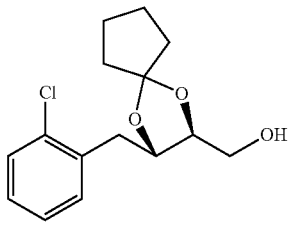 [SMILES: OC[C@@H]1OC2(CCCC2)O[C@H]1Cc1ccccc1Cl]

The substantially same method as described in Example 331 was conducted, except that (2R,3S)-methyl-3-(2-chlorobenzyl)-1,4-dioxaspiro[4.4]nonane-2-carboxylate (Preparation example 332) was used instead of (4R,5S)-methyl-5-(2-chlorobenzyl)-2,2-dimethyl-1,3-dioxolane-4-carboxylate (Preparation example 330), to obtain the title compound (0.6 g, 70~95%)

$^1$H NMR (400 MHz, CDCl$_3$): δ=1.69~1.74 (m, 3H), 1.77~1.85 (m, 5H), 3.11 (ddd, J=6.3, 14.1, 31.3, 2H), 3.42~3.48 (m, 1H), 3.61~3.66 (m, 1H), 3.87~3.91 (m, 1H), 4.19 (q, J=6.8, 1H), 7.19~7.26 (m, 2H), 7.34~7.40 (m, 2H)

Preparation Example 334

(2R,3S)-methyl-3-(2-chlorobenzyl)-1,4-dioxaspiro[4.5]decane-2-carboxylate

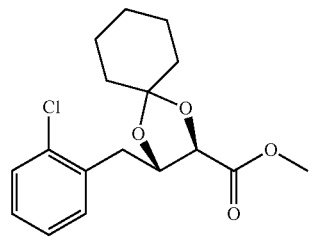 [SMILES: COC(=O)[C@@H]1OC2(CCCCC2)O[C@H]1Cc1ccccc1Cl]

The substantially same method as described in Example 332 was conducted, except that cyclohexanone was used instead of cyclopetanone, to obtain the title compound (0.5 g, 60~85%)

$^1$H NMR (400 MHz, CDCl$_3$): δ=1.54~1.77 (m, 10H), 3.12 (dd, J=7.6, 14.4, 1H), 3.32 (dd, J=4.4, 14.4, 1H), 3.72 (s, 3H), 4.30 (d, J=7.6, 1H), 4.46~4.51 (m, 1H), 7.18~7.26 (m, 2H), 7.37~7.39 (m, 2H)

Preparation Example 335

((2S,3S)-3-(2chlorobenzyl)-1,4-dioxaspiro[4.5]decan-2-yl)methanol

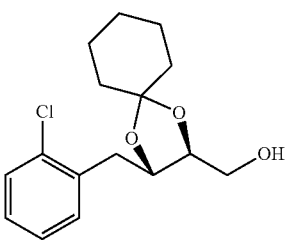 [SMILES: OC[C@@H]1OC2(CCCCC2)O[C@H]1Cc1ccccc1Cl]

The substantially same method as described in Example 333 was conducted, except that (2R,3S)-methyl-3-(2-chlorobenzyl)-1,4-dioxaspiro[4.5]decane-2-carboxylate (Preparation example 334) was used instead of (2R,3S)-methyl-3-(2-chlorobenzyl)-1,4-dioxaspiro[4.4]nonane-2-carboxylate (Preparation example 332), to obtain the title compound (0.5 g, 70~95%)

$^1$H NMR (400 MHz, CDCl$_3$): δ=1.38~1.45 (m, 2H), 1.58~1.63 (m, 8H), 1.84 (q, J=4.3, 1H), 3.11 (ddd, J=7.9, 15.9, 22.1, 2H), 3.43 (ddd, J=4.6, 7.6, 12.1, 1H), 3.66~3.71 (m, 1H), 3.88~3.92 (m, 1H), 4.21~4.26 (m, 1H), 7.18~7.26 (m, 2H), 7.37~7.39 (m, 2H)

Preparation Example 336

(2S,3R)-methyl-4-(2chlorophenyl)-2,3-dihydroxybutanoate

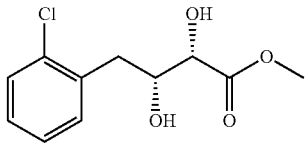 [SMILES: COC(=O)[C@@H](O)[C@H](O)Cc1ccccc1Cl]

The substantially same method as described in Example 269 was conducted, except that (E)-methyl-4-(2-chlorophenyl)but-2-enoate (Preparation example 326) was used instead of (E)-methyl-4-phenylbut-2-enoate (Preparation example 259), to obtain the title compound (3.5 g, 70~95%)

$^1$H NMR (400 MHz, CDCl$_3$): δ=3.08~3.17 (m, 2H), 3.84 (s, 3H), 4.12 (dd, J=1.6, 5.2, 1H), 4.28~4.34 (m, 1H), 7.20~7.27 (m, 2H), 7.33~7.36 (m, 1H), 7.39~7.41 (m, 1H)

Preparation Example 337

(4S,5R)-methyl-5-(2-chlorobenzyl)-2,2-dimethyl-1,3-dioxolane-4-carboxylate

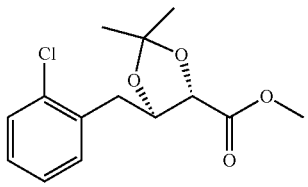 [SMILES: COC(=O)[C@H]1OC(C)(C)O[C@@H]1Cc1ccccc1Cl]

The substantially same method as described in Example 328 was conducted, except that (2S,3R)-methyl-4-(2chlorophenyl)-2,3-dihydroxybutanoate (Preparation example 336) was used instead of (2R,3S)-methyl-4-(2chlorophenyl)-2,3-dihydroxybutanoate (Preparation example 327), to obtain the title compound (3.4 g, 70~95%)

$^1$H NMR (400 MHz, CDCl$_3$): δ=1.41 (s, 6H), 1.79 (q, J=4.3, 1H), 2.83 (dd, J=6.2, 13.8, 1H), 3.07 (dd, J=6.4, 14.0, 1H), 3.29 (ddd, J=4.7, 7.5, 12.1, 1H), 3.54 (ddd, J=2.8, 5.2, 12.0, 1H), 3.83 (ddd, J=3.9, 3.9, 7.1, 1H), 4.15 (q, J=7.1, 1H), 7.22~7.32 (m, 5H)

Preparation Example 338

((4R,5R)-5-(2chlorobenzyl)-2,2-dimethyl-1,3-dioxolan-4-yl)methanol

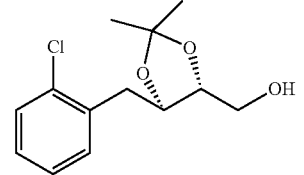 [SMILES: CC1(C)O[C@H](CO)[C@@H](Cc2ccccc2Cl)O1]

The substantially same method as described in Example 335 was conducted, except that (4S,5R)-methyl-5-(2-chlorobenzyl)-2,2-dimethyl-1,3-dioxolane-4-carboxylate (Preparation example 337) was used instead of (2R,3S)-methyl-3-(2-chlorobenzyl)-1,4-dioxaspiro[4.5]decane-2-carboxylate (Preparation example 334), to obtain the title compound (2.7 g, 70~95%).

$^1$H NMR (400 MHz, CDCl$_3$): δ=1.41 (s, 6H), 1.79 (q, J=4.3, 1H), 2.83 (dd, J=6.2, 13.8, 1H), 3.07 (dd, J=6.4, 14.0, 1H), 3.29 (ddd, J=4.7, 7.5, 12.1, 1H), 3.54 (ddd, J=2.8, 5.2, 12.0, 1H), 3.83 (ddd, J=3.9, 3.9, 7.1, 1H), 4.15 (q, J=7.1, 1H), 7.22~7.32 (m, 5H)

Preparation Example 339

(4S,5R)-methyl-(5-2-chlprp)benzyl-2,2-diethyl-1,3-dioxolane-4-carboxylate

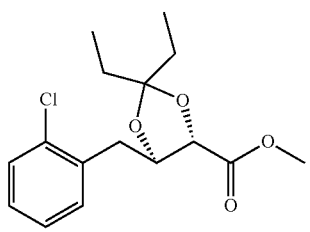 [SMILES: CCC1(CC)O[C@H](C(=O)OC)[C@@H](Cc2ccccc2Cl)O1]

The substantially same method as described in Example 330 was conducted, except that (2S,3R)-methyl-2,3-dihydroxy-4-phenylbutanoate (Preparation example 336) was used instead of that (2R,3S)-methyl-4-(2chlorophenyl)-2,3-dihydroxybutanoate (Preparation example 327), to obtain the title compound (0.6 g, 50~75%)

$^1$H NMR (400 MHz, CDCl$_3$): δ=0.93 (t, J=7.4, 6H), 1.67~1.74 (m, 4H), 3.10 (dd, J=8.0, 14.4, 1H), 3.35 (dd, J=4.0, 14.4, 1H), 3.73 (s, 3H), 4.27 (d, J=8.4, 1H), 4.42~4.47 (m, 1H), 7.18~7.26 (m, 2H), 7.37~7.40 (m, 2H)

Preparation Example 340

((4R,5R)-5-(2-chlorobenzyl)-2,2-diethyl-1,3-dioxolan-4-yl)methanol

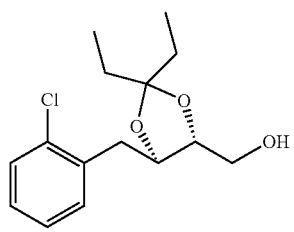 [SMILES: CCC1(CC)O[C@H](CO)[C@@H](Cc2ccccc2Cl)O1]

The substantially same method as described in Example 338 was conducted, except that (4S,5R)-methyl-(5-2-chlprp)benzyl-2,2-diethyl-1,3-dioxolane-4-carboxylate (Preparation example 339) was used instead of (4S,5R)-methyl-5-(2-chlrobenzyl)-2,2-dimethyl-1,3-dioxolane-4-carboxylate (Preparation example 337), to obtain the title compound (0.5 g, 70~95%)

$^1$H NMR (400 MHz, CDCl$_3$): δ=0.93 (dt, J=2.1, 7.5, 6H), 1.62~1.70 (m, 4H), 1.83 (q, J=4.3, 1H), 3.11 (ddd, J=6.0, 14.2, 28.0, 2H), 3.44 (ddd, J=4.8, 7.2, 12.0, 1H), 3.64~3.69

(m, 1H), 3.88 (ddd, J=3.3, 4.9, 8.3, 1H), 4.18~4.24 (m, 1H), 7.19~7.26 (m, 2H), 7.36~7.39 (m, 2H)

Preparation Example 341

(2S,3R)-methyl-3-(2-chlorobenzyl)-1,4-dioxaspiro[4.4]nonane-2-carboxylate

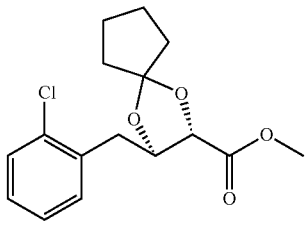 [SMILES: COC(=O)[C@H]1OC2(CCCC2)O[C@@H]1Cc1ccccc1Cl]

The substantially same method as described in Example 339 was conducted, except that cyclopetanone was used instead of 3-pantanone, to obtain the title compound (0.5 g, 60~85%)

$^1$H NMR (400 MHz, CDCl$_3$): δ=1.65~1.80 (m, 5H), 1.89~2.00 (m, 3H), 3.13 (dd, J=7.8, 14.2, 1H), 3.32 (dd, J=4.6, 14.2, 1H), 3.72 (s, 3H), 4.28 (d, J=7.2, 1H), 4.41~4.46 (m, 1H), 7.19~7.26 (m, 2H), 7.35~7.40 (m, 2H)

Preparation Example 342

((2R,3R)-3-(2-chlorobenzyl)-1,4-dioxaspiro[4.4]nonan-2-yl)methanol

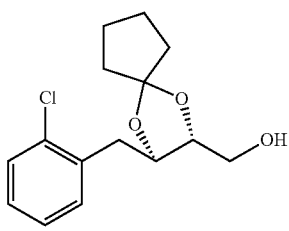 [SMILES: OC[C@H]1OC2(CCCC2)O[C@@H]1Cc1ccccc1Cl]

The substantially same method as described in Example 340 was conducted, except that (2S,3R)-methyl-3-(2-chlorobenzyl)-1,4-dioxaspiro[4.4]nonane-2-carboxylate (Preparation example 341) was used instead of that (4S,5R)-methyl-(5-2-chlprp)benzyl-2,2-diethyl-1,3-dioxolane-4-carboxylate (Preparation example 339), to obtain the title compound (0.4 g, 70~95%)

$^1$H NMR (400 MHz, CDCl$_3$): δ=1.69~1.74 (m, 3H), 1.77~1.85 (m, 5H), 3.11 (ddd, J=6.3, 14.1, 31.3, 2H), 3.42~3.48 (m, 1H), 3.61~3.66 (m, 1H), 3.87~3.91 (m, 1H), 4.19 (q, J=6.8, 1H), 7.19~7.26 (m, 2H), 7.34~7.40 (m, 2H)

Preparation Example 343

(2S,3R)-methyl-3-(2-chlorobenzyl)-1,4-dioxasoiro[4.5]decane-2-carboxylate

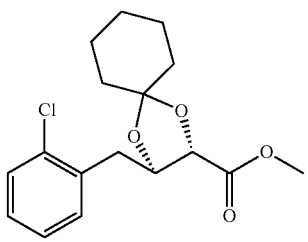 [SMILES: COC(=O)[C@H]1OC2(CCCCC2)O[C@@H]1Cc1ccccc1Cl]

The substantially same method as described in Example 341 was conducted, except that cyclohexanone was used instead of cyclopetanone, to obtain the title compound (0.9 g, 60~85%)

$^1$H NMR (400 MHz, CDCl$_3$): δ=1.54~1.77 (m, 10H), 3.12 (dd, J=7.6, 14.4, 1H), 3.32 (dd, J=4.4, 14.4, 1H), 3.72 (s, 3H), 4.30 (d, J=7.6, 1H), 4.46~4.51 (m, 1H), 7.18~7.26 (m, 2H), 7.37~7.39 (m, 2H)

Preparation Example 344

((2R,3R)-3-(2-chlorobenzyl)-1,4-dioxaspiro[4.5]decan-2-yl)methanol

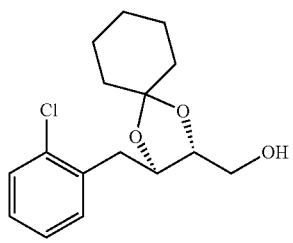 [SMILES: OC[C@H]1OC2(CCCCC2)O[C@@H]1Cc1ccccc1Cl]

The substantially same method as described in Example 342 was conducted, except that (2S,3R)-methyl-3-(2-chlorobenzyl)-1,4-dioxaspiro[4.5]decane-2-carboxylate (Preparation example 343) was used instead of (2S,3R)-methyl-3-(2-chlorobenzyl)-1,4-dioxaspiro[4.4]nonane-2-carboxylate (Preparation example 341), to obtain the title compound (0.7 g, 70~95%)

$^1$H NMR (400 MHz, CDCl$_3$): δ=1.38~1.45 (m, 2H), 1.58~1.63 (m, 8H), 1.84 (q, J=4.3, 1H), 3.11 (ddd, J=7.9, 15.9, 22.1, 2H), 3.43 (ddd, J=4.6, 7.6, 12.1, 1H), 3.66~3.71 (m, 1H), 3.88~3.92 (m, 1H), 4.21~4.26 (m, 1H), 7.18~7.26 (m, 2H), 7.37~7.39 (m, 2H)

Preparation Example 345

(E)-4-(2chlorophenyl)but-3-enoic acid

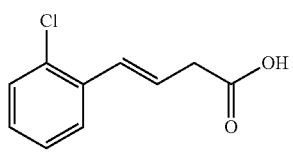 [SMILES: O=C(O)C/C=C/c1ccccc1Cl]

The substantially same method as described in Example 278 was conducted, except that 2-(2-chlorophenyl)acetaldehyde was used instead of phenylacetaldehyde, to obtain the title compound (4.0 g, 55~80%)

$^1$H NMR (400 MHz, CDCl$_3$): δ=3.39 (d, J=8.8, 2H), 6.31 (td, J=7.9, 14.8, 1H), 6.94 (d, J=16, 1H), 7.17~7.45 (m, 3H), 7.56~7.59 (m, 1H)

Preparation Example 346

(E)-4-(2-chlorophenyl)but-3-en-1-ol

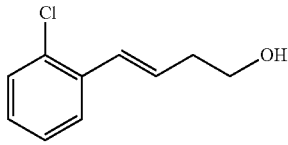 [SMILES: OCC/C=C/c1ccccc1Cl]

The substantially same method as described in Example 279 was conducted, except that (E)-4-(2chlorophenyl)but-3-enoic acid (Preparation example 345) was used instead of (E)-4-phenylbut-3-enoic acid (Preparation example 278), to obtain the title compound (1.2 g, 55~80%)

$^1$H NMR (400 MHz, CDCl$_3$): δ=2.55 (ddd, J=4.1, 11.9, 21.5, 2H), 3.82 (t, J=5.8, 2H), 6.24 (td, J=7.2, 15.7, 1H), 6.87 (d, J=14.8, 1H), 7.12~7.25 (m, 3H), 7.36 (dd, J=1.2, 8.0, 1H), 7.52 (dd, J=1.6, 9.2, 1H)

Preparation Example 347

(E)-tert-butyldimethyl(4-(2-chlorophenyl)but-3-enyloxy)silane

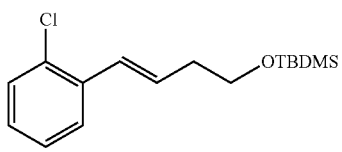 [SMILES: CC(C)(C)[Si](C)(C)OCC/C=C/c1ccccc1Cl]

The substantially same method as described in Example 280 was conducted, except that (E)-4-(2-chlorophenyl)but-3-en-1-ol (Preparation example 346) was used instead of (E)-4-phenylbut-3-en-1-ol (Preparation example 279), to obtain the title compound (1.1 g, 80~98%)

$^1$H NMR (400 MHz, CDCl$_3$): δ=0.07 (s, 3H), 0.10 (s, 3H), 0.92 (d, J=6.4, 9H), 2.51 (q, J=4.5, 2H), 3.78 (t, J=6.6, 2H), 6.26 (td, J=7.2, 15.7, 1H), 6.84 (d, J=15.6, 1H), 7.13~7.24 (m, 3H), 7.36 (dd, J=5.6, 12.4, 1H), 7.53 (dd, J=1.4, 7.8, 1H)

Preparation Example 348

(E)-4-(2-chlorophenyl)but-3-enyl pivalate

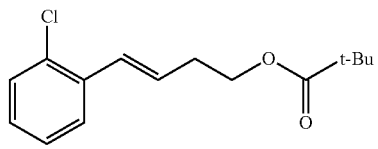 [SMILES: CC(C)(C)C(=O)OCC/C=C/c1ccccc1Cl]

The substantially same method as described in Example 281 was conducted, except that (E)-4-(2-chlorophenyl)but-3-en-1-ol (Preparation example 346) was used instead of (E)-4-phenylbut-3-en-1-ol (Preparation example 279), to obtain the title compound (3.5 g, 75~95%)

$^1$H NMR (400 MHz, CDCl$_3$): δ=1.21 (s, 9H), 2.55~2.64 (m, 2H), 4.24 (t, J=6.4, 2H), 6.18 (td, J=7.9, 14.8, 1H), 6.86 (d, J=16.0, 1H), 7.22~7.26 (m, 2H), 7.38 (dd, J=3.6, 10.8, 1H), 7.51 (dd, J=1.6, 7.6, 1H)

Preparation Example 349

(1R,2R)-4-(tert-butyldimethylsilyloxy)-1-(2-chlorophenyl)butane-1,2-diol

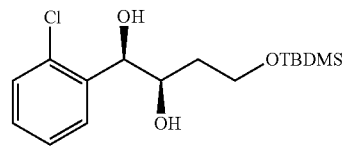 [SMILES: CC(C)(C)[Si](C)(C)OCC[C@@H](O)[C@H](O)c1ccccc1Cl]

The substantially same method as described in Example 282 was conducted, except that (E)-tert-butyldimethyl(4-2-chlorophenyl)but-3-enyloxy)silane (Preparation example 347) was used instead of (E)-tert-butyldimethyl (5-phenyl-pent-3-enyloxy)silane (Preparation example 237), to obtain the title compound (0.7 g, 70~95%)

$^1$H NMR (400 MHz, CDCl$_3$): δ=0.10 (s, 3H), 0.11 (s, 3H), 0.92 (s, 9H), 1.69~1.70 (m, 1H), 1.93~2.07 (m, 1H), 3.51 (d, J=4.8, 1H), 3.86 (d, J=3.2, 1H), 3.87 (dd, J=3.2, 9.2, 1H), 3.91~3.96 (m, 1H), 4.01~4.06 (m, 1H), 5.05 (t, J=4.6, 1H), 7.22~7.26 (m, 1H), 7.31~7.37 (m, 2H), 7.59 (dd, J=1.2, 7.6, 1H)

Preparation Example 350

(3R,4R)-3,4-dihydroxy-4-(2-chlorophenyl)butyl pivalate

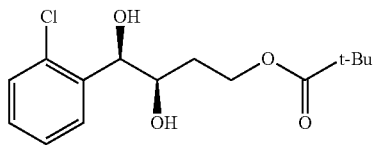 [SMILES: CC(C)(C)C(=O)OCC[C@@H](O)[C@H](O)c1ccccc1Cl]

The substantially same method as described in Example 349 was conducted, except that (E)-4-(2-chlorophenyl)but-3-enyl pivalate (Preparation example 348) was used instead of (E)-tert-butyldimethyl(4-2-chlorophenyl)but-3-enyloxy)silane (Preparation example 347), to obtain the title compound (3.2 g, 70~95%)

$^1$H NMR (400 MHz, CDCl$_3$): δ=1.19 (s, 9H), 1.76~1.84 (m, 1H), 1.90~1.98 (m, 1H), 2.70 (d, J=4.4, 1H), 2.86 (d, J=5.2, 1H), 3.84~3.90 (m, 1H), 4.14~4.21 (m, 1H), 4.35~4.41 (m, 1H), 5.05 (t, J=5.0, 1H), 7.23~7.39 (m, 3H), 7.54 (dd, J=1.6, 7.6, 1H)

Preparation Example 351 tert-butyl(2-((4R,5R)-5-(2-chlorophenyl)-2,2-dimethyl-1,3-dioxolan-4-yl)ethoxy)dimethylsilane

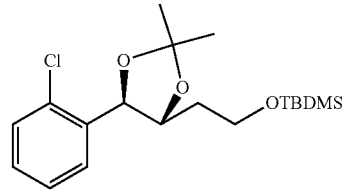 [SMILES: CC1(C)O[C@H](c2ccccc2Cl)[C@@H](CCO[Si](C)(C)C(C)(C)C)O1]

The substantially same method as described in Example 284 was conducted, except that (1R,2R)-4-(tert-butyldimethylsilyloxy)-1-(2-chlorophenyl)butane-1,2-diol (Preparation example 349) was used instead of (1R,2R)-4-(tert-butyldimethylsilyloxy)-1-phenylbutane-1,2-diol (Preparation example 282), to obtain the title compound (0.8 g, 70~95%)

¹H NMR (400 MHz, CDCl₃): δ=0.02 (s, 3H), 0.07 (s, 3H), 0.86 (s, 9H), 1.50 (s, 3H), 1.58 (s, 3H), 1.82~1.99 (m, 2H), 3.68~3.78 (m, 2H), 3.95 (dt, J=3.3, 8.7, 1H), 5.16 (d, J=8.4, 1H), 7.21~7.27 (m, 1H), 7.31~7.38 (m, 2H), 7.60 (dd, J=1.6, 7.6, 1H)

Preparation Example 352

2-((4R,5R)-5-(2-chlorophenyl)-2,2-dimethyl-1,3-dioxolan-4-yl)ethanol

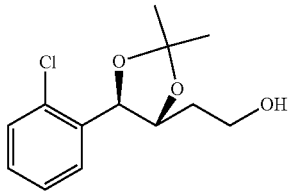 [SMILES: CC1(C)O[C@H](c2ccccc2Cl)[C@@H](CCO)O1]

The substantially same method as described in Example 285 was conducted, except tert-butyl(2-((4R,5R)-5-(2-chlorophenyl)-2,2-dimethyl-1,3-dioxolan-4-yl)ethoxy)dimethylsilane (Preparation example 351) was used instead of tert-butyl(2-((4R,5R)-5-phenyl-2,2-dimethyl-1,3-dioxolan-4-yl)ethoxy)dimethylsilane (Preparation example 284), to obtain the title compound (0.7 g, 80~95%)

¹H NMR (400 MHz, CDCl₃): δ=1.56 (s, 3H), 1.62 (s, 3H), 1.92~2.04 (m, 2H), 2.26 (q, J=3.7, 1H), 3.75~3.90 (m, 2H), 3.94 (td, J=3.9, 8.5, 1H), 5.23 (d, J=15.6, 1H), 7.22~7.27 (m, 1H), 7.33~7.39 (m, 2H), 7.62 (dd, J=1.6, 7.6, 1H)

Preparation Example 353

(1S,2S)-4-(tert-butyldimethylsilyloxy)-1-(2-chlorophenyl)butane-1,2-diol

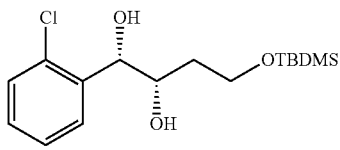 [SMILES: CC(C)(C)[Si](C)(C)OCC[C@H](O)[C@@H](O)c1ccccc1Cl]

The substantially same method as described in Example 286 was conducted, except that (E)-tert-butyldimethyl(4-(2-chlorophenyl)but-3-enyloxy)silane (Preparation example 347) was used instead of (E)-tert-butyldimethyl(4-phenylbut-3-enyloxy)silane (Preparation example 280), to obtain the title compound (0.7 g, 70~95%)

¹H NMR (400 MHz, CDCl₃): δ=1.19 (s, 9H), 1.76~1.84 (m, 1H), 1.90~1.98 (m, 1H), 2.70 (d, J=4.4, 1H), 2.86 (d, J=5.2, 1H), 3.84~3.90 (m, 1H), 4.14~4.21 (m, 1H), 4.35~4.41 (m, 1H), 5.05 (t, J=5.0, 1H), 7.23~7.39 (m, 3H), 7.54 (dd, J=1.6, 7.6, 1H)

Preparation Example 354

(3S,4S)-3,4-dihydroxy-4-(2-chlorophenyl)butyl pivalate

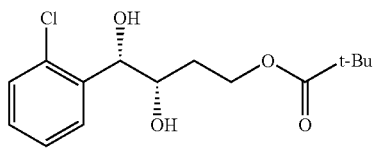 [SMILES: CC(C)(C)C(=O)OCC[C@H](O)[C@@H](O)c1ccccc1Cl]

The substantially same method as described in Example 353 was conducted, except that (E)-4-(2-chlorophenyl)but-3-enyl pivalate (Preparation example 348) was used instead of ((E)-tert-butyldimethyl(4-(2-chlorophenyl)but-3-enyloxy)silane (Preparation example 347), to obtain the title compound (3.0 g, 70~95%)

¹H NMR (400 MHz, CDCl₃): δ=1.19 (s, 9H), 1.76~1.84 (m, 1H), 1.90~1.98 (m, 1H), 2.70 (d, J=4.4, 1H), 2.86 (d, J=5.2, 1H), 3.84~3.90 (m, 1H), 4.14~4.21 (m, 1H), 4.35~4.41 (m, 1H), 5.05 (t, J=5.0, 1H), 7.23~7.39 (m, 3H), 7.54 (dd, J=1.6, 7.6, 1H)

Preparation Example 355 tert-butyl(2-((4S,5S)-5-(2-chlorophenyl)-2,2-dimethyl-1,3-dioxolan-4-yl)ethoxy)dimethylsilane

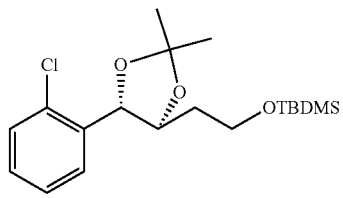 [SMILES: CC1(C)O[C@@H](CCO[Si](C)(C)C(C)(C)C)[C@H](c2ccccc2Cl)O1]

The substantially same method as described in Example 351 was conducted, except that (1S,2S)-4-(tert-butyldimethylsilyloxy)-1-(2-chlorophenyl)butane-1,2-diol (Preparation example 353) was used instead of 1R, 2R)-4-(tert-butyldimethylsilyloxy)-1-(2-chlorophenyl)butane-1,2-diol (Preparation example 349), to obtain the title compound (0.7 g, 70~95%)

¹H NMR (400 MHz, CDCl₃): δ=0.02 (s, 3H), 0.07 (s, 3H), 0.86 (s, 9H), 1.50 (s, 3H), 1.58 (s, 3H), 1.82~1.99 (m, 2H), 3.68~3.78 (m, 2H), 3.95 (dt, J=3.3, 8.7, 1H), 5.16 (d, J=8.4, 1H), 7.21~7.27 (m, 1H), 7.31~7.38 (m, 2H), 7.60 (dd, J=1.6, 7.6, 1H)

Preparation Example 356

2-((4S,5S)-5-(2-chlorophenyl)-2,2-dimethyl-1,3-dioxolan-4-yl)ethanol

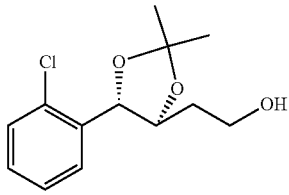 [SMILES: CC1(C)O[C@@H](CCO)[C@H](c2ccccc2Cl)O1]

The substantially same method as described in Example 352 was conducted, except that tert-butyl(2-((4S,5S)-5-(2-chlorophenyl)-2,2-dimethyl-1,3-dioxolan-4-yl)ethoxy)dimethylsilane (Preparation example 355) was used instead of that tert-butyl(2-((4R,5R)-5-(2-chlorophenyl)-2,2-dimethyl-1,3-dioxolan-4-yl)ethoxy)dimethyl silane (Preparation example 351), to obtain the title compound (0.3 g, 80~95%).

$^1$H NMR (400 MHz, CDCl$_3$): δ=1.56 (s, 3H), 1.62 (s, 3H), 1.92~2.04 (m, 2H), 2.26 (q, J=3.7, 1H), 3.75~3.90 (m, 2H), 3.94 (td, J=3.9, 8.5, 1H), 5.23 (d, J=15.6, 1H), 7.22~7.27 (m, 1H), 7.33~7.39 (m, 2H), 7.62 (dd, J=1.6, 7.6, 1H)

Preparation Example 357

2-((4R,5R)-2,2-diethyl-5-(2-chlorophenyl)-1,3-dioxolan-4-yl)ethyl pivalate

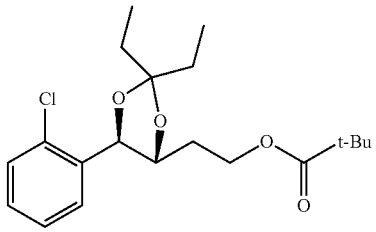 [SMILES: CCC1(CC)O[C@H](c2ccccc2Cl)[C@@H](CCOC(=O)C(C)(C)C)O1]

The substantially same method as described in Example 290 was conducted, except that (3R,4R)-3,4-dihydroxy-4-(2-chlorophenyl)butyl pivalate (Preparation example 350) was used instead of (3R,4R)-3,4-dihydroxy-4-phenylbutyl pivalate(Preparation example 283), to obtain the title compound (0.8 g, 70~95%)

$^1$H NMR (400 MHz, CDCl$_3$): δ=1.15 (s, 9H), 1.76 (q, J=7.6, 2H), 1.84~1.90 (m, 2H), 2.00~2.07 (m, 2H), 3.85 (dt, J=3.7, 8.5, 1H), 4.14~4.27 (m, 2H), 5.17 (d, J=8.4, 1H), 7.22~7.28 (m, 1H), 7.32~7.38 (m, 2H), 7.64 (dd, J=1.4, 7.8, 1H)

Preparation Example 358

2-((4R,5R)-2,2-diethyl-5-(2-chlorophenyl)-1,3-dioxolan-4-yl)ethanol

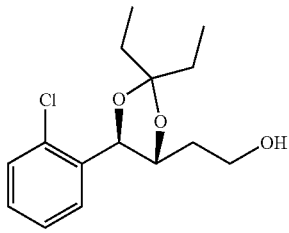 [SMILES: CCC1(CC)O[C@H](c2ccccc2Cl)[C@@H](CCO)O1]

The substantially same method as described in Example 291 was conducted, except that 2-((4R,5R)-2,2-diethyl-5-(2-chlorophenyl)-1,3-dioxolan-4-yl)ethyl pivalate (Preparation example 357) was used instead of 2-((4R,5R)-2,2-diethyl-5-phenyl-1,3-dioxolan-4-yl)ethyl pivalate(Preparation example 290), to obtain the title compound (0.6 g, 80~95%)

$^1$H NMR (400 MHz, CDCl$_3$): δ=1.02 (t, J=7.4, 3H), 1.08 (t, J=7.4, 3H), 1.80 (q, J=7.5, 2H), 1.86~1.91 (m, 2H), 1.96~2.00 (m, 2H), 2.37 (q, J=3.7, 1H), 3.76~3.95 (m, 3H), 5.23 (d, J=8.4, 1H), 7.25~7.27 (m, 1H), 7.32~7.39 (m, 2H), 7.65 (dd, J=1.8, 7.8, 1H)

Preparation Example 359

2-((2R,3R)-3-(2-chlorophenyl)-1,4-dioxaspiro[4.4]nonan-2-yl)ethyl pivalate

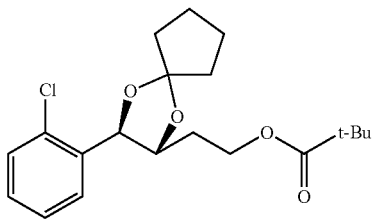 [SMILES: CC(C)(C)C(=O)OCC[C@H]1OC2(CCCC2)O[C@@H]1c1ccccc1Cl]

The substantially same method as described in Example 357 was conducted, except that cyclopetanone was used instead of 3-pantanone, to obtain the title compound (0.8 g, 60~85%)

$^1$H NMR (400 MHz, CDCl$_3$): δ=1.17 (s, 9H), 1.58~2.02 (m, 10H), 3.86 (ddd, J=3.8, 8.2, 8.2, 1H), 4.11~4.28 (m, 2H), 5.13 (d, J=8.0, 1H), 7.20~7.39 (m, 3H), 7.58 (dd, J=1.6, 8.0, 1H)

Preparation Example 360

2-((2R,3R)-3-(2-chlorophenyl)-1,4-dioxaspiro[4.4]nonan-2-yl)ethanol

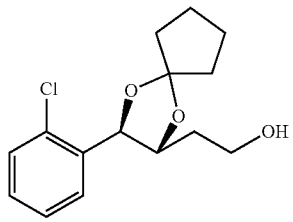 [SMILES: OCC[C@H]1OC2(CCCC2)O[C@@H]1c1ccccc1Cl]

The substantially same method as described in Example 358 was conducted, except that 2-((2R,3R)-3-(2-chlorophenyl)-1,4-dioxaspiro[4.4]nonan-2-yl)ethyl pivalate (Preparation example 359) was used instead of that 2-((4R,5R)-2,2-diethyl-5-(2-chlorophenyl)-1,3-dioxolan-4-yl)ethyl pivalate (Preparation example 357), to obtain the title compound (0.5 g, 80~95%)

$^1$H NMR (400 MHz, CDCl$_3$): δ=1.72~1.90 (m, 4H), 1.93~1.98 (m, 6H), 2.28 (q, J=3.7, 1H), 3.76~3.93 (m, 3H), 5.18 (d, J=8.0, 1H), 7.24~7.29 (m, 1H), 7.32~7.38 (m, 2H), 7.60 (dd, J=1.8, 7.8, 1H)

Preparation Example 361

2-((2R,3R)-3-(2-chlorophenyl)-1,4-dioxaspiro[4.5]decan-2-yl)ethyl pivalate

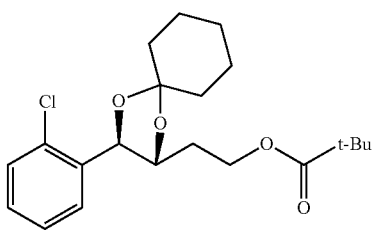 [SMILES: CC(C)(C)C(=O)OCC[C@H]1OC2(CCCCC2)O[C@@H]1c1ccccc1Cl]

The substantially same method as described in Example 359 was conducted, except that cyclohexanone was used instead of cyclopetanone, to obtain the title compound (1.0 g, 60~85%)

$^1$H NMR (400 MHz, CDCl$_3$): δ=1.15 (s, 9H), 1.70~1.94 (m, 10H), 2.06~2.09 (m, 2H), 3.86 (dt, J=3.5, 8.5, 1H), 4.16~4.26 (m, 2H), 5.18 (d, J=8.4, 1H), 7.22~7.28 (m, 1H), 7.32~7.38 (m, 2H), 7.61 (dd, J=1.4, 7.8, 1H)

Preparation Example 362

2-((2R,3R)-3-(2-chlorophenyl)-1,4-dioxaspiro[4.45]decan-2-yl)ethanol

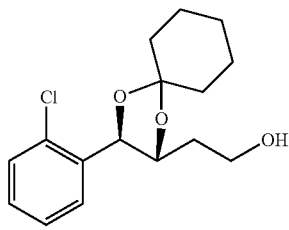 [SMILES: OCC[C@H]1OC2(CCCCC2)O[C@@H]1c1ccccc1Cl]

The substantially same method as described in Example 360 was conducted, except that 2-((2R,3R)-3-(2-chlorophenyl)-1,4-dioxaspiro[4.5]decan-2-yl)ethyl pivalate (Preparation example 361) was used instead of that 2-((2R,3R)-3-(2-chlorophenyl)-1,4-dioxaspiro[4.4]nonan-2-yl)ethyl pivalate (Preparation example 359), to obtain the title compound (0.6 g, 80~95%)

$^1$H NMR (400 MHz, CDCl$_3$): δ=1.42~1.50 (m, 2H), 1.63~1.77 (m, 5H), 1.82~1.89 (m, 5H), 2.41 (q, J=3.9, 1H), 3.78~3.96 (m, 3H), 5.25 (d, J=8.4, 1H), 7.21~7.28 (m, 1H), 7.32~7.38 (m, 2H), 7.63 (dd, J=1.4, 7.8, 1H)

Preparation Example 363

2-((4S,5S)-2,2-diethyl-5-(2-chlorophenyl)-1,3-dioxolan-4-yl)ethyl pivalate

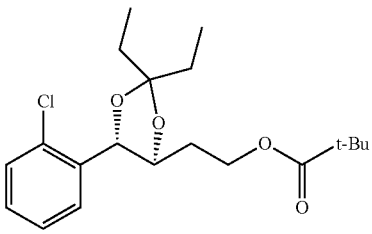 [SMILES: CCC1(CC)O[C@@H](CCOC(=O)C(C)(C)C)[C@H](c2ccccc2Cl)O1]

The substantially same method as described in Example 357 was conducted, except that (3S,4S)-3,4-dihydroxy-4-(2-chlorophenyl)butyl pivalate (Preparation example 354) was used instead of (3R,4R)-3,4-dihydroxy-4-(2-chlorophenyl)butyl pivalate (Preparation example 350), to obtain the title compound (0.7 g, 70~95%).

$^1$H NMR (400 MHz, CDCl$_3$): δ=1.15 (s, 9H), 1.76 (q, J=7.6, 2H), 1.84~1.90 (m, 2H), 2.00~2.07 (m, 2H), 3.85 (dt, J=3.7, 8.5, 1H), 4.14~4.27 (m, 2H), 5.17 (d, J=8.4, 1H), 7.22~7.28 (m, 1H), 7.32~7.38 (m, 2H), 7.64 (dd, J=1.4, 7.8, 1H)

Preparation Example 364

2-((4S,5S)-2,2-diethyl-5-(2-chlorophenyl)-1,3-dioxolan-4-yl)ethyl pivalate

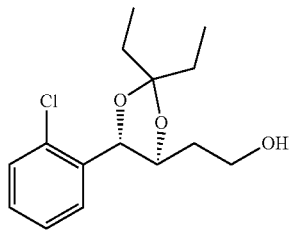 [SMILES: CCC1(CC)O[C@@H](CCO)[C@H](c2ccccc2Cl)O1]

The substantially same method as described in Example 358 was conducted, except that 2-((4S,5S)-2,2-diethyl-5-(2-chlorophenyl)-1,3-dioxolan-4-yl)ethyl pivalate(Preparation example 363) was used instead of 2-((4R,5R)-2,2-diethyl-5-(2-chlorophenyl)-1,3-dioxolan-4-yl)ethyl pivalate (Preparation example 357), to obtain the title compound (0.5 g, 80~95%)

$^1$H NMR (400 MHz, CDCl$_3$): δ=1.02 (t, J=7.4, 3H), 1.08 (t, J=7.4, 3H), 1.80 (q, J=7.5, 2H), 1.86~1.91 (m, 2H), 1.96~2.00 (m, 2H), 2.37 (q, J=3.7, 1H), 3.76~3.95 (m, 3H), 5.23 (d, J=8.4, 1H), 7.25~7.27 (m, 1H), 7.32~7.39 (m, 2H), 7.65 (dd, J=1.8, 7.8, 1H)

Preparation Example 365

2-((2S,3S)-3-(2-chlorophenyl)-1,4-dioxaspiro[4.4]nonan-2-yl)ethyl pivalate

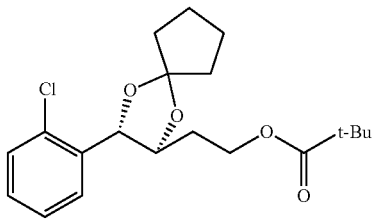 [SMILES: CC(C)(C)C(=O)OCC[C@@H]1OC2(CCCC2)O[C@H]1c1ccccc1Cl]

The substantially same method as described in Example 363 was conducted, except that cyclopetanone was used instead of 3-pantanone, to obtain the title compound (0.6 g, 60~85%)

$^1$H NMR (400 MHz, CDCl$_3$): δ=1.17 (s, 9H), 1.58~2.02 (m, 10H), 3.86 (ddd, J=3.8, 8.2, 8.2, 1H), 4.11~4.28 (m, 2H), 5.13 (d, J=8.0, 1H), 7.20~7.39 (m, 3H), 7.58 (dd, J=1.6, 8.0, 1H)

Preparation Example 366

2-((2S,3S)-3-(2-chlorophenyl)-1,4-dioxaspiro[4.4]nonan-2-yl)ethanol

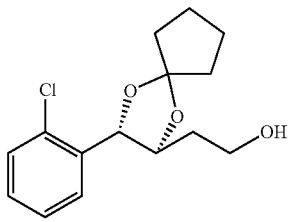 [SMILES: OCC[C@@H]1OC2(CCCC2)O[C@H]1c1ccccc1Cl]

The substantially same method as described in Example 364 was conducted, except that 2-((2S,3S)-3-(2-chlorophenyl)-1,4-dioxaspiro[4.4]nonan-2-yl)ethyl pivalate (Preparation example 365) was used instead of that 2-((4S,5S)-2,2-diethyl-5-(2-chlorophenyl)-1,3-dioxolan-4-yl)ethyl pivalate (Preparation example 363), to obtain the title compound (0.4 g, 80~95%)

$^1$H NMR (400 MHz, CDCl$_3$): δ=1.72~1.90 (m, 4H), 1.93~1.98 (m, 6H), 2.28 (q, J=3.7, 1H), 3.76~3.93 (m, 3H), 5.18 (d, J=8.0, 1H), 7.24~7.29 (m, 1H), 7.32~7.38 (m, 2H), 7.60 (dd, J=1.8, 7.8, 1H)

Preparation Example 367

2-((2S,3S)-3-(2-chlorophenyl)-1,4-dioxaspiro[4.5]decan-2-yl)ethyl pivalate

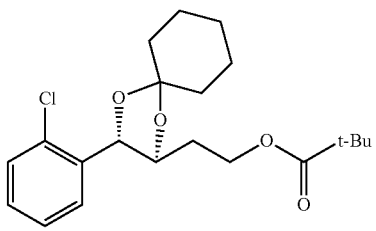 [SMILES: CC(C)(C)C(=O)OCC[C@@H]1OC2(CCCCC2)O[C@H]1c1ccccc1Cl]

The substantially same method as described in Example 366 was conducted, except that cyclohexanone was used instead of cyclopetanone, to obtain the title compound (0.7 g, 60~85%)

$^1$H NMR (400 MHz, CDCl$_3$): δ=1.15 (s, 9H), 1.70~1.94 (m, 10H), 2.06~2.09 (m, 2H), 3.86 (dt, J=3.5, 8.5, 1H), 4.16~4.26 (m, 2H), 5.18 (d, J=8.4, 1H), 7.22~7.28 (m, 1H), 7.32~7.38 (m, 2H), 7.61 (dd, J=1.4, 7.8, 1H)

Preparation Example 368

2-((2R,3R)-3-(2-chlorophenyl)-1,4-dioxaspiro[4.45]decan-2-yl)ethanol

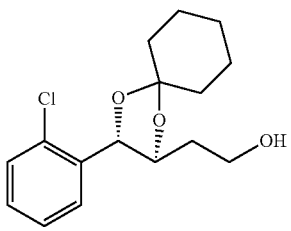 [SMILES: OCC[C@@H]1OC2(CCCCC2)O[C@H]1c1ccccc1Cl]

The substantially same method as described in Example 366 was conducted, except that 2-((2S,3S)-3-(2-chlorophenyl)-1,4-dioxaspiro[4.5]decan-2-yl)ethyl pivalate (Preparation example 367) was used instead of that 2-((2S,3S)-3-(2-chlorophenyl)-1,4-dioxaspiro[4.4]nonan-2-yl)ethyl pivalate (Preparation example 365), to obtain the title compound (0.4 g, 80~95%).

$^1$H NMR (400 MHz, CDCl$_3$): δ=1.42~1.50 (m, 2H), 1.63~1.77 (m, 5H), 1.82~1.89 (m, 5H), 2.41 (q, J=3.9, 1H), 3.78~3.96 (m, 3H), 5.25 (d, J=8.4, 1H), 7.21~7.28 (m, 1H), 7.32~7.38 (m, 2H), 7.63 (dd, J=1.4, 7.8, 1H)

Preparation Example 367

(E)-1-(3 (benzyloxy)prop-1enyl)2-chlorobenzen

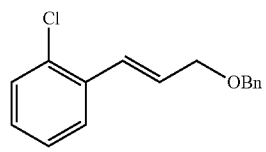 [SMILES: Clc1ccccc1/C=C/COCc1ccccc1]

To a solution of (E)-3-(2-chlorophenyl) prop-2-en-1-ol (Preparation example 1, 5.3 g, 31.6 mmole) in THF was added NaH (60% in mineral oil, 0.91 g, 37.7 mmole) and Benzyl bromide (4.12 mL, 34.8 mmole), sequently at 0° C. The reaction mixture was stirred at room temperature for 18 hr. The TLC showed complete consumption of SM. The reaction mixture was quenched with H$_2$O at 0° C. then extracted with EtOAc. The aqueous layer was extracted with EtOAc and separated. The combined organic layer was washed with H$_2$O, then dried over MgSO$_4$ and evaporated under reduced pressure. The crude compound was purified by silica ge column to produce the title compound (4.94 g, 70~90%).

¹H NMR (400 MHz, CDCl₃) δ 7.57 (dd, J=7.76, 2, 1H), 7.42~7.13 (m, 3H), 7.05 (d, J=16 Hz, 1H), 6.37~6.30 (m, 1H), 4.62 (s, 2H), 4.26 (dd, J=6, 1.6, 2H).

Preparation Example 368

(±)-2-(benzyloxymethyl)-3-(2-chlorophenyl)oxirane

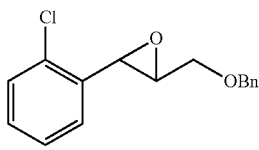 [SMILES: Clc1ccccc1C1OC1COCc1ccccc1]

To a solution of (E)-1-(3-(benzyloxy)prop-1-enyl)-2-chlorobenzene(Preparation example 367, 4.94 g, 22 mmole) in CH₂Cl₂ (110 mL) was added 3-chloroperoxybenzoic acid (70~75%, 8 g, 33 mmole) portionwise at 0° C. The mixture was stirred for 18 hr at room temperature. The TLC showed complete consumption of SM. The reaction mixture was quenched with H₂O at 0° C. then extracted with EtOAc. The aqueous layer was extracted with EtOAc and separated. The combined organic layer was washed with sat' NaHCO₃, H₂O, then dried over MgSO₄ and evaporated under reduced pressure. The crude compound was purified by silica ge column to produce the title compound (4.3 g, 60~80%).

¹H NMR (400 MHz, CDCl₃) δ 7.42~7.24 (m, 9H), 4.68 (d, J=14.8, 2H), 4.18 (d, J=2 Hz, 1H), 3.96 (dd, J=11.6, 2.8 Hz, 1H), 3.69~3.64 (m, 1H), 3.14 (qt, J=2.4 Hz, 1H)

Preparation Example 369

(±)-3-(benzyloxy)-1-(2-chlorophenyl)-2-hydroxypropyl & (±)-3-(benzyloxy)-1-(2-chlorophenyl)-1-hydroxypropan-2-yl acetate

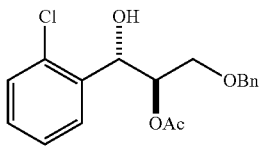

(1)

&

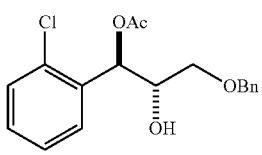

(2)

To a solution of (±)-2-(benzyloxymethyl)-3-(2-chlorophenyl)oxirane (Preparation example 368, 4.3 g, 15.6 mmole) in Acetic acid (78 mL) was added Cerium Ammonium Nitrate (1.71 g, 3.1 mmole) at room temperature. The mixture was stirred for 18 hr at room temperature. The TLC showed complete consumption of SM. The reaction mixture was quenched with sat'NaHCO₃ to pH7 at 0° C. then extracted with EtOAc. The aqueous layer was extracted with EtOAc and separated. The combined organic layer was washed with H₂O, then dried over MgSO₄ and evaporated under reduced pressure. The crude compound was purified by silica ge column to produce the title compound (1) (1.2 g, 23%). (2)(1.8 g, 34%).

(1) ¹H NMR (400 MHz, CDCl₃) δ 7.55~7.22 (m, 9H), 5.41 (t, J=5 Hz, 1H), 5.33-5.29 (m, 1H), 4.61~4.47 (m, 2H), 3.70~3.63 (m, 2H, —OH), 2.09 (s, 3H).

(2) ¹H NMR (400 MHz, CDCl₃) δ 7.46~7.24 (m, 9H), 6.31 (d, J=5.6 Hz, 1H), 4.55 (d, J=9.6 Hz, 2H), 4.24~4.22 (m, 1H), 3.67~3.55 (m, 2H), 2.52 (d, J=5.2 Hz, —OH), 2.10 (s, 3H).

Preparation Example 370

(±)-3-(benzyloxy)-1-(2-chlorophenyl)propane-1,2-diol (Anti mixture)

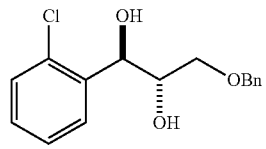 [SMILES: O[C@H](c1ccccc1Cl)[C@@H](O)COCc1ccccc1]

To a solution of (±)-3-(benzyloxy)-1-(2-chlorophenyl)-2-hydroxypropyl and (±)-3-(benzyloxy)-1-(2-chlorophenyl)-1-hydroxypropan-2-yl acetate (Preparation example 369, 3 g, 8.9 mmole) in MeOH (36 mL) and H₂O (4 mL) was added K₂CO₃ (3.69 g, 26.7 mmole) at 0° C. The mixture was stirred for 1.5 hr at 0° C. The TLC showed complete consumption of SM. The reaction mixture was quenched with H₂O at 0° C. then extracted with EtOAc. The aqueous layer was extracted with EtOAc and separated. The combined organic layer was washed with H₂O, then dried over MgSO₄ and evaporated under reduced pressure. The crude compound was purified by silica gel column to produce the title compound (2.4 g, 80~95%).

¹H NMR (400 MHz, CDCl₃) δ 7.50 (dd, J=7.6, 1.2 Hz, 1H), 7.35-7.19 (m, 8H), 5.28 (t, J=4.8 Hz, 1H), 4.46 (d, J=6 Hz, 2H), 4.18-4.13 (m, 1H), 3.55-3.42 (m, 3H, —OH), 3.02 (d, J=5.2 Hz, —OH).

Preparation Example 371

(±)-4-(benzyloxymethyl)-5-(2-chlorophenyl)-2,2-dimethyl-1,3-dioxolane

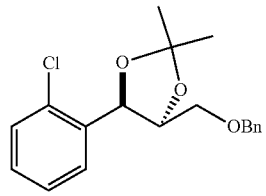 [SMILES: CC1(C)O[C@@H](COCc2ccccc2)[C@@H](c2ccccc2Cl)O1]

To a solution of (±)-3-(benzyloxy)-1-(2-chlorophenyl)propane-1,2-diol (Preparation example 370, 2.4 g, 8.2 mmole) in CH₂Cl₂ (40 mL) was added p-toluenesulfonyl chloride (15.2 g, 0.08 mmole), and dimethoxypropan (8.4 mL, 9.84 mmole) at 0° C. sequently. The mixture was stirred for 1.5 hr at room temperature. The TLC showed complete consumption of SM. The reaction mixture was quenched with H₂O then extracted with EtOAc. The aqueous layer was extracted with EtOAc and separated. The combined organic layer was washed with H₂O, then dried over MgSO₄ and evaporated under reduced pressure. The crude compound was purified by silica ge column to produce the title compound (2.2 g, 75~90%).

$^1$H NMR (400 MHz, CDCl₃) δ 7.61 (dd, J=7.4, 1.6 Hz, 1H), 7.35-7.16 (m, 8H), 5.63 (d, J=6.8, 1H), 4.83-4.78 (m, 1H). 4.26 (d, J=12 Hz, 2H), 3.14-3.06 (m, 2H), 1.66 (s, 3H), 1.53 (s, 3H).

Preparation Example 372

5-(2-chlorophenyl)-2,2-dimethyl-1,3-dioxolan-4-yl) methanol (SR & RS mixture)

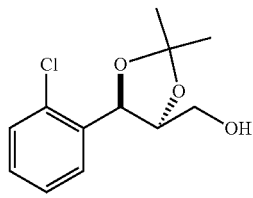 [SMILES: CC1(C)O[C@@H](CO)[C@@H](c2ccccc2Cl)O1]

To a solution of (±)-4-(benzyloxymethyl)-5-(2-chlorophenyl)-2,2-dimethyl-1,3-dioxolane (Preparation example 371, 2.2 g, 6.6 mmole) in EtOAc (33 mL) was added 10% Pd/C on carbon (0.11 g) at room temperature. The mixture was stirred for 1 hr at room temperature under H₂ (g). The TLC showed complete consumption of SM. The reaction mixture was filtered through celite pad then evaporated under reduced pressure. The crude compound was purified by silica ge column to produce the title compound (1.5 g, 80~95%).

$^1$H NMR (400 MHz, CDCl₃) δ 7.61 (dd, J=7.4, 1.6, 1H), 7.35~7.16 (m, 8H), 5.63 (d, J=6.8 Hz, 1H), 4.83-4.78 (m, 1H), 4.26 (d, J=12 Hz, 2H), 3.14-3.06 (m, 2H), 1.66 (s, 3H), 1.53 (s, 3H).

Preparation Example 373

(2R,3R)-2-(benzyloxymethyl)-3-(2-chlorophenyl) oxirane

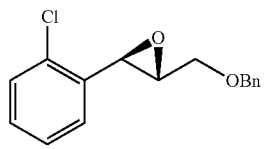 [SMILES: Clc1ccccc1[C@H]1O[C@@H]1COCc1ccccc1]

To a solution of (E)-1-(3-(benzyloxy)prop-1-enyl)-2-chlorobenzene (Preparation example 367, 4.16 g, 18.58 mmole) and 1,2;4,5-di-O-isopropylidene-β-D-erythro-2,3-hexodiulo-2,6-pyranose (5.76 g, 22.30 mmole) in DME-DMM (3:1, v/v) (185 mL) was added buffer (0.2M K₂CO₃—AcOH in 4×10-4 aq. EDTA, buffer pH=8.0) (185 mL) and Bu₄NHSO₄ (0.26 g, 0.75 mmole). After the mixture was cooled to 0° C., a solution of Oxone (15.76 g, 25.64 mmole) in 4×10-4 aq. EDTA (100 mL) and a solution of K₂CO₃ (13.6 g, 98.47 mmole) in 4×10-4 aq. EDTA (100 mL) were added dropwise separately over a period of 3.5 hr via a syringe pump at 0° C. The reaction mixture was stirred for 14 hr at 0° C. The reaction mixture was quenched with H₂O then extracted with EtOAc. The aqueous layer was extracted with EtOAc and separated. The combined organic layer was washed with H₂O then dried over MgSO₄ and evaporated under reduced pressure The crude compound was purified by silica ge column to produce the title compound (2.9 g, 56%).

$^1$H NMR (400 MHz, CDCl₃) δ3.14 (qt, J=2.4 Hz, 1H). 3.69-3.64 (m, 1H), 3.96 (dd, J=11.6, 2.8 Hz, 1H), 4.18 (d, J=2 Hz, 1H), 4.68 (d, J=14.8, 2H), 7.42-7.24 (m, 9H),

Preparation Example 374

(1S,2R)-3-(benzyloxy)-1-(2-chlorophenyl)-1-hydroxypropan-2-yl acetate

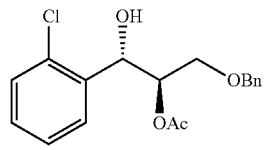 [SMILES: CC(=O)O[C@H](COCc1ccccc1)[C@@H](O)c1ccccc1Cl]

To a solution of (±)-2-(benzyloxymethyl)-3-(2-chlorophenyl)oxirane (Preparation example 373, 2.9 g, 10.55 mmole) in Acetic acid (55 mL) was added Cerium Ammonium Nitrate (1.15 g, 2.11 mmole) at room temperature. The mixture was stirred for 18 hr at room temperature. The TLC showed complete consumption of SM. The reaction mixture was quenched with sat'NaHCO₃ to pH7 at 0° C. then extracted with EtOAc. The aqueous layer was extracted with EtOAc and separated. The combined organic layer was washed with H₂O, then dried over MgSO₄ and evaporated under reduced pressure. The crude compound was purified by silica ge column to produce the title compound (1.2 g, 34%).

$^1$H NMR (400 MHz, CDCl₃) δ2.10 (s, 3H), 2.52 (d, J=5.2 Hz, —OH), 3.67-3.55 (m, 2H), 4.24-4.22 (m, 1H), 4.55 (d, J=9.6 Hz, 2H), 6.31 (d, J=5.6 Hz, 1H), 7.46-7.24 (m, 9H).

Preparation Example 375

(1S,2R)-3-(benzyloxy)-1-(2-chlorophenyl)propane-1,2-diol

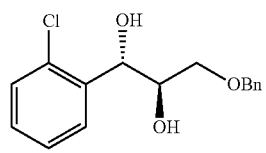 [SMILES: O[C@H](COCc1ccccc1)[C@@H](O)c1ccccc1Cl]

To a solution of (1S,2R)-3-(benzyloxy)-1-(2-chlorophenyl)-1-hydroxypropan-2-yl acetate (Preparation example 374, 1.2 g, 3.58 mmole) in MeOH (16.2 mL) and H₂O (1.8 mL) was added K₂CO₃ (1.48 g, 10.74 mmole) at 0° C. The mixture was stirred for 1.5 hr at 0° C. The TLC showed complete consumption of SM. The reaction mixture was quenched with H₂O at 0° C. then extracted with EtOAc. The aqueous layer was extracted with EtOAc and separated. The combined organic layer was washed with H₂O, then dried over MgSO₄ and evaporated under reduced pressure. The crude compound was purified by silica ge column to produce the title compound (1.0 g, 94%).

¹H NMR (400 MHz, CDCl₃) δ3.02 (d, J=5.2 Hz, 1H), 3.55-3.42 (m, 3H, —OH), 4.18-4.13 (m, 1H), 4.46 (d, J=6 Hz, 2H), 5.28 (t, J=4.8 Hz, 1H), 7.35-7.19 (m, 8H), 7.50 (dd, J=7.6, 1.2 Hz, 1H).

Preparation Example 376

(4S,5R)-4-(benzyloxymethyl)-5-(2-chlorophenyl)-2,2-dimethyl-1,3-dioxolane

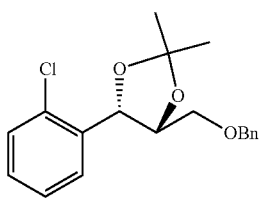 [SMILES: CC1(C)O[C@H](COCc2ccccc2)[C@H](c2ccccc2Cl)O1]

The substantially same method as described in Example 371 was conducted, except that (1S,2R)-3-(benzyloxy)-1-(2-chlorophenyl)propane-1,2-diol (Preparation example 375) was used instead of that (±)-3-(benzyloxy)-1-(2-chlorophenyl)propane-1,2-diol (Preparation example 370), to obtain the title compound (0.84 g, 85%).

¹H NMR (400 MHz, CDCl₃) δ1.53 (s, 3H), 1.66 (s, 3H), 3.14-3.06 (m, 2H), 4.26 (d, J=12 Hz, 2H), 4.83-4.78 (m, 1H), 5.63 (d, J=6.8 Hz, 1H), 7.35-7.16 (m, 8H), 7.61 (dd, J=7.4, 1.6 Hz, 1H).

Preparation Example 377

((4S,5R)-5-(2-chlorophenyl)-2,2-dimethyl-1,3-dioxolan-4-yl)methanol

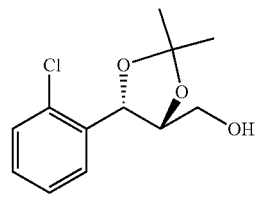 [SMILES: CC1(C)O[C@H](CO)[C@H](c2ccccc2Cl)O1]

The substantially same method as described in Example 372 was conducted, except that ((4S,5R)-4-(benzyloxymethyl)-5-(2-chlorophenyl)-2,2-dimethyl-1,3-dioxolane (Preparation example 376) was used instead of that (±)-4-(benzyloxymethyl)-5-(2-chlorophenyl)-2,2-dimethyl-1,3-dioxolane (Preparation example 371), to obtain the title compound (0.58 g, 95%).

¹H NMR (400 MHz, CDCl₃) δ1.66 (s, 3H), 1.53 (s, 3H), 3.14-3.06 (m, 2H), 4.26 (d, J=12, 2H), 4.83-4.78 (m, 1H), 5.63 (d, J=6.8 Hz, 1H), 7.35-7.16 (m, 8H), 7.61 (dd, J=7.4, 1.6, 1H).

TABLE 1

Example of sulfamate compound

| No | $R_3$-$R_7$ | n | m | $R_1$ | $R_2$ | $R_8$ | $R_9$ | Chiral-1 | Chiral-2 |
|---|---|---|---|---|---|---|---|---|---|
| 1 | 2-Cl | 0 | 0 | Me | Me | H | H | R | R |
| 2 | 2-Cl | 0 | 0 | Me | Me | H | H | S | S |
| 3 | 2-Cl | 0 | 0 | Me | Me | H | H | Rac. (syn) | Rac. (syn) |
| 4 | 2-Cl | 0 | 0 | Me | Me | H | H | Rac. (anti) | Rac. (anti) |
| 5 | 2-Cl | 0 | 0 | Me | H | H | H | R | R |
| 6 | 2-Cl | 0 | 0 | Me | H | H | H | S | S |
| 7 | 2-Cl | 0 | 0 | Et | Et | H | H | R | R |
| 8 | 2-Cl | 0 | 0 | Et | Et | H | H | S | S |
| 9 | 2-Cl | 0 | 0 | Cyclopentyl | | H | H | R | R |
| 10 | 2-Cl | 0 | 0 | Cyclopentyl | | H | H | S | S |
| 11 | 2-Cl | 0 | 0 | Cyclohexyl | | H | H | R | R |
| 12 | 2-Cl | 0 | 0 | Cyclohexyl | | H | H | S | S |
| 13 | 2-Cl | 0 | 0 | Methylbenzene | | H | H | R | R |
| 14 | 2-Cl | 0 | 0 | Methylbenzene | | H | H | S | S |
| 15 | 2-F | 0 | 0 | Me | Me | H | H | R | R |
| 16 | 2-F | 0 | 0 | Me | Me | H | H | S | S |
| 17 | 2-F | 0 | 0 | Me | H | H | H | R | R |
| 18 | 2-F | 0 | 0 | Me | H | H | H | S | S |
| 19 | 2-F | 0 | 0 | Et | Et | H | H | R | R |
| 20 | 2-F | 0 | 0 | Et | Et | H | H | S | S |
| 21 | 2-F | 0 | 0 | Cyclopentyl | | H | H | R | R |
| 22 | 2-F | 0 | 0 | Cyclopentyl | | H | H | S | S |
| 23 | 2-F | 0 | 0 | Cyclohexyl | | H | H | R | R |
| 24 | 2-F | 0 | 0 | Cyclohexyl | | H | H | S | S |
| 25 | 2-F | 0 | 0 | Methylbenzene | | H | H | R | R |
| 26 | 2-F | 0 | 0 | Methylbenzene | | H | H | S | S |
| 27 | 2-I | 0 | 0 | Me | Me | H | H | R | R |
| 28 | 2-I | 0 | 0 | Me | Me | H | H | S | S |
| 29 | 2-I | 0 | 0 | Me | H | H | H | R | R |
| 30 | 2-I | 0 | 0 | Me | H | H | H | S | S |
| 31 | 2-I | 0 | 0 | Et | Et | H | H | R | R |
| 32 | 2-I | 0 | 0 | Et | Et | H | H | S | S |
| 33 | 2-I | 0 | 0 | Cyclopentyl | | H | H | R | R |
| 34 | 2-I | 0 | 0 | Cyclopentyl | | H | H | S | S |
| 35 | 2-I | 0 | 0 | Cyclohexyl | | H | H | R | R |
| 36 | 2-I | 0 | 0 | Cyclohexyl | | H | H | S | S |
| 37 | 2-I | 0 | 0 | Methylbenzene | | H | H | R | R |
| 38 | 2-I | 0 | 0 | Methylbenzene | | H | H | S | S |
| 39 | 2,4-Cl | 0 | 0 | Me | Me | H | H | R | R |
| 40 | 2,4-Cl | 0 | 0 | Me | Me | H | H | S | S |
| 41 | 2,4-Cl | 0 | 0 | Me | H | H | H | R | R |
| 42 | 2,4-Cl | 0 | 0 | Me | H | H | H | S | S |
| 43 | 2,4-Cl | 0 | 0 | Et | Et | H | H | R | R |
| 44 | 2,4-Cl | 0 | 0 | Et | Et | H | H | S | S |
| 45 | 2,4-Cl | 0 | 0 | Cyclopentyl | | H | H | R | R |
| 46 | 2,4-Cl | 0 | 0 | Cyclopentyl | | H | H | S | S |
| 47 | 2,4-Cl | 0 | 0 | Cyclohexyl | | H | H | R | R |
| 48 | 2,4-Cl | 0 | 0 | Cyclohexyl | | H | H | S | S |
| 49 | 2,4-Cl | 0 | 0 | Methylbenzene | | H | H | R | R |
| 50 | 2,4-Cl | 0 | 0 | Methylbenzene | | H | H | S | S |
| 51 | 2,6-Cl | 0 | 0 | Me | Me | H | H | R | R |
| 52 | 2,6-Cl | 0 | 0 | Me | Me | H | H | S | S |
| 53 | 2,6-Cl | 0 | 0 | Me | H | H | H | R | R |
| 54 | 2,6-Cl | 0 | 0 | Me | H | H | H | S | S |
| 55 | 2,6-Cl | 0 | 0 | Et | Et | H | H | R | R |
| 56 | 2,6-Cl | 0 | 0 | Et | Et | H | H | S | S |
| 57 | 2,6-Cl | 0 | 0 | Cyclopentyl | | H | H | R | R |
| 58 | 2,6-Cl | 0 | 0 | Cyclopentyl | | H | H | S | S |
| 59 | 2,6-Cl | 0 | 0 | Cyclohexyl | | H | H | R | R |
| 60 | 2,6-Cl | 0 | 0 | Cyclohexyl | | H | H | S | S |
| 61 | 2,6-Cl | 0 | 0 | Methylbenzene | | H | H | R | R |
| 62 | 2,6-Cl | 0 | 0 | Methylbenzene | | H | H | S | S |
| 63 | 2-NH2 | 0 | 0 | Me | Me | H | H | R | R |
| 64 | 2-NH2 | 0 | 0 | Me | Me | H | H | S | S |
| 65* | 2-NH2 | 0 | 0 | Me | Me | H | H | R | R |
| 66* | 2-NH2 | 0 | 0 | Me | Me | H | H | S | S |
| 67 | 2-NH2 | 0 | 0 | Me | H | H | H | R | R |
| 68 | 2-NH2 | 0 | 0 | Me | H | H | H | S | S |
| 69 | 2-NH2 | 0 | 0 | Et | Et | H | H | R | R |
| 70 | 2-NH2 | 0 | 0 | Et | Et | H | H | S | S |
| 71 | 2-NH2 | 0 | 0 | Cyclopentyl | | H | H | R | R |
| 72 | 2-NH2 | 0 | 0 | Cyclopentyl | | H | H | S | S |
| 73 | 2-NH2 | 0 | 0 | Cyclohexyl | | H | H | R | R |
| 74 | 2-NH2 | 0 | 0 | Cyclohexyl | | H | H | S | S |
| 75 | 2-NH2 | 0 | 0 | Methylbenzene | | H | H | R | R |

TABLE 1-continued

Example of sulfamate compound

| No | R₃-R₇ | n | m | R₁ | R₂ | R₈ | R₉ | Chiral-1 | Chiral-2 |
|---|---|---|---|---|---|---|---|---|---|
| 76 | 2-NH2 | 0 | 0 | Methylbenzene | | H | H | S | S |
| 77 | 2-NO2 | 0 | 0 | Me | Me | H | H | R | R |
| 78 | 2-NO2 | 0 | 0 | Me | Me | H | H | S | S |
| 79 | 2-NO2 | 0 | 0 | Me | H | H | H | R | R |
| 80 | 2-NO2 | 0 | 0 | Me | H | H | H | S | S |
| 81 | 2-NO2 | 0 | 0 | Et | Et | H | H | R | R |
| 82 | 2-NO2 | 0 | 0 | Et | Et | H | H | S | S |
| 83 | 2-NO2 | 0 | 0 | Cyclopentyl | | H | H | R | R |
| 84 | 2-NO2 | 0 | 0 | Cyclopentyl | | H | H | S | S |
| 85 | 2-NO2 | 0 | 0 | Cyclohexyl | | H | H | R | R |
| 86 | 2-NO2 | 0 | 0 | Cyclohexyl | | H | H | S | S |
| 87 | 2-NO2 | 0 | 0 | Methylbenzene | | H | H | R | R |
| 88 | 2-NO2 | 0 | 0 | Methylbenzene | | H | H | S | S |
| 89 | 2-NO2 | 0 | 0 | Cyclocarbonyl | | H | H | R | R |
| 90 | 2-NO2 | 0 | 0 | Cyclocarbonyl | | H | H | S | S |
| 91 | 2-Me | 0 | 0 | Me | Me | H | H | R | R |
| 92 | 2-Me | 0 | 0 | Me | Me | H | H | S | S |
| 93 | 2-Me | 0 | 0 | Me | H | H | H | R | R |
| 94 | 2-Me | 0 | 0 | Me | H | H | H | S | S |
| 95 | 2-Me | 0 | 0 | Et | Et | H | H | R | R |
| 96 | 2-Me | 0 | 0 | Et | Et | H | H | S | S |
| 97 | 2-Me | 0 | 0 | Cyclopentyl | | H | H | R | R |
| 98 | 2-Me | 0 | 0 | Cyclopentyl | | H | H | S | S |
| 99 | 2-Me | 0 | 0 | Cyclohexyl | | H | H | R | R |
| 100 | 2-Me | 0 | 0 | Cyclohexyl | | H | H | S | S |
| 101 | 2-Me | 0 | 0 | Methylbenzene | | H | H | R | R |
| 102 | 2-Me | 0 | 0 | Methylbenzene | | H | H | S | S |
| 103 | 2-MeNH | 0 | 0 | Me | Me | Me | H | R | R |
| 104 | 2-MeNH | 0 | 0 | Me | Me | Me | H | S | S |
| 105 | H | 0 | 0 | Me | Me | H | H | R | R |
| 106 | H | 0 | 0 | Me | Me | H | H | S | S |
| 107 | H | 0 | 0 | Et | Et | H | H | R | R |
| 108 | H | 0 | 0 | Et | Et | H | H | S | S |
| 109 | H | 0 | 0 | Cyclopentyl | | H | H | R | R |
| 110 | H | 0 | 0 | Cyclopentyl | | H | H | S | S |
| 111 | H | 0 | 0 | Cyclohexyl | | H | H | R | R |
| 112 | H | 0 | 0 | Cyclohexyl | | H | H | S | S |
| 113 | H | 1 | 1 | Me | Me | H | H | R | R |
| 114 | H | 1 | 1 | Me | Me | H | H | S | S |
| 115 | H | 1 | 1 | Et | Et | H | H | R | R |
| 116 | H | 1 | 1 | Et | Et | H | H | S | S |
| 117 | H | 1 | 1 | Cyclopentyl | | H | H | R | R |
| 118 | H | 1 | 1 | Cyclopentyl | | H | H | S | S |
| 119 | H | 1 | 1 | Cyclohexyl | | H | H | R | R |
| 120 | H | 1 | 1 | Cyclohexyl | | H | H | S | S |
| 121 | H | 1 | 0 | Me | Me | H | H | R | R |
| 122 | H | 1 | 0 | Me | Me | H | H | S | S |
| 123 | H | 1 | 0 | Et | Et | H | H | R | R |
| 124 | H | 1 | 0 | Et | Et | H | H | S | S |
| 125 | H | 1 | 0 | Cyclopentyl | | H | H | R | R |
| 126 | H | 1 | 0 | Cyclopentyl | | H | H | S | S |
| 127 | H | 1 | 0 | Cyclohexyl | | H | H | R | R |
| 128 | H | 1 | 0 | Cyclohexyl | | H | H | S | S |
| 129 | H | 0 | 1 | Me | Me | H | H | R | R |
| 130 | H | 0 | 1 | Me | Me | H | H | S | S |
| 131 | H | 0 | 1 | Et | Et | H | H | R | R |
| 132 | H | 0 | 1 | Et | Et | H | H | S | S |
| 133 | H | 0 | 1 | Cyclopentyl | | H | H | R | R |
| 134 | H | 0 | 1 | Cyclopentyl | | H | H | S | S |
| 135 | H | 0 | 1 | Cyclohexyl | | H | H | R | R |
| 136 | H | 0 | 1 | Cyclohexyl | | H | H | S | S |
| 137 | Cl | 1 | 1 | Me | Me | H | H | R | R |
| 138 | Cl | 1 | 1 | Me | Me | H | H | S | S |
| 139 | Cl | 1 | 1 | Et | Et | H | H | R | R |
| 140 | Cl | 1 | 1 | Et | Et | H | H | S | S |
| 141 | Cl | 1 | 1 | Cyclopentyl | | H | H | R | R |
| 142 | Cl | 1 | 1 | Cyclopentyl | | H | H | S | S |
| 143 | Cl | 1 | 1 | Cyclohexyl | | H | H | R | R |
| 144 | Cl | 1 | 1 | Cyclohexyl | | H | H | S | S |
| 145 | Cl | 1 | 0 | Me | Me | H | H | R | R |
| 146 | Cl | 1 | 0 | Me | Me | H | H | S | S |
| 147 | Cl | 1 | 0 | Et | Et | H | H | R | R |
| 148 | Cl | 1 | 0 | Et | Et | H | H | S | S |
| 149 | Cl | 1 | 0 | Cyclopentyl | | H | H | R | R |
| 150 | Cl | 1 | 0 | Cyclopentyl | | H | H | S | S |
| 151 | Cl | 1 | 0 | Cyclohexyl | | H | H | R | R |
| 152 | Cl | 1 | 0 | Cyclohexyl | | H | H | S | S |
| 153 | Cl | 0 | 1 | Me | Me | H | H | R | R |
| 154 | Cl | 0 | 1 | Me | Me | H | H | S | S |
| 155 | Cl | 0 | 1 | Et | Et | H | H | R | R |
| 156 | Cl | 0 | 1 | Et | Et | H | H | S | S |
| 157 | Cl | 0 | 1 | Cyclopentyl | | H | H | R | R |
| 158 | Cl | 0 | 1 | Cyclopentyl | | H | H | S | S |
| 159 | Cl | 0 | 1 | Cyclohexyl | | H | H | R | R |
| 160 | Cl | 0 | 1 | Cyclohexyl | | H | H | S | S |
| 161 | Cl | 0 | 0 | Me | Me | H | H | S | R |

*Sodium salt

Example 1-1

((4R,5R)-5-(2-chlorophenyl)-2,2-dimethyl-1,3-dioxolan-4-yl)methyl sulfamate

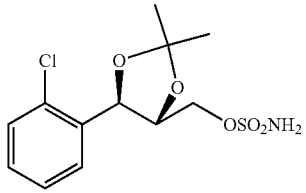

To a 100 ml flask, Acetonitrile (2.26 ml, 43.2 mmol) was added and cooled to 0° C. Chlorosulfonyl isocyanate (1.5 ml, 17.3 mmol), and formic acid (0.65 ml, 17.3 mmol) was added dropwise and stirred at room temperature for 6 hours. ((4R, 5R)-5-(2-chlorophenyl)-2,2-dimethyl-1,3-dioxolan-4-yl) methanol (Preparation example 6, 1.05 g, 4.3 mmol) in N,N-dimethyl acetamide (13.2 ml, 142.7 mmol) was slowly added at 0° C. and stirred at room temperature for 1 hours. The reaction mixture was quenched with $H_2O$, extracted with EtOAc, and washed with $H_2O$. The organic layer was dried over anhydrous magnesium sulfate ($MgSO_4$), filtered and concentrated. The crude compound was purified by a silica gel column to produce the title compound (1.00 g, 50~80%).

$^1$H NMR (400 MHz, $CDCl_3$) δ 1.57 (s, 3H), 1.63 (s, 3H), 4.11~4.10 (m, 1H), 4.53~4.42 (m, 2H), 4.88 (s, 2H), 5.37 (d, J=8.4, 1H), 7.28~7.56 (m, 4H)

Example 1-2

((4R,5R)-5-(2-chlorophenyl)-2,2-dimethyl-1,3-dioxolan-4-yl)methyl sulfamate

To a 100 mL RB flask 10.0 g (41.2 mmol) of acetonide alcohol 3, 50 ml of toluene, 7.92 g (82.4 mmol) of sulfamide and 13.0 g (165 mmol) of pyridine were added at RT. The mixture was refluxed for 1.5 hr (bath temperature 135). The reaction mixture cooled to room temperature then solution was extracted with 27.5 ml (82.4 mmol) of 3N NaOH solution. The aqueous layer was washed with 50 mL of toluene. To the mixture 50 ml of methanol and 35 ml of water was

Example 2

((4S,5S)-5-(2-chlorophenyl)-2,2-dimethyl-1,3-dioxolan-4-yl)methyl sulfamate

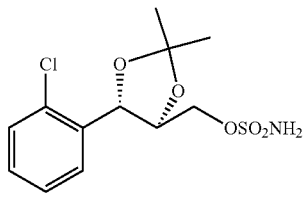

The substantially same method as described in Example 1 was conducted, except that ((4S,5S)-5-(2-chlorophenyl)-2,2-dimethyl-1,3-dioxolan-4-yl)methanol (Preparation example 7, 27) was used instead of ((4R,5R)-5-(2-chlorophenyl)-2,2-dimethyl-1,3-dioxolan-4-yl)methanol (Preparation example 6), to obtain the title compound (2.30 g, 50~80%).

$^1$H NMR (400 MHz, CDCl$_3$) δ 1.59 (s, 3H), 1.65 (s, 3H), 4.12~4.07 (m, 1H), 4.54~4.42 (m, 2H), 4.91 (s, 2H), 5.37 (d, J=8.8, 1H), 7.29~7.65 (m, 4H)

Example 3

(5-(2-chlorophenyl)-2,2-dimethyl-1,3-dioxolan-4-yl)methyl sulfamate (SS & RR mixture)

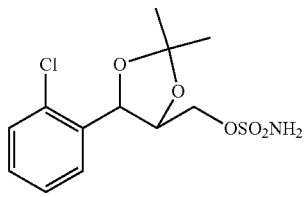

The substantially same method as described in Example 1 was conducted, except that (5-(2-chlorophenyl)-2,2-dimethyl-1,3-dioxolan-4-yl)methanol (Preparation example 8) was used instead of ((4R,5R)-5-(2-chlorophenyl)-2,2-dimethyl-1,3-dioxolan-4-yl)methanol (Preparation example 6), to obtain the title compound (1.74 g, 50~80%).

$^1$H NMR (400 MHz, CDCl$_3$) δ 1.57 (s, 3H), 1.63 (s, 3H), 4.11~4.10 (m, 1H), 4.53~4.42 (m, 2H), 4.88 (s, 2H), 5.37 (d, J=8.4, 1H) 7.28~7.65 (m, 4H)

Example 4

(5-(2-chlorophenyl)-2,2-dimethyl-1,3-dioxolan-4-yl)methyl sulfamate (SR & RS mixture)

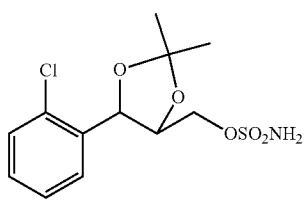

The substantially same method as described in Example 1 was conducted, except that 5-(2-chlorophenyl)-2,2-dimethyl-1,3-dioxolan-4-yl)methanol (Preparation example 372 (SR&RS mixture)) was used instead of ((4R,5R)-5-(2-chlorophenyl)-2,2-dimethyl-1,3-dioxolan-4-yl)methanol (Preparation example 6), to obtain the title compound (1.3 g, 50~80%).

$^1$H NMR (400 MHz, CDCl$_3$) δ 1.59 (s, 3H), 1.65 (s, 3H), 4.11~4.10 (m, 1H), 4.50~4.42 (m, 2H), 4.85 (s, 2H), 5.35 (d, J=8.4, 1H) 7.28~7.65 (m, 4H)

Example 5

((4R,5R)-5-(2-chlorophenyl)-2-methyl-1,3-dioxolan-4-yl)methyl sulfamate

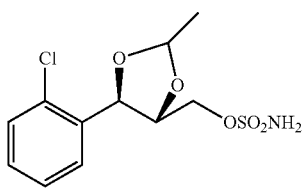

The substantially same method as described in Example 1 was conducted, except that ((4S,5S)-5-(2-chlorophenyl)-2-methyl-1,3-dioxolan-4-yl)methanol (Preparation example 61) was used instead of ((4R,5R)-5-(2-chlorophenyl)-2,2-dimethyl-1,3-dioxolan-4-yl)methanol (Preparation example 6), to obtain the title compound (2.8 g, 55~75%)

$^1$H NMR (400 MHz, DMSO) δ 1.40 (d, J=6.4, 3H), 4.22 (dt, J=7.0, J=3.3, 1H), 4.7 (d, J=3.2, 2H), 5.08 (d, J=7.0, 1H), 5.46 (m, J=6.4, 1H), 7.26~7.40 (m, 3H), 7.49 (s, 2H), 7.61 (dd, J=1.2, J=7.6, 1H).

Example 6

((4S,5S)-5-(2-chlorophenyl)-2-methyl-1,3-dioxolan-4-yl)methyl sulfamate

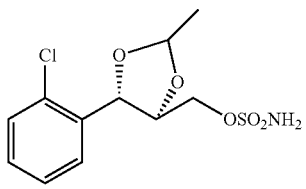

The substantially same method as described in Example 1 was conducted, except that ((4R,5R)-5-(2-chlorophenyl)-2-methyl-1,3-dioxolan-4-yl)methanol (Preparation example 63) was used instead of ((4R,5R)-5-(2-chlorophenyl)-2,2-dimethyl-1,3-dioxolan-4-yl)methanol (Preparation example 6), to obtain the title compound (2.1 g, 55~75%)

$^1$H NMR (400 MHz, DMSO) δ 1.40 (d, J=6.4, 3H), 4.22 (dt, J=7.0, J=3.3, 1H), 4.7 (d, J=3.2, 2H), 5.08 (d, J=7.0, 1H), 5.46 (m, J=6.4, 1H), 7.26~7.40 (m, 3H), 7.49 (s, 2H), 7.61 (dd, J=1.2, J=7.6, 1H).

Example 7

((4R,5R)-5-(2-chlorophenyl)-2,2-diethyl-1,3-dioxolan-4-yl)methyl sulfamate

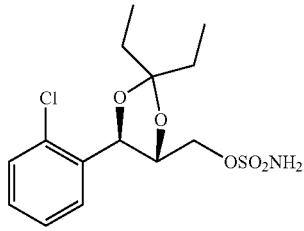

The substantially same method as described in Example 1 was conducted, except that ((4R,5R)-5-(2-chlorophenyl)-2,2-diethyl-1,3-dioxolan-4-yl)methanol (Preparation example 65) was used instead of ((4R,5R)-5-(2-chlorophenyl)-2,2-dimethyl-1,3-dioxolan-4-yl)methanol (Preparation example 6), to obtain the title compound (1.5 g, 50~80%).

$^1$H NMR (400 MHz, CDCl$_3$) δ 1.59 (s, 10H), 4.17 (m, 3H), 4.98 (d, J=8.4, 1H), 5.08 (s, 2H), 6.59 (t, J=8.4, 1H), 6.68 (d, J=8.4, 1H), 7.04~7.56 (m, 4H)

Example 8

((4S,4S)-5-(2-chlorophenyl)-2,2-diethyl-1,3-dioxolan-4-yl)methyl sulfamate

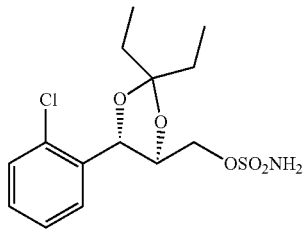

The substantially same method as described in Example 1 was conducted, except that ((4S,5S)-5-(2-chlorophenyl)-2,2-diethyl-1,3-dioxolan-4-yl)methanol (Preparation example 67) was used instead of ((4R,5R)-5-(2-chlorophenyl)-2,2-dimethyl-1,3-dioxolan-4-yl)methanol (Preparation example 6), to obtain the title compound (1.2 g, 50~80%).

$^1$H NMR (400 MHz, CDCl$_3$) δ 1.59 (s, 10H), 4.17 (m, 3H), 4.96 (d, J=8.4, 1H), 5.08 (s, 2H), 6.59 (t, J=8.4, 1H), 6.68 (d, J=8.4, 1H), 7.04~7.56 (m, 4H)

Example 9

((2R,3R)-3-(2-chlorophenyl)-1,4-dioxaspiro[4,4]nonan-2-yl)methyl sulfamate

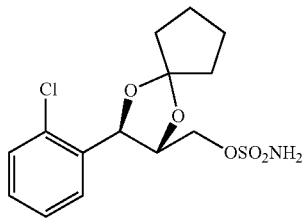

The substantially same method as described in Example 1 was conducted, except that ((4R,5R)-5-(2-chlorophenyl)-1,4-dioxaspiro[4,4]nonane-2-yl)methanol (Preparation example 69) was used instead of ((4R,5R)-5-(2-chlorophenyl)-2,2-dimethyl-1,3-dioxolan-4-yl)methanol (Preparation example 6), to obtain the title compound (2.2 g, 50~80%).

$^1$H NMR (400 MHz, DMSO) δ 1.64~1.72 (m, 4H), 1.85-19.8 (m, 4H), 4.10~4.16 (m, 2H), 4.17~4.25 (m, 1H), 5.20 (d, J=7.2, 1H), 7.34~7.62 (m, 6H)

Example 10

((2S,3S)-3-(2-chlorophenyl)-1,4-dioxaspiro[4,4]nonan-2-yl)methyl sulfamate

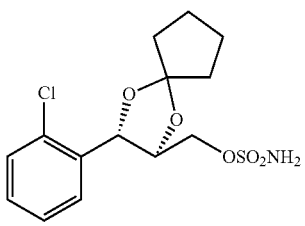

The substantially same method as described in Example 1 was conducted, except that ((4S,5S)-5-(2-chlorophenyl)-1,4-dioxaspiro[4,4]nonane-2-yl)methanol (Preparation example 71) was used instead of ((4R,5R)-5-(2-chlorophenyl)-2,2-dimethyl-1,3-dioxolan-4-yl)methanol (Preparation example 6), to obtain the title compound (2.1 g, 50~80%).

$^1$H NMR (400 MHz, DMSO) δ 1.64~1.75 (m, 4H), 1.85~19.9 (m, 4H), 4.10~4.16 (m, 2H), 4.17~4.25 (m, 1H), 5.20 (d, J=7.2, 1H), 7.34~7.62 (m, 6H)

Example 11

((2R,3R)-3-(2-chlorophenyl)-1,4-dioxaspiro[4,5]decan-2-yl)methyl sulfamate

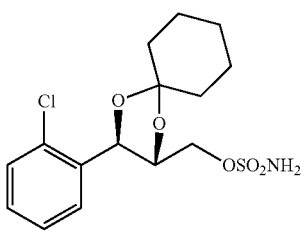

The substantially same method as described in Example 1 was conducted, except that ((4R,5R)-5-(2-chlorophenyl)-1,4-dioxaspiro[4,5]decane-2-yl)methanol (Preparation example 73) was used instead of ((4R,5R)-5-(2-chlorophenyl)-2,2-dimethyl-1,3-dioxolan-4-yl)methanol (Preparation example 6), to obtain the title compound (1.4 g, 50~80%).

¹H NMR (400 MHz, DMSO) δ 1.51~1.67 (m, 10H), 4.11~4.23 (m, 3H), 4.98 (d, J=8.0, 2H), 5.08 (s, 1H), 6.59 (t, J=8.0, 1H), 6.68 (d, J=8.0, 1H), 7.04~7.56 (m, 4H)

Example 12

((2S,3S)-3-(2-chlorophenyl)-1,4-dioxaspiro[4,5]decan-2-yl)methyl sulfamate

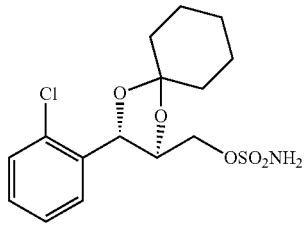

The substantially same method as described in Example 1 was conducted, except that ((4S,5S)-5-(2-chlorophenyl)-1,4-dioxaspiro[4,5]decane-2-yl)methanol (Preparation example 75) was used instead of ((4R,5R)-5-(2-chlorophenyl)-2,2-dimethyl-1,3-dioxolan-4-yl)methanol (Preparation example 6), to obtain the title compound (1.2 g, 50~80%).
¹H NMR (400 MHz, DMSO) δ 1.51~1.67 (m, 10H), 4.11~4.23 (m, 3H), 4.98 (d, J=8.0, 2H), 5.08 (s, 1H), 6.59 (t, J=8.0, 1H), 6.68 (d, J=8.0, 1H), 7.04~7.56 (m, 4H)

Example 13

((4R,5R)-5-(2-chlorophenyl)-2-phenyl-1,3-dioxolan-4-yl)methyl sulfamate

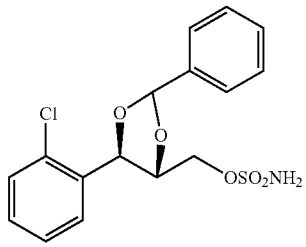

The substantially same method as described in Example 1 was conducted, except that ((4R,5R)-5-(2-chlorophenyl)-2-phenyl-1,3-dioxolan-4-yl)methanol (Preparation example 77) was used instead of ((4R,5R)-5-(2-chlorophenyl)-2,2-dimethyl-1,3-dioxolan-4-yl)methanol (Preparation example 6), to obtain the title compound (1.3 g, 50~80%).
¹H NMR (400 MHz, DMSO) δ 4.25 (dt, J=3.3, J=5.7, 1H), 4.55 (d, J=5.7, 1H), 4.75 (d, J=3.3, 2H), 5.59 (m, 1H), 6.72~7.75 (m, 2H), 6.92~7.33 (m, 5H), 7.29 (m, 1H), 7.76 (m, 1H)

Example 14

((4S,5S)-5-(2-chlorophenyl)-2-phenyl-1,3-dioxolan-4-yl)methyl sulfamate

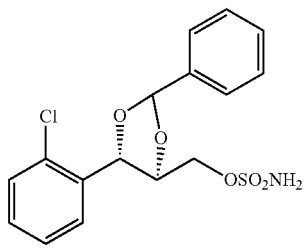

The substantially same method as described in Example 1 was conducted, except that ((4S,5S)-5-(2-chlorophenyl)-2-phenyl-1,3-dioxolan-4-yl)methanol (Preparation example 79) was used instead of ((4R,5R)-5-(2-chlorophenyl)-2,2-dimethyl-1,3-dioxolan-4-yl)methanol (Preparation example 6), to obtain the title compound (2.1 g, 50~80%).
¹H NMR (400 MHz, DMSO) δ 4.28 (dt, J=3.3, J=5.7, 1H), 4.58 (d, J=5.7, 1H), 4.75 (d, J=3.3, 2H), 5.62 (m, 1H), 6.72~7.75 (m, 2H), 6.92~7.33 (m, 5H), 7.29 (m, 1H), 7.76 (m, 1H)

Example 15

((4R,5R)-5-(2-fluorophenyl)-2,2-dimethyl-1,3-dioxolan-4-yl)methyl sulfamate

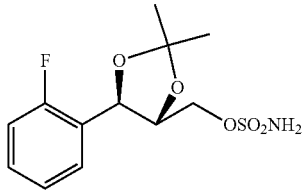

The substantially same method as described in Example 1 was conducted, except that ((4R,5R)-5-(2-fluorophenyl)-2,2-dimethyl-1,3-dioxolan-4-yl)methanol (Preparation example 13) was used instead of ((4R,5R)-5-(2-chlorophenyl)-2,2-dimethyl-1,3-dioxolan-4-yl)methanol (Preparation example 6), to obtain the title compound (1.8 g, 50~80%).
¹H NMR (400 MHz, DMSO) δ 1.47 (d, J=11.6, 6H), 3.35~3.94 (m, 1H), 4.02~4.20 (m, 1H), 4.23 (d, J=2.0 1H), 5.07 (d, J=8.4, 1H), 7.21~7.58 (m, 4H)

Example 16

((4S,5S)-5-(2-fluorophenyl)-2,2-dimethyl-1,3-dioxolan-4-yl)methyl sulfamate

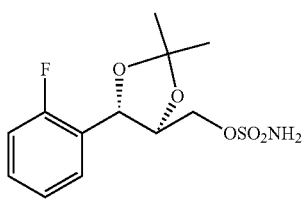

The substantially same method as described in Example 1 was conducted, except that ((4S,5S)-5-(2-fluorophenyl)-2,2-dimethyl-1,3-dioxolan-4-yl)methanol (Preparation example 15) was used instead of ((4R,5R)-5-(2-chlorophenyl)-2,2-dimethyl-1,3-dioxolan-4-yl)methanol (Preparation example 6), to obtain the title compound (1.2 g, 50~80%).
¹H NMR (400 MHz, DMSO) δ 1.47 (d, J=11.6, 6H), 3.35~3.94 (m, 1H), 4.02~4.20 (m, 1H), 4.23 (d, J=2.0 1H), 5.07 (d, J=8.4, 1H), 7.21~7.58 (m, 4H)

Example 17

((4R,5R)-5-(2-fluorophenyl)-2-methyl-1,3-dioxolan-4-yl)methyl sulfamate

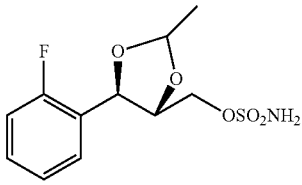

The substantially same method as described in Example 1 was conducted, except that ((4S,5S)-5-(2-fluorophenyl)-2-methyl-1,3-dioxolan-4-yl)methanol (Preparation example 84) was used instead of ((4R,5R)-5-(2-chlorophenyl)-2,2-dimethyl-1,3-dioxolan-4-yl)methanol (Preparation example 6), to obtain the title compound (2.5 g, 55~75%)

$^1$H NMR (400 MHz, DMSO) δ 1.40 (d, J=6.4, 3H), 4.7 (d, J=3.2, 2H), 5.46 (m, J=6.4, 1H), 4.22 (dt, J=3.3, J=7.0, 1H), 5.08 (d, J=7.0, 1H), 7.26~7.40 (m, 3H), 7.49 (s, 2H), 7.61 (dd, J=1.2, J=7.6, 1H).

Example 18

((4S,5S)-5-(2-fluorophenyl)-2-methyl-1,3-dioxolan-4-yl)methyl sulfamate

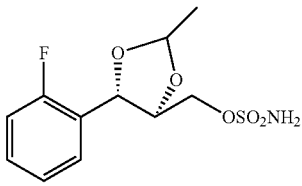

The substantially same method as described in Example 1 was conducted, except that ((4R,5R)-5-(2-fluorophenyl)-2,2-dimethyl-1,3-dioxolan-4-yl)methanol (Preparation example 86) was used instead of ((4R,5R)-5-(2-chlorophenyl)-2,2-dimethyl-1,3-dioxolan-4-yl)methanol (Preparation example 6), to obtain the title compound (2.1 g, 55~75%)

$^1$H NMR (400 MHz, DMSO) δ 1.40 (d, J=6.4, 3H), 4.7 (d, J=3.2, 2H), 5.46 (m, J=6.4, 1H), 4.22 (dt, J=3.3, J=7.0, 1H), 5.18 (d, J=7.0, 1H), 7.26~7.40 (m, 3H), 7.52 (s, 2H), 7.61 (dd, J=1.2, J=7.6, 1H).

Example 19

((4R,5R)-5-(2-fluorophenyl)-2,2-diethyl-1,3-dioxolan-4-yl)methyl sulfamate

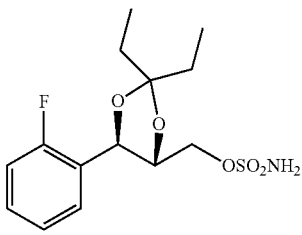

The substantially same method as described in Example 1 was conducted, except that ((4R,5R)-5-(2-fluorophenyl)-2,2-diethyl-1,3-dioxolan-4-yl)methanol (Preparation example 88) was used instead of ((4R,5R)-5-(2-chlorophenyl)-2,2-dimethyl-1,3-dioxolan-4-yl)methanol (Preparation example 6), to obtain the title compound (1.3 g, 50~80%).

$^1$H NMR (400 MHz, CDCl$_3$) δ 1.59 (s, 10H), 4.17 (m, 3H), 4.98 (d, J=8.4, 1H), 5.08 (s, 2H), 6.59 (t, J=8.4, 1H), 6.68 (d, J=8.4, 1H), 7.04~7.56 (m, 4H)

Example 20

((4S,5S)-5-(2-fluorophenyl)-2,2-diethyl-1,3-dioxolan-4-yl)methyl sulfamate

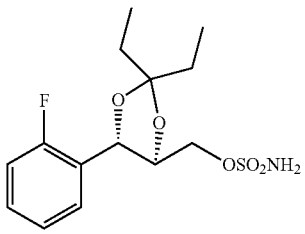

The substantially same method as described in Example 1 was conducted, except that ((4S,5S)-5-(2-fluorophenyl)-2,2-diethyl-1,3-dioxolan-4-yl)methanol (Preparation example 90) was used instead of ((4R,5R)-5-(2-chlorophenyl)-2,2-dimethyl-1,3-dioxolan-4-yl)methanol (Preparation example 6), to obtain the title compound (1.6 g, 50~80%).

$^1$H NMR (400 MHz, CDCl$_3$) δ 1.59 (s, 10H), 4.14 (m, 3H), 4.98 (d, J=8.4, 1H), 5.05 (s, 2H), 6.59 (t, J=8.4, 1H), 6.65 (d, J=8.4, 1H), 7.04~7.60 (m, 4H)

Example 21

((2R,3R)-3-(2-fluorophenyl)-1,4-dioxaspiro[4,4]nonan-2-yl)methyl sulfamate

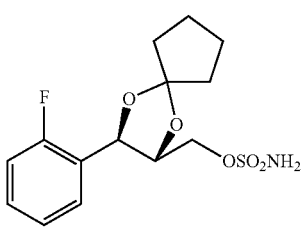

The substantially same method as described in Example 1 was conducted, except that ((4R,5R)-5-(2-fluorophenyl)-1,4-dioxapiro[4,4]nonane-2-yl)methanol (Preparation example 92) was used instead of ((4R,5R)-5-(2-chlorophenyl)-2,2-dimethyl-1,3-dioxolan-4-yl)methanol (Preparation example 6), to obtain the title compound (1.5 g, 50~80%).

¹H NMR (400 MHz, DMSO) δ 1.64~1.72 (m, 4H), 1.84~19.8 (m, 4H), 4.10~4.16 (m, 2H), 4.19~4.25 (m, 1H), 5.25 (d, J=7.2, 1H), 7.34~7.62 (m, 6H)

Example 22

((2S,3S)-3-(2-fluorophenyl)-1,4-dioxaspiro[4,4]nonan-2-yl)methyl sulfamate

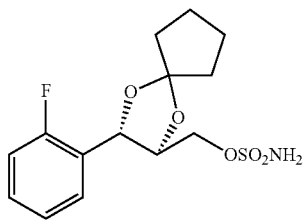

The substantially same method as described in Example 1 was conducted, except that ((4S,5S)-5-(2-fluorophenyl)-1,4-dioxapiro[4,4]nonane-2-yl)methanol (Preparation example 94) was used instead of ((4R,5R)-5-(2-chlorophenyl)-2,2-dimethyl-1,3-dioxolan-4-yl)methanol (Preparation example 6), to obtain the title compound (1.0 g, 50~80%).

¹H NMR (400 MHz, DMSO) δ 1.64~1.72 (m, 4H), 1.85~19.8 (m, 4H), 4.10~4.16 (m, 2H), 4.17~4.25 (m, 1H), 5.20 (d, J=7.2, 1H), 7.34~7.62 (m, 6H)

Example 23

((2R,3R)-3-(2-fluorophenyl)-1,4-dioxaspiro[4,5]decan-2-yl)methyl sulfamate

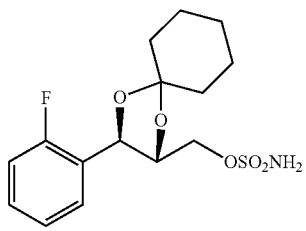

The substantially same method as described in Example 1 was conducted, except that ((4R,5R)-5-(2-fluorophenyl)-1,4-dioxapiro[4,5]decane-2-yl)methanol (Preparation example 96) was used instead of ((4R,5R)-5-(2-chlorophenyl)-2,2-dimethyl-1,3-dioxolan-4-yl)methanol (Preparation example 6), to obtain the title compound (0.9 g, 50~80%).

¹H NMR (400 MHz, DMSO) δ 1.51~1.67 (m, 10H), 4.11~4.23 (m, 3H), 4.98 (d, J=8.0, 2H), 5.08 (s, 1H), 6.59 (t, J=8.0, 1H), 6.68 (d, J=8.0, 1H), 7.04~7.56 (m, 4H)

Example 24

((2S,3S)-3-(2-fluorophenyl)-1,4-dioxaspiro[4,5]decan-2-yl)methyl sulfamate

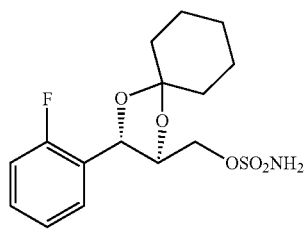

The substantially same method as described in Example 1 was conducted, except that ((4S,5S)-5-(2-fluorophenyl)-1,4-dioxapiro[4,5]decane-2-yl)methanol (Preparation example 98) was used instead of ((4R,5R)-5-(2-chlorophenyl)-2,2-dimethyl-1,3-dioxolan-4-yl)methanol (Preparation example 6), to obtain the title compound (0.9 g, 50~80%).

¹H NMR (400 MHz, DMSO) δ 1.51~1.67 (m, 10H), 4.11~4.23 (m, 3H), 4.98 (d, J=8.0, 2H), 5.08 (s, 1H), 6.59 (t, J=8.0, 1H), 6.68 (d, J=8.0, 1H), 7.04~7.56 (m, 4H)

Example 25

((4R,5R)-5-(2-fluorophenyl)-2-phenyl-1,3-dioxolan-4-yl)methyl sulfamate

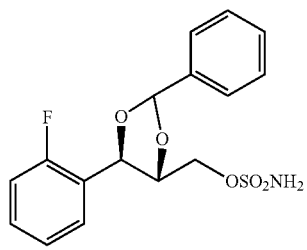

The substantially same method as described in Example 1 was conducted, except that ((4R,5R)-5-(2-fluorophenyl)-2-phenyl-1,3-dioxolane-4-yl)methanol (Preparation example 100) was used instead of ((4R,5R)-5-(2-chlorophenyl)-2,2-dimethyl-1,3-dioxolan-4-yl)methanol (Preparation example 6), to obtain the title compound (1.0 g, 50~80%).

¹H NMR (400 MHz, DMSO) δ 4.25 (dt, J=5.7, J=3.3, 1H), 4.59 (d, J=5.7, 1H), 4.75 (d, J=3.3, 2H), 5.59 (m, 1H), 6.72~7.75 (m, 2H), 6.92~7.33 (m, 5H), 7.25 (m, 1H), 7.76 (m, 1H)

Example 26

((4S,5S)-5-(2-fluorophenyl)-2-phenyl-1,3-dioxolan-4-yl)methyl sulfamate

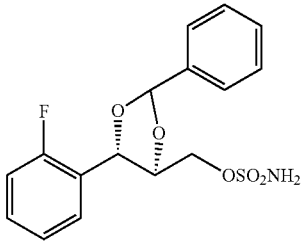

The substantially same method as described in Example 1 was conducted, except that ((4S,5S)-5-(2-fluorophenyl)-2-phenyl-1,3-dioxolane-4-yl)methanol (Preparation example 102) was used instead of ((4R,5R)-5-(2-chlorophenyl)-2,2-dimethyl-1,3-dioxolan-4-yl)methanol (Preparation example 6), to obtain the title compound (0.8 g, 50~80%).

$^1$H NMR (400 MHz, DMSO) δ 1.51~1.67 (m, 10H), 4.11~4.23 (m, 3H), 4.98 (d, J=8.0, 2H), 5.08 (s, 1H), 6.59 (t, J=8.0, 1H), 6.68 (d, J=8.0, 1H), 7.04~7.56 (m, 4H)

Example 27

((4R,5R)-5-(2-iodophenyl)-2,2-dimethyl-1,3-dioxolan-4-yl)methyl sulfamate

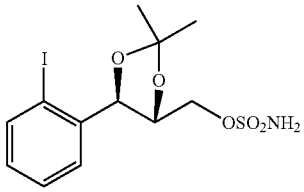

The substantially same method as described in Example 1 was conducted, except that ((4R,5R)-5-(2-iodophenyl)-2,2-dimethyl-1,3-dioxolan-4-yl)methanol (Preparation example 21) was used instead of ((4R,5R)-5-(2-chlorophenyl)-2,2-dimethyl-1,3-dioxolan-4-yl)methanol (Preparation example 6), to obtain the title compound (3.23 g, 50~80%).

$^1$H NMR (400 MHz, DMSO) δ 1.55 (s, 3H), 1.47 (s, 3H) 4.21~4.11 (m, 3H), 5.10 (d, J=7.6, 1H), 7.56~7.13 (m, 3H) 7.60 (s, 2H), 7.91 (d, J=8.0, 1H)

Example 28

((4S,5S)-5-(2-iodophenyl)-2,2-dimethyl-1,3-dioxolan-4-yl)methyl sulfamate

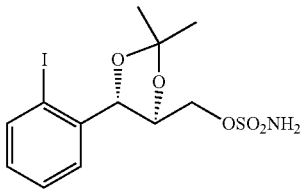

The substantially same method as described in Example 1 was conducted, except that ((4S,5S)-5-(2-iodophenyl)-2,2-dimethyl-1,3-dioxolan-4-yl)methanol (Preparation example 23) was used instead of ((4R,5R)-5-(2-chlorophenyl)-2,2-dimethyl-1,3-dioxolan-4-yl)methanol (Preparation example 6), to obtain the title compound (1.0 g, 50~80%).

$^1$H NMR (400 MHz, DMSO) δ 1.53 (s, 3H), 1.47 (s, 3H), 4.21~4.11 (m, 3H), 5.04 (d, J=7.6, 1H), 7.56~7.13 (m, 3H), 7.59 (s, 2H), 7.91 (d, J=8.0, 1H)

Example 29

((4R,5R)-5-(2-iodophenyl)-2-methyl-1,3-dioxolan-4-yl)methyl sulfamate

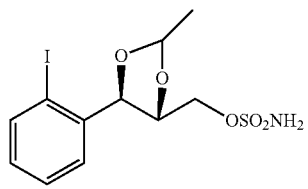

The substantially same method as described in Example 1 was conducted, except that ((4R,5R)-5-(2-iodophenyl)-2-methyl-1,3-dioxolan-4-yl)methanol (Preparation example 107) was used instead of ((4R,5R)-5-(2-chlorophenyl)-2,2-dimethyl-1,3-dioxolan-4-yl)methanol (Preparation example 6), to obtain the title compound (1.7 g, 50~80%).

$^1$H NMR (400 MHz, DMSO) δ 1.40 (d, J=6.4, 3H), 4.7 (d, J=3.2, 2H), 5.46 (m, J=6.4, 1H), 4.22 (dt, J=3.3, J=7.0, 1H), 5.10 (d, J=7.0, 1H), 7.26~7.40 (m, 3H), 7.49 (s, 2H), 7.61 (dd, J=1.2, J=7.6, 1H).

Example 30

((4S,5S)-5-(2-iodophenyl)-2-methyl-1,3-dioxolan-4-yl)methyl sulfamate

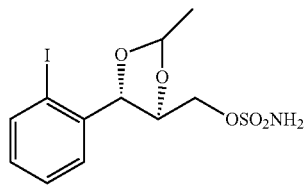

The substantially same method as described in Example 1 was conducted, except that ((4S,5S)-5-(2-iodophenyl)-2-methyl-1,3-dioxolan-4-yl)methanol (Preparation example 109) was used instead of ((4R,5R)-5-(2-chlorophenyl)-2,2-dimethyl-1,3-dioxolan-4-yl)methanol (Preparation example 6), to obtain the title compound (1.8 g, 50~80%).

$^1$H NMR (400 MHz, DMSO) δ 1.40 (d, J=6.4, 3H), 4.7 (d, J=3.2, 2H), 5.46 (m, J=6.4, 1H), 4.22 (dt, J=3.3, J=7.0, 1H), 5.08 (d, J=7.0, 1H), 7.30~7.40 (m, 3H), 7.61 (s, 2H), 7.65 (dd, J=1.2, J=7.6, 1H).

Example 31

(((4R,5R)-5-(2-iodophenyl)-2,2-diethyl-1,3-dioxolan-4-yl)methyl sulfamate

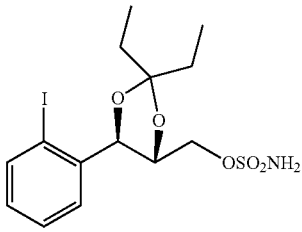

The substantially same method as described in Example 1 was conducted, except that ((4R,5R)-5-(2-iodophenyl)-2,2-methyl-1,3-dioxolan-4-yl)methanol (Preparation example 111) was used instead of ((4R,5R)-5-(2-chlorophenyl)-2,2-dimethyl-1,3-dioxolan-4-yl)methanol (Preparation example 6), to obtain the title compound (1.6 g, 50~80%).

$^1$H NMR (400 MHz, CDCl$_3$) δ 0.90 (t, J=8.0, 6H), 1.59 (q, J=8.0, 4H), 3.96~4.21 (m, 2H), 4.42 (q, J=7.0, 1H), 4.88 (s, 2H), 5.17 (d, J=7.0, 1H), 7.13~7.56 (m, 4H)

Example 32

(((4S,5S)-5-(2-iodophenyl)-2,2-diethyl-1,3-dioxolan-4-yl)methyl sulfamate

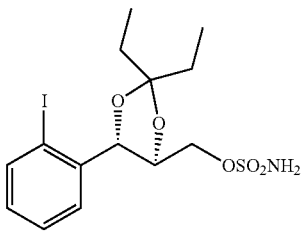

The substantially same method as described in Example 1 was conducted, except that ((4S,5S)-5-(2-iodophenyl)-2,2-methyl-1,3-dioxolan-4-yl)methanol (Preparation example 113) was used instead of ((4R,5R)-5-(2-chlorophenyl)-2,2-dimethyl-1,3-dioxolan-4-yl)methanol (Preparation example 6), to obtain the title compound (1.3 g, 50~80%).

$^1$H NMR (400 MHz, CDCl$_3$) δ 0.90 (t, J=8.0, 6H), 1.59 (q, J=8.0, 4H), 3.96~4.21 (m, 2H), 4.42 (q, J=7.0, 1H), 4.88 (s, 2H), 5.17 (d, J=7.0, 1H), 7.12~7.57 (m, 4H)

Example 33

((2R,3R)-3-(2-iodophenyl)-1,4-dioxaspiro[4,4]nonan-2-yl)methyl sulfamate

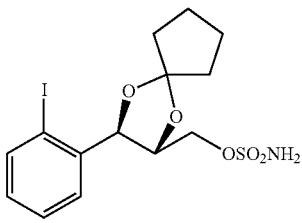

The substantially same method as described in Example 1 was conducted, except that ((4R,5R)-5-(2-iodophenyl)-1,4-dioxapiro[4,4]nonane-2-yl)methanol (Preparation example 115) was used instead of ((4R,5R)-5-(2-chlorophenyl)-2,2-dimethyl-1,3-dioxolan-4-yl)methanol (Preparation example 6), to obtain the title compound (1.6 g, 50~80%).

$^1$H NMR (400 MHz, DMSO) δ 1.46~1.90 (m, 8H), 3.96~4.21 (m, 2H), 4.42 (q, J=7.0, 1H), 4.88 (s, 2H), 5.17 (d, J=7.0, 1H), 7.13~7.56 (m, 4H)

Example 34

((2S,3S)-3-(2-iodophenyl)-1,4-dioxaspiro[4,4]nonan-2-yl)methyl sulfamate

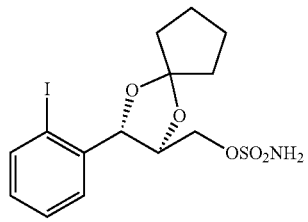

The substantially same method as described in Example 1 was conducted, except that ((4S,5S)-5-(2-iodophenyl)-1,4-dioxapiro[4,4]nonane-2-yl)methanol (Preparation example 117) was used instead of ((4R,5R)-5-(2-chlorophenyl)-2,2-dimethyl-1,3-dioxolan-4-yl)methanol (Preparation example 6), to obtain the title compound (1.2 g, 50~80%).

$^1$H NMR (400 MHz, DMSO) δ 1.46~1.92 (m, 8H), 3.96~4.21 (m, 2H), 4.42 (q, J=7.0, 1H), 4.88 (s, 2H), 5.22 (d, J=7.0, 1H), 7.13~7.59 (m, 4H)

Example 35

((2R,3R)-3-(2-iodophenyl)-1,4-dioxaspiro[4,5]decan-2-yl)methyl sulfamate

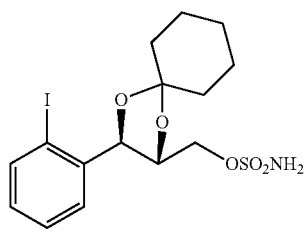

The substantially same method as described in Example 1 was conducted, except that ((4R,5R)-5-(2-iodophenyl)-1,4-dioxapiro[4,5]decane-2-yl)methanol (Preparation example 119) was used instead of ((4R,5R)-5-(2-chlorophenyl)-2,2-dimethyl-1,3-dioxolan-4-yl)methanol (Preparation example 6), to obtain the title compound (0.9 g, 50~80%).

$^1$H NMR (400 MHz, DMSO) δ 1.33~1.72 (m, 10H), 4.02~4.31 (m, 2H), 4.51 (q, J=7.0, 1H), 4.97 (s, 2H), 5.25 (d, J=7.0, 1H), 7.19~7.65 (m, 4H)

Example 36

((2S,3S)-3-(2-iodophenyl)-1,4-dioxaspiro[4,5]decan-2-yl)methyl sulfamate

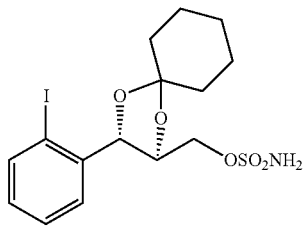

The substantially same method as described in Example 1 was conducted, except that ((4S,5S)-5-(2-iodophenyl)-1,4-dioxapiro[4,5]decane-2-yl)methanol (Preparation example 121) was used instead of ((4R,5R)-5-(2-chlorophenyl)-2,2-dimethyl-1,3-dioxolan-4-yl)methanol (Preparation example 6), to obtain the title compound (0.9 g, 50~80%).

$^1$H NMR (400 MHz, DMSO) δ 1.33~1.72 (m, 10H), 4.02~4.31 (m, 2H), 4.51 (q, J=7.0, 1H), 4.97 (s, 2H), 5.25 (d, J=7.0, 1H), 7.19~7.6 m, 4H)

Example 37

((4R,5R)-5-(2-iodophenyl)-2-phenyl-1,3-dioxolan-4-yl)methyl sulfamate

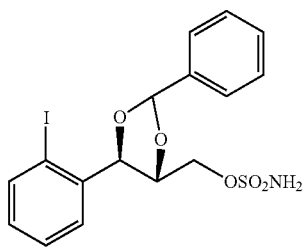

The substantially same method as described in Example 1 was conducted, except that ((4R,5R)-5-(2-iodophenyl)-2-phenyl-1,3-dioxolane-4-yl)methanol (Preparation example 123) was used instead of ((4R,5R)-5-(2-chlorophenyl)-2,2-dimethyl-1,3-dioxolan-4-yl)methanol (Preparation example 6), to obtain the title compound (1.1 g, 50~80%).

$^1$H NMR (400 MHz, DMSO) δ 3.96~4.21 (m, 2H), 4.42 (q, J=7.0, 1H), 4.92 (s, 2H), 5.20 (d, J=7.0, 1H), 5.97 (s, 1H), 7.14~7.38 (m, 9H)

Example 38

((4S,5S)-5-(2-iodophenyl)-2-phenyl-1,3-dioxolan-4-yl)methyl sulfamate

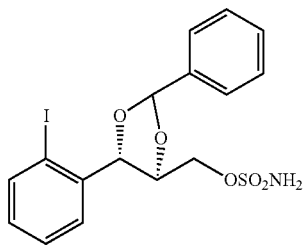

The substantially same method as described in Example 1 was conducted, except that ((4S,5S)-5-(2-iodophenyl)-2-phenyl-1,3-dioxolane-4-yl)methanol (Preparation example 125) was used instead of ((4R,5R)-5-(2-chlorophenyl)-2,2-dimethyl-1,3-dioxolan-4-yl)methanol (Preparation example 6), to obtain the title compound (0.9 g, 50~80%).

$^1$H NMR (400 MHz, DMSO) δ 3.96~4.21 (m, 2H), 4.42 (q, J=7.0, 1H), 4.92 (s, 2H), 5.20 (d, J=7.0, 1H), 5.97 (s, 1H), 7.14~7.38 (m, 9H)

Example 39

((4R,5R)-5-(2,4-dichlorophenyl)-2,2-dimethyl-1,3-dioxolan-4-yl)methyl sulfamate

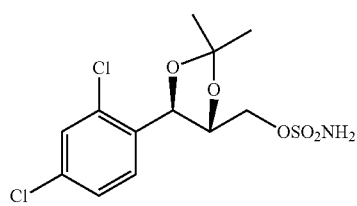

The substantially same method as described in Example 1 was conducted, except that ((4R,5R)-5-(2,4-dichlorophenyl)-2,2-dimethyl-1,3-dioxolan-4-yl)methanol (Preparation example 38) was used instead of ((4R,5R)-5-(2-chlorophenyl)-2,2-dimethyl-1,3-dioxolan-4-yl)methanol (Preparation example 6), to obtain the title compound (2.8 g, 50~80%).

$^1$H NMR (400 MHz, CDCl$_3$) δ 1.27 (s, 6H), 3.90~4.15 (m, 2H), 4.37 (q, J=7.0, 1H), 4.79 (s, 2H), 5.12 (d, J=7.0, 1H), 7.29~7.42 (m, 2H), 7.79 (s, 1H).

Example 40

((4S,5S)-5-(2,4-dichlorophenyl)-2,2-dimethyl-1,3-dioxolan-4-yl)methyl sulfamate

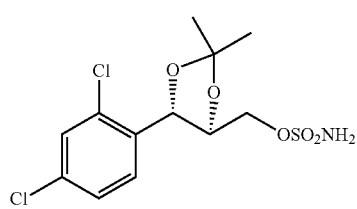

The substantially same method as described in Example 1 was conducted, except that ((4S,5S)-5-(2,4-dichlorophenyl)-2,2-dimethyl-1,3-dioxolan-4-yl)methanol (Preparation example 31) was used instead of ((4R,5R)-5-(2-chlorophenyl)-2,2-dimethyl-1,3-dioxolan-4-yl)methanol (Preparation example 6), to obtain the title compound (2.5 g, 50~80%).

$^1$H NMR (400 MHz, CDCl$_3$) δ 1.27 (s, 6H), 3.90~4.15 (m, 2H), 4.37 (q, J=7.0, 1H), 4.79 (s, 2H), 5.12 (d, J=7.0, 1H), 7.29~7.42 (m, 2H), 7.79 (s, 1H).

Example 41

(((4R,5R)-5-(2,4-dichlorophenyl)-2-methyl-1,3-dioxolan-4-yl)methyl sulfamate

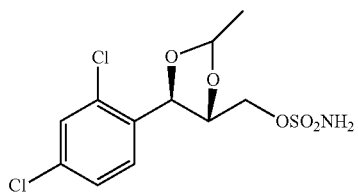

The substantially same method as described in Example 1 was conducted, except that ((4R,5R)-5-(2,4-dichlorophenyl)-2-methyl-1,3-dioxolan-4-yl)methanol (Preparation example 127) was used instead of ((4R,5R)-5-(2-chlorophenyl)-2,2-dimethyl-1,3-dioxolan-4-yl)methanol (Preparation example 6), to obtain the title compound (1.5 g, 50~80%).

$^1$H NMR (400 MHz, CDCl$_3$) δ 1.40 (s, 3H), 3.81~4.08 (m, 2H), 4.25 (q, J=7.0, 1H), 4.81 (s, 2H), 5.03 (q, J=6.8, 1H), 5.12 (d, J=7.0, 1H), 7.21~7.27 (m, 2H), 7.70 (s, 1H).

Example 42

((4S,5S)-5-(2,4-dichlorophenyl)-2-methyl-1,3-dioxolan-4-yl)methyl sulfamate

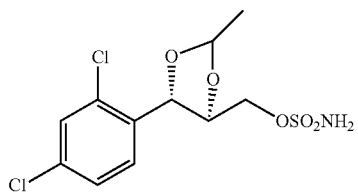

The substantially same method as described in Example 1 was conducted, except that ((4S,5S)-5-(2,4-dichlorophenyl)-2-methyl-1,3-dioxolan-4-yl)methanol (Preparation example 129) was used instead of ((4R,5R)-5-(2-chlorophenyl)-2,2-dimethyl-1,3-dioxolan-4-yl)methanol (Preparation example 6), to obtain the title compound (1.1 g, 50~80%).

$^1$H NMR (400 MHz, CDCl$_3$) δ 1.40 (s, 3H), 3.81~4.08 (m, 2H), 4.25 (q, J=7.0, 1H), 4.81 (s, 2H), 5.03 (q, J=6.8, 1H), 5.12 (d, J=7.0, 1H), 7.21~7.27 (m, 2H), 7.70 (s, 1H).

Example 43

((4R,5R)-5-(2,4-dichlorophenyl)-2,2-diethyl-1,3-dioxolan-4-yl)methyl sulfamate

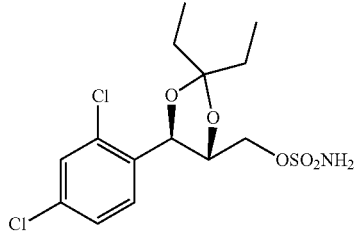

The substantially same method as described in Example 1 was conducted, except that ((4R,5R)-5-(2,4-dichlorophenyl)-2,2-diethyl-1,3-dioxolan-4-yl)methanol (Preparation example 131) was used instead of ((4R,5R)-5-(2-chlorophenyl)-2,2-dimethyl-1,3-dioxolan-4-yl)methanol (Preparation example 6), to obtain the title compound (0.9 g, 50~80%).

$^1$H NMR (400 MHz, CDCl$_3$) δ 0.90 (t, J=8.0, 6H), 1.59 (q, J=8.0, 4H), 3.96~4.21 (m, 2H), 4.42 (q, J=7.0, 1H), 4.88 (s, 2H), 5.17 (d, J=7.0, 1H), 7.24~7.30 (m, 2H), 7.73 (s, 1H).

Example 44

((4S,5S)-5-(2,4-dichlorophenyl)-2,2-diethyl-1,3-dioxolan-4-yl)methyl sulfamate

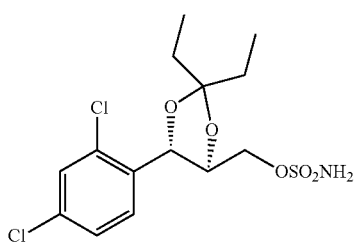

The substantially same method as described in Example 1 was conducted, except that ((4S,5S)-5-(2,4-dichlorophenyl)-2,2-diethyl-1,3-dioxolan-4-yl)methanol (Preparation example 133) was used instead of ((4R,5R)-5-(2-chlorophenyl)-2,2-dimethyl-1,3-dioxolan-4-yl)methanol (Preparation example 6), to obtain the title compound (0.8 g, 50~80%).

$^1$H NMR (400 MHz, CDCl$_3$) δ 0.90 (t, J=8.0, 6H), 1.59 (q, J=8.0, 4H), 3.96~4.21 (m, 2H), 4.42 (q, J=7.0, 1H), 4.88 (s, 2H), 5.17 (d, J=7.0, 1H), 7.24~7.30 (m, 2H), 7.73 (s, 1H).

Example 45

((2R,3R)-3-(2,4-dichlorophenyl)-1,4-dioxaspiro[4,4]nonan-2-yl)methyl sulfamate

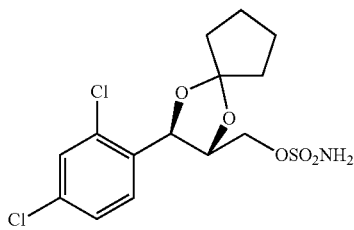

The substantially same method as described in Example 1 was conducted, except that ((4R,5R)-5-(2,4-dichlorophenyl)-1,4-dioxaspiro[4,4]nonane-2-yl)methanol (Preparation example 135) was used instead of ((4R,5R)-5-(2-chlorophenyl)-2,2-dimethyl-1,3-dioxolan-4-yl)methanol (Preparation example 6), to obtain the title compound (0.8 g, 50~80%).

$^1$H NMR (400 MHz, DMSO) δ 1.46~1.90 (m, 8H), 3.79~4.05 (m, 2H), 4.25 (q, J=7.0, 1H), 4.80 (s, 2H), 5.11 (d, J=7.0, 1H), 7.28~7.34 (m, 2H), 7.76 (s, 1H).

Example 46

((2S,3S)-3-(2,4-dichlorophenyl)-1,4-dioxaspiro[4,4]nonan-2-yl)methyl sulfamate

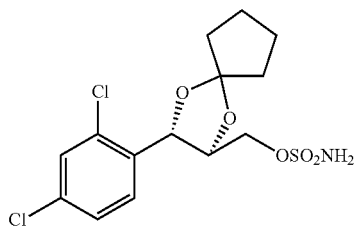

The substantially same method as described in Example 1 was conducted, except that ((4S,5S)-5-(2,4-dichlorophenyl)-1,4-dioxaspiro[4,4]nonane-2-yl)methanol (Preparation example 137) was used instead of ((4R,5R)-5-(2-chlorophenyl)-2,2-dimethyl-1,3-dioxolan-4-yl)methanol (Preparation example 6), to obtain the title compound (0.8 g, 50~80%).

$^1$H NMR (400 MHz, DMSO) δ 1.46~1.90 (m, 8H), 3.79~4.05 (m, 2H), 4.25 (q, J=7.0, 1H), 4.80 (s, 2H), 5.11 (d, J=7.0, 1H), 7.28~7.34 (m, 2H), 7.76 (s, 1H).

Example 47

((2R,3R)-3-(2,4-dichlorophenyl)-1,4-dioxaspiro[4,5]decan-2-yl)methyl sulfamate

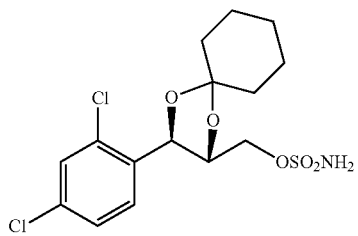

The substantially same method as described in Example 1 was conducted, except that ((4R,5R)-5-(2,4-dichlorophenyl)-1,4-dioxaspiro[4,5]decane-2-yl)methanol (Preparation example 139) was used instead of ((4R,5R)-5-(2-chlorophenyl)-2,2-dimethyl-1,3-dioxolan-4-yl)methanol (Preparation example 6), to obtain the title compound (0.7 g, 50~80%).

$^1$H NMR (400 MHz, DMSO) δ 1.33~1.72 (m, 10H), 3.78~4.03 (m, 2H), 4.22 (q, J=7.0, 1H), 4.78 (s, 2H), 5.07 (d, J=7.0, 1H), 7.26~7.32 (m, 2H), 7.77 (s, 1H).

Example 48

((2S,3S)-3-(2,4-dichlorophenyl)-1,4-dioxaspiro[4,5]decan-2-yl)methyl sulfamate

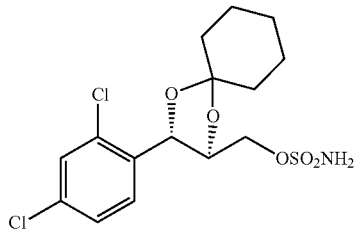

The substantially same method as described in Example 1 was conducted, except that ((4S,5S)-5-(2,4-dichlorophenyl)-1,4-dioxaspiro[4,5]decane-2-yl)methanol (Preparation example 141) was used instead of ((4R,5R)-5-(2-chlorophenyl)-2,2-dimethyl-1,3-dioxolan-4-yl)methanol (Preparation example 6), to obtain the title compound (0.7 g, 50~80%).

$^1$H NMR (400 MHz, DMSO) δ 1.33~1.72 (m, 10H), 3.78~4.03 (m, 2H), 4.22 (q, J=7.0, 1H), 4.78 (s, 2H), 5.07 (d, J=7.0, 1H), 7.26~7.32 (m, 2H), 7.77 (s, 1H).

Example 49

((4R,5R)-5-(2,4-dichlorophenyl)-2-phenyl-1,3-dioxolan-4-yl)methyl sulfamate

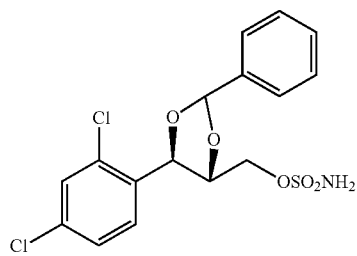

The substantially same method as described in Example 1 was conducted, except that ((4R,5R)-5-(2,4-dichlorophenyl)-2-phenyl-1,3-dioxolane-4-yl)methanol (Preparation example 143) was used instead of ((4R,5R)-5-(2-chlorophenyl)-2,2-dimethyl-1,3-dioxolan-4-yl)methanol (Preparation example 6), to obtain the title compound (1.1 g, 50~80%).

$^1$H NMR (400 MHz, DMSO) δ 3.96~4.21 (m, 2H), 4.42 (q, J=7.0, 1H), 4.88 (s, 2H), 5.17 (d, J=7.0, 1H), 5.97 (s, 1H), 7.14~7.386 (m, 8H)

Example 50

((4S,5S)-5-(2,4-dichlorophenyl)-2-phenyl-1,3-dioxolan-4-yl)methyl sulfamate

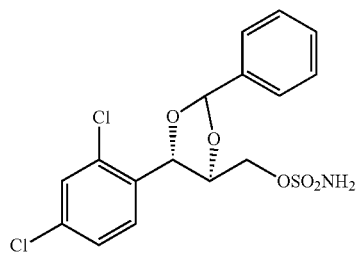

The substantially same method as described in Example 1 was conducted, except that ((4S,5S)-5-(2,4-dichlorophenyl)-2-phenyl-1,3-dioxolane-4-yl)methanol (Preparation example 145) was used instead of ((4R,5R)-5-(2-chlorophenyl)-2,2-dimethyl-1,3-dioxolan-4-yl)methanol (Preparation example 6), to obtain the title compound (0.6 g, 50~80%).

$^1$H NMR (400 MHz, DMSO) δ 3.96~4.21 (m, 2H), 4.42 (q, J=7.0, 1H), 4.88 (s, 2H), 5.17 (d, J=7.0, 1H), 5.97 (s, 1H), 7.14~7.386 (m, 8H)

Example 51

((4R,5R)-5-(2,6-dichlorophenyl)-2,2-dimethyl-1,3-dioxolan-4-yl)methyl sulfamate

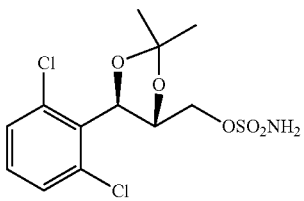

The substantially same method as described in Example 1 was conducted, except that ((4R,5R)-5-(2,6-dichlorophenyl)-2,2-dimethyl-1,3-dioxolane-4-yl)methanol (Preparation example 41) was used instead of ((4R,5R)-5-(2-chlorophenyl)-2,2-dimethyl-1,3-dioxolan-4-yl)methanol (Preparation example 6), to obtain the title compound (2.5 g, 50~80%).

$^1$H NMR (400 MHz, CDCl$_3$) δ 1.27 (s, 6H), 3.96~4.21 (m, 2H), 4.42 (q, J=7.0, 1H), 4.88 (s, 2H), 5.17 (d, J=7.0, 1H), 7.45~7.58 (m, 3H).

Example 52

((4S,5S)-5-(2,6-dichlorophenyl)-2,2-dimethyl-1,3-dioxolan-4-yl)methyl sulfamate

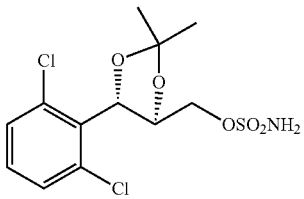

The substantially same method as described in Example 1 was conducted, except that ((4S,5S)-5-(2,6-dichlorophenyl)-2,2-dimethyl-1,3-dioxolane-4-yl)methanol (Preparation example 35) was used instead of ((4R,5R)-5-(2-chlorophenyl)-2,2-dimethyl-1,3-dioxolan-4-yl)methanol (Preparation example 6), to obtain the title compound (2.2 g, 50~80%).

$^1$H NMR (400 MHz, CDCl$_3$) δ 1.27 (s, 6H), 3.96~4.21 (m, 2H), 4.42 (q, J=7.0, 1H), 4.88 (s, 2H), 5.17 (d, J=7.0, 1H), 7.45~7.58 (m, 3H).

Example 53

((4R,5R)-5-(2,6-dichlorophenyl)-2-methyl-1,3-dioxolan-4-yl)methyl sulfamate

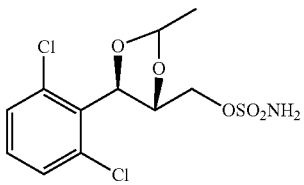

The substantially same method as described in Example 1 was conducted, except that ((4R,5R)-5-(2,6-dichlorophenyl)-2-methyl-1,3-dioxolane-4-yl)methanol (Preparation example 147) was used instead of ((4R,5R)-5-(2-chlorophenyl)-2,2-dimethyl-1,3-dioxolan-4-yl)methanol (Preparation example 6), to obtain the title compound (0.7 g, 50~80%).

$^1$H NMR (400 MHz, DMSO) δ 1.40 (s, 3H), 3.88~4.13 (m, 2H), 4.42 (q, J=7.0, 1H), 4.88 (s, 2H), 5.07 (q, J=6.8, 1H), 5.21 (d, J=7.0, 1H), 5.97 (s, 1H), 7.45~7.58 (m, 3H).

Example 54

((4S,5S)-5-(2,6-dichlorophenyl)-2-methyl-1,3-dioxolan-4-yl)methyl sulfamate

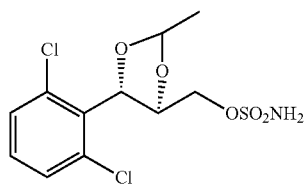

The substantially same method as described in Example 1 was conducted, except that ((4S,5S)-5-(2,6-dichlorophenyl)-2-methyl-1,3-dioxolane-4-yl)methanol (Preparation example 149) was used instead of ((4R,5R)-5-(2-chlorophenyl)-2,2-dimethyl-1,3-dioxolan-4-yl)methanol (Preparation example 6), to obtain the title compound (0.9 g, 50~80%).

$^1$H NMR (400 MHz, DMSO) δ 1.40 (s, 3H), 3.88~4.13 (m, 2H), 4.42 (q, J=7.0, 1H), 4.88 (s, 2H), 5.07 (q, J=6.8, 1H), 5.21 (d, J=7.0, 1H), 5.97 (s, 1H), 7.45~7.58 (m, 3H).

Example 55

((4R,5R)-5-(2,6-dichlorophenyl)-2,2-diethyl-1,3-dioxolan-4-yl)methyl sulfamate

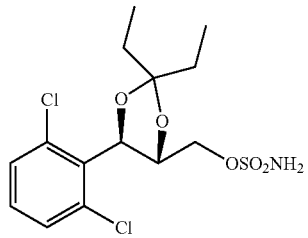

The substantially same method as described in Example 1 was conducted, except that ((4R,5R)-5-(2,6-dichlorophenyl)-2,2-diethyl-1,3-dioxolane-4-yl)methanol (Preparation example 151) was used instead of ((4R,5R)-5-(2-chlorophenyl)-2,2-dimethyl-1,3-dioxolan-4-yl)methanol (Preparation example 6), to obtain the title compound (0.7 g, 50~80%).

$^1$H NMR (400 MHz, CDCl$_3$)) O 0.90 (t, J=8.0, 6H), 1.59 (q, J=8.0, 4H), 3.86~4.11 (m, 2H), 4.49 (q, J=7.0, 1H), 4.88 (s, 2H), 5.15 (d, J=7.0, 1H), 7.45~7.58 (m, 3H).

Example 56

((4S,5S)-5-(2,6-dichlorophenyl)-2,2-diethyl-1,3-dioxolan-4-yl)methyl sulfamate

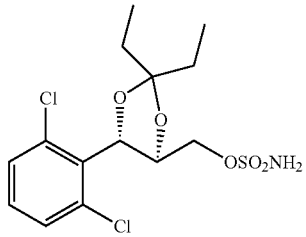

The substantially same method as described in Example 1 was conducted, except that ((4S,5S)-5-(2,6-dichlorophenyl)-2,2-diethyl-1,3-dioxolane-4-yl)methanol (Preparation example 153) was used instead of ((4R,5R)-5-(2-chlorophenyl)-2,2-dimethyl-1,3-dioxolan-4-yl)methanol (Preparation example 6), to obtain the title compound (1.5 g, 50~80%).

$^1$H NMR (400 MHz, CDCl$_3$)) O 0.90 (t, J=8.0, 6H), 1.59 (q, J=8.0, 4H), 3.86~4.11 (m, 2H), 4.49 (q, J=7.0, 1H), 4.88 (s, 2H), 5.15 (d, J=7.0, 1H), 7.45~7.58 (m, 3H).

Example 57

((2R,3R)-3-(2,6-dichlorophenyl)-1,4-dioxaspiro[4,4]nonan-2-yl)methyl sulfamate

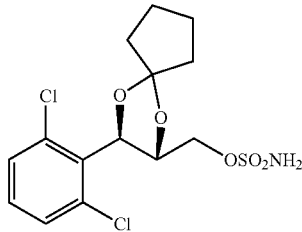

The substantially same method as described in Example 1 was conducted, except that ((2R,3R)-3-(2,6-dichlorophenyl)-1,4-dioxaspiro[4,4]nonane-2-yl)methanol (Preparation example 155) was used instead of ((4R,5R)-5-(2-chlorophenyl)-2,2-dimethyl-1,3-dioxolan-4-yl)methanol (Preparation example 6), to obtain the title compound (1.2 g, 50~80%).

$^1$H NMR (400 MHz, DMSO) δ 1.46~1.90 (m, 8H), 3.98~4.24 (m, 2H), 4.45 (q, J=7.0, 1H), 4.88 (s, 2H), 5.20 (d, J=7.0, 1H), 7.45~7.58 (m, 3H).

Example 58

((2S,3S)-3-(2,6-dichlorophenyl)-1,4-dioxaspiro[4,4]nonan-2-yl)methyl sulfamate

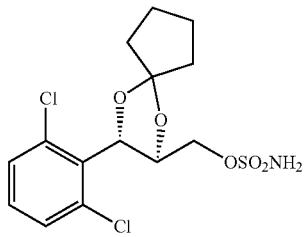

The substantially same method as described in Example 1 was conducted, except that ((2S,3S)-3-(2,6-dichlorophenyl)-1,4-dioxaspiro[4,4]nonane-2-yl)methanol (Preparation example 157) was used instead of ((4R,5R)-5-(2-chlorophenyl)-2,2-dimethyl-1,3-dioxolan-4-yl)methanol (Preparation example 6), to obtain the title compound (1.4 g, 50~80%).

$^1$H NMR (400 MHz, DMSO) δ 1.46~1.90 (m, 8H), 3.98~4.24 (m, 2H), 4.45 (q, J=7.0, 1H), 4.88 (s, 2H), 5.20 (d, J=7.0, 1H), 7.45~7.58 (m, 3H).

Example 59

((2R,3R)-3-(2,6-dichlorophenyl)-1,4-dioxaspiro[4,5]decan-2-yl)methyl sulfamate

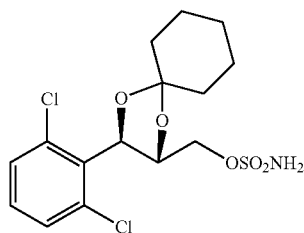

The substantially same method as described in Example 1 was conducted, except that ((2R,3R)-3-(2,6-dichlorophenyl)-1,4-dioxaspiro[4,45]decane-2-yl)methanol (Preparation example 159) was used instead of ((4R,5R)-5-(2-chlorophenyl)-2,2-dimethyl-1,3-dioxolan-4-yl)methanol (Preparation example 6), to obtain the title compound (1.1 g, 50~80%).

$^1$H NMR (400 MHz, DMSO) δ 1.33~1.72 (m, 10H), 3.96~4.21 (m, 2H), 4.42 (q, J=7.0, 1H), 4.88 (s, 2H), 5.17 (d, J=7.0, 1H), 7.45~7.58 (m, 3H).

Example 60

((2S,3S)-3-(2,6-dichlorophenyl)-1,4-dioxaspiro[4,5]decan-2-yl)methyl sulfamate

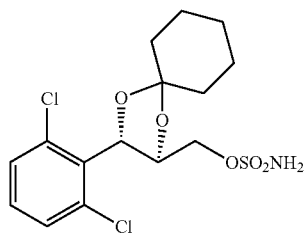

The substantially same method as described in Example 1 was conducted, except that ((4S,5S)-5-(2,6-dichlorophenyl)-1,4-dioxaspiro[4,4]decane-2-yl)methanol (Preparation example 161) was used instead of ((4R,5R)-5-(2-chlorophenyl)-2,2-dimethyl-1,3-dioxolan-4-yl)methanol (Preparation example 6), to obtain the title compound (1.1 g, 50~80%).

¹H NMR (400 MHz, DMSO) δ 1.33~1.72 (m, 10H), 3.96~4.21 (m, 2H), 4.42 (q, J=7.0, 1H), 4.88 (s, 2H), 5.17 (d, J=7.0, 1H), 7.45~7.58 (m, 3H).

Example 61

((4R,5R)-5-(2,6-dichlorophenyl)-2-phenyl-1,3-dioxolan-4-yl)methyl sulfamate

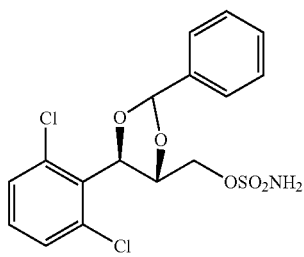

The substantially same method as described in Example 1 was conducted, except that ((4R,5R)-5-(2,6-dichlorophenyl)-2-phenyl-1,3-dioxolane-4-yl)methanol (Preparation example 163) was used instead of ((4R,5R)-5-(2-chlorophenyl)-2,2-dimethyl-1,3-dioxolan-4-yl)methanol (Preparation example 6), to obtain the title compound (1.3 g, 50~80%).

¹H NMR (400 MHz, DMSO) δ 2.0 (s, 2H), 3.96~4.21 (m, 2H), 4.42 (dd, J=7.0, J=7.0, 1H), 5.17 (d, J=7.0, 1H), 5.79 (s, 1H), 7.36~7.38 (m, 5H), 7.57~7.58 (m, 3H).

Example 62

((4S,5S)-5-(2,6-dichlorophenyl)-2-phenyl-1,3-dioxolan-4-yl)methyl sulfamate

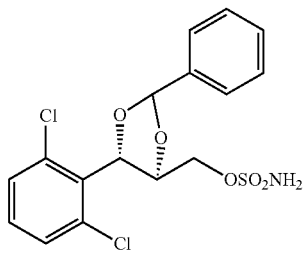

The substantially same method as described in Example 1 was conducted, except that ((4S,5S)-5-(2,6-dichlorophenyl)-2-phenyl-1,3-dioxolane-4-yl)methanol (Preparation example 165) was used instead of ((4R,5R)-5-(2-chlorophenyl)-2,2-dimethyl-1,3-dioxolan-4-yl)methanol (Preparation example 6), to obtain the title compound (1.0 g, 50~80%).

¹H NMR (400 MHz, DMSO) δ 2.0 (s, 2H), 3.96~4.21 (m, 2H), 4.42 (dd, J=7.0, J=7.0, 1H), 5.17 (d, J=7.0, 1H), 5.79 (s, 1H), 7.36~7.38 (m, 5H), 7.57~7.58 (m, 3H).

Example 63

((4R,5R)-5-(2-aminophenyl)-2,2-dimethyl-1,3-dioxolan-4-yl)methyl sulfamate

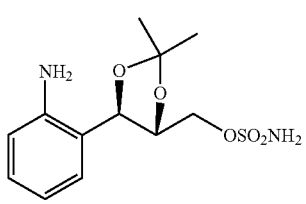

The substantially same method as described in Example 1 was conducted, except that ((4R,5R)-5-(2-aminophenyl)-2,2-dimethyl-1,3-dioxolane-4-yl)methanol (Preparation example 47) was used instead of ((4R,5R)-5-(2-chlorophenyl)-2,2-dimethyl-1,3-dioxolan-4-yl)methanol (Preparation example 6), to obtain the title compound (5.3 g, 50~80%).

¹H NMR (400 MHz, DMSO) δ 1.27 (s, 6H), 2.0 (s, 2H), 3.96~4.21 (m, 2H), 4.42 (dt, J=7.02, J=3.27, 1H), 5.17 (d, J=7.0, 1H), 6.27 (s, 2H), 6.73~7.13 (m, 4H).

Example 64

((4S,5S)-5-(2-aminophenyl)-2,2-dimethyl-1,3-dioxolan-4-yl)methyl sulfamate

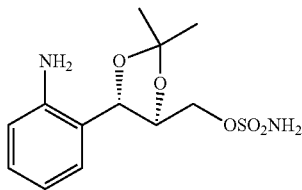

The substantially same method as described in Example 1 was conducted, except that ((4S,5S)-5-(2-aminophenyl)-2,2-dimethyl-1,3-dioxolane-4-yl)methanol (Preparation example 51) was used instead of ((4R,5R)-5-(2-chlorophenyl)-2,2-dimethyl-1,3-dioxolan-4-yl)methanol (Preparation example 6), to obtain the title compound (8.2 g, 50~80%).

¹H NMR (400 MHz, DMSO) δ 1.27 (s, 6H), 2.0 (s, 2H), 3.96~4.21 (m, 2H), 4.42 (dt, J=7.02, J=3.27, 1H), 5.17 (d, J=7.0, 1H), 6.27 (s, 2H), 6.73~7.13 (m, 4H).

Example 65

((4R,5R)-5-(2-aminophenyl)-2,2-dimethyl-1,3-dioxolan-4-yl)methyl sulfamate Sodium salt

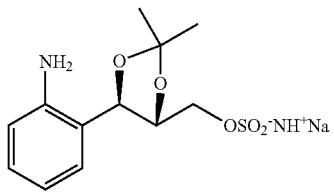

To stirred solution of ((4R,5R)-5-(2-aminophenyl)-2,2-dimethyl-1,3-dioxolan-4-yl)methyl sulfamate (Example 63, 5.5 g) in distilled water (55 ml) was added 1N NaOH(23 ml) then heated. After 30 min, the resulting mixture cooled to room temperature and concentrated under reduced pressure. The crude product in EA(ethyl acetate, 16.5 ml) was slowly added to Ether(200 ml) at low temperature. The precipitate was filtered off, washed with Hexane, and dried under vacuum to obtain the title compound (4.7 g, 65~85%)

$^1$H NMR (400 MHz, DMSO) δ 1.42 (s, 3H), 1.46 (s, 3H), 3.79~3.81 (m, 2H), 3.99~4.00 (m, 1H), 4.94 (d, J=8.4, 1H), 6.59~7.16 (m, 4H).

Example 66

((4S,5S)-5-(2-aminophenyl)-2,2-dimethyl-1,3-dioxolan-4-yl)methyl sulfamate Sodium salt

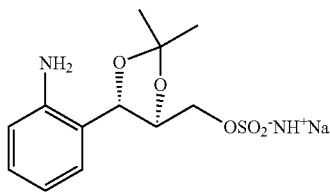

The substantially same method as described in Example 65 was conducted, except that ((4S,5S)-5-(2-aminophenyl)-2,2-dimethyl-1,3-dioxolan-4-yl)methyl sulfamate (Example 64) was used instead of ((4R,5R)-5-(2-aminophenyl)-2,2-dimethyl-1,3-dioxolan-4-yl)methyl sulfamate (Example 63), to obtain the title compound (4.23 g, 65~85%).

$^1$H NMR (400 MHz, DMSO) δ 1.42 (s, 3H), 1.46 (s, 3H), 3.79~3.81 (m, 2H), 3.99~4.00 (m, 1H), 4.94 (d, J=8.4, 1H), 6.59~7.16 (m, 4H).

Example 67

((4R,5R)-5-(2-aminophenyl)-2-methyl-1,3-dioxolan-4-yl)methyl sulfamate

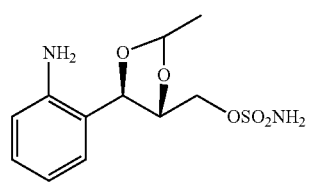

The substantially same method as described in Example 1 was conducted, except that ((4R,5R)-5-(2-aminophenyl)-2,2-dimethyl-1,3-dioxolane-4-yl)methanol (Preparation example 206) was used instead of ((4R,5R)-5-(2-chlorophenyl)-2,2-dimethyl-1,3-dioxolan-4-yl)methanol (Preparation example 6), to obtain the title compound (1.2 g, 50~80%).

$^1$H NMR (400 MHz, DMSO): δ 1.40 (d, J=6.8, 3H), 2.0 (s, 2H), 3.96~4.21 (m, 2H), 4.42 (q, J=7.0, 1H), 5.07 (q, J=7.0, 1H), 5.17 (d, J=7.0, 1H), 6.27 (s, 2H), 6.73~7.13 (m, 4H).

Example 68

((4S,5S)-5-(2-aminophenyl)-2-methyl-1,3-dioxolan-4-yl)methyl sulfamate

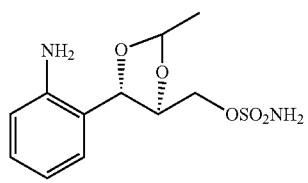

The substantially same method as described in Example 1 was conducted, except that ((4S,5S)-5-(2-aminophenyl)-2,2-dimethyl-1,3-dioxolane-4-yl)methanol (Preparation example 207) was used instead of ((4R,5R)-5-(2-chlorophenyl)-2,2-dimethyl-1,3-dioxolan-4-yl)methanol (Preparation example 6), to obtain the title compound (0.7 g, 50~80%).

$^1$H NMR (400 MHz, DMSO): δ 1.40 (d, J=6.8, 3H), 2.0 (s, 2H), 3.96~4.21 (m, 2H), 4.42 (q, J=7.0, 1H), 5.07 (q, J=7.0, 1H), 5.17 (d, J=7.0, 1H), 6.27 (s, 2H), 6.73~7.13 (m, 4H).

Example 69

((4R,5R)-5-(2-aminophenyl)-2,2-diethyl-1,3-dioxolan-4-yl)methyl sulfamate

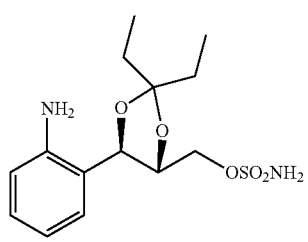

The substantially same method as described in Example 1 was conducted, except that ((4R,5R)-5-(2-aminophenyl)-2,2-diethyl-1,3-dioxolane-4-yl)methanol (Preparation example 208) was used instead of ((4R,5R)-5-(2-chlorophenyl)-2,2-dimethyl-1,3-dioxolan-4-yl)methanol (Preparation example 6), to obtain the title compound (1.1 g, 50~80%).

$^1$H NMR (400 MHz, CDCl$_3$) δ 0.90 (t, J=8.0, 6H), 1.59 (q, J=8.0, 4H), 2.0 (s, 2H), 3.96~4.21 (m, 2H), 4.42 (dt, J=7.02, J=3.27, 1H), 5.17 (d, J=7.0, 1H), 6.27 (s, 2H), 6.71~7.14 (m, 4H).

Example 70

((4S,5S)-5-(2-aminophenyl)-2,2-diethyl-1,3-dioxolan-4-yl)methyl sulfamate

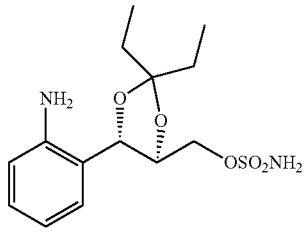

The substantially same method as described in Example 1 was conducted, except that ((4S,5S)-5-(2-aminophenyl)-2,2-diethyl-1,3-dioxolane-4-yl)methanol (Preparation example 209) was used instead of ((4R,5R)-5-(2-chlorophenyl)-2,2-dimethyl-1,3-dioxolan-4-yl)methanol (Preparation example 6), to obtain the title compound (1.1 g, 50~80%).

$^1$H NMR (400 MHz, CDCl$_3$) δ 0.90 (t, J=8.0, 6H), 1.59 (q, J=8.0, 4H), 2.0 (s, 2H), 3.96~4.21 (m, 2H), 4.42 (dt, J=7.02, J=3.27, 1H), 5.17 (d, J=7.0, 1H), 6.27 (s, 2H), 6.71~7.14 (m, 4H).

Example 71

((2R,3R)-3-(2-aminophenyl)-1,4-dioxaspiro[4,4]nonan-2-yl)methyl sulfamate

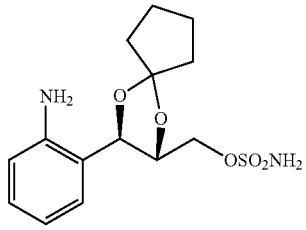

The substantially same method as described in Example 1 was conducted, except that ((2R,3R)-3-(2-aminophenyl)-1,4-dioxaspiro[4,4]nonane-2-yl)methanol (Preparation example 210) was used instead of ((4R,5R)-5-(2-chlorophenyl)-2,2-dimethyl-1,3-dioxolan-4-yl)methanol (Preparation example 6), to obtain the title compound (1.2 g, 50~80%).

$^1$H NMR (400 MHz, DMSO) δ 1.46~1.56 (m, 6H), 1.65~1.90 (m, 2H), 2.0 (s, 2H), 3.96~4.21 (m, 2H), 4.42 (dt, J=7.02, J=3.27, 1H), 5.17 (d, J=7.0, 1H), 6.27 (s, 2H), 6.70~7.11 (m, 4H).

Example 72

((2S,3S)-3-(2-aminophenyl)-1,4-dioxaspiro[4,4]nonan-2-yl)methyl sulfamate

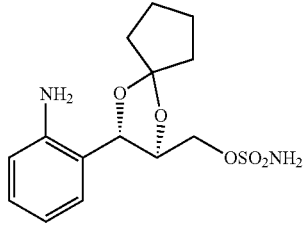

The substantially same method as described in Example 1 was conducted, except that ((2S,3S)-3-(2-aminophenyl)-1,4-dioxaspiro[4,4]nonane-2-yl)methanol (Preparation example 211) was used instead of ((4R,5R)-5-(2-chlorophenyl)-2,2-dimethyl-1,3-dioxolan-4-yl)methanol (Preparation example 6), to obtain the title compound (1.0 g, 50~80%).

$^1$H NMR (400 MHz, DMSO) δ 1.46~1.56 (m, 6H), 1.65~1.90 (m, 2H), 2.0 (s, 2H), 3.96~4.21 (m, 2H), 4.42 (dt, J=7.02, J=3.27, 1H), 5.17 (d, J=7.0, 1H), 6.27 (s, 2H), 6.70~7.11 (m, 4H).

Example 73

((2R,3R)-3-(2-aminophenyl)-1,4-dioxaspiro[4,5]decan-2-yl)methyl sulfamate

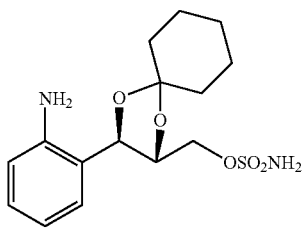

The substantially same method as described in Example 1 was conducted, except that ((2R,3R)-3-(2-aminophenyl)-1,4-dioxaspiro[4,5]dacane-2-yl)methanol (Preparation example 212) was used instead of ((4R,5R)-5-(2-chlorophenyl)-2,2-dimethyl-1,3-dioxolan-4-yl)methanol (Preparation example 6), to obtain the title compound (0.6 g, 50~80%).

$^1$H NMR (400 MHz, DMSO) δ 1.33~1.72 (m, 10H), 2.0 (s, 2H), 3.96~4.21 (m, 2H), 4.43 (dt, J=7.02, J=3.27, 1H), 5.17 (d, J=7.0, 1H), 6.25 (s, 2H), 6.71~7.12 (m, 4H).

Example 74

((2S,3S)-3-(2-aminophenyl)-1,4-dioxaspiro[4,5]decan-2-yl)methyl sulfamate

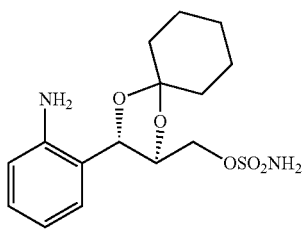

The substantially same method as described in Example 1 was conducted, except that ((3S,3S)-3-(2-aminophenyl)-1,4-dioxaspiro[4,5]dacane-2-yl)methanol (Preparation example 213) was used instead of ((4R,5R)-5-(2-chlorophenyl)-2,2-dimethyl-1,3-dioxolan-4-yl)methanol (Preparation example 6), to obtain the title compound (0.6 g, 50~80%).

$^1$H NMR (400 MHz, DMSO) δ 1.33~1.72 (m, 10H), 2.0 (s, 2H), 3.96~4.21 (m, 2H), 4.43 (dt, J=7.02, J=3.27, 1H), 5.17 (d, J=7.0, 1H), 6.25 (s, 2H), 6.71~7.12 (m, 4H).

Example 75

((4R,5R)-5-(2-aminophenyl)-2-phenyl-1,3-dioxolan-4-yl)methyl sulfamate

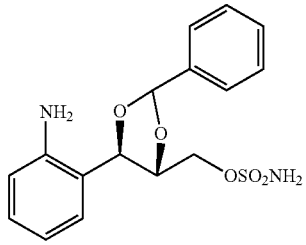

The substantially same method as described in Example 1 was conducted, except that ((4R,5R)-5-(2-aminophenyl)-2-phenyl-1,3-dioxalane-4-yl)methanol (Preparation example 214) was used instead of ((4R,5R)-5-(2-chlorophenyl)-2,2-dimethyl-1,3-dioxolan-4-yl)methanol (Preparation example 6), to obtain the title compound (0.7 g, 50~80%).

$^1$H NMR (400 MHz, DMSO) δ 2.0 (s, 2H), 3.96~4.21 (m, 2H), 4.42 (dt, J=7.02, J=3.27, 1H), 5.17 (d, J=7.0, 1H), 5.79 (s, 1H), 6.27 (s, 2H), 6.73~6.74 (m, 2H), 7.11~7.13 (m, 2H), 7.36~7.38 (m, 5H).

Example 76

((4S,5S)-5-(2-aminophenyl)-2-phenyl-1,3-dioxolan-4-yl)methyl sulfamate

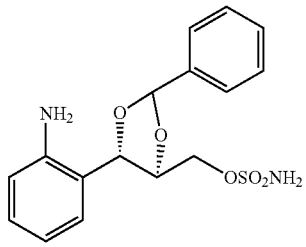

The substantially same method as described in Example 1 was conducted, except that ((4S,5S)-5-(2-aminophenyl)-2-phenyl-1,3-dioxalane-4-yl)methanol (Preparation example 215) was used instead of ((4R,5R)-5-(2-chlorophenyl)-2,2-dimethyl-1,3-dioxolan-4-yl)methanol (Preparation example 6), to obtain the title compound (0.7 g, 50~80%).

$^1$H NMR (400 MHz, DMSO) δ 2.0 (s, 2H), 3.96~4.21 (m, 2H), 4.42 (dt, J=7.02, J=3.27, 1H), 5.17 (d, J=7.0, 1H), 5.79 (s, 1H), 6.27 (s, 2H), 6.73~6.74 (m, 2H), 7.11~7.13 (m, 2H), 7.36~7.38 (m, 5H).

Example 77

((4R,5R)-5-(2-nitrophenyl)-2,2-dimethyl-1,3-dioxolan-4-yl)methyl sulfamate

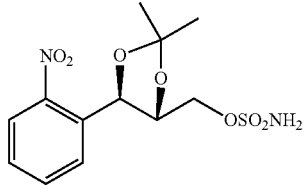

The substantially same method as described in Example 1 was conducted, except that ((4R,5R)-5-(2-nitrophenyl)-2,2-dimethyl-1,3-dioxolan-4-yl)methanol (Preparation example 46) was used instead of ((4R,5R)-5-(2-chlorophenyl)-2,2-dimethyl-1,3-dioxolan-4-yl)methanol (Preparation example 6), to obtain the title compound (1.3 g, 50~80%).

$^1$H NMR (400 MHz, DMSO) δ 1.27 (s, 6H), 1.40 (s, 3H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 78

((4S,5S)-5-(2-nitrophenyl)-2,2-dimethyl-1,3-dioxolan-4-yl)methyl sulfamate

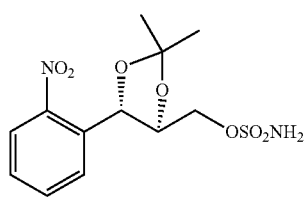

The substantially same method as described in Example 1 was conducted, except that ((4S,5S)-5-(2-nitrophenyl)-2,2-dimethyl-1,3-dioxolan-4-yl)methanol (Preparation example 50) was used instead of ((4R,5R)-5-(2-chlorophenyl)-2,2-dimethyl-1,3-dioxolan-4-yl)methanol (Preparation example 6), to obtain the title compound (3.2 g, 50~80%).

$^1$H NMR (400 MHz, DMSO) δ 1.27 (s, 6H), 1.40 (s, 3H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 79

((4R,5R)-5-(2-nitrophenyl)-2-methyl-1,3-dioxolan-4-yl)methyl sulfamate

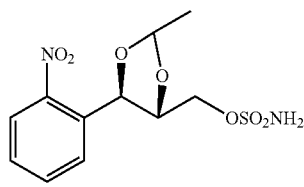

The substantially same method as described in Example 1 was conducted, except that ((4R,5R)-5-(2-nitrophenyl)-2-methyl-1,3-dioxolan-4-yl)methanol (Preparation example 167) was used instead of ((4R,5R)-5-(2-chlorophenyl)-2,2-dimethyl-1,3-dioxolan-4-yl)methanol (Preparation example 6), to obtain the title compound (1.2 g, 50~80%)

$^1$H NMR (400 MHz, DMSO): δ 1.40 (d, J=6.8, 3H), 2.0 (s, 2H), 3.96~4.21 (m, 2H), 4.42 (q, J=7.0, 1H), 5.07 (q, J=7.0, 1H), 5.17 (d, J=7.0, 1H), 7.62~7.64 (m, 2H), 7.77~7.90 (m, 2H).

Example 80

((4S,5S)-5-(2-nitrophenyl)-2-methyl-1,3-dioxolan-4-yl)methyl sulfamate

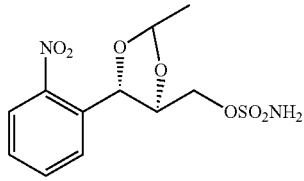

The substantially same method as described in Example 1 was conducted, except that ((4S,5S)-5-(2-nitrophenyl)-2-methyl-1,3-dioxolan-4-yl)methanol (Preparation example 169) was used instead of ((4R,5R)-5-(2-chlorophenyl)-2,2-dimethyl-1,3-dioxolan-4-yl)methanol (Preparation example 6), to obtain the title compound (1.1 g, 50~80%)

$^1$H NMR (400 MHz, DMSO): δ 1.40 (d, J=6.8, 3H), 2.0 (s, 2H), 3.96~4.21 (m, 2H), 4.42 (q, J=7.0, 1H), 5.07 (q, J=7.0, 1H), 5.17 (d, J=7.0, 1H), 7.62~7.64 (m, 2H), 7.77~7.90 (m, 2H).

Example 81

((4R,5R)-5-(2-nitrophenyl)-2,2-diethyl-1,3-dioxolan-4-yl)methyl sulfamate

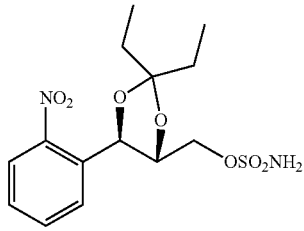

The substantially same method as described in Example 1 was conducted, except that ((4R,5R)-5-(2-nitrophenyl)-2,2-diethyl-1,3-dioxolan-4-yl)methanol (Preparation example 171) was used instead of ((4R,5R)-5-(2-chlorophenyl)-2,2-dimethyl-1,3-dioxolan-4-yl)methanol (Preparation example 6), to obtain the title compound (1.4 g, 50~80%)

$^1$H NMR (400 MHz, CDCl$_3$) δ 0.90 (t, J=8.0, 6H), 1.59 (q, J=8.0, 4H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 82

((4S,5S)-5-(2-nitrophenyl)-2,2-diethyl-1,3-dioxolan-4-yl)methyl sulfamate

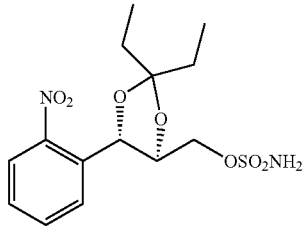

The substantially same method as described in Example 1 was conducted, except that ((4S,5S)-5-(2-nitrophenyl)-2,2-diethyl-1,3-dioxolan-4-yl)methanol (Preparation example 173) was used instead of ((4R,5R)-5-(2-chlorophenyl)-2,2-dimethyl-1,3-dioxolan-4-yl)methanol (Preparation example 6), to obtain the title compound (1.4 g, 50~80%)

$^1$H NMR (400 MHz, CDCl$_3$) δ 0.90 (t, J=8.0, 6H), 1.59 (q, J=8.0, 4H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 83

((2R,3R)-3-(2-nitrophenyl)-1,4-dioxaspiro[4,4]nonane-2-yl)methyl sulfamate

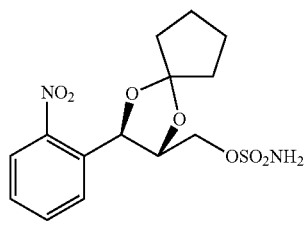

The substantially same method as described in Example 1 was conducted, except that ((2R,3R)-3-(2-nitrophenyl)-1,4-dioxapiro[4,4]nonane-2-yl)methanol (Preparation example 175) was used instead of ((4R,5R)-5-(2-chlorophenyl)-2,2-dimethyl-1,3-dioxolan-4-yl)methanol (Preparation example 6), to obtain the title compound (1.6 g, 50~80%)

$^1$H NMR (400 MHz, DMSO) δ 1.46~1.56 (m, 6H), 1.65~1.90 (m, 2H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 84

((2S,3S)-3-(2-nitrophenyl)-1,4-dioxaspiro[4,4]nonan-2-yl)methyl sulfamate

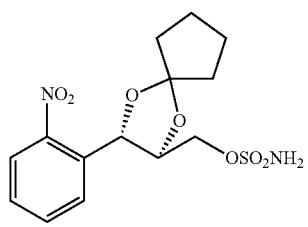

The substantially same method as described in Example 1 was conducted, except that ((2S,3S)-3-(2-nitrophenyl)-1,4-dioxapiro[4,4]nonane-2-yl)methanol (Preparation example 177) was used instead of ((4R,5R)-5-(2-chlorophenyl)-2,2-dimethyl-1,3-dioxolan-4-yl)methanol (Preparation example 6), to obtain the title compound (1.5 g, 50~80%)

$^1$H NMR (400 MHz, DMSO) δ 1.46~1.56 (m, 6H), 1.65~1.90 (m, 2H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 85

((2R,3R)-3-(2-nitrophenyl)-1,4-dioxaspiro[4,5]decan-2-yl)methyl sulfamate

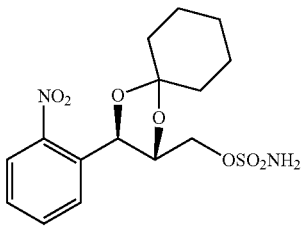

The substantially same method as described in Example 1 was conducted, except that ((2R,3R)-3-(2-nitrophenyl)-1,4-dioxapiro[4,5]decane-2-yl)methanol (Preparation example 179) was used instead of ((4R,5R)-5-(2-chlorophenyl)-2,2-dimethyl-1,3-dioxolan-4-yl)methanol (Preparation example 6), to obtain the title compound (1.0 g, 50~80%)

$^1$H NMR (400 MHz, DMSO) δ 1.33~1.72 (m, 10H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 86

((2S,3S)-3-(2-nitrophenyl)-1,4-dioxaspiro[4,5]decan-2-yl)methyl sulfamate

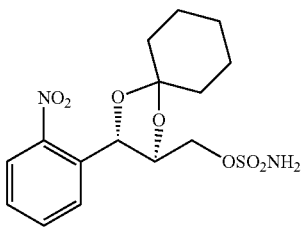

The substantially same method as described in Example 1 was conducted, except that ((2S,3S)-3-(2-nitrophenyl)-1,4-dioxapiro[4,5]decane-2-yl)methanol (Preparation example 181) was used instead of ((4R,5R)-5-(2-chlorophenyl)-2,2-dimethyl-1,3-dioxolan-4-yl)methanol (Preparation example 6), to obtain the title compound (0.8 g, 50~80%)

$^1$H NMR (400 MHz, DMSO) δ 1.33~1.72 (m, 10H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 87

((4R,5R)-5-(2-nitrophenyl)-2-phenyl-1,3-dioxolan-4-yl)methyl sulfamate

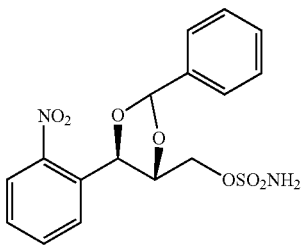

The substantially same method as described in Example 1 was conducted, except that ((4R,5R)-5-(2-nitrophenyl)-2-phenyl-1,3-dioxolane-4-yl)methanol (Preparation example 183) was used instead of ((4R,5R)-5-(2-chlorophenyl)-2,2-dimethyl-1,3-dioxolan-4-yl)methanol (Preparation example 6), to obtain the title compound (0.9 g, 50~80%)

$^1$H NMR (400 MHz, DMSO) δ 2.0 (s, 2H), 3.96~4.21 (m, 2H), 4.42 (dt, J=7.02, J=3.27, 1H), 5.17 (d, J=7.0, 1H), 5.79 (s, 1H), 6.73~6.74 (m, 2H), 7.11~7.13 (m, 2H), 7.36~7.38 (m, 5H).

Example 88

((4S,5S)-5-(2-nitrophenyl)-2-phenyl-1,3-dioxolan-4-yl)methyl sulfamate

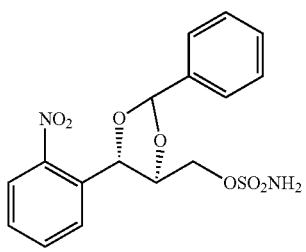

The substantially same method as described in Example 1 was conducted, except that ((4S,5S)-5-(2-nitrophenyl)-2-phenyl-1,3-dioxolane-4-yl)methanol (Preparation example 185) was used instead of ((4R,5R)-5-(2-chlorophenyl)-2,2-dimethyl-1,3-dioxolan-4-yl)methanol (Preparation example 6), to obtain the title compound (0.7 g, 50~80%)

$^1$H NMR (400 MHz, DMSO) δ 2.0 (s, 2H), 3.96~4.21 (m, 2H), 4.42 (dt, J=7.02, J=3.27, 1H), 5.17 (d, J=7.0, 1H), 5.79 (s, 1H), 6.73~6.74 (m, 2H), 7.11~7.13 (m, 2H), 7.36~7.38 (m, 5H).

Example 89

((4R,5R)-5-(2-nitrophenyl)-2-oxo-1,3-dioxolan-4-yl)methyl sulfamate

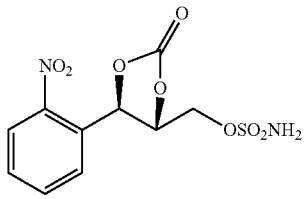

To a stirred solution of ((4R,5R)-5-(2-nitrophenyl)-2,2-dimethyl-1,3-dioxolan-4-yl)methyl sulfamate (Example 77, 5.2 g, 16 mmol) in EtOAc (50 mL) was added 3N HCl (24.6 mL, 80.0 mmol) at room temperature. The mixture was stirred for 5 h. The resulting mixture was diluted with EtOAc, washed with sat. NaHCO$_3$, dried over MgSO$_4$, filtered, and concentrated under reduced pressure. The crude product stirred in THF (35 mL) was added CDI (2.91 g, 17.9 mmol) at room temperature. The mixture was stirred for 1 h. The resulting mixture was diluted with EtOAc, washed with water, dried over MgSO$_4$, filtered, and concentrated under reduced pressure. The crude product was purified by SiO$_2$ gel column chromatography to produce the title compound (2.6 g, 60~80%)

¹H NMR (400 MHz, CDCl₃) δ 2.0 (s, 2H), 4.08~4.33 (m, 2H), 4.72 (dt, J=7.02, J=3.27, 1H), 5.47 (d, J=7.0, 1H), 7.62~7.64 (m, 2H), 7.77~7.90 (m, 2H).

Example 90

((4S,5S)-5-(2-nitrophenyl)-2-oxo-1,3-dioxolan-4-yl)methyl sulfamate

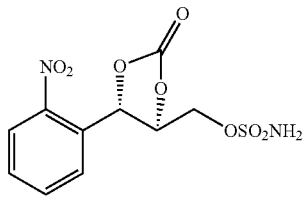

The substantially same method as described in Example 89 was conducted, except that ((4S,5S)-5-(2-nitrophenyl)-2,2-dimethyl-1,3-dioxolan-4-yl)methyl sulfamate (Example 78) was used instead of ((4R,5R)-5-(2-nitrophenyl)-2,2-dimethyl-1,3-dioxolan-4-yl)methyl sulfamate (Example 77), to obtain the title compound (0.9 g, 50~80%)

¹H NMR (400 MHz, CDCl₃) δ 2.0 (s, 2H), 4.08~4.33 (m, 2H), 4.72 (dt, J=7.02, J=3.27, 1H), 5.47 (d, J=7.0, 1H), 7.62~7.64 (m, 2H), 7.77~7.90 (m, 2H).

Example 91

((4R,5R)-5-(2-methylphenyl)-2,2-dimethyl-1,3-dioxolan-4-yl)methyl sulfamate

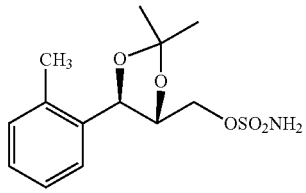

The substantially same method as described in Example 1 was conducted, except that ((4R,5R)-5-(2-methylphenyl)-2,2-dimethyl-1,3-dioxolan-4-yl)methanol (Preparation example 56) was used instead of ((4R,5R)-5-(2-chlorophenyl)-2,2-dimethyl-1,3-dioxolan-4-yl)methanol (Preparation example 6), to obtain the title compound (0.8 g, 50~80%).

¹H NMR (400 MHz, CDCl₃) δ1.38 (s, 3H), 1.40 (s, 3H), 2.24 (s, 3H), 4.29 (d, J=3.3, 2H), 4.74 (dt, J=7.0, J=3.3, 1H), 5.06 (d, J=7.0, 1H), 5.52 (s, 2H), 7.13~7.29 (m, 4H)

Example 92

((4S,5S)-5-(2-methylphenyl)-2,2-dimethyl-1,3-dioxolan-4-yl)methyl sulfamate

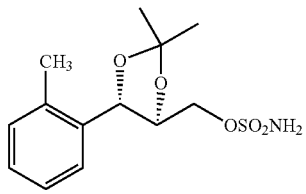

The substantially same method as described in Example 1 was conducted, except that ((4S,5S)-5-(2-methylphenyl)-2,2-dimethyl-1,3-dioxolan-4-yl)methanol (Preparation example 59) was used instead of ((4R,5R)-5-(2-chlorophenyl)-2,2-dimethyl-1,3-dioxolan-4-yl)methanol (Preparation example 6), to obtain the title compound (0.8 g, 50~80%)

¹H NMR (400 MHz, CDCl₃) δ1.38 (s, 3H), 1.40 (s, 3H), 2.24 (s, 3H), 4.29 (d, J=3.3, 2H), 4.74 (dt, J=7.0, J=3.3, 1H), 5.06 (d, J=7.0, 1H), 5.52 (s, 2H), 7.13~7.29 (m, 4H)

Example 93

((4R,5R)-5-(2-methylphenyl)-2-methyl-1,3-dioxolan-4-yl)methyl sulfamate

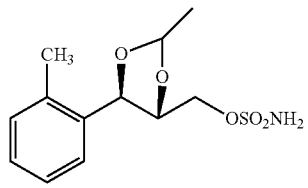

The substantially same method as described in Example 1 was conducted, except that ((4R,5R)-5-(2-methylphenyl)-2-methyl-1,3-dioxolan-4-yl)methanol (Preparation example 187) was used instead of ((4R,5R)-5-(2-chlorophenyl)-2,2-dimethyl-1,3-dioxolan-4-yl)methanol (Preparation example 6), to obtain the title compound (1.4 g, 50~80%)

¹H NMR (400 MHz, CDCl₃) δ1.40 (d, J=6.4, 3H), 2.24 (s, 3H), 4.27 (dt, J=7.0, J=3.3, 1H), 4.70 (d, J=3.3, 2H), 5.13 (d, J=7.0, 1H), 5.40 (q, J=6.4, 1H), 5.52 (s, 2H), 7.13~7.29 (m, 4H)

Example 94

((4S,5S)-5-(2-methylphenyl)-2-methyl-1,3-dioxolan-4-yl)methyl sulfamate

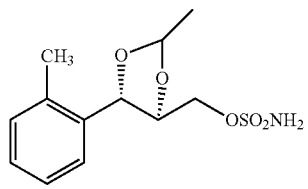

The substantially same method as described in Example 1 was conducted, except that ((4S,5S)-5-(2-methylphenyl)-2-methyl-1,3-dioxolan-4-yl)methanol (Preparation example 189) was used instead of ((4R,5R)-5-(2-chlorophenyl)-2,2-dimethyl-1,3-dioxolan-4-yl)methanol (Preparation example 6), to obtain the title compound (1.2 g, 50~80%)

¹H NMR (400 MHz, CDCl₃) δ1.40 (cl, J=6.4, 3H), 2.24 (s, 3H), 4.27 (dt, J=7.0, J=3.3, 1H), 4.70 (d, J=3.3, 2H), 5.13 (d, J=7.0, 1H), 5.40 (q, J=6.4, 1H), 5.52 (s, 2H), 7.13~7.29 (m, 4H)

Example 95

((4R,5R)-5-(2-methylphenyl)-2,2-diethyl-1,3-dioxolan-4-yl)methyl sulfamate

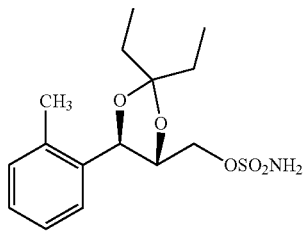

The substantially same method as described in Example 1 was conducted, except that ((4R,5R)-5-(2-methylphenyl)-2,2-diethyl-1,3-dioxolan-4-yl)methanol (Preparation example 191) was used instead of ((4R,5R)-5-(2-chlorophenyl)-2,2-dimethyl-1,3-dioxolan-4-yl)methanol (Preparation example 6), to obtain the title compound (1.3 g, 50~80%)

$^1$H NMR (400 MHz, CDCl$_3$) δ1.05 (t, J=6.8, 3H), 1.15 (t, J=6.8, 3H), 1.77~1.85 (m, 4H), 2.24 (s, 3H), 4.35 (d, J=3.3, 2H), 4.75 (dt, J=7.0, J=3.3, 1H), 5.10 (d, J=7.0, 1H), 5.52 (s, 2H), 7.18~7.30 (m, 4H)

Example 96

((4S,5S)-5-(2-methylphenyl)-2,2-diethyl-1,3-dioxolan-4-yl)methyl sulfamate

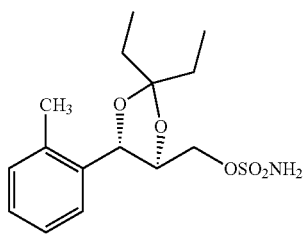

The substantially same method as described in Example 1 was conducted, except that ((4S,5S)-5-(2-methylphenyl)-2,2-diethyl-1,3-dioxolan-4-yl)methanol (Preparation example 193) was used instead of ((4R,5R)-5-(2-chlorophenyl)-2,2-dimethyl-1,3-dioxolan-4-yl)methanol (Preparation example 6), to obtain the title compound (1.4 g, 50~80%)

$^1$H NMR (400 MHz, CDCl$_3$) δ1.05 (t, J=6.8, 3H), 1.15 (t, J=6.8, 3H), 1.77~1.85 (m, 4H), 2.24 (s, 3H), 4.35 (d, J=3.3, 2H), 4.75 (dt, J=7.0, J=3.3, 1H), 5.10 (d, J=7.0, 1H), 5.52 (s, 2H), 7.18~7.30 (m, 4H)

Example 97

((2R,3R)-3-(2-methylphenyl)-1,4-dioxaspiro[4,4]nonane-2-yl)methyl sulfamate

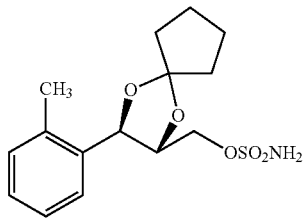

The substantially same method as described in Example 1 was conducted, except that ((2R,3R)-3-(2-methylphenyl)-1,4-dioxaspiro[4,4]nonane-2-yl)methanol (Preparation example 195) was used instead of ((4R,5R)-5-(2-chlorophenyl)-2,2-dimethyl-1,3-dioxolan-4-yl)methanol (Preparation example 6), to obtain the title compound (1.1 g, 50~80%)

$^1$H NMR (400 MHz, CDCl$_3$) δ1.60~1.70 (m, 4H), 1.74~1.99 (m, 4H), 2.24 (s, 3H), 4.75 (d, J=3.267, 2H), 4.36 (dt, J=7.1, J=3.3, 1H), 5.13 (d, J=7.0, 1H), 5.52 (s, 2H), 7.13~7.30 (m, 4H)

Example 98

((2S,3S)-3-(2-methylphenyl)-1,4-dioxaspiro[4,4]nonane-2-yl)methyl sulfamate

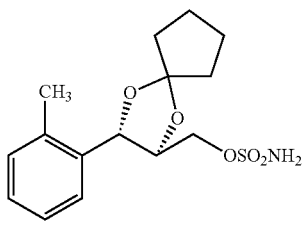

The substantially same method as described in Example 1 was conducted, except that ((2S,3S)-3-(2-methylphenyl)-1,4-dioxaspiro[4,4]nonane-2-yl)methanol (Preparation example 197) was used instead of ((4R,5R)-5-(2-chlorophenyl)-2,2-dimethyl-1,3-dioxolan-4-yl)methanol (Preparation example 6), to obtain the title compound (1.4 g, 50~80%)

$^1$H NMR (400 MHz, CDCl$_3$) δ1.60~1.70 (m, 4H), 1.74~1.99 (m, 4H), 2.24 (s, 3H), 4.75 (d, J=3.267, 2H), 4.36 (dt, J=7.1, J=3.3, 1H), 5.13 (d, J=7.0, 1H), 5.52 (s, 2H), 7.13~7.30 (m, 4H)

Example 99

((2R,3R)-3-(2-methylphenyl)-1,4-dioxaspiro[4,5]decane-2-yl)methyl sulfamate

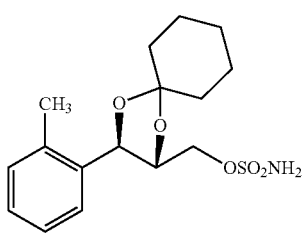

The substantially same method as described in Example 1 was conducted, except that ((2R,3R)-3-(2-methylphenyl)-1,4-dioxaspiro[4,5]decane-2-yl)methanol (Preparation example 199) was used instead of ((4R,5R)-5-(2-chlorophenyl)-2,2-dimethyl-1,3-dioxolan-4-yl)methanol (Preparation example 6), to obtain the title compound (1.0 g, 50~80%)

¹H NMR (400 MHz, CDCl₃) δ1.40~1.49 (m, 2H), 1.53~1.60 (m, 4H), 1.61~2.09 (m, 4H), 2.24 (s, 3H), 4.23 (d, J=3.3, 2H), 4.75 (dt, J=7.0, J=3.3, 1H), 5.10 (d, J=7.0, 1H), 5.62 (s, 2H), 7.13~7.30 (m, 4H)

Example 100

((2S,3S)-3-(2-methylphenyl)-1,4-dioxaspiro[4,5]decan-2-yl)methyl sulfamate

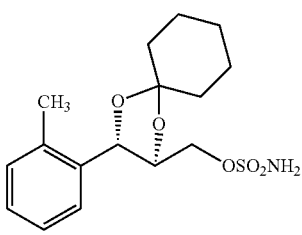

The substantially same method as described in Example 1 was conducted, except that ((2S,3S)-3-(2-methylphenyl)-1,4-dioxaspiro[4,5]decan-2-yl)methanol (Preparation example 201) was used instead of ((4R,5R)-5-(2-chlorophenyl)-2,2-dimethyl-1,3-dioxolan-4-yl)methanol (Preparation example 6), to obtain the title compound (1.3 g, 50~80%)

¹H NMR (400 MHz, CDCl₃) δ1.40~1.49 (m, 2H), 1.53~1.60 (m, 4H), 1.61~2.09 (m, 4H), 2.24 (s, 3H), 4.23 (d, J=3.3, 2H), 4.75 (dt, J=7.0, J=3.3, 1H), 5.10 (d, J=7.0, 1H), 5.62 (s, 2H), 7.13~7.30 (m, 4H)

Example 101

((4R,5R)-5-(2-methylphenyl)-2-phenyl-1,3-dioxolan-4-yl)methyl sulfamate

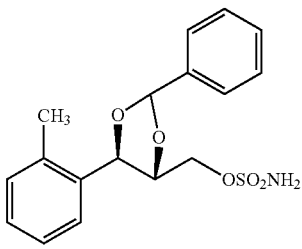

The substantially same method as described in Example 1 was conducted, except that ((4R,5R)-5-(2-methylphenyl)-2-phenyl-1,3-dioxolane-4-yl)methanol (Preparation example 203) was used instead of ((4R,5R)-5-(2-chlorophenyl)-2,2-dimethyl-1,3-dioxolan-4-yl)methanol (Preparation example 6), to obtain the title compound (1.1 g, 50~80%)

¹H NMR (400 MHz, CDCl₃) δ2.24 (s, 3H), 4.35 (d, J=3.3, 2H), 4.64 (d, J=5.7, 1H), 4.75 (dt, J=5.7, J=3.3, 1H), 5.59 (m, 1H), 5.78 (s, 2H), 7.13~7.29 (m, 4H), 7.33 (ddt, J=7.7, J=7.5, J=1.5, 1H), 7.40~7.75 (m, 4H)

Example 102

((4S,5S)-5-(2-methylphenyl)-2-phenyl-1,3-dioxolan-4-yl)methyl sulfamate

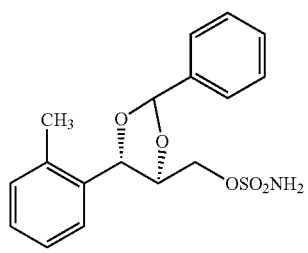

The substantially same method as described in Example 1 was conducted, except that ((4S,5S)-5-(2-methylphenyl)-2-phenyl-1,3-dioxolane-4-yl)methanol (Preparation example 205) was used instead of ((4R,5R)-5-(2-chlorophenyl)-2,2-dimethyl-1,3-dioxolan-4-yl)methanol (Preparation example 6), to obtain the title compound (0.6 g, 50~80%)

¹H NMR (400 MHz, CDCl₃) δ2.24 (s, 3H), 4.35 (d, J=3.3, 2H), 4.64 (d, J=5.7, 1H), 4.75 (dt, J=5.7, J=3.3, 1H), 5.59 (m, 1H), 5.78 (s, 2H), 7.13~7.29 (m, 4H), 7.33 (ddt, J=7.7, J=7.5, J=1.5, 1H), 7.40~7.75 (m, 4H)

Example 103

((4R,5R)-5-(2-methylaminophenyl)-2,2-dimethyl-1,3-dioxolan-4-yl)methyl methylsulfamate

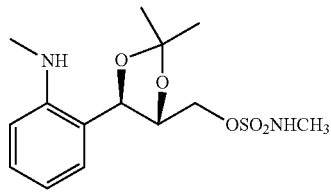

To a stirred solution of ((4R,5R)-5-(2-aminophenyl)-2,2-dimethyl-1,3-dioxolan-4-yl)methyl sulfamate (Example 63, 0.68 g, 2.25 mmol) and benzotriazole (0.27 g, 2.25 mmol) in EtOH (10 mL) was slowly added formaldehyde (10 wt % in H₂O, 0.62 mL, 2.25 mmol) and NaBH₄ (0.085 g, 2.25 mmol) at 0° C. The resulting mixture was diluted with EtOAc, washed with water, dried over MgSO₄, filtered, and concentrated under reduced pressure. The crude product was purified by SiO₂ gel column chromatography to obtain the title compound (0.3 g, 30~50%)

¹H NMR (400 MHz, CDCl₃) δ1.40 (s, 6H), 2.62 (s, 3H), 2.96 (s, 3H), 4.25 (dt, J=7.0, J=3.3, 1H), 4.75 (d, J=3.3, 2H), 4.84 (d, J=7.0, 1H), 6.99~7.20 (m, 4H)

Example 104

((4S,5S)-5-(2-methylaminophenyl)-2,2-dimethyl-1,3-dioxolan-4-yl)methyl methylsulfamate

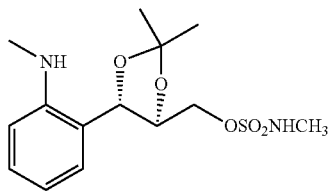

The substantially same method as described in Example 103 was conducted, except that ((4S,5S)-5-(2-aminophenyl)-2,2-dimethyl-1,3-dioxolan-4-yl)methyl sulfamate (Example 64) was used instead of ((4R,5R)-5-(2-aminophenyl)-2,2-dimethyl-1,3-dioxolan-4-yl)methyl sulfamate (Example 63), to obtain the title compound (0.5 g, 50~80%)

$^1$H NMR (400 MHz, CDCl$_3$) δ1.40 (s, 6H), 2.62 (s, 3H), 2.96 (s, 3H), 4.25 (dt, J=7.0, J=3.3, 1H), 4.75 (d, J=3.3, 2H), 4.84 (d, J=7.0, 1H), 6.99~7.20 (m, 4H)

Example 105

((4R,5R)-5-phenyl-2,2-dimethyl-1,3-dioxolan-4-yl)methyl sulfamate

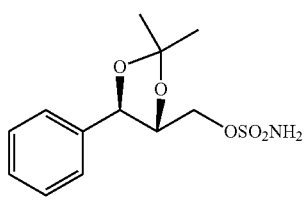

The substantially same method as described in Example 1 was conducted, except that ((4R,5R)-5-phenyl-2,2-dimethyl-1,3-dioxolan-4-yl)methanol (Preparation example 219) was used instead of ((4R,5R)-5-(2-chlorophenyl)-2,2-dimethyl-1,3-dioxolan-4-yl)methanol (Preparation example 6), to obtain the title compound (3.5 g, 50~80%)

$^1$H NMR (400 MHz, DMSO) δ 1.27 (s, 6H), 1.40 (s, 3H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 106

((4S,5S)-5-phenyl-2,2-dimethyl-1,3-dioxolan-4-yl)methyl sulfamate

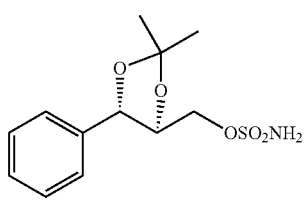

The substantially same method as described in Example 1 was conducted, except that ((4S,5S)-5-phenyl-2,2-dimethyl-1,3-dioxolan-4-yl)methanol (Preparation example 222) was used instead of ((4R,5R)-5-(2-chlorophenyl)-2,2-dimethyl-1,3-dioxolan-4-yl)methanol (Preparation example 6), to obtain the title compound (4.7 g, 50~80%)

$^1$H NMR (400 MHz, DMSO) δ 1.27 (s, 6H), 1.40 (s, 3H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 107

((4R,5R)-5-phenyl-2,2-diethyl-1,3-dioxolan-4-yl)methyl sulfamate

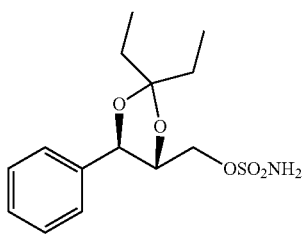

The substantially same method as described in Example 1 was conducted, except that ((4R,5R)-5-phenyl-2,2-diethyl-1,3-dioxolan-4-yl)methanol (Preparation example 224) was used instead of ((4R,5R)-5-(2-chlorophenyl)-2,2-dimethyl-1,3-dioxolan-4-yl)methanol (Preparation example 6), to obtain the title compound (0.8 g, 50~80%)

$^1$H NMR (400 MHz, CDCl$_3$) b 0.90 (t, J=8.0, 6H), 1.59 (q, J=8.0, 4H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 108

((4S,5S)-5-phenyl-2,2-diethyl-1,3-dioxolan-4-yl)methyl sulfamate

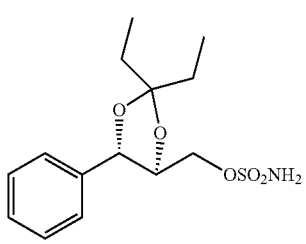

The substantially same method as described in Example 1 was conducted, except that ((4S,5S)-5-phenyl-2,2-diethyl-1,3-dioxolan-4-yl)methanol (Preparation example 226) was used instead of ((4R,5R)-5-(2-chlorophenyl)-2,2-dimethyl-1,3-dioxolan-4-yl)methanol (Preparation example 6), to obtain the title compound (4.3 g, 50~80%)

¹H NMR (400 MHz, CDCl₃) b 0.90 (t, J=8.0, 6H), 1.59 (q, J=8.0, 4H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 109

((2R 3R)-3-phenyl-1,4-dioxaspiro[4,4]nonan-2-yl)methyl sulfamate

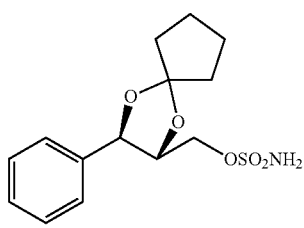

The substantially same method as described in Example 1 was conducted, except that ((4R,5R)-5-phenyl-1,4-dioxapiro[4,4]nonane-2-yl)methanol (Preparation example 228) was used instead of ((4R,5R)-5-(2-chlorophenyl)-2,2-dimethyl-1,3-dioxolan-4-yl)methanol (Preparation example 6), to obtain the title compound (0.4 g, 50~80%)

¹H NMR (400 MHz, DMSO) δ 1.46~1.56 (m, 6H), 1.65~1.90 (m, 2H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 110

((2S,3S)-3-phenyl-1,4-dioxaspiro[4,4]nonan-2-yl) methyl sulfamate

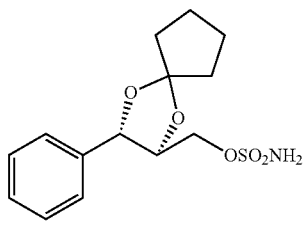

The substantially same method as described in Example 1 was conducted, except that ((4S,5S)-5-phenyl-1,4-dioxapiro[4,4]nonane-2-yl)methanol (Preparation example 230) was used instead of ((4R,5R)-5-(2-chlorophenyl)-2,2-dimethyl-1,3-dioxolan-4-yl)methanol (Preparation example 6), to obtain the title compound (0.2 g, 50~80%)

¹H NMR (400 MHz, DMSO) δ 1.46~1.56 (m, 6H), 1.65~1.90 (m, 2H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 111

((2R,3R)-3-phenyl-1,4-dioxaspiro[4,5]decan-2-yl) methyl sulfamate

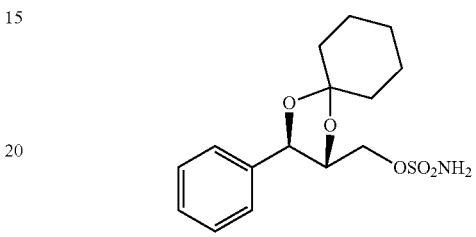

The substantially same method as described in Example 1 was conducted, except that ((4R,5R)-5-phenyl-1,4-dioxapiro[4,5]decane-2-yl)methanol (Preparation example 232) was used instead of ((4R,5R)-5-(2-chlorophenyl)-2,2-dimethyl-1,3-dioxolan-4-yl)methanol (Preparation example 6), to obtain the title compound (0.6 g, 50~80%)

¹H NMR (400 MHz, DMSO) δ 1.33~1.72 (m, 10H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 112

((2S,3S)-3-phenyl-1,4-dioxaspiro[4,5]decan-2-yl) methyl sulfamate

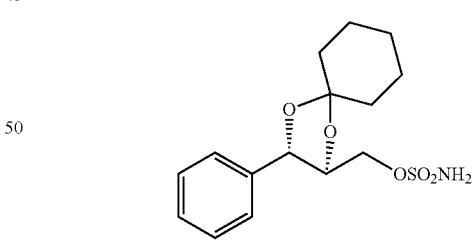

The substantially same method as described in Example 1 was conducted, except that ((4S,5S)-5-phenyl-1,4-dioxapiro[4,5]decane-2-yl)methanol (Preparation example 234) was used instead of ((4R,5R)-5-(2-chlorophenyl)-2,2-dimethyl-1,3-dioxolan-4-yl)methanol (Preparation example 6), to obtain the title compound (0.3 g, 50~80%)

¹H NMR (400 MHz, DMSO) δ 1.33~1.72 (m, 10H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 113

2-((4S,5S)-5-benzyl-2,2-dimethyl-1,3-dioxolan-4-yl)ethyl sulfamate

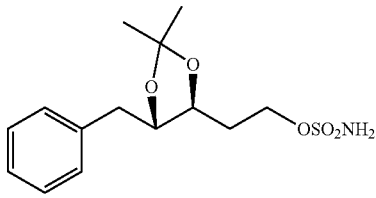

The substantially same method as described in Example 1 was conducted, except that 2-((4S,5S)-5-benzyl-2,2-dimethyl-1,3-dioxolan-4-yl)ethanol (Preparation example 241) was used instead of ((4R,5R)-5-(2-chlorophenyl)-2,2-dimethyl-1,3-dioxolan-4-yl)methanol (Preparation example 6), to obtain the title compound (4.2 g, 50~80%)

$^1$H NMR (400 MHz, DMSO) δ 1.27 (s, 6H), 1.40 (s, 3H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 114

2-((4R,5R)-5-benzyl-2,2-dimethyl-1,3-dioxolan-4-yl)ethyl sulfamate

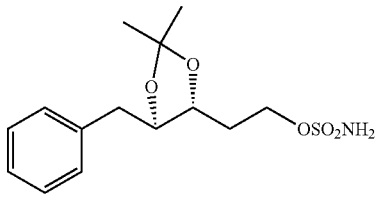

The substantially same method as described in Example 1 was conducted, except that 2-((4R,5R)-5-benzyl-2,2-dimethyl-1,3-dioxolan-4-yl)ethanol (Preparation example 244) was used instead of ((4R,5R)-5-(2-chlorophenyl)-2,2-dimethyl-1,3-dioxolan-4-yl)methanol (Preparation example 6), to obtain the title compound (4.2 g, 50~80%)

$^1$H NMR (400 MHz, DMSO) δ 1.27 (s, 6H), 1.40 (s, 3H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 115

2-((4S,5S)-5-benzyl-2,2-diethyl-1,3-dioxolan-4-yl)ethyl sulfamate

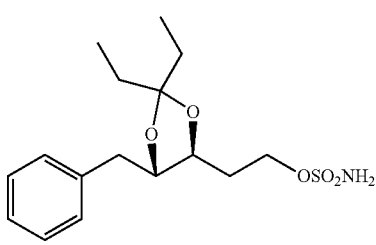

The substantially same method as described in Example 1 was conducted, except that 2-((4S,5S)-5-benzyl-2,2-diethyl-1,3-dioxolan-4-yl)ethanol (Preparation example 247) was used instead of ((4R,5R)-5-(2-chlorophenyl)-2,2-dimethyl-1,3-dioxolan-4-yl)methanol (Preparation example 6), to obtain the title compound (0.3 g, 50~80%)

$^1$H NMR (400 MHz, CDCl$_3$) δ 0.90 (t, J=8.0, 6H), 1.59 (q, J=8.0, 4H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 116

2-((4R,5R)-5-benzyl-2,2-diethyl-1,3-dioxolan-4-yl)ethyl sulfamate

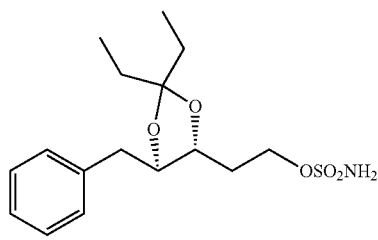

The substantially same method as described in Example 1 was conducted, except that 2-((4R,5R)-5-benzyl-2,2-diethyl-1,3-dioxolan-4-yl)ethanol (Preparation example 250) was used instead of ((4R,5R)-5-(2-chlorophenyl)-2,2-dimethyl-1,3-dioxolan-4-yl)methanol (Preparation example 6), to obtain the title compound (0.5 g, 50~80%)

$^1$H NMR (400 MHz, CDCl$_3$) δ 0.90 (t, J=8.0, 6H), 1.59 (q, J=8.0, 4H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 117

2-((2S,3S)-3-benzyl-1,4-dioxaspiro[4,4]nonan-2-yl)ethyl sulfamate

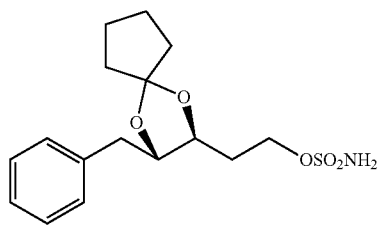

The substantially same method as described in Example 1 was conducted, except that 2-((2S,3S)-3-benzyl-1,4-dioxaspiro[4,4]nonane-2-yl)ethanol (Preparation example 252) was used instead of ((4R,5R)-5-(2-chlorophenyl)-2,2-dimethyl-1,3-dioxolan-4-yl)methanol (Preparation example 6), to obtain the title compound (0.5 g, 50~80%)

$^1$H NMR (400 MHz, DMSO) δ 1.46~1.56 (m, 6H), 1.65~1.90 (m, 2H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 118

2-((2R,3R)-3-benzyl-1,4-dioxaspiro[4,4]nonan-2-yl)ethyl sulfamate

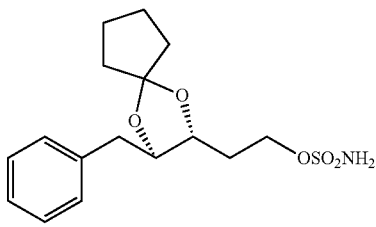

The substantially same method as described in Example 1 was conducted, except that 2-((2R,3R)-5-benzyl-1,4-dioxaspiro[4,4]nonane-2-yl)ethanol (Preparation example 254) was used instead of ((4R,5R)-5-(2-chlorophenyl)-2,2-dimethyl-1,3-dioxolan-4-yl)methanol (Preparation example 6), to obtain the title compound (0.6 g, 50~80%)

$^1$H NMR (400 MHz, DMSO) δ 1.46~1.56 (m, 6H), 1.65~1.90 (m, 2H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 119

2-((2S,3S)-3-benzyl-1,4-dioxaspiro[4,5]decane-2-yl)ethyl sulfamate

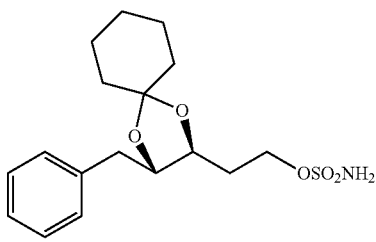

The substantially same method as described in Example 1 was conducted, except that 2-((2S,3S)-3-benzyl-1,4-dioxaspiro[4,5]decane-2-yl)ethanol (Preparation example 256) was used instead of ((4R,5R)-5-(2-chlorophenyl)-2,2-dimethyl-1,3-dioxolan-4-yl)methanol (Preparation example 6), to obtain the title compound (0.5 g, 50~80%)

$^1$H NMR (400 MHz, DMSO) δ 1.33~1.72 (m, 10H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 120

2-((2R,3R)-3-benzyl-1,4-dioxaspiro[4,5]decan-2-yl)ethyl sulfamate

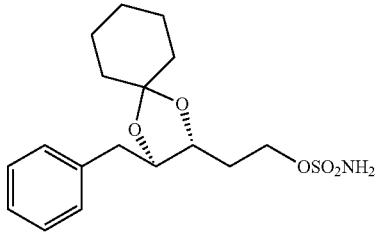

The substantially same method as described in Example 1 was conducted, except that 2-((2R,3R)-3-benzyl-1,4-dioxaspiro[4,5]decane-2-yl)ethanol (Preparation example 258) was used instead of ((4R,5R)-5-(2-chlorophenyl)-2,2-dimethyl-1,3-dioxolan-4-yl)methanol (Preparation example 6), to obtain the title compound (1.2 g, 50~80%)

$^1$H NMR (400 MHz, DMSO) δ 1.33~1.72 (m, 10H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 121

((4S,5S)-5-benzyl-2,2-dimethyl-1,3-dioxolan-4-yl)methyl sulfamate

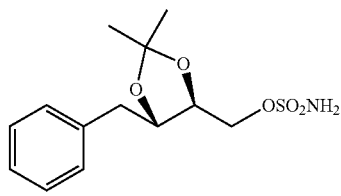

The substantially same method as described in Example 1 was conducted, except that ((4S,5S)-5-benzyl-2,2-dimethyl-1,3-dioxolan-4-yl)methanol (Preparation example 262) was used instead of ((4R,5R)-5-(2-chlorophenyl)-2,2-dimethyl-1,3-dioxolan-4-yl)methanol (Preparation example 6), to obtain the title compound (1.5 g, 50~80%)

$^1$H NMR (400 MHz, DMSO) δ 1.27 (s, 6H), 1.40 (s, 3H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 122

((4R,5R)-5-benzyl-2,2-dimethyl-1,3-dioxolan-4-yl)methyl sulfamate

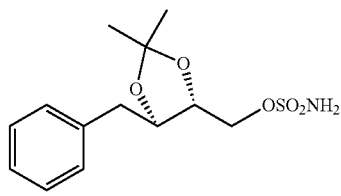

The substantially same method as described in Example 1 was conducted, except that ((4R,5R)-5-benzyl-2,2-dimethyl-1,3-dioxolan-4-yl)methanol (Preparation example 271) was used instead of ((4R,5R)-5-(2-chlorophenyl)-2,2-dimethyl-1,3-dioxolan-4-yl)methanol (Preparation example 6), to obtain the title compound (2.0 g, 50~80%)

$^1$H NMR (400 MHz, DMSO) δ 1.27 (s, 6H), 1.40 (s, 3H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 123

((4S,5S)-5-benzyl-2,2-diethyl-1,3-dioxolan-4-yl)
methyl sulfamate

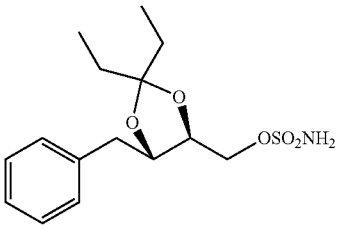

The substantially same method as described in Example 1 was conducted, except that ((4S,5S)-5-benzyl-2,2-diethyl-1,3-dioxolan-4-yl)methanol (Preparation example 264) was used instead of ((4R,5R)-5-(2-chlorophenyl)-2,2-dimethyl-1,3-dioxolan-4-yl)methanol (Preparation example 6), to obtain the title compound (0.3 g, 50~80%)

$^1$H NMR (400 MHz, CDCl$_3$) b 0.90 (t, J=8.0, 6H), 1.59 (q, J=8.0, 4H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 124

((4R,5R)-5-benzyl-2,2-diethyl-1,3-dioxolan-4-yl)
methyl sulfamate

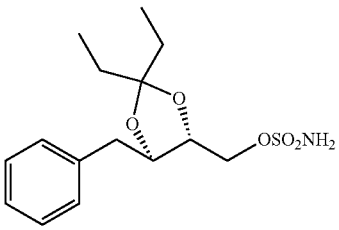

The substantially same method as described in Example 1 was conducted, except that ((4R,5R)-5-benzyl-2,2-diethyl-1,3-dioxolan-4-yl)methanol (Preparation example 273) was used instead of ((4R,5R)-5-(2-chlorophenyl)-2,2-dimethyl-1,3-dioxolan-4-yl)methanol (Preparation example 6), to obtain the title compound (0.5 g, 50~80%)

$^1$H NMR (400 MHz, CDCl$_3$) b 0.90 (t, J=8.0, 6H), 1.59 (q, J=8.0, 4H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 125

((2S,3S)-3-benzyl-1,4-dioxaspiro[4,4]nonan-2-yl)
methyl sulfamate

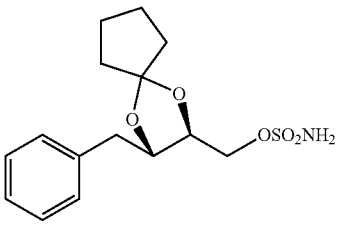

The substantially same method as described in Example 1 was conducted, except that ((2S,3S)-3-benzyl-1,4-dioxaspiro[4,4]nonan-2-yl)methanol (Preparation example 266) was used instead of ((4R,5R)-5-(2-chlorophenyl)-2,2-dimethyl-1,3-dioxolan-4-yl)methanol (Preparation example 6), to obtain the title compound (0.6 g, 50~80%)

$^1$H NMR (400 MHz, DMSO) δ 1.46~1.56 (m, 6H), 1.65~1.90 (m, 2H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 126

((2R,3R)-3-benzyl-1,4-dioxaspiro[4,4]nonan-2-yl)
methyl sulfamate

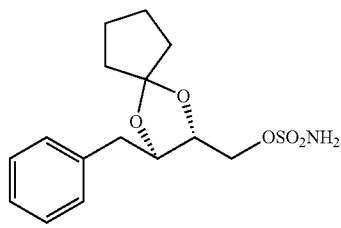

The substantially same method as described in Example 1 was conducted, except that ((2R,3R)-3-benzyl-1,4-dioxaspiro[4,4]nonan-2-yl)methanol (Preparation example 266) was used instead of ((4R,5R)-5-(2-chlorophenyl)-2,2-dimethyl-1,3-dioxolan-4-yl)methanol (Preparation example 6), to obtain the title compound (0.9 g, 50~80%)

$^1$H NMR (400 MHz, DMSO) δ 1.46~1.56 (m, 6H), 1.65~1.90 (m, 2H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 127

((2S,3S)-3-benzyl-1,4-dioxaspiro[4,5]decan-2-yl)
methyl sulfamate

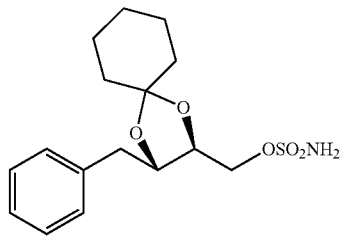

The substantially same method as described in Example 1 was conducted, except that ((2S,3S)-3-benzyl-1,4-dioxaspiro[4,5]decan-2-yl)methanol (Preparation example 268) was used instead of ((4R,5R)-5-(2-chlorophenyl)-2,2-dimethyl-1,3-dioxolan-4-yl)methanol (Preparation example 6), to obtain the title compound (0.7 g, 50~80%)

$^1$H NMR (400 MHz, DMSO) δ 1.33~1.72 (m, 10H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 128

((2R,3R)-3-benzyl-1,4-dioxaspiro[4,5]decan-2-yl)methyl sulfamate

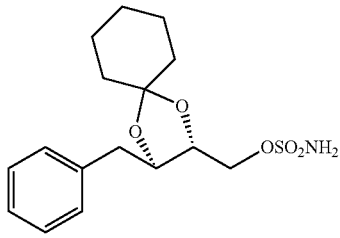

The substantially same method as described in Example 1 was conducted, except that ((2R,3R)-3-benzyl-1,4-dioxaspiro[4,5]decan-2-yl)methanol (Preparation example 277) was used instead of ((4R,5R)-5-(2-chlorophenyl)-2,2-dimethyl-1,3-dioxolan-4-yl)methanol (Preparation example 6), to obtain the title compound (1.2 g, 50~80%)

$^1$H NMR (400 MHz, DMSO) δ 1.33~1.72 (m, 10H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 129

2-((4R,5R)-5-phenyl-2,2-dimethyl-1,3-dioxolan-4-yl)ethyl sulfamate

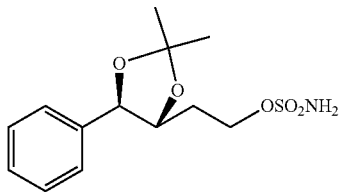

The substantially same method as described in Example 1 was conducted, except that 2-((4R,5S)-5-phenyl-2,2-dimethyl-1,3-dioxolan-4-yl)ethanol (Preparation example 285) was used instead of ((4R,5R)-5-(2-chlorophenyl)-2,2-dimethyl-1,3-dioxolan-4-yl)methanol (Preparation example 6), to obtain the title compound (1.2 g, 50~80%)

$^1$H NMR (400 MHz, DMSO) δ 1.27 (s, 6H), 1.40 (s, 3H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 130

2-((4S,5S)-5-phenyl-2,2-dimethyl-1,3-dioxolan-4-yl)ethyl sulfamate

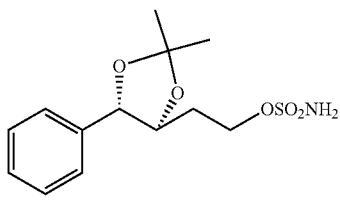

The substantially same method as described in Example 1 was conducted, except that 2-((4S,5S)-5-phenyl-2,2-dimethyl-1,3-dioxolan-4-yl)ethanol (Preparation example 289) was used instead of ((4R,5R)-5-(2-chlorophenyl)-2,2-dimethyl-1,3-dioxolan-4-yl)methanol (Preparation example 6), to obtain the title compound (0.3 g, 50~80%)

$^1$H NMR (400 MHz, DMSO) δ 1.27 (s, 6H), 1.40 (s, 3H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 131

2-((4R,5R)-5-phenyl-2,2-diethyl-1,3-dioxolan-4-yl)methyl sulfamate

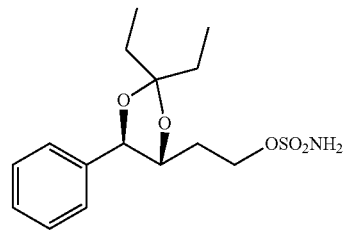

The substantially same method as described in Example 1 was conducted, except that 2-((4R,5R)-5-phenyl-2,2-diethyl-1,3-dioxolan-4-yl)ethanol (Preparation example 291) was used instead of ((4R,5R)-5-(2-chlorophenyl)-2,2-dimethyl-1,3-dioxolan-4-yl)methanol (Preparation example 6), to obtain the title compound (0.7 g, 50~80%)

$^1$H NMR (400 MHz, CDCl$_3$) δ 0.90 (t, J=8.0, 6H), 1.59 (q, J=8.0, 4H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 132

2-((4S,5S)-5-phenyl-2,2-diethyl-1,3-dioxolan-4-yl)ethyl sulfamate

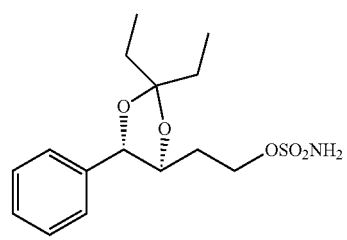

The substantially same method as described in Example 1 was conducted, except that 2-((4S,5S)-5-phenyl-2,2-diethyl-1,3-dioxolan-4-yl)ethanol (Preparation example 297) was used instead of ((4R,5R)-5-(2-chlorophenyl)-2,2-dimethyl-1,3-dioxolan-4-yl)methanol (Preparation example 6), to obtain the title compound (0.6 g, 50~80%)

$^1$H NMR (400 MHz, CDCl$_3$) δ 0.90 (t, J=8.0, 6H), 1.59 (q, J=8.0, 4H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 133

2-((2R,3R)-3-phenyl-1,4-dioxaspiro[4,4]nonan-2-yl)ethyl sulfamate

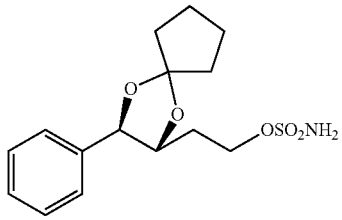

The substantially same method as described in Example 1 was conducted, except that 2-((2R,3R)-3-phenyl-1,4-dioxaspiro[4,4]nonan-2-yl)ethanol (Preparation example 293) was used instead of ((4R,5R)-5-(2-chlorophenyl)-2,2-dimethyl-1,3-dioxolan-4-yl)methanol (Preparation example 6), to obtain the title compound (0.5 g, 50~80%)

$^1$H NMR (400 MHz, DMSO) δ 1.46~1.56 (m, 6H), 1.65~1.90 (m, 2H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 134

2-((2S,3S)-3-phenyl-1,4-dioxaspiro[4,4]nonan-2-yl)ethyl sulfamate

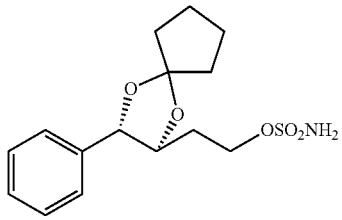

The substantially same method as described in Example 1 was conducted, except that 2-((2S,3S)-3-phenyl-1,4-dioxaspiro[4,4]nonan-2-yl)methanol (Preparation example 299) was used instead of ((4R,5R)-5-(2-chlorophenyl)-2,2-dimethyl-1,3-dioxolan-4-yl)methanol (Preparation example 6), to obtain the title compound (0.5 g, 50~80%)

$^1$H NMR (400 MHz, DMSO) δ 1.46~1.56 (m, 6H), 1.65~1.90 (m, 2H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 135

2-((2R,3R)-3-phenyl-1,4-dioxaspiro[4,5]decan-2-yl)ethyl sulfamate

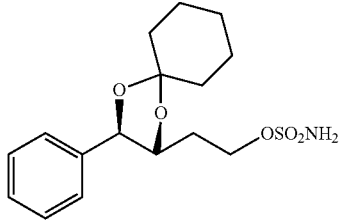

The substantially same method as described in Example 1 was conducted, except that 2-((2R,3R)-3-phenyl-1,4-dioxaspiro[4,5]decan-2-yl)ethanol (Preparation example 295) was used instead of ((4R,5R)-5-(2-chlorophenyl)-2,2-dimethyl-1,3-dioxolan-4-yl)methanol (Preparation example 6), to obtain the title compound (0.6 g, 50~80%)

$^1$H NMR (400 MHz, DMSO) δ 1.33~1.72 (m, 10H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 136

2-((2S,3S)-3-phenyl-1,4-dioxaspiro[4,5]decan-2-yl)ethyl sulfamate

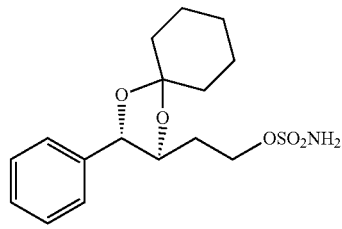

The substantially same method as described in Example 1 was conducted, except that 2-(2S,3S)-3-phenyl-1,4-dioxaspiro[4,5]decan-2-yl)ethanol (Preparation example 301) was used instead of ((4R,5R)-5-(2-chlorophenyl)-2,2-dimethyl-1,3-dioxolan-4-yl)methanol (Preparation example 6), to obtain the title compound (0.7 g, 50~80%)

$^1$H NMR (400 MHz, DMSO) δ 1.33~1.72 (m, 10H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 137

2-((4S,5S)-5-(2-chlorobenzyl)-2,2-dimethyl-1,3-dioxolan-4-yl)ethyl sulfamate

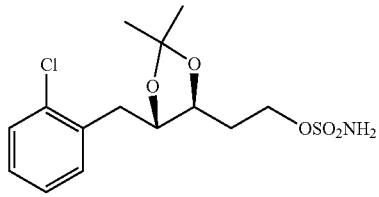

The substantially same method as described in Example 1 was conducted, except that 2-((4S,5S)-5-(2-chlorobenzyl)-2,2-dimethyl-1,3-dioxolan-4-yl)ethanol (Preparation example 308) was used instead of ((4R,5R)-5-(2-chlorophenyl)-2,2-dimethyl-1,3-dioxolan-4-yl)methanol (Preparation example 6), to obtain the title compound (2.7 g, 50~80%)

$^1$H NMR (400 MHz, DMSO) δ 1.27 (s, 6H), 1.40 (s, 3H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 138

2-((4R,5R)-5-(2-chlorobenzyl)-2,2-dimethyl-1,3-dioxolan-4-yl)ethyl sulfamate

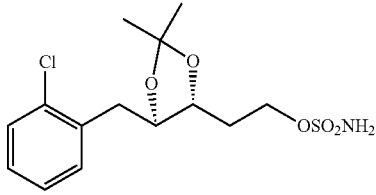

The substantially same method as described in Example 1 was conducted, except that 2-((4R,5R)-5-(2-chlorobenzyl)-2,2-dimethyl-1,3-dioxolan-4-yl)ethanol (Preparation example 311) was used instead of ((4R,5R)-5-(2-chlorophenyl)-2,2-dimethyl-1,3-dioxolan-4-yl)methanol (Preparation example 6), to obtain the title compound (2.4 g, 50~80%)

$^1$H NMR (400 MHz, DMSO) δ 1.27 (s, 6H), 1.40 (s, 3H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 139

2-((4S,5S)-5-(2-chlorobenzyl)-2,2-diethyl-1,3-dioxolan-4-yl)ethyl sulfamate

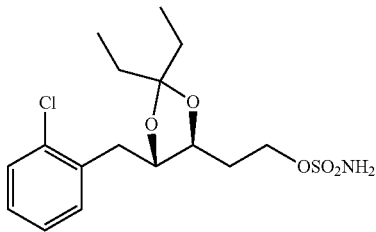

The substantially same method as described in Example 1 was conducted, except that 2-((4S,5S)-5-(2-chlorobenzyl)-2,2-diethyl-1,3-dioxolan-4-yl)ethanol (Preparation example 314) was used instead of ((4R,5R)-5-(2-chlorophenyl)-2,2-dimethyl-1,3-dioxolan-4-yl)methanol (Preparation example 6), to obtain the title compound (0.7 g, 50~80%)

$^1$H NMR (400 MHz, CDCl$_3$) δ 0.90 (t, J=8.0, 6H), 1.59 (q, J=8.0, 4H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 140

2-((4R,5R)-5-(2-chlorobenzyl)-2,2-diethyl-1,3-dioxolan-4-yl)ethyl sulfamate

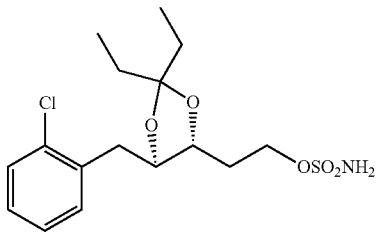

The substantially same method as described in Example 1 was conducted, except that 2-((4R,5R)-5-(2-chlorobenzyl)-2,2-diethyl-1,3-dioxolan-4-yl)ethanol (Preparation example 317) was used instead of ((4R,5R)-5-(2-chlorophenyl)-2,2-dimethyl-1,3-dioxolan-4-yl)methanol (Preparation example 6), to obtain the title compound (0.5 g, 50~80%)

$^1$H NMR (400 MHz, CDCl$_3$) δ 0.90 (t, J=8.0, 6H), 1.59 (q, J=8.0, 4H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 141

2-((2S,3S)-3-(2-chlorobenzyl)-1,4-dioxaspiro[4,4]nonan-2-yl)ethyl sulfamate

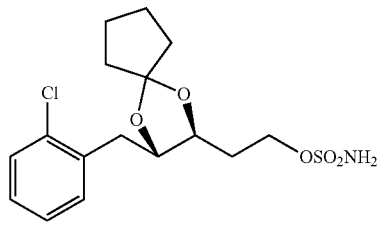

The substantially same method as described in Example 1 was conducted, except that 2-((2S,3S)-3-(2-chlorobenzyl)-1,4-dioxaspiro[4,4]nonan-2-yl)ethanol (Preparation example 319) was used instead of ((4R,5R)-5-(2-chlorophenyl)-2,2-dimethyl-1,3-dioxolan-4-yl)methanol (Preparation example 6), to obtain the title compound (0.5 g, 50~80%)

$^1$H NMR (400 MHz, DMSO) δ 1.46~1.56 (m, 6H), 1.65~1.90 (m, 2H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 142

2-((2R,3R)-3-(2-chlorobenzyl)-1,4-dioxaspiro[4,4]nonan-2-yl)ethyl sulfamate

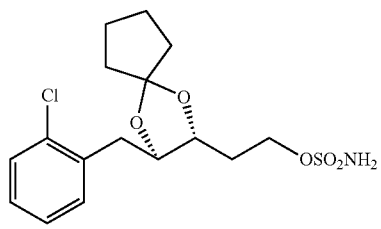

The substantially same method as described in Example 1 was conducted, except that 2-((2R,3R)-3-(2-chlorobenzyl)-1,4-dioxaspiro[4,4]nonan-2-yl)ethanol (Preparation example 321) was used instead of ((4R,5R)-5-(2-chlorophenyl)-2,2-dimethyl-1,3-dioxolan-4-yl)methanol (Preparation example 6), to obtain the title compound (0.6 g, 50~80%)

$^1$H NMR (400 MHz, DMSO) δ 1.46~1.56 (m, 6H), 1.65~1.90 (m, 2H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 143

2-((2S,3S)-3-(2-chlorobenzyl)-1,4-dioxaspiro[4,5]decan-2-yl)ethyl sulfamate

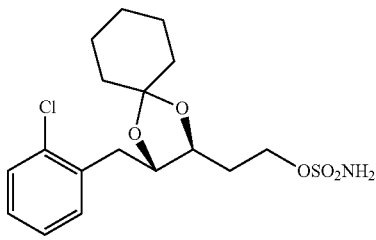

The substantially same method as described in Example 1 was conducted, except that 2-((2S,3S)-3-(2-chlorobenzyl)-1,4-dioxaspiro[4,5]decan-2-yl)ethanol (Preparation example 323) was used instead of ((4R,5R)-5-(2-chlorophenyl)-2,2-dimethyl-1,3-dioxolan-4-yl)methanol (Preparation example 6), to obtain the title compound (0.3 g, 50~80%)

$^1$H NMR (400 MHz, DMSO) δ 1.33~1.72 (m, 10H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 144

2-((2R,3R)-3-(2-chlorobenzyl)-1,4-dioxaspiro[4,5]decan-2-yl)ethyl sulfamate

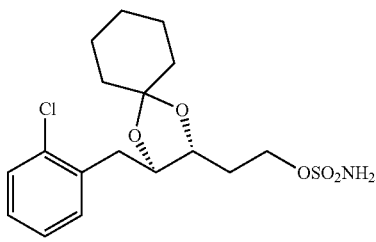

The substantially same method as described in Example 1 was conducted, except that 2-((2R,3R)-3-(2-chlorobenzyl)-1,4-dioxaspiro[4,5]decan-2-yl)ethanol (Preparation example 325) was used instead of ((4R,5R)-5-(2-chlorophenyl)-2,2-dimethyl-1,3-dioxolan-4-yl)methanol (Preparation example 6), to obtain the title compound (0.6 g, 50~80%)

$^1$H NMR (400 MHz, DMSO) δ 1.33~1.72 (m, 10H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 145

((4S,5S)-5-(2-chlorobenzyl)-2,2-dimethyl-1,3-dioxolan-4-yl)methyl sulfamate

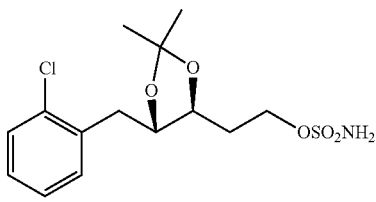

The substantially same method as described in Example 1 was conducted, except that ((4S,5S)-5-(2-chlorobenzyl)-2,2-dimethyl-1,3-dioxolan-4-yl)methanol (Preparation example 329) was used instead of ((4R,5R)-5-(2-chlorophenyl)-2,2-dimethyl-1,3-dioxolan-4-yl)methanol (Preparation example 6), to obtain the title compound (0.4 g, 50~80%)

$^1$H NMR (400 MHz, DMSO) δ 1.27 (s, 6H), 1.40 (s, 3H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 146

((4R,5R)-5-(2-chlorobenzyl)-2,2-dimethyl-1,3-dioxolan-4-yl)methyl sulfamate

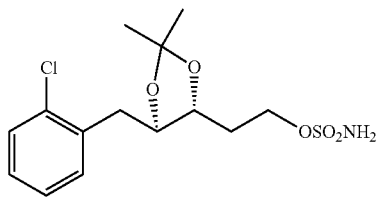

The substantially same method as described in Example 1 was conducted, except that ((4R,5R)-5-(2-chlorobenzyl)-2,2-dimethyl-1,3-dioxolan-4-yl)methanol (Preparation example 338) was used instead of ((4R,5R)-5-(2-chlorophenyl)-2,2-dimethyl-1,3-dioxolan-4-yl)methanol (Preparation example 6), to obtain the title compound (1.4 g, 50~80%)

$^1$H NMR (400 MHz, DMSO) δ 1.27 (s, 6H), 1.40 (s, 3H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 147

((4S,5S)-5-(2-chlorobenzyl)-2,2-diethyl-1,3-dioxolan-4-yl)methyl sulfamate

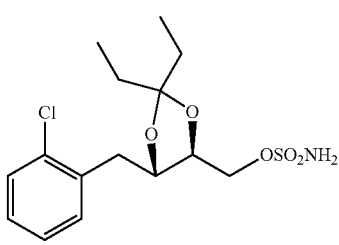

The substantially same method as described in Example 1 was conducted, except that ((4S,5S)-5-(2-chlorobenzyl)-2,2-diethyl-1,3-dioxolan-4-yl)methanol (Preparation example 331) was used instead of ((4R,5R)-5-(2-chlorophenyl)-2,2-dimethyl-1,3-dioxolan-4-yl)methanol (Preparation example 6), to obtain the title compound (0.2 g, 50~80%)

$^1$H NMR (400 MHz, CDCl$_3$) δ 0.90 (t, J=8.0, 6H), 1.59 (q, J=8.0, 4H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 148

((4R,5R)-5-(2-chlorobenzyl)-2,2-diethyl-1,3-dioxolan-4-yl)methyl sulfamate

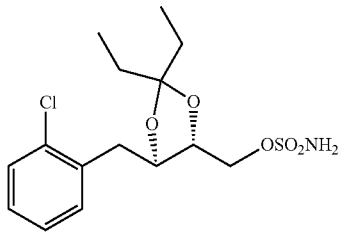

The substantially same method as described in Example 1 was conducted, except that ((4R,5R)-5-(2-chlorobenzyl)-2,2-diethyl-1,3-dioxolan-4-yl)methanol (Preparation example 340) was used instead of ((4R,5R)-5-(2-chlorophenyl)-2,2-dimethyl-1,3-dioxolan-4-yl)methanol (Preparation example 6), to obtain the title compound (0.3 g, 50~80%)

$^1$H NMR (400 MHz, CDCl$_3$) δ 0.90 (t, J=8.0, 6H), 1.59 (q, J=8.0, 4H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 149

((2S,3S)-3-(2-chlorobenzyl)-1,4-dioxaspiro[4,4]nonan-2-yl)methyl sulfamate

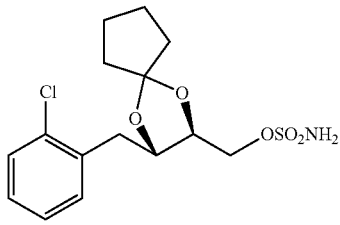

The substantially same method as described in Example 1 was conducted, except that ((2S,3S)-3-(2-chlorobenzyl)-1,4-dioxaspiro[4,4]nonan-2-yl)methanol (Preparation example 333) was used instead of ((4R,5R)-5-(2-chlorophenyl)-2,2-dimethyl-1,3-dioxolan-4-yl)methanol (Preparation example 6), to obtain the title compound (0.3 g, 50~80%)

$^1$H NMR (400 MHz, DMSO) δ 1.46~1.56 (m, 6H), 1.65~1.90 (m, 2H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 150

((2R,3R)-3-(2-chlorobenzyl)-1,4-dioxaspiro[4,4]nonan-2-yl)methyl sulfamate

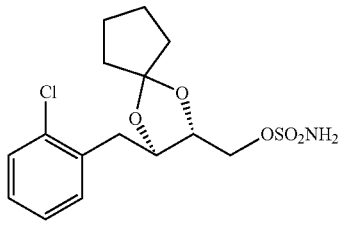

The substantially same method as described in Example 1 was conducted, except that ((2R,3R)-3-(2-chlorobenzyl)-1,4-dioxaspiro[4,4]nonan-2-yl)methanol (Preparation example 342) was used instead of ((4R,5R)-5-(2-chlorophenyl)-2,2-dimethyl-1,3-dioxolan-4-yl)methanol (Preparation example 6), to obtain the title compound (0.3 g, 50~80%)

$^1$H NMR (400 MHz, DMSO) δ 1.46~1.56 (m, 6H), 1.65~1.90 (m, 2H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 151

((2S,3S)-3-(2-chlorobenzyl)-1,4-dioxaspiro[4,5]decan-2-yl)methyl sulfamate

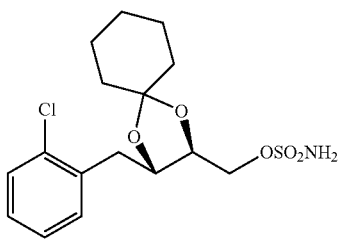

The substantially same method as described in Example 1 was conducted, except that ((2S,3S)-3-(2-chlorobenzyl)-1,4-dioxaspiro[4,5]decan-2-yl)methanol (Preparation example 335) was used instead of ((4R,5R)-5-(2-chlorophenyl)-2,2-dimethyl-1,3-dioxolan-4-yl)methanol (Preparation example 6), to obtain the title compound (0.4 g, 50~80%)

$^1$H NMR (400 MHz, DMSO) δ 1.33~1.72 (m, 10H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 152

((2R,3R)-3-(2-chlorobenzyl)-1,4-dioxaspiro[4,5]decan-2-yl)methyl sulfamate

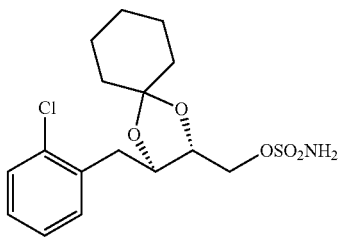

The substantially same method as described in Example 1 was conducted, except that ((2R,3R)-3-(2-chlorobenzyl)-1,4-dioxaspiro[4,5]decan-2-yl)methanol (Preparation example 344) was used instead of ((4R,5R)-5-(2-chlorophenyl)-2,2-dimethyl-1,3-dioxolan-4-yl)methanol (Preparation example 6), to obtain the title compound (0.4 g, 50~80%)

¹H NMR (400 MHz, DMSO) δ 1.33~1.72 (m, 10H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 153

(4R,5R)-5-(2-chlorophenyl)-2,2-dimethyl-1,3-dioxolan-4-yl)ethyl sulfamate

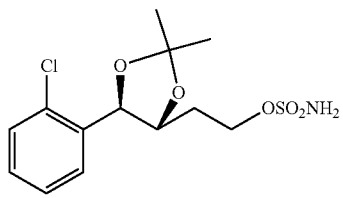

The substantially same method as described in Example 1 was conducted, except that 2-((4R,5R)-5-(2-chlorophenyl)-2,2-dimethyl-1,3-dioxolan-4-yl)ethanol (Preparation example 352) was used instead of ((4R,5R)-5-(2-chlorophenyl)-2,2-dimethyl-1,3-dioxolan-4-yl)methanol (Preparation example 6), to obtain the title compound (0.3 g, 50~80%)

¹H NMR (400 MHz, DMSO) δ 1.27 (s, 6H), 1.40 (s, 3H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 154

((4S,5S)-5-(2-chlorophenyl)-2,2-dimethyl-1,3-dioxolan-4-yl)ethyl sulfamate

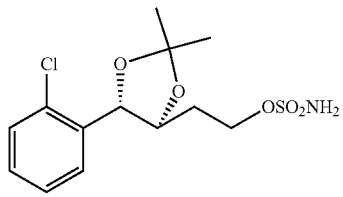

The substantially same method as described in Example 1 was conducted, except that 2-((4S,5S)-5-(2-chlorophenyl)-2,2-dimethyl-1,3-dioxolan-4-yl)ethanol (Preparation example 356) was used instead of ((4R,5R)-5-(2-chlorophenyl)-2,2-dimethyl-1,3-dioxolan-4-yl)methanol (Preparation example 6), to obtain the title compound (0.2 g, 50~80%)

¹H NMR (400 MHz, DMSO) δ 1.27 (s, 6H), 1.40 (s, 3H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 155

2-((4R,5R)-5-(2-chlorophenyl)-2,2-diethyl-1,3-dioxolan-4-yl)ethyl sulfamate

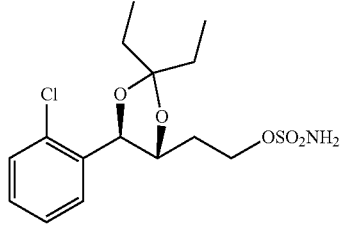

The substantially same method as described in Example 1 was conducted, except that 2-((4R,5R)-5-(2-chlorophenyl)-2,2-diethyl-1,3-dioxolan-4-yl)ethanol (Preparation example 358) was used instead of ((4R,5R)-5-(2-chlorophenyl)-2,2-dimethyl-1,3-dioxolan-4-yl)methanol (Preparation example 6), to obtain the title compound (0.5 g, 50~80%)

¹H NMR (400 MHz, CDCl₃) δ 0.90 (t, J=8.0, 6H), 1.59 (q, J=8.0, 4H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 156

2-((4S,5S)-5-(2-chlorophenyl)-2,2-diethyl-1,3-dioxolan-4-yl)ethyl sulfamate

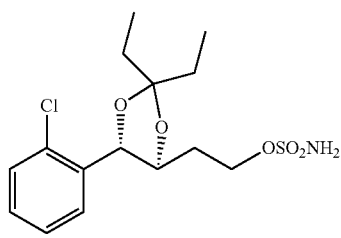

The substantially same method as described in Example 1 was conducted, except that 2-((4S,5S)-5-(2-chlorophenyl)-2,2-diethyl-1,3-dioxolan-4-yl)ethanol (Preparation example 364) was used instead of ((4R,5R)-5-(2-chlorophenyl)-2,2-dimethyl-1,3-dioxolan-4-yl)methanol (Preparation example 6), to obtain the title compound (0.5 g, 50~80%)

¹H NMR (400 MHz, CDCl₃) δ 0.90 (t, J=8.0, 6H), 1.59 (q, J=8.0, 4H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 157

2-((2R,3R)-3-(2-chlorophenyl)-1,4-dioxaspiro[4,4]nonan-2-yl)ethyl sulfamate

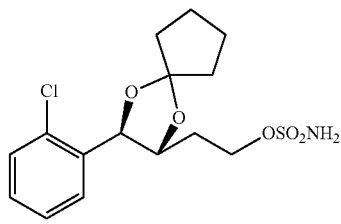

The substantially same method as described in Example 1 was conducted, except that 2-((2R,3R)-3-(2-chlorophenyl)-1,4-dioxaspiro[4,4]nonan-2-yl)ethanol (Preparation example 360) was used instead of ((4R,5R)-5-(2-chlorophenyl)-2,2-dimethyl-1,3-dioxolan-4-yl)methanol (Preparation example 6), to obtain the title compound (0.4 g, 50~80%)

¹H NMR (400 MHz, DMSO) δ 1.46~1.56 (m, 6H), 1.65~1.90 (m, 2H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 158

2-((2S,3S)-3-(2-chlorophenyl)-1,4-dioxaspiro[4,4]nonan-2-yl)ethyl sulfamate

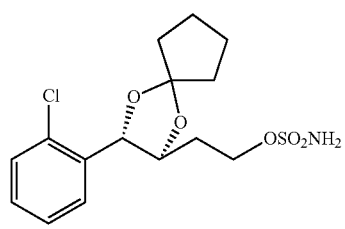

The substantially same method as described in Example 1 was conducted, except that 2-((2R,3R)-3-(2-chlorophenyl)-1,4-dioxaspiro[4,4]nonan-2-yl)ethanol (Preparation example 366) was used instead of ((4R,5R)-5-(2-chlorophenyl)-2,2-dimethyl-1,3-dioxolan-4-yl)methanol (Preparation example 6), to obtain the title compound (0.3 g, 50~80%)

¹H NMR (400 MHz, DMSO) δ 1.46~1.56 (m, 6H), 1.65~1.90 (m, 2H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 159

2-((2R,3R)-3-(2-chlorophenyl)-1,4-dioxaspiro[4,5]decan-2-yl)ethyl sulfamate

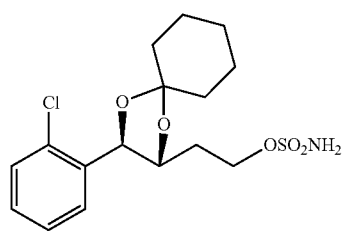

The substantially same method as described in Example 1 was conducted, except 2-((2R,3R)-3-(2-chlorophenyl)1,4-dioxaspiro[4,5]decan-2-yl)ethanol (Preparation example 362) was used instead of ((4R,5R)-5-(2-chlorophenyl)-2,2-dimethyl-1,3-dioxolan-4-yl)methanol (Preparation example 6), to obtain the title compound (0.3 g, 50~80%)

¹H NMR (400 MHz, DMSO) δ 1.33~1.72 (m, 10H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 160

2-((2S,3S)-3-(2-chlorophenyl)-1,4-dioxaspiro[4,5]decan-2-yl)ethyl sulfamate

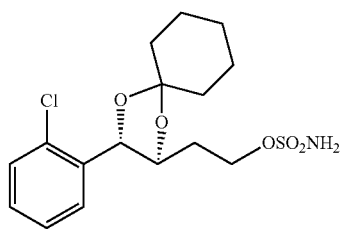

The substantially same method as described in Example 1 was conducted, except that 2-((2S,3S)-3-(2-chlorophenyl)-1,4-dioxaspiro[4,5]decan-2-yl)ethanol (Preparation example 368) was used instead of ((4R,5R)-5-(2-chlorophenyl)-2,2-dimethyl-1,3-dioxolan-4-yl)methanol (Preparation example 6), to obtain the title compound (0.4 g, 50~80%)

¹H NMR (400 MHz, DMSO) δ 1.33~1.72 (m, 10H), 2.0 (s, 2H), 3.96~4.21 (m, 2H), 4.42 (dt, J=7.02, J=3.27, 1H), 5.17 (d, J=7.0, 1H), 7.62~7.64 (m, 2H), 7.77~7.90 (m, 2H).

Example 161

((4S,5R)-5-(2-chlorophenyl)-2,2-dimethyl-1,3-dioxolan-4-yl)methyl sulfamate

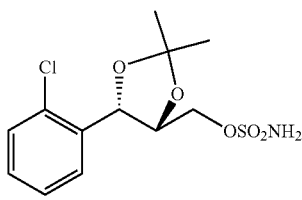

The substantially same method as described in Example 1 was conducted, except that ((4S,5R)-5-(2-chlorophenyl)-2,2-dimethyl-1,3-dioxolan-4-yl)methanol (Preparation example 377) was used instead of ((4R,5R)-5-(2-chlorophenyl)-2,2-dimethyl-1,3-dioxolan-4-yl)methanol (Preparation example 6), to obtain the title compound (0.58 g, 50~80%).

¹H NMR (400 MHz, CDCl₃) δ1.53 (s, 3H), 1.66 (s, 3H), 3.14~3.06 (m, 2H), 4.26 (d, J=12, 2H), 4.83~4.78 (m, 1H), 5.63 (d, J=6.8 Hz, 1H), 7.35~7.16 (m, 8H), 7.61 (dd, J=7.4, 1.6, 1H).

ANIMAL TESTING EXAMPLES

For testing, male mice (ICR) were purchased from ORIENT BIO INC. (Korea), divided into several groups with 6 mice in each group, and were adapted for 4-5 days. The mice having the weight ranging from 19 g to 26 g were employed for the test. The pharmacological effect of the test compounds on muscle relaxation was evaluated by Rotarod test, grip strength test, and muscular force (wire hang) test. All mice were adapted to the test environment at one hour before starting the tests. The pharmacological effects of all the test compounds were evaluated by administration through peritoneal cavity of the mice (10 ul/g, bw).

Experimental Example 1

Measurement of Muscle Relaxation Activity by Grip Strength

A grip strength test using the test animals' forelimbs was performed using an instrument equipped with triangle ring and designed so as to easily grip with the forelimbs of experimental animals, manufactured from Ugo Basile Inc. (Ugo Basile, Model 47106, Italy). The test was conducted before and after administration of the compounds to evaluate the effects thereof. All the test compounds were intraperitoneally administered (10 ul/g, bw) at 15 minutes, 30 minutes, 1 hour, and 2 hours before test, and the median effective concentration (ED50) was determined at the time (generally 15 min, 30 min or 60 min) that the compounds exhibits therir maximum pharmacological effect. The mouse was made to grip the rod with its forelimbs, and its tail was pulled, where the force at which the mouse detached from the rod was recorded. The instrument indicated the force in grams. All of the mice were given 3 opportunities for test, and the 3 highest values among the test opportunities were selected and the mean value was used as the test result. The obtained results are shown in Table 3. This experimentation was conducted according to the method described in the reference, 'Nevins et al. (1993) Quantitative grip strength assessment as a means of evaluating muscle relaxation in mice. Psychopharmacol. 110: 92-96'.

Experimental Example 2

Measurement of Muscle Relaxation Activity by Wire Hang

This experimentation was conducted using a metal wire of 30 cm in length, which was suspended between two pillars at a height of about 40 cm from the bottom covered with a soft pad. All the test compounds were administered to the mice through peritoneal cavity (10 ul/g, bw) at 15 minutes, 30 minutes, 1 hour, and 2 hours prior to the testing, and the median effective concentration (ED50) was determined at the time that the compound exhibits the maximum pharmacological effect. Each mouse was made to grip the wire using two forelimbs, and the elapse time before the mouse fell off from the wire to the pad on the bottom was recorded in seconds. Each mouse was given 5 opportunities for this test at an interval of 2 minutes period. The highest 3 records among the test opportunities were selected and the mean value was used as the test result. The obtained results are shown in Table 3. This experimentation was conducted according to the method described in the reference, 'Jacqueline N. Crawley (1999) Behavioral phenotyping of transgenic and knockout mice: experimental design and evaluation of general health, sensory functions, motor abilities, and specific behavioral tests. Brain Res. 835: 18-26'.

Experimental Example 3

Measurement of Muscle Relaxation Activity by Residence Time on a Rotarod Rotating at a Fixed Speed All the mice to be tested were preliminarily trained for 5 minutes on a rod rotating at the rate of 15 revolutions per a minute. The mice that could not remain on the rod without falling off therefrom for a minimum of 2 minutes were excluded from this testing. After the training, all the mice were allowed to rest for 45-60 minutes. Before the administration of the test compounds, the mice were subjected to a further training for one minute on the rod rotating under the same condition, where the mice falling off from the rod were excluded from this experimentation. All the test compounds were intraperitoneally administered (10 ul/g, bw) to the mice at 15 minutes, 30 minutes, 1 hour, and 2 hours prior to the testing, and the median effective concentration (ED50) was determined at the time (generally 15 min, 30 min or 60 min) that the compounds exhibit their maximum pharmacological effect. In case a mouse stays on the rod until the test is finished, the time was recorded as 10 minutes. As test time for evaluation, a maximum of 10 minutes was applied. The obtained results were shown in following Table 3. This experimentation was conducted according to the method described in the reference, 'Yasuda et al. (2005) Antipyretic, analgesic and muscle relaxant activities of Pueraria isoflavonoids and their metabolites from Pueraria lobata Ohwi—a traditional Chinese drug. Biol. Pharm. Bull. 28: 1224-1228.

[Statistical Analysis]

The obtained results are shown as mean±sem. The difference between the groups was statistically analyzed by ANOVA, and then, further examined by Dunnett's test or Bonferroni test. If p is less than 0.05, it was determined that the difference between the groups had statistical significance.

[Results]

The results of muscle relaxation activity of the phenylalkyl sulfamate compounds measured in above Experimental Examples 1 to 43 are shown in following Table 2. In the Table 2, the ED50 was represented by the concentration where the compound shows the 50% of muscle relaxation activity compared to the vehicle only (100%).

TABLE 2

Results of the measurements of muscle relaxation activity of the phenylalkyl sulfamate compounds

| No | Grip strength | Wire suspension | Fixed rotarod |
|---|---|---|---|
| 1 | 211.9 (0.5 h) | 96.7 (0.5 h) | 108.2 (0.5 h) |
| 2 | 211.4 (0.5 h) | 81.4 (0.5 h) | 73.6 (0.5 h) |
| 3 | 205.0 (0.25 h) | 116.2 (1 h) | 99.2 (0.5 h) |
| 4 | 200 (56.5%) | 100 (41.3%) | 100 (76.6%) |
| 6 | 200 (44.8%) | 100 (70.0%) | 100 (50.4%) |
| 8 | 200 (59.6%) | | |
| 10 | 200 (91.2%) | | |
| 12 | 200 (57.7%) | | |
| 15 | | | 140 (22.7%) |
| 16 | 161.1 (0.5 h) | 99.1 (0.5 h) | |
| 27 | 377.8 (0.5 h) | | |
| 28 | 261.1 (0.5 h) | 100 (66.8%) | 102.4 (0.5 h) |
| 40 | 200 (79.3%) | | |
| 52 | 200 (28.2%) | | |
| 66 | 200 (69.5%) | | |
| 70 | 200 (78.6%) | | |
| 72 | 200 (87.0%) | | |
| 74 | 200 (88.1%) | | |
| 76 | 200 (78.5%) | | |
| 90 | 200 (43.8%) | | |
| 92 | 200 (46.2%) | | |
| 104 | 200 (71.3%) | | |
| 106 | 200 (62.8%) | | |
| 108 | 200 (66.8%) | | |
| 110 | 200 (62.9%) | | |
| 112 | 200 (33.2%) | | |
| 114 | 200 (75.4%) | | |
| 116 | 200 (81.6%) | | |
| 118 | 200 (83.7%) | | |
| 120 | 200 (80.5%) | | |

TABLE 2-continued

Results of the measurements of muscle relaxation activity of the phenylalkyl sulfamate compounds

| No | Grip strength | Wire suspension | Fixed rotarod |
|---|---|---|---|
| 122 | 200 (61.6%) | | |
| 124 | 200 (81.0%) | | |
| 126 | 200 (76.7%) | | |
| 128 | 200 (81.4%) | | |
| 130 | 200 (91.4%) | | |
| 132 | 200 (25.7%) | | |
| 134 | 200 (90.1%) | | |
| 136 | 200 (80.8%) | | |
| 138 | 200 (70.1%) | | |
| 140 | 200 (73.4%) | | |
| 142 | 200 (66.8%) | | |
| 144 | 200 (62.0%) | | |
| 146 | 200 (79.2%) | | |
| 148 | 200 (70.2%) | | |
| 150 | 200 (89.8%) | | |
| 152 | 200 (77.2%) | | |
| 154 | 200 (70.4%) | | |
| 156 | 200 (73.2%) | | |
| 158 | 200 (74.2%) | | |
| 160 | 200 (86.8%) | | |

% = the percentage of grip strength, wire suspension, and residence time on a rotating rotarod compared to the vehicle only (100%), respectively.

What is claimed is:

1. A compound represented by the following formula 1 or pharmaceutically acceptable salt thereof:

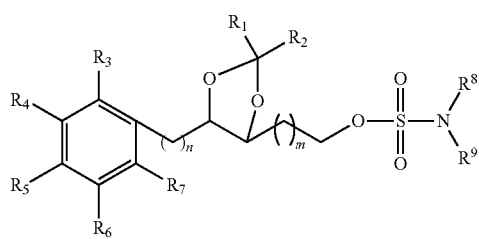

(1)

wherein $R_1$ and $R_2$ are each independently selected from the group consisting of hydrogen, $C_1$-$C_5$ alkyl group and $C_6$-$C_{10}$ aryl group or $R^1$ and $R^2$ together with the carbon atom to which they attach form $C_5$-$C_6$ cycloalkyl group; $R^3$, $R^4$, $R^5$, $R^6$ and $R^7$ are each independently selected from the group consisting of hydrogen, halogen, $C_1$-$C_5$ alkyl group, nitro group and unsubstituted or $C_1$-$C_3$ alkyl-substituted amine group; $R^8$ and $R^9$ are each independently hydrogen or $C_1$-$C_3$ alkyl group; n and m are each independently integer of 0-2.

2. The compound or pharmaceutically acceptable salt thereof according to claim 1, wherein $R^1$ and $R^2$ are each independently selected from the group consisting of hydrogen, $C_1$-$C_3$ alkyl group and phenyl group or $R^1$ and $R^2$ together with the carbon atom to which they attach form $C_5$-$C_6$ cycloalkyl group, and wherein $R^1$ and $R^2$ are not hydrogen at the same time.

3. The compound or pharmaceutically acceptable salt thereof according to claim 1, wherein $R^3$, $R^4$, $R^5$, $R^6$ and $R^7$ are each independently selected from the group consisting of hydrogen, chlorine, fluorine, iodine, $C_1$-$C_3$ alkyl group, nitro group and unsubstituted or methyl-substituted amine group.

4. The compound or pharmaceutically acceptable salt thereof according to claim 1, wherein $R^8$ and $R^9$ are hydrogen.

5. The compound or pharmaceutically acceptable salt thereof according to claim 1, wherein n and m are each independently integer of 0-1.

6. The compound or pharmaceutically acceptable salt thereof according to claim 1, wherein the compound is selected from the group consisting of:

(1) (5-(2-chlorophenyl)-2,2-dimethyl-1,3-dioxolan-4-yl) methylsulfamate;
(2) (5-(2-chlorophenyl)-2-methyl-1,3-dioxolan-4-yl) methyl sulfamate;
(3) (5-(2-chlorophenyl)-2,2-diethyl-1,3-dioxolan-4-yl) methyl sulfamate;
(4) (3-(2-chlorophenyl)-1,4-dioxaspiro[4,4]nonan-2-yl) methyl sulfamate;
(5) (3-(2-chlorophenyl)-1,4-dioxaspiro[4,5]decan-2-yl) methyl sulfamate;
(6) (5-(2-chlorophenyl)-2-phenyl-1,3-dioxolan-4-yl)methyl sulfamate;
(7) (5-(2-fluorophenyl)-2,2-dimethyl-1,3-dioxolan-4-yl) methyl sulfamate;
(8) (5-(2-fluorophenyl)-2-methyl-1,3-dioxolan-4-yl) methyl sulfamate;
(9) (5-(2-fluorophenyl)-2,2-diethyl-1,3-dioxolan-4-yl) methyl sulfamate;
(10) (3-(2-fluorophenyl)-1,4-dioxaspiro[4,4]nonan-2-yl) methyl sulfamate;
(11) (3-(2-fluorophenyl)-1,4-dioxaspiro[4,5]decan-2-yl) methyl sulfamate;
(12) (5-(2-fluorophenyl)-2-phenyl-1,3-dioxolan-4-yl)methyl sulfamate;
(13) (5-(2-iodophenyl)-2,2-dimethyl-1,3-dioxolan-4-yl) methyl sulfamate;
(14) (5-(2-iodophenyl)-2-methyl-1,3-dioxolan-4-yl) methyl sulfamate;
(15) (5-(2-iodophenyl)-2,2-diethyl-1,3-dioxolan-4-yl) methyl sulfamate;
(16) (3-(2-iodophenyl)-1,4-dioxaspiro[4,4]nonan-2-yl) methyl sulfamate;
(17) (3-(2-iodophenyl)-1,4-dioxaspiro[4,5]decan-2-yl) methyl sulfamate;
(18) (5-(2-iodophenyl)-2-phenyl-1,3-dioxolan-4-yl)methyl sulfamate;
(19) (5-(2,4-dichlorophenyl)-2,2-dimethyl-1,3-dioxolan-4-yl)methyl sulfamate;
(20) (5-(2,4-dichlorophenyl)-2-methyl-1,3-dioxolan-4-yl) methyl sulfamate;
(21) (5-(2,4-dichlorophenyl)-2,2-diethyl-1,3-dioxolan-4-yl)methyl sulfamate;
(22) (3-(2,4-dichlorophenyl)-1,4-dioxaspiro[4,4]nonan-2-yl)methyl sulfamate;
(23) (3-(2,4-dichlorophenyl)-1,4-dioxaspiro[4,5]decan-2-yl)methyl sulfamate;
(24) (5-(2,4-dichlorophenyl)-2-phenyl-1,3-dioxolan-4-yl) methyl sulfamate;
(25) (5-(2,6-dichlorophenyl)-2,2-dimethyl-1,3-dioxolan-4-yl)methylsulfamate;
(26) (5-(2,6-dichlorophenyl)-2-methyl-1,3-dioxolan-4-yl) methyl sulfamate;
(27) (5-(2,6-dichlorophenyl)-2,2-diethyl-1,3-dioxolan-4-yl)methyl sulfamate;
(28) (3-(2,6-dichlorophenyl)-1,4-dioxaspiro[4,4]nonan-2-yl)methyl sulfamate;
(29) (3-(2,6-dichlorophenyl)-1,4-dioxaspiro[4,5]decan-2-yl)methyl sulfamate;
(30) (5-(2,6-dichlorophenyl)-2-phenyl-1,3-dioxolan-4-yl) methyl sulfamate;
(31) (5-(2-aminophenyl)-2,2-dimethyl-1,3-dioxolan-4-yl) methyl sulfamate;
(32) (5-(2-aminophenyl)-2-methyl-1,3-dioxolan-4-yl)methyl sulfamate;

(33) (5-(2-aminophenyl)-2,2-diethyl-1,3-dioxolan-4-yl)methyl sulfamate;
(34) (3-(2-aminophenyl)-1,4-dioxaspiro[4,4]nonan-2-yl)methyl sulfamate;
(35) (3-(2-aminophenyl)-1,4-dioxaspiro[4,5]decan-2-yl)methyl sulfamate;
(36) (5-(2-aminophenyl)-2-phenyl-1,3-dioxolan-4-yl)methyl sulfamate;
(37) (5-(2-nitrophenyl)-2,2-dimethyl-1,3-dioxolan-4-yl)methyl sulfamate;
(38) (5-(2-nitrophenyl)-2-methyl-1,3-dioxolan-4-yl)methyl sulfamate;
(39) (5-(2-nitrophenyl)-2,2-diethyl-1,3-dioxolan-4-yl)methyl sulfamate;
(40) (3-(2-nitrophenyl)-1,4-dioxaspiro[4,4]nonan-2-yl)methyl sulfamate;
(41) (3-(2-nitrophenyl)-1,4-dioxaspiro[4,5]decan-2-yl)methyl sulfamate;
(42) (5-(2-nitrophenyl)-2-phenyl-1,3-dioxolan-4-yl)methyl sulfamate;
(43) (5-(2-nitrophenyl)-2-oxo-1,3-dioxolan-4-yl)methyl sulfamate;
(44) (5-(2-methylphenyl)-2,2-dimethyl-1,3-dioxolan-4-yl)methyl sulfamate;
(45) (5-(2-methylphenyl)-2-methyl-1,3-dioxolan-4-yl)methyl sulfamate;
(46) (5-(2-methylphenyl)-2,2-diethyl-1,3-dioxolan-4-yl)methyl sulfamate;
(47) (3-(2-methylphenyl)-1,4-dioxaspiro[4,4]nonan-2-yl)methyl sulfamate;
(48) (3-(2-methylphenyl)-1,4-dioxaspiro[4,5]decan-2-yl)methyl sulfamate;
(49) (5-(2-methylphenyl)-2-phenyl-1,3-dioxolan-4-yl)methyl sulfamate;
(50) (5-(2-methylaminophenyl)-2,2-dimethyl-1,3-dioxolan-4-yl)methyl methyl sulfamate;
(51) (5-phenyl-2,2-dimethyl-1,3-dioxolan-4-yl)methyl sulfamate;
(52) (5-phenyl-2,2-diethyl-1,3-dioxolan-4-yl)methyl sulfamate;
(53) (3-phenyl-1,4-dioxaspiro[4,4]nonan-2-yl)methyl sulfamate;
(54) (3-phenyl-1,4-dioxaspiro[4,5]decan-2-yl)methyl sulfamate;
(55) 2-(5-benzyl-2,2-dimethyl-1,3-dioxolan-4-yl)ethyl sulfamate;
(56) 2-(5-benzyl-2,2-diethyl-1,3-dioxolan-4-yl)ethyl sulfamate;
(57) 2-(3-benzyl-1,4-dioxaspiro[4,4]nonan-2-yl)ethyl sulfamate;
(58) 2-(3-benzyl-1,4-dioxaspiro[4,5]decane-2-yl)ethyl sulfamate;
(59) (5-benzyl-2,2-dimethyl-1,3-dioxolan-4-yl)methyl sulfamate;
(60) (5-benzyl-2,2-diethyl-1,3-dioxolan-4-yl)methyl sulfamate;
(61) (3-benzyl-1,4-dioxaspiro[4,4]nonan-2-yl)methyl sulfamate;
(62) (3-benzyl-1,4-dioxaspiro[4,5]decan-2-yl)methyl sulfamate;
(63) 2-(5-phenyl-2,2-dimethyl-1,3-dioxolan-4-yl)ethyl sulfamate;
(64) 2-(5-phenyl-2,2-diethyl-1,3-dioxolan-4-yl)ethyl sulfamate;
(65) 2-(3-phenyl-1,4-dioxaspiro[4,4]nonan-2-yl)ethyl sulfamate;
(66) 2-(3-phenyl-1,4-dioxaspiro[4,5]decan-2-yl)ethyl sulfamate;
(67) 2-(5-(2-chlorobenzyl)-2,2-dimethyl-1,3-dioxolan-4-yl)ethyl sulfamate;
(68) 2-(5-(2-chlorobenzyl)-2,2-diethyl-1,3-dioxolan-4-yl)ethyl sulfamate;
(69) 2-(3-(2-chlorobenzyl)-1,4-dioxaspiro[4,4]nonan-2-yl)ethyl sulfamate;
(70) 2-(3-(2-chlorobenzyl)-1,4-dioxaspiro[4,5]decan-2-yl)ethyl sulfamate;
(71) (5-(2-chlorobenzyl)-2,2-dimethyl-1,3-dioxolan-4-yl)methyl sulfamate;
(72) (5-(2-chlorobenzyl)-2,2-diethyl-1,3-dioxolan-4-yl)methyl sulfamate;
(73) (3-(2-chlorobenzyl)-1,4-dioxaspiro[4,4]nonan-2-yl)methyl sulfamate;
(74) (3-(2-chlorobenzyl)-1,4-dioxaspiro[4,5]decan-2-yl)methyl sulfamate;
(75) 2-(5-(2-chlorophenyl)-2,2-dimethyl-1,3-dioxolan-4-yl)ethyl sulfamate;
(76) 2-(5-(2-chlorophenyl)-2,2-diethyl-1,3-dioxolan-4-yl)ethyl sulfamate;
(77) 2-(3-(2-chlorophenyl)-1,4-dioxaspiro[4,4]nonan-2-yl)ethyl sulfamate; and
(78) 2-(3-(2-chlorophenyl)-1,4-dioxaspiro[4,5]decan-2-yl)ethyl sulfamate.

7. The compound or pharmaceutically acceptable salt thereof according to claim 6, wherein the compound is selected from the group consisting of:
(1) (5-(2-chlorophenyl)-2,2-dimethyl-1,3-dioxolan-4-yl)methylsulfamate;
(2) (5-(2-chlorophenyl)-2-methyl-1,3-dioxolan-4-yl)methyl sulfamate;
(3) (5-(2-chlorophenyl)-2,2-diethyl-1,3-dioxolan-4-yl)methyl sulfamate;
(5) (3-(2-chlorophenyl)-1,4-dioxaspiro[4,5]decan-2-yl)methyl sulfamate;
(25) (5-(2,6-dichlorophenyl)-2,2-dimethyl-1,3-dioxolan-4-yl)methylsulfamate;
(43) (5-(2-nitrophenyl)-2-oxo-1,3-dioxolan-4-yl)methyl sulfamate;
(44) (5-(2-methylphenyl)-2,2-dimethyl-1,3-dioxolan-4-yl)methyl sulfamate;
(54) (3-phenyl-1,4-dioxaspiro[4,5]decan-2-yl)methyl sulfamate; and
(64) 2-(5-phenyl-2,2-diethyl-1,3-dioxolan-4-yl)ethyl sulfamate.

8. The compound or pharmaceutically acceptable salt thereof according to claim 1, wherein the compound is in the form of racemate, enantiomer, diastereomer, a mixture of enantiomer or a mixture of diastereomer.

9. The compound or pharmaceutically acceptable salt thereof according to claim 1, wherein the pharmaceutically acceptable salt is produced by reacting the compound with an inorganic acid, an organic acid, an amino acid, sulfonic acid, an alkali metal or ammonium ion.

10. A method for muscle relaxation comprising administering pharmaceutically effective amount of the compound or pharmaceutically acceptable salt thereof according to claim 1 to a subject in need thereof.

11. A method for preventing or treating a disease associated with muscle spasm comprising administering pharmaceutically effective amount of the compound or pharmaceutically acceptable salt thereof according to claim 1 to a subject in need thereof.

12. The method according to claim 11, wherein the disease associated with muscle spasm is selected from the group consisting of herniation of intervertebral disk, vascular disorders of the spinal cord, spastic spinal paralysis, cervical spondylosis, cerebral palsy, sequelae of spinal cord injuries, sequelae of head injuries and spinocerebellar degeneration.

13. A composition for preventing or treating a disease associated with muscle spasm, comprising the compound or pharmaceutically acceptable salt thereof according to claim 1 as an active ingredient.

14. The composition according to claim 13, wherein the disease associated with muscle spasm is selected from the group consisting of herniation of intervertebral disk, vascular disorders of the spinal cord, spastic spinal paralysis, cervical spondylosis, cerebral palsy, sequelae of spinal cord injuries, sequelae of head injuries and spinocerebellar degeneration.

15. A method for preparing a compound represented by the following formula 2:

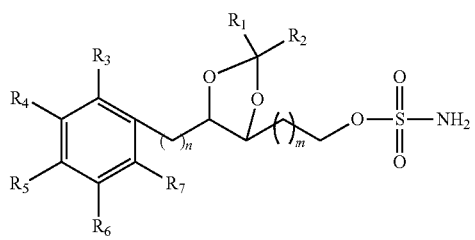

(2)

comprising:
(a) performing sulfamation of a compound represented by the following formula 3:

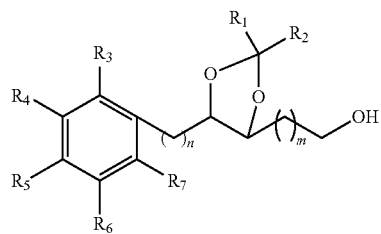

(3)

wherein $R^1$ to $R^7$, n and m are same as defined in claim 1.

16. The method according to claim 15, wherein the method further comprises reacting a compound represented by the following formula 4:

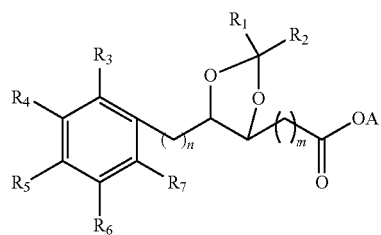

(4)

with a reducing agent to form the compound of formula 3 prior to the step (a), wherein $R^1$ to R', n and m are same as defined in claim 1, and, wherein A is $C_1$-$C_3$ alkoxy $C_1$-$C_3$ alkyl.

17. The method according to claim 16, wherein the method further comprises reacting a compound represented by the following formula 5:

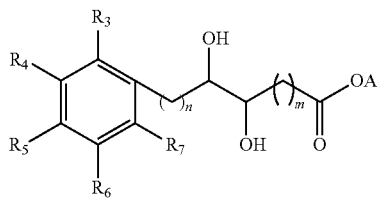

(5)

with and acid and a compound represented by the following formula 6-1 or formula 6-2 to form the compound of formula 4:

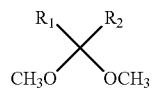

(6-1)

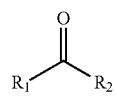

(6-2)

wherein $R_1$ to $R_7$, n, m and A are same as defined in claim 16.

18. The method according to claim 17, wherein the method further comprises performing dihydroxylation of a compound represented by the following formula 7:

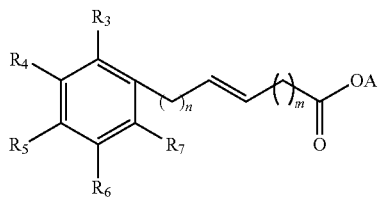

(7)

with an oxidant to form the compound of formula 5, wherein $R^3$ to $R^7$, n, m and A are same as defined in claim 16.

19. A compound represented by the following formula 3 or 4:

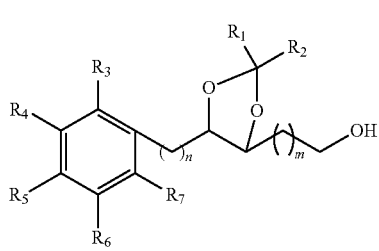

(3)

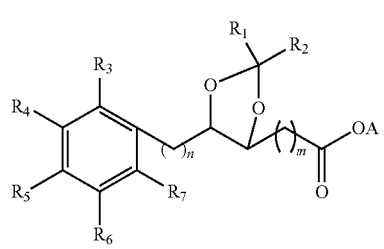
(4)
wherein $R^1$ to $R^7$, n, m and A are same as defined in claim 16.
* * * * *